US010556936B2

(12) United States Patent
Peters et al.

(10) Patent No.: US 10,556,936 B2
(45) Date of Patent: Feb. 11, 2020

(54) IMMUNOGENIC PROTEINS AND FRAGMENTS THEREOF FROM ALLERGENIC MITES

(71) Applicants: ALK-ABELLÓ A/S, Hørsholm (DK); LA JOLLA INSTITUTE FOR ALLERGY AND IMMUNOLOGY, La Jolla, CA (US)

(72) Inventors: Bjoern Peters, La Jolla, CA (US); Gitte Lund, Allerød (DK); Lars Harder Christensen, Allerød (DK); Thomas Stranzl, Farum (DK); Alessandro Sette, La Jolla, CA (US)

(73) Assignees: ALK ABELLÓ, Hørsholm (DK); LA JOLLA INSTITUTE FOR ALLERGY AND IMMUNOLOGY, La Jolla, CA (US)

(*) Notice: Subject to any disclaimer, the term of this patent is extended or adjusted under 35 U.S.C. 154(b) by 0 days.

(21) Appl. No.: 16/303,980

(22) PCT Filed: May 29, 2017

(86) PCT No.: PCT/EP2017/062866
§ 371 (c)(1),
(2) Date: Nov. 21, 2018

(87) PCT Pub. No.: WO2017/203057
PCT Pub. Date: Nov. 30, 2017

(65) Prior Publication Data
US 2019/0202875 A1 Jul. 4, 2019

Related U.S. Application Data

(60) Provisional application No. 62/342,421, filed on May 27, 2016.

(51) Int. Cl.
C07K 14/435 (2006.01)
A61K 39/35 (2006.01)
A61P 37/08 (2006.01)
C12Q 1/02 (2006.01)
G01N 33/68 (2006.01)
C12N 15/70 (2006.01)
C12N 15/86 (2006.01)

(52) U.S. Cl.
CPC ........ *C07K 14/43531* (2013.01); *A61K 39/35* (2013.01); *A61P 37/08* (2018.01); *C12N 15/70* (2013.01); *C12N 15/86* (2013.01); *C12Q 1/025* (2013.01); *G01N 33/6878* (2013.01)

(58) Field of Classification Search
None
See application file for complete search history.

(56) References Cited

FOREIGN PATENT DOCUMENTS

| JP | 2007-244216 A | 9/2007 |
|---|---|---|
| WO | WO 2007/031080 A1 | 3/2007 |
| WO | WO 2012/049310 A1 | 4/2012 |
| WO | WO 2015/100360 A1 | 7/2015 |
| WO | WO 2017/055235 A1 | 4/2017 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinfornnatics.' Science. 290 (5491):471-473.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allerg. Clin. Immunol. 119:965-72, 2007.*
Schein et al. 'Bioinformatics approaches to classifying allergens and predicting cross-reactivity.' Immunol. Allergy Clin. North Am. 27 (1):1-27, 2007.*
Friedl-Hajek et al. 'Identification of a highly promiscuous and an HLA allele-specific T-cell epitope in the birch major allergen Bet v 1 :HLA restriction, epitope mapping and TCR sequence comparisons.' Clin. Exp. Allergy 29:478-487, 1999.*
Banerjee, S., et al., "Conversion of Der p 23, a New Major House Dust Mite Allergen, into a Hypoallergenic Vaccine," *The Journal of Immunology*, 2014, vol. 192, pp. 4867-4875.
Cooper, B., et al., "Relative, Label-free Protein Quantitation: Spectral Counting Error Statistics from Nine Replicate MudPIT Samples," *J Am Soc Mass Spectrom*, 2010, vol. 21, pp. 1534-1546.
Goodman, R., et al., "Criteria used to categorise proteins as allergens for inclusion in allergenonline.org: a curated database for risk assessment," *Clinical and Transitional Allergy*, 2014, vol. 4(Suppl 2), p. 12.
Haqqani, A., et al., "Chapter 16—Quantitative Protein Profiling by Mass Spectrometry Using Isotope-Coded Affinity Tags," *Methods Mol. Biol.*, 2008, vol. 439, pp. 241-256.
Henmar, H., et al., "Allergenicity, immunogenicity and dose-relationship of three intact allergen vaccines and four allergoid vaccines for subcutaneous grass pollen immunotherapy," *Clinical and Experimental Immunology*, 2008, vol. 153, pp. 316-323.
Ishihama, Y., et al., "Exponentially Modified Protein Abundance Index (emPAI) for Extimation of Absolute Protein Amount in Proteomics by the Number of Sequenced Peptides per Protein" *Molecular & Cellular Proteomics*, 2005, vol. 4, pp. 1265-1272.

(Continued)

*Primary Examiner* — Nora M Rooney
(74) *Attorney, Agent, or Firm* — Womble Bond Dickinson (US) LLP

(57) ABSTRACT

The invention relates to novel immunogenic polypeptides identified in house dust mites and storage mites, which have the potential to be used in allergy immunotherapy, for diagnostic purposes, eventually via production of antibodies binding the polypeptide or for characterising allergen extracts of house dust mites and storage mites.

11 Claims, No Drawings

Specification includes a Sequence Listing.

(56) References Cited

OTHER PUBLICATIONS

Jeong, K., et al., "Immunoglobulin E Reactivity of Recombinant Allergen Tyr p 13 from *Tyrophagus putrescentiae* Homologous to Fatty Acid Binding Protein," *Clinical And Diagnostic Laboratory Immunology*, 2005, vol. 12(5), pp. 581-585.
NCBI, Accession No. XP_005494816, 2015, pp. 1-2.
NCBI, Accession No. XP_012788259, 2015, pp. 1-2.
Rider, S., et al., "Draft genome of the scabies mite," *Parasites & Vectors*, 2015, vol. 8(585), pp. 1-14.
Tang, V., et al., Identification and Characterization of a Group of Polymorphic, Single Domain Peptidoglycan Hydrolases of the N1pC/P60 Superfamily in Dust Mites, *The FASEB Journal*, 2015, vol. 29(1, Supplement 720.2), pp. 1-2.
Trauger, S., et al., "Peptide and protein analysis with mass spectrometry," *Spectroscopy*, 2002, vol. 16, pp. 15-28.
UNIPROT, Accession No. Q09JE3, 2006, pp. 1-2.
UNIPROT, Accession No. A2I463, 2007, 1 page.
UNIPROT, Accession No. T2B4F3, 2013, 1 page.
UNIPROT, Accession No. A0A132AL66, 2016, 1 page.
Wells, W., et al., "Comparative Study of Three Proteomic Quantitative Methods, DIGEm cICAT, and iTRAQm Using 2D Gel- or LC-MALDI TOF/TOF," *Journal of Proteome Research*, 2006, vol. 5, pp. 651-658.

\* cited by examiner

IMMUNOGENIC PROTEINS AND FRAGMENTS THEREOF FROM ALLERGENIC MITES

CROSS-REFERENCE TO RELATED APPLICATIONS

This application is a national stage filing under 35 U.S.C. 371 of PCT/EP2017/062866 filed May 29, 2017, which International Application was published by the International Bureau in English on Nov. 30, 2017, and claims priority from U.S. Provisional Application No. 62/342,421, filed May 27, 2016, which applications are hereby incorporated by reference in their entirety in this application.

FIELD OF THE INVENTION

The present invention relates to the field of medicine, in particular allergy immunotherapy against mite allergy. The present invention deals with a group of immunogenic polypeptides with low IgE antibody reactivity but considerable T cell reactivity in a mite allergic population. The immunogenic polypeptides are conserved across important species of house dust mites as well as storage mites, and may be usable in the field of allergy immunotherapy against mite allergy.

BACKGROUND OF THE INVENTION

House dust mites of the genus *Dermatophagoides* are one of the most frequent indoor allergen sources worldwide and are potent inducers of perennial asthma and rhinitis. Several groups of allergens from the most important species (*Dermatophagoides pteronyssinus* (Der p) and *Dermatophagoides farinae* (Der f)) are reported (http\www.allergen.org). The group 1 allergens (e.g. Der p 1 and Der f 1) and the group 2 allergens (e.g. Der p 2 and Der f 2) are considered the clinically most important allergens among house dust mites with IgE binding frequencies of more than 80 percent. Other known allergens from the genus *Dermatophagoides* have variable levels of IgE antibody titers, e.g. Der p 4, 5, 7, 8, 10, 11, 13-15, 18, 20, 21 and 23. In some tropical and subtropical regions of the world, the clinically most important mite allergens may be from both house dust mites and storage mites of which storage mites of the genus *Blomia* (e.g. of the species *Blomia tropicalis*) may be more clinically important than of the genus *Dermatophagoides*. While the major allergens of the species Der p and Der f are highly cross-reactive and have sequence identity of above 80-85%, the sequence identity to the corresponding allergens in storage mite species are much lower (below 40-50%).

Allergen-specific immunotherapy (SIT) represents a causative and disease-modifying approach with long-lasting effects with the efficacy of reducing the symptom burden and concomitant medication use. SIT is based on the administration of increasing doses of the disease-eliciting allergens into sensitized subjects in order to achieve a state of clinical tolerance to subsequent exposure. Conventionally, SIT includes subcutaneous injection (SCIT) or sublingual administration (SLIT) of a pharmaceutical formulation of an allergen extract of the disease-eliciting allergen source, e.g. an allergen extract of house dust mite bodies and fecal particles. Conventional SIT may induce severe side-effects in allergic patients, e.g. anaphylaxis, though SLIT has been proven to have a superior safety profile to SCIT. However, the risk of inducing anaphylaxis is still not negligible because the allergen extracts contains considerable amounts of IgE-reactive allergens. This may limit the broad applicability of this treatment approach.

Current SIT products on the market target either house dust mite allergy or storage mite allergy. Thus, patients with dual sensitization to both house dust mite species and storage mite species may not be well treated by current SIT products.

Accordingly, an unmet need exists in the art for allergy immunotherapeutic products with high safety profile and efficacy to both house dust mites and optionally storage mites.

OBJECT OF THE INVENTION

It is an object of embodiments of the invention to provide proteins and fragments thereof with low or absent IgE reactivity, but T cell reactivity in a high fraction of a mite allergic population and which have sequences with high sequence identity to proteins present in house dust mites and optionally also storage mites.

SUMMARY OF THE INVENTION

The present inventors have identified a number of proteins present in house dust mites. The proteins share the feature of being immunogenic in the sense that they, at least, elicit T cell responses in a high fraction of a mite allergic population, while only a low or insignificant fraction of the same population has raised an IgE antibody immune response against these proteins as such. This renders the use of these proteins and optionally peptides thereof relevant for treatment of allergy, optionally by exploitation of the bystander suppression effect, e.g. as disclosed in WO 2012/049310: effective immunization of a patient to obtain a tolerogenic immune response with a first immunogenic protein, preferably a protein the patient has not raised IgE antibodies against, which is present in a material (e.g. an allergen-source material) which causes allergy in the patient due to the presence of at least one protein allergen (e.g. a protein to which the patient has raised IgE antibodies), followed by later exposure of the patient to both the first protein and the allergen-source material has the consequence that the tolerogenic immune response induced by the first protein suppresses the undesired allergic immune response induced by the protein allergen. So, somewhat paradoxically, immunization with a protein immunogen different from the protein allergen can reduce a later immune response against a protein allergen to which the patient is exposed, provided that this later exposure is accompanied by exposure to the protein immunogen. Thus, in a first aspect the present invention relates to a polypeptide comprising or consisting of (a) an amino acid sequence selected from the group consisting of any one of SEQ ID NOs: 1-44 and 261-332, or (b) an amino acid sequence consisting of at least or exactly 9 contiguous amino acid residues from the amino acid sequence of (a), or (c) an amino acid sequence having a sequence identity of at least 60% with the amino acid sequence of (a), or (d) an amino acid sequence having a sequence identity of at least 60% with the amino acid sequence of (b).

In a related second aspect, the present invention relates to a composition, such as a pharmaceutical composition, comprising one or more of the polypeptides of the first aspect of the invention.

A third aspect of the invention relates to a method of treating allergy (i.e. IgE-mediated allergy) in a patient, where signs and/or symptoms of said allergy are elicited in the patient by exposure to house dust mites or storage mites and/or exposure to at least one protein allergen present in house dust mites or storage mites, the method comprising administering, to the patient, a therapeutically effective amount of a polypeptide of the first aspect of the invention or a composition of the second aspect of the invention.

Consequently, in related aspects, the invention relates to the polypeptides of the first aspect and/or the composition of the second aspect for use as a pharmaceutical, in particular for use in a method of the third aspect of the invention. Likewise, in related aspects the invention relates to use of a polypeptide of the first aspect of the invention or the composition of the second aspect of the invention in a method of the third aspect of the invention. And, in related aspects, the invention relates to use of the polypeptides of the first aspect of the invention in the preparation of a pharmaceutical composition for use in a method of the second aspect of the invention.

A fourth aspect of the invention relates to an in vitro method of determining whether T cells of a subject are responsive to one or more of the polypeptides of the first aspect of the invention and/or the composition of the second aspect of the invention, comprising a step of contacting T cells obtained from the subject with said one or more polypeptides of the first aspect of the invention and/or the composition of the second aspect of the invention and detecting whether the T cells are stimulated.

A fifth aspect of the invention relates to an in vitro method of diagnosing a subject for sensitization or allergy to house dust mites or storage mites, comprising contacting T cells obtained from the subject with one or more of the polypeptides of the first aspect of the invention and/or the composition of the second aspect of the invention and determining whether the T cells are stimulated.

A sixth aspect of the invention relates to an in vitro method for determining whether a subject has, or is at risk of developing, an allergy to house dust mites or storage mites, comprising contacting T cells obtained from the subject with one or more of the polypeptides of the first aspect of the invention and/or the composition of the second aspect of the invention and determining whether the T cells are stimulated.

A seventh aspect relates to an in vitro method of diagnosing a subject for allergy or sensitivity to house dust mites or storage mites, comprising determining the presence of specific IgE against one or more of the polypeptides of the first aspect of the invention and/or the composition of the second aspect of the invention in a biological sample (e.g. serum) obtained from the subject.

An eighth aspect of the invention relates to a diagnostic kit comprising one or more of the polypeptides of the first aspect of the invention and/or the composition of the second aspect of the invention.

A ninth aspect of the invention relates to a nucleic acid fragment, which encodes a polypeptide of the first aspect of the invention.

A tenth aspect of the invention relates to a vector comprising a nucleic acid fragment of the ninth aspect of the invention.

An eleventh aspect of the invention relates to a transformed cell carrying a nucleic acid fragment of the ninth aspect of the invention or a vector of the tenth aspect of the invention. Included in this aspect is also a cell line derived from the transformed cell.

A twelfth aspect of the invention relates to a method of preparing a polypeptide of the first aspect of the invention, the method comprising culturing a transformed cell of the tenth aspect of the invention under conditions that facilitate expression of the nucleic acid fragment of the ninth aspect, and subsequently recovering the expression product (a polypeptide of the second aspect of the invention) from the culture medium.

A thirteenth aspect of the invention relates to an antibody (polyclonal, monoclonal) or an antibody fragment or analogue that specifically binds the polypeptide of the first aspect of the invention.

Finally, a fourteenth aspect relates to a method for qualitative or quantitative determination of the presence in a sample of the polypeptide of the first aspect, the method comprising any one of the following approaches:

contacting the sample with an antibody of the thirteenth aspect and detecting specific binding of material in said sample to said antibody, contacting the sample with a system comprising a solid phase with an antibody of the thirteenth aspect coupled thereto and comprising a labelled polypeptide of the first aspect, where said labelled polypeptide specifically binds said antibody, and gauging the degree of competition exerted by material in the sample on the binding between said labelled polypeptide and said antibody, contacting the sample with a system comprising 1) a solid phase with a polypeptide of the first aspect coupled thereto and comprising 2) a labelled antibody of the thirteenth aspect, where said polypeptide specifically binds said labelled antibody, and gauging the degree of competition exerted by material in the sample on the binding between said polypeptide and said antibody, subjecting polypeptide material from the sample to proteolytic treatment and subjecting the thus obtained material to quantitative MS, optionally using at least one polypeptide described herein as useful as a standard calibration peptide.

DETAILED DISCLOSURE OF THE INVENTION

Definitions

The term "antigen" is an agent that is recognized (i.e. bound by) an antibody and/or a T cell receptor. The latter is normally only possible when the antigen is presented in the context of an MHC Class I or II molecule and after being processed by an antigen presenting cell such as a macrophage or a dendritic cell. This means that relatively large polypeptides may be antigens even though they do not directly bind a T cell receptor but since shorter peptides that are products of antigen presenting cell-processing are recognized by T cell receptors, such proteins are nevertheless termed "antigens".

An "immunogen" is a type of antigen, which is capable of eliciting a specific adaptive immune response that targets the antigen, i.e. immunogens are able to induce the production by the animal body of the antibodies and T cells that recognize antigens. This is in contrast to "haptens", which denote antigens that are not themselves capable of inducing an immune response but which are capable of being recognized by antibodies and/or T-cell receptors.

Of particular interest are "protein antigens", "protein immunogens", "polypeptide antigens", "polypeptide immunogens", "peptide antigens", and "peptide immunogens", which are each characterized by comprising or consisting of a protein, polypeptide or peptide, which in itself is an antigen or immunogen.

The terms "protein", "polypeptide", "oligopeptide", and "peptide" are used interchangeably herein if no other characteristics are used to describe these molecules in terms of molecule size or length: where a polypeptide and protein typically is of a larger size (e.g. >100 amino acid residues), an oligopeptide has between 10 and 100 amino acid residues, and a peptide is an even shorter molecule, the present description and claims will as a rule indicate the relevant length of the proteins, polypeptides, oligopeptides and peptides disclosed herein. These molecules are characterized by being constituted of multiple amino acid residues linked via peptide bonds. Typically all the amino acid residues (except for glycine, which is achiral) are in the L-form (since this allows for processing of the polypeptides by antigen presenting cells), but the presence of D-amino acid residues is not excluded.

A "protein" is also meant to designate a biomolecule comprising or consisting of at least one polypeptide, oligopeptide, or peptide, but which optionally may include other molecular entities, such as prosthetic groups, sugars, lipids, and various other derivatizations of the side groups in the amino acid chain(s). For example, the human adult protein hemoglobin is composed of 4 (2+2) polypeptides (2 identical a chains and 2 identical 13 chains), which are each tightly associated to a heme group (a prosthetic group).

As used herein an "epitope" refers to a region or part of an antigen, such as a poly(peptide) or protein disclosed herein, that elicits an immune response when administered to a subject. An epitope may be a T cell epitope, i.e., an epitope that elicits, stimulates, induces, promotes, increases or enhances a T cell activity, function or response; for example a Th2 cell epitope. Any peptide or combination of peptides of interest can be analyzed to determine whether they include at least one T cell epitope using any number of assays known in the art (e.g. T cell proliferation assays, lymphokine secretion assays, T cell non-responsiveness studies, etc.).

The term "allergen" refers to an antigen which elicits, induces, stimulates, or enhances an immune response, e.g. $Th_2$-immune response, by a cell of the immune system of an exposed animal (e.g., human). An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies and histamine release from mast cells or basophil cells in predisposed subjects.

If no other meaning is given specifically, the term "T cell response" refers to induction of cytokines or proliferation of a T cell in response to an immunogen. It may be determined as explained in Example 2. It may in some instances be referred to simply as a "response" to an immunogen, such as a peptide, polypeptide or a protein.

The term "allergic response" is intended to refer to the hypersensitive immune reaction to a normally innocuous environmental substance known as an allergen. The most common mechanism of allergic reactions is the binding of IgE to the FcεRI on the surface of mast cells and basophils, which in turn causes asthma, hay fever and other common allergic reactions due to release of cytokines, notably histamine.

The term "identity" and "identical" and grammatical variations thereof, as used herein, mean that two or more referenced entities are the same (e.g., amino acid sequences). Thus, where two proteins, polypeptides or peptides are identical, they have the same amino acid sequence. The identity can be over a defined area, e.g. over at least 12, 13, 14, 15, 16, 17, 18, 19, 20, or more contiguous amino acids, such as 50, 100, 150, 200 or the entire length of the parent protein, polypeptide or peptide, optionally wherein the alignment is the best fit with gaps permitted.

Identity can be determined by comparing each position in aligned sequences. A degree of identity between amino acid sequences is a function of the number of identical or matching amino acids at positions shared by the sequences, i.e. over a specified region. Optimal pairwise alignment of sequences for comparisons of identity may be conducted using a variety of algorithms, as are known in the art, including the Clustal Omega program available at http://www.ebi.ac.uk/Tools/msa/clustalo/, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). Such algorithms that calculate percent sequence identity generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol. Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)). Thus, a polypeptide having an amino acid sequence with at least, for example, 85 percent identity to the sequence with SEQ ID NO: 1, it is intended that the amino acid sequence of the polypeptide, after global pairwise alignment with the sequence SEQ ID NO: 1, may include up to 15 amino acid modifications per each 100 amino acids of the sequence SEQ ID NO: 1. That is to say that to obtain a polypeptide having an amino acid sequence at least 85 percent identical to the sequence SEQ ID NO: 1, up to 15 percent (15 of 100) of the amino acid residues in the subject sequence may be inserted, deleted, or substituted with another amino acid.

As used herein, the term "immune response" includes T cell (cellular) mediated and/or B cell (humoral) mediated immune responses, or both cellular and humoral responses. In particular, the term "immune response" may include an IgE-mediated immune response (i.e. an allergic immune response). Exemplary immune responses include T cell responses, such as Th2 responses resulting in cytokine production and/or cellular cytotoxicity. In addition, the term "immune response" includes responses that are indirectly affected by T cell activation, e.g., antibody production (humoral responses) and activation of cytokine responsive cells, e.g., eosinophils, macrophages. Immune cells involved in the immune response include lymphocytes, such as T cells (CD4+, CD8+, Th1 and Th2 cells, memory T cells, regulatory T cells) and B cells; antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer (NK) cells; and myeloid cells, such as macrophages, eosinophils, mast cells, basophils, and granulocytes. A particular immune response is production of immunoglobulin (Ig) isotype antibodies or decreasing IgE antibodies.

SPECIFIC EMBODIMENTS OF THE INVENTION

Embodiments of the First Aspect of the Invention

The polypeptide comprising or consisting of
(a) an amino acid sequence selected from the group consisting of any one of SEQ ID NOs: 1-44 and 261-332,
(b) an amino acid sequence consisting of at least or exactly 9 contiguous amino acid residues from the amino acid sequence of (a), or
(c) an amino acid sequence having a sequence identity of at least 60% with the amino acid sequence of (a), or
(d) an amino acid sequence having a sequence identity of at least 60% with the amino acid sequence of (b)
constitutes the first aspect of the invention. In other words, apart from the polypeptides defined by SEQ ID NOs: 1-44 and 261-332, the invention also provides fragments and amino acid sequence variants of these proteins which can be useful in eliciting an immune response such as for example a specific T-cell response and IgG production.

Thus, a first aspect of the invention includes the option that a polypeptide of option (a) comprises an amino acid sequence variant of any one of SEQ ID NOs: 1-44 and 261-332. Hence, the sequence identity specified in option (c) is in some embodiments at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. The variant sequence may have the same biological activity or functionality as the parent polypeptide of option (a). For example, a variant sequence may have the same enzymatic functionality. The variant sequence may optionally have the same, greater or less ability to elicit, stimulate or induce an immune response (e.g. in vitro T cell proliferation or T cell cytokine production, such as the cytokines, IL-4, IL-5, IL-13 and/or IL-10); to induce immunological tolerance against the original polypeptide and/or to bind or interact with IgE, IgG or IgA antibodies raised against the parent polypeptide.

As mentioned, a first aspect of the invention includes the option (b) that polypeptides are fragments of the polypeptides of option (a) as well as the option (d) which comprises an amino acid sequence variant of polypeptides of option (b) that may still be useful in eliciting an immune response such as for example a specific T-cell response and IgG production. Hence, the sequence identity specified in option (d) is in some embodiments at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%. The variant sequence defined in option (d) may have the same biological activity or functionality as the parent sequence defined in option (b). For example, a variant sequence may have the same enzymatic functionality (i.e. ability to act on the same substrate(s)). The variant sequence may optionally have the same, greater or less ability to
elicit, stimulate or induce an immune response (e.g. effecting in vitro T cell proliferation or T cell cytokine production (for example of the cytokines, IL-4, IL-5, IL-13 and/or IL-10)) in blood from mite allergic individuals;
to induce immunological tolerance against mites, a mite allergen or the parent polypeptide of option (b); and/or
to bind or interact with IgE, IgG or IgA antibodies raised against the parent polypeptide.

For polypeptides of more limited length, for example in the range of 9-30 amino acids in length, the variant sequence may result in the same, greater or less ability to bind a Class HLA II allele or a group of Class HLA II alleles. For example, a variant sequence may bind to at least 70%, such as at least 75%, 80%, 85%, 90% or 95% of the Class HLA II alleles that the parent polypeptide of option (b) binds to. The ability of the parent polypeptide and the variant sequence to bind HLA Class II alleles may be tested under the same test conditions, for example by use of HLA binding prediction tool or in-vitro HLA binding assay. For example, the binding of polypeptide of the invention may be investigated to one or more of the following Class HLA II alleles: DPA1*02:01-DPB1*01:01, DPA1*01:03-DPB1*02:01, DPA1*01:03-DPB1*03:01, DPA1*01:03-DPB1*04:01, DPA1*01:03-DPB1*04:02, DPA1*02:02-DPB1*05:01, DPA1*02:01-DPB1*14:01, DQA1*05:01-DQB1*02:01, DQA1*05:01-DQB1*03:01, DQA1*03:01-DQB1*03:02, DQA1*04:01-DQB1*04:02, DQA1*01:01-DQB1*05:01, DQA1*01:02-DQB1*06:02, DRB1*01:01, DRB1*03:01, DRB1*04:01, DRB1*04:05, DRB1*07:01, DRB1*09:01, DRB1*11:01, DRB1*12:01, DRB1*13:02, DRB1*15:01, DRB3*01:01, DRB3*02:02, DRB4*01:01 and DRB5*01:01.

A polypeptide of option (b) and (d) may be of any length. In some embodiments, the polypeptides may be useful for peptide immunotherapy and comprise a limited number of amino acid residues. For example, a polypeptide of option (b) and (d) may consist of 9 to 30 amino acid residues, such as having a length of 9, 10, 11, 12, 13, 14, 15, 16, 17, 18, 19, 20, 21, 22, 23, 24, 25, 26, 27, 28, 29, or 30 amino acid residues. As mentioned, such polypeptides of option (b) or (d) may comprise at least or exactly 9 contiguous amino acid residues, such as at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30 contiguous amino acid residues. In such embodiments, the consecutive amino acids of option (b) and (d) may comprise a T cell epitope, optionally a Th$_2$ cell epitope.

In other embodiments, a polypeptide of option (b) or (d) may comprise several amino acid residues. Hence, in option (b) or (d), the at least or exactly 9 contiguous amino acid residues may constitute at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, or at least or exactly or at most 125 contiguous amino acid residues.

The number of contiguous amino acids in option (b) and (d) can be higher for all of SEQ ID NOs: 1-44 and 261-304, 306-318, and 320-332. Another way to phrase this is that for each of SEQ ID NOs: 2-44 and 262-304, the number of the contiguous amino acid residues is at least or exactly or at most N–n, where N is the length of the sequence ID in question and n is any integer between 1 and N–9; that is, the at least 9 contiguous amino acids can be at least any number between 9 and the length of the reference sequence minus one, in increments of one. Consequently:

Insofar as embodiment (b) and (d) relate to SEQ ID NOs: 1-44, 261-304, 306-318, and 320-332, the at least 9 contiguous amino acids referred to in option (b) in the definition of the first aspect of the invention may also constitute at least or exactly or at most 126, at least or exactly or at most 127, at least or exactly or at most 128, or at least or exactly or at most 129 contiguous amino acid residues.

Insofar as embodiment (b) and (d) relate to SEQ ID NOs: 2-44 262-304, 306-318, and 320-332, the at least 9 contiguous amino acids referred to in option (b) in the definition of the first aspect of the invention may also constitute at least or exactly or at most 130 or at least or exactly or at most 131 contiguous amino acid residues.

Insofar as embodiment (b) and (d) relate to SEQ ID NOs: 4-44, 264-304, 306-318, and 320-332, the at least 9 contiguous amino acids referred to in option (b) in the definition of the first aspect of the invention may also constitute at least or exactly or at most 132 or at least or exactly or at most 133 contiguous amino acid residues.

Insofar as embodiment (b) and (d) relate to SEQ ID NOs: 5-44, 265-304, 306-318, and 320-332, the at least 9 contiguous amino acids referred to in option (b) in the definition of the first aspect of the invention may also constitute at least or exactly or at most 134, at least or exactly or at most 135, or at least or exactly or at most 136 contiguous amino acid residues.

Insofar as embodiment (b) and (d) relate to SEQ ID NOs: 5-44, 265-304, 306-314. 316-318, 320-328, and 330-332, the at least 9 contiguous amino acids referred to in option (b) in the definition of the first aspect of the invention may also constitute at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, or at least or exactly or at most 149 contiguous amino acid residues.

Insofar as embodiment (b) and (d) relate to SEQ ID NOs: 5-44 265-304, 306-313, 316-318, 320-327, and 330-332, the at least 9 contiguous amino acids referred to in option (b) in the definition of the first aspect of the invention may also constitute, at least or exactly or at most 150, at least or exactly or at most 151 contiguous amino acid residues.

Insofar as embodiment (b) and (d) relate to SEQ ID NOs: 7-44, 267-304, 306-313, 316-318, 320-327, and 330-332, the at least 9 contiguous amino acids referred to in option (b) in the definition of the first aspect of the invention may also constitute at least or exactly or at most 152 or at least or exactly or at most 153 contiguous amino acid residues.

Insofar as embodiment (b) and (d) relate to SEQ ID NOs: 9-44, 269-304, 306-313, 316-318, 320-327, and 330-332 the at least 9 contiguous amino acids referred to in option (b) in the definition of the first aspect of the invention may also constitute at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, or at least or exactly or at most 170 contiguous amino acid residues.

Insofar as embodiment (b) and (d) relate to SEQ ID NOs: 10-44, 270-304, 306-313, 316-318, 320-327, and 330-332, the at least 9 contiguous amino acids referred to in option (b)

in the definition of the first aspect of the invention may also constitute at least or exactly or at most 171 contiguous amino acid residues.

Insofar as embodiment (b) and (d) relate to SEQ ID NOs: 11-44, 271-304, 306-313, 316-318, 320-327, and 330-332, the at least 9 contiguous amino acids referred to in option (b) in the definition of the first aspect of the invention may also constitute at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, or at least or exactly or at most 185 contiguous amino acid residues Insofar as embodiment (b) and (d) relate to SEQ ID NOs: 11-44, 271-304, 306-313, 316-317, 320-327, and 330-331, the at least 9 contiguous amino acids referred to in option (b) in the definition of the first aspect of the invention may also constitute at least or exactly or at most 186, or at least or exactly or at most 187 contiguous amino acid residues.

Insofar as embodiment (b) and (d) relate to SEQ ID NOs: 13-44, 273-304, 306-313, 316-317, 320-327, and 330-331, the at least 9 contiguous amino acids referred to in option (b) in the definition of the first aspect of the invention may also constitute at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, or at least or exactly or at most 221 contiguous amino acid residues.

Insofar as embodiment (b) and (d) relate to SEQ ID NOs: 15-44, 275-304, 306-313, 316-317, 320-327, and 330-331, the at least 9 contiguous amino acids referred to in option (b) in the definition of the first aspect of the invention may also constitute at least or exactly or at most 222, at least or exactly or at most 223, at least or exactly or at most 224, at least or exactly or at most 225, at least or exactly or at most 226, or at least or exactly or at most 227 contiguous amino acid residues.

Insofar as embodiment (b) and (d) relate to SEQ ID NOs: 17-44, 277-304, 306-313, 316-317, 320-327, and 330-331, the at least 9 contiguous amino acids referred to in option (b) in the definition of the first aspect of the invention may also constitute at least or exactly or at most 228 contiguous amino acid residues.

Insofar as embodiment (b) and (d) relate to SEQ ID NOs: 17, 19-44, 277, 279-304, 306-313, 316-317, 320-327, and 330-331, the at least 9 contiguous amino acids referred to in option (b) in the definition of the first aspect of the invention may also constitute at least or exactly or at most 229, at least or exactly or at most 230, or at least or exactly or at most 231 contiguous amino acid residues.

Insofar as embodiment (b) and (d) relate to SEQ ID NOs: 17, 19-44, 277, 279-304, 306-313, 317, 320-327, and 331, the at least 9 contiguous amino acids referred to in option (b) in the definition of the first aspect of the invention may also constitute at least or exactly or at most 232 contiguous amino acid residues.

Insofar as embodiment (b) and (d) relate to SEQ ID NOs: 19-44, 279-304, 306-313, 317, 320-327, and 331, the at least 9 contiguous amino acids referred to in option (b) in the definition of the first aspect of the invention may also constitute at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, or at least or exactly or at most 251 contiguous amino acid residues.

Insofar as embodiment (b) and (d) relate to SEQ ID NOs: 20-44, 280-304, 306-313, and 320-327, the at least 9 contiguous amino acids referred to in option (b) in the definition of the first aspect of the invention may also constitute at least or exactly or at most 252 contiguous amino acid residues.

Insofar as embodiment (b) and (d) relate to SEQ ID NOs: 21-44 and 281-304, 306-313, and 320-327, the at least 9 contiguous amino acids referred to in option (b) in the definition of the first aspect of the invention may also constitute at least or exactly or at most 253, at least or exactly or at most 254, at least or exactly or at most 255, at least or exactly or at most 256, at least or exactly or at most 257, at least or exactly or at most 258, or at least or exactly or at most 259 contiguous amino acid residues.

Insofar as embodiment (b) and (d) relate to SEQ ID NOs: 21-44 and 281-304, 306-312, and 320-326, the at least 9 contiguous amino acids referred to in option (b) in the definition of the first aspect of the invention may also constitute at least or exactly or at most 260 contiguous amino acid residues.

Insofar as embodiment (b) and (d) relate to SEQ ID NOs: 22-44, 282-304, 306-312, and 320-326, the at least 9 contiguous amino acids referred to in option (b) in the definition of the first aspect of the invention may also constitute at least or exactly or at most 261 contiguous amino acid residues.

Insofar as embodiment (b) and (d) relate to SEQ ID NOs: 23-44, 283-304, 306-312, and 320-326, the at least 9 contiguous amino acids referred to in option (b) in the definition of the first aspect of the invention may also constitute at least or exactly or at most 262, at least or exactly or at most 263, at least or exactly or at most 264, at least or exactly or at most 265, at least or exactly or at most 266, at least or exactly or at most 267, at least or exactly or at most 268, or at least or exactly or at most 269 contiguous amino acid residues.

Insofar as embodiment (b) and (d) relate to SEQ ID NOs: 24-44, 284-304, 306-312, and 320-326, the at least 9 contiguous amino acids referred to in option (b) in the definition of the first aspect of the invention may also constitute at least or exactly or at most 270 contiguous amino acid residues.

Insofar as embodiment (b) and (d) relate to SEQ ID NOs: 25-44, 285-304, 306-312, and 320-326, the at least 9 contiguous amino acids referred to in option (b) in the definition of the first aspect of the invention may also constitute at least or exactly or at most 271, at least or exactly or at most 272, at least or exactly or at most 273, or at least or exactly or at most 274 contiguous amino acid residues.

Insofar as embodiment (b) and (d) relate to SEQ ID NOs: 26-44, 286-304, 306-312, and 320-326, the at least 9 contiguous amino acids referred to in option (b) in the definition of the first aspect of the invention may also constitute at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, or at least or exactly or at most 308 contiguous amino acid residues.

Insofar as embodiment (b) and (d) relate to SEQ ID NOs: 26-44, 286-304, 306-311, and 320-325, the at least 9 contiguous amino acids referred to in option (b) in the definition of the first aspect of the invention may also constitute at least or exactly or at most 309 contiguous amino acid residues.

Insofar as embodiment (b) and (d) relate to SEQ ID NOs: 27-44, 287-304, 306-311, and 320-325, the at least 9 contiguous amino acids referred to in option (b) in the definition of the first aspect of the invention may also constitute at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, or at least or exactly or at most 320 contiguous amino acid residues.

Insofar as embodiment (b) and (d) relate to SEQ ID NOs: 28-44, 288-304, 306-311, and 320-325, the at least 9 contiguous amino acids referred to in option (b) in the definition of the first aspect of the invention may also constitute at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, or at least or exactly or at most 331 contiguous amino acid residues.

Insofar as embodiment (b) and (d) relate to SEQ ID NOs: 30-44, 290-304, 306-311, and 320-325, the at least 9 contiguous amino acids referred to in option (b) in the definition of the first aspect of the invention may also constitute at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, or at least or exactly or at most 360 contiguous amino acid residues.

Insofar as embodiment (b) and (d) relate to SEQ ID NOs: 31-44, 291-304, 306-311, and 320-325, the at least 9 contiguous amino acids referred to in option (b) in the definition of the first aspect of the invention may also constitute at least or exactly or at most 361 contiguous amino acid residues.

Insofar as embodiment (b) and (d) relate to SEQ ID NOs: 32-44 and 292-304, 306-311, and 320-325, the at least 9 contiguous amino acids referred to in option (b) in the definition of the first aspect of the invention may also constitute at least or exactly or at most 362 contiguous amino acid residues.

Insofar as embodiment (b) and (d) relate to SEQ ID NOs: 32-44 and 292-304, 307-311, and 321-325, the at least 9 contiguous amino acids referred to in option (b) in the definition of the first aspect of the invention may also constitute at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, or at least or exactly or at most 428 contiguous amino acid residues.

Insofar as embodiment (b) and (d) relate to SEQ ID NOs: 33-44, 293-304, 307-311, and 321-325, the at least 9 contiguous amino acids referred to in option (b) in the definition of the first aspect of the invention may also constitute at least or exactly or at most 429, at least or exactly or at most 430, at least or exactly or at most 431, at least or exactly or at most 432, at least or exactly or at most 433 contiguous amino acid residues.

Insofar as embodiment (b) and (d) relate to SEQ ID NOs: 34-44, 294-304, 307-311, and 321-325, the at least 9 contiguous amino acids referred to in option (b) in the definition of the first aspect of the invention may also constitute at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, or at least or exactly or at most 458 contiguous amino acid residues.

Insofar as embodiment (b) and (d) relate to SEQ ID NOs: 34-44, 294-304, 307-310, and 321-324, the at least 9 contiguous amino acids referred to in option (b) in the definition of the first aspect of the invention may also constitute at least or exactly or at most 459, at least or exactly or at most 460, or at least or exactly or at most 461 contiguous amino acid residues.

Insofar as embodiment (b) and (d) relate to SEQ ID NOs: 36-44, 296-304, 307-310, and 321-324, the at least 9 contiguous amino acids referred to in option (b) in the definition of the first aspect of the invention may also constitute at least or exactly or at most 462 contiguous amino acid residues.

Insofar as embodiment (b) and (d) relate to SEQ ID NOs: 37-44, 297-304, the at least 9 contiguous amino acids referred to in option (b) in the definition of the first aspect of the invention may also constitute at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, or at least or exactly or at most 473 contiguous amino acid residues.

Insofar as embodiment (b) and (d) relate to SEQ ID NOs: 38-44, 298-304, 307-310, and 321-324, the at least 9 contiguous amino acids referred to in option (b) in the definition of the first aspect of the invention may also constitute at least or exactly or at most 474, at least or exactly or at most 475, at least or exactly or at most 476, at least or exactly or at most 477, at least or exactly or at most 478, at least or exactly or at most 479, at least or exactly or at most 480, or at least or exactly or at most 481 contiguous amino acid residues.

Insofar as embodiment (b) and (d) relate to SEQ ID NOs: 38-44, 298-304, 307, 308, 310, 321, 322, and 324, the at least 9 contiguous amino acids referred to in option (b) in the definition of the first aspect of the invention may also constitute at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, or at least or exactly or at most 490 contiguous amino acid residues.

Insofar as embodiment (b) and (d) relate to SEQ ID NOs: 38-44, 298-304, 307, 308, 321, and 322, the at least 9 contiguous amino acids referred to in option (b) in the definition of the first aspect of the invention may also constitute at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, or at least or exactly or at most 508 contiguous amino acid residues.

Insofar as embodiment (b) and (d) relate to SEQ ID NOs: 39-44, 299-304, 307, 308, 321, and 321, the at least 9 contiguous amino acids referred to in option (b) in the definition of the first aspect of the invention may also constitute at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518 contiguous amino acid residues.

Insofar as embodiment (b) and (d) relate to SEQ ID NOs: 39, 41-44, 299, 301-304, 307, 308, 321, and 321, the at least 9 contiguous amino acids referred to in option (b) in the definition of the first aspect of the invention may also constitute at least or exactly or at most 519 contiguous amino acid residues.

Insofar as embodiment (b) and (d) relate to SEQ ID NOs: 41-44, 301-304, 307, 308, 321, and 322, the at least 9 contiguous amino acids referred to in option (b) in the definition of the first aspect of the invention may also constitute at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, or at least or exactly or at most 884 contiguous amino acid residues.

Insofar as embodiment (b) and (d) relate to SEQ ID NOs: 41, 43, 44, 302, 303, and 304, the at least 9 contiguous amino acids referred to in option (b) in the definition of the first aspect of the invention may also constitute at least or exactly or at most 885 or at least or exactly or at most 886 contiguous amino acid residues.

Insofar as embodiment (b) and (d) relate to SEQ ID NOs: 43-44, 303-304, 307, 308, 321, and 322, the at least 9 contiguous amino acids referred to in option (b) in the definition of the first aspect of the invention may also constitute at least or exactly or at most 887 or at least or exactly or at most 888 contiguous amino acid residues.

Insofar as embodiment (b) and (d) relate to SEQ ID NOs: 43-44, 303-304, 307, and 321, the at least 9 contiguous amino acids referred to in option (b) in the definition of the first aspect of the invention may also constitute at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, or at least or exactly or at most 972 contiguous amino acid residues.

Insofar as embodiment (b) and (d) relate to SEQ ID NOs: 43-44, and 303-304, the at least 9 contiguous amino acids referred to in option (b) in the definition of the first aspect of the invention may also constitute at least or exactly or at most 973, or at least or exactly or at most 974 contiguous amino acid residues.

Finally, insofar as embodiment (b) and (d) relate to SEQ ID NOs: 44 and 304, the at least 9 contiguous amino acids referred to in option (b) in the definition of the first aspect of the invention may also constitute at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, or at least or exactly or at most 989 contiguous amino acid residues.

In any one of the embodiments of option (b) and (d) above, the polypeptide of the invention is also one that has at least or exactly 9 contiguous amino acid residues defined for option (b) above in any one of the embodiments and wherein the contiguous amino acid residues commence at amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117 in any one of SEQ ID NOs: 1-44 and 261-332; or at amino acid residue 118, 119, 120, 121, or 122 in any one of SEQ ID NOs: 1-44, 261-304, 306-318, and 320-332; or at amino acid residue 123 or 124 in any one of SEQ ID NOs: 2-44, 262-304, 306-318, and 320-332; or at amino acid residue 125 or 126 in any one of SEQ ID NOs: 4-44, 264-304, 306-318, and 320-332; or at amino acid residue 127, 128, or 129 in any one of SEQ ID NOs: 5-44, 265-304, 306-318, and 320-332; or at amino acid residue 130, 131, 132, 133, 134, 135, 136, 135, 136, 137, 138, 139, 140, 141, 142 in any one of SEQ ID NOs: 5-44, 265-304, 306-314, 316-318, 320-328, and 330-332; or at amino acid residue, 143 or 144 in any one of SEQ ID NOs: 5-44, 265-304, 306-313, 316-318, 320-327, and 330-332; or at amino acid residue 145 and 146 in any one of SEQ ID NOs: 7-44, 267-304, 306-313, 316-318, 320-327, and 330-332; or at amino acid residue 147, 148, 149, 150, 151, 152, 153, 154, 155, 156, 157, 158, 159, 160, 161, 162, or 163 in any one of SEQ ID NOs: 9-44, 269-304, 306-313, 316-318, 320-327, and 330-332; or at amino acid residue 164 in any one of SEQ ID NOs: 10-44, 270-304, 306-313, 316-318, 320-327, and 330-332; or at amino acid residue 165, 166, 167, 168, 169, 170, 171, 172, 173, 174, 175, 176, 177, 178 in any one of SEQ ID NOs: 11-44, 271-304, 306-313, 316-318, 320-327, and 330-332; or at amino acid residue 179 or 180 in any one of SEQ ID NOs: 11-44 and 271-304, 306-313, 316-317, 320-327, and 330-331; or at amino acid residue 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, or 214 in any one of SEQ ID NOs: 13-44, 273-304, 306-313, 316-317, 320-327, and 330-331; or at amino acid residue 215, 216, 217, 218, 219, or 220 in any one of SEQ ID NOs: in any one of SEQ ID NOs: 15-44, 275-304, 306-313, 316-317, 320-327, and 330-331; or at amino acid residue 221 in any one of SEQ ID NOs: 17-44 and 275-304; or at amino acid residue 222, 223, or 224 in any one of SEQ ID NOs: 17, 19-44, 277, 279-304, 306-313, 316-317, 320-327, and 330-331; or at amino acid residue 225 in any one of SEQ ID NOs: 17, 19-44, 277, 279-304, 306-313, 317, 320-327, and 331; or at amino acid residue 226, 227, 228, 229, 230, 231, 232, 233, 234, 235, 236, 237, 238, 239, 240, 241, 242, 243, or 244 in any one of SEQ ID NOs: 19-44, 279-304, 306-313, 317, 320-327, and 331; or at amino acid residue 245 in any one of SEQ ID NOs: 20-44, 280-304, 306-313, and 320-327; or at amino acid residue 246, 247, 248, 249, 250, 251, or 252 in any one of SEQ ID NOs: 21-44 and 281-304, 306-313, and 320-327; or at amino acid residue 253 in any one of SEQ ID NOs: 21-44, 281-304, 306-312, and 320-326; or at amino acid residue 254 in any one of SEQ ID NOs: 22-44 and 282-304; or at amino acid residue 255, 256, 257, 258, 259, 260, 261, or 262 in any one of SEQ ID NOs: 23-44, 283-304, 306-312, and 320-326; or at amino acid residue 263 in any one of SEQ ID NOs: in any one of SEQ ID NOs: 24-44, 284-304, 306-312, and 320-326; or at amino acid residue 264, 265, 266, or 267 in any one of SEQ ID NOs: 25-44, 285-304, 306-312, and 320-326; or at amino acid residue 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301 in any one of SEQ ID NOs: 26-44, 286-304, 306-312, and 320-326; or at amino acid residue 302 in any one of SEQ ID NOs: 26-44, 286-304, 306-311, and 320-325; or at amino acid residue, 303, 304, 305, 306, 307, 308, 309, 310, 311, 312, or 313 in any one of SEQ ID NOs: 27-44, 287-304, 306-311, and 320-325; or at amino acid residue 314, 315, 316, 317, 318, 319, 320, 321, 322, 323, or 324 in any one of SEQ ID NOs: 28-44, 288-304, 306-311, and 320-325; or at amino acid residue 325, 326, 327, 328, 329, 330, 331, 332, 333, 334, 335, 336, 337, 338, 339, 340, 341, 342, 343, 344, 345, 346, 347, 348, 349, 350, 351, 352, or 353 in any one of SEQ ID NOs: 30-44, 290-304, 306-311, and 320-325; or at amino acid residue 354 in any one of SEQ ID NOs: 31-44 291-304, 306-311, and 320-325; or at amino acid residue 355 in any one of SEQ ID NOs: 32-44 292-304, 306-311, and 320-325; or at amino acid residue 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, or 421 in any one of SEQ ID NOs: 32-44, 292-304, 307-311, and 321-325; or at amino acid residue 422, 423, 424, 425, or 426 in any one of SEQ ID NOs: 33-44, 293-304, 307-311, and 321-325; or at amino acid residue 427, 428, 429, 430, 431, 432, 433, 434, 435, 436, 437, 438, 439, 440, 441, 442, 443, 444, 445, 446, 447, 448, 449, 450, 451 in any one of SEQ ID NOs: 34-44, 294-304, 307-311, and 321-325; or at amino acid residue 452, 453, or 454 in any one of SEQ ID NOs: 34-44, 294-304, 307-310, and 321-324; or at amino acid residue 455 in any one of SEQ ID NOs: 36-44, 296-304, 307-310, and 321-324; or at amino acid residue 456, 457, 458, 459, 460, 461, 462, 463, 464, 465, or 466 in any one of SEQ ID NOs: 37-44, 297-304, 307-310, and 321-324; or at amino acid residue 467, 468, 469, 470, 471, 472, 473, or 474 in any one of SEQ ID NOs: 38-44, 298-304, 307-310, and 321-324; or at amino acid residue 475, 476, 477, 478, 479, 480, 481, 482, or 483 in any one of SEQ ID NOs: 38-44, 298-304, 307, 308, 310, 321, 323, and 324; or at amino acid residue 484, 485, 486, 487, 488, 489, 490, 491, 492, 493, 494, 495, 496, 497, 498, 499, 500, or 501 in any one of SEQ ID NOs: 38-44, 298-304, 307, 308, 321, and 323; or at amino acid residue 502, 503, 504, 505, 506, 507, 508, 509, 510, or 511 in any one of SEQ ID NOs: 39-44, 299-304, 307, 308, 321, and 323; or at amino acid residue 512 in any one of SEQ ID NOs: 39, 41-44, 299, 301-304, 307, 308, 321, and 323; or at amino acid residue 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, or 877 in any one of SEQ ID NOs: 41-44 301-304, 307, 308, 321, and 323; or at amino acid residue 878 or 879 in any one of SEQ ID NOs: 41, 43, 44, 301, 303, 304, 307, 308, 321, and 323; or at amino acid residue 880 or 881 in any one of SEQ ID NOs: 43, 44, 303, 304, 307, 308, 321, and 323; or at amino acid residue, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965 in any one of SEQ ID NOs: 43, 44, 303, 304, 307, and 321; or at amino acid residue, 966 or 967 in any one of SEQ ID NOs: 43, 44, 303, and 304; or at amino acid residue, 968, 969, 970, 971, 972, 973, 974, 975, 976, 977, 978, 979, 980, 981, or 982 in SEQ ID NO: 44 or 304.

The possible commencement point in the sequences listed above is of course dependent on the number of contiguous amino acid residues (L) selected: the N-terminal first residue cannot in any case be higher numbered than N-L+1, where N is the number of amino acid residues of the sequence among SEQ ID NOs: 1-44 and 261-332 in which the contiguous amino acid residues are found.

As will be apparent from the examples, certain peptides are particularly interesting embodiments of the first aspect of the invention: These embodiments of the first aspect relate to a polypeptide, optionally of 9 to 30 amino acid residues in length, comprise or consist of an amino acid sequence consisting of 9, 10, 11, 12, 13, 14 or 15 consecutive amino acid residues from a parent sequence selected from any one of SEQ ID NOs: 45-260 and any one of SEQ ID NOs: 45, 61, 63, 80, 100, 113, 147, 154, 170, 172, 191, 215, 225, 226, 248, and 260, wherein any cysteine residue is/are substituted with a serine residue, an alanine residue or a 2-aminobutyric acid residue, or a variant of 9 consecutive amino acid residues from a parent sequence selected from any one of SEQ ID NOs: 45-260, wherein 1 or 2 or 3 amino acid residues are substituted with a different amino acid residue in the variant relative to the parent sequence, or a variant of 10 consecutive amino acid residues from a parent sequence selected from any one of SEQ ID NOs: 45-260, wherein 1 or 2 or 3 or 4 amino acid residues are substituted with a different amino acid residue in the variant relative to the parent sequence, or a variant of 11 consecutive amino acid residues from a parent sequence selected from any one of SEQ ID NOs: 45-260, wherein 1 or 2 or 3 or 4 amino acid residues are substituted with a different amino acid residue in the variant relative to the parent sequence, or a variant of 12 consecutive amino acid residues from a parent sequence selected from any one of SEQ ID NOs: 45-260, wherein 1 or 2 or 3 or 4 amino acid residues are substituted with a different amino acid residue in the variant relative to the parent sequence, or a variant of 13 consecutive amino acid residues from a parent sequence selected from any one of SEQ ID NOs: 45-260, wherein 1, 2, 3, 4, or 5 amino acid residues are substituted with a different amino acid residue in the variant relative to the parent sequence, or a variant of 14 consecutive amino acid residues from a parent sequence selected from any one of SEQ ID NOs: 45-260, wherein 1, 2, 3, 4, or 5 amino acid residues are substituted with a different amino acid residue in the variant relative to the parent sequence, or a variant of a parent sequence selected from any one of SEQ ID NOs: 45-260, wherein 1, 2, 3, 4, 5, or 6 amino acids are substituted with a different amino acid in the variant relative to the parent sequence.

In these embodiments, the parent sequence may commence at residue 1, 2, 3, 4, 5, 6, or 7 in any one of SEQ ID NOs: 45-260 when the peptide is 9 amino acids in length, or residue 1, 2, 3, 4, 5, or 6 in any one of SEQ ID NOs: 45-260 when the peptide is 10 amino acids in length, or residue 1, 2, 3, 3, 4, or 5 in any one of SEQ ID NOs: 45-260 when the peptide is 11 amino acids in length, or residue 1, 2, 3, or 4 in any one of SEQ ID NOs: 45-260 when the peptide is 12 amino acids in length, or residue 1, 2, or 3 in any one of SEQ ID NOs: 45-260 when the peptide is 13 amino acids in length, or residue 1 or 2 in any one of SEQ ID NOs: 45-260 when the peptide is 14 amino acids in length.

Thus, in some embodiments of the polypeptide of the first aspect of the invention, the polypeptide comprises or consists of 9 to 15 consecutive amino acid residues of an amino acid sequence set forth in any one of SEQ ID NOs: 45-260 or a variant sequence thereof wherein 1, 2, 3, 4, 5, or 6 amino acids are substituted with a different amino acid in the variant relative to the parent sequence. In such embodiments, the polypeptide may have a length of 9-30 amino acid residues or more, for example 9, 10, 11, 12, 13, 14, 15, 16, 17, 18, 19, 20, 21, 22, 23, 24, 25, 26, 27, 28, 29, or 30, or optionally more amino acid residues. The variant sequence may have the same biological activity or functionality as the parent sequence as defined of polypeptides of option (b) of the first aspect. For example, the variant sequence may result in the same, greater or less ability to bind a Class HLA II allele or a group of Class HLA II alleles or the variant sequence may comprise a T cell epitope, optionally a $Th_2$ cell epitope. Optionally, the Class HLA II binding is determined with respect to a particular group of Class HLA II alleles, for example one or more or all of the following alleles: DPA1*02:01-DPB1*01:01, DPA1*01:03-DPB1*02:01, DPA1*01:03-DPB1*03:01, DPA1*01:03-DPB1*04:01, DPA1*01:03-DPB1*04:02, DPA1*02:02-DPB1*05:01, DPA1*02:01-DPB1*14:01, DQA1*05:01-DQB1*02:01, DQA1*05:01-DQB1*03:01, DQA1*03:01-DQB1*03:02, DQA1*04:01-DQB1*04:02, DQA1*01:01-DQB1*05:01, DQA1*01:02-DQB1*06:02, DRB1*01:01, DRB1*03:01, DRB1*04:01, DRB1*04:05, DRB1*07:01, DRB1*09:01, DRB1*11:01, DRB1*12:01, DRB1*13:02, DRB1*15:01, DRB3*01:01, DRB3*02:02, DRB4*01:01 and DRB5*01:01.

The polypeptide of the first aspect of the invention may in certain embodiments find special use in qualitative or quantitative mass spectrometric determination of polypeptides. In these embodiments, the polypeptide of the invention typically consists of an amino acid sequence identical with the amino acid sequence of a proteolytic fragment of a protein consisting of an amino acid sequence selected from any one of SEQ ID NOs: 1-44, and 261-332 (preferably SEQ ID NOs 1-44 and 305-318, i.e. proteolytic fragments of naturally occurring proteins). Such a proteolytic fragment is typically a tryptic or chymotryptic fragment, but any suitable protease can be used to provide the proteolytic fragment: papain, pepsin, ArgC, LysC, V8 protease, AspN, pronase, and carboxypeptidease C. In certain embodiments, the polypeptide, which has the amino acid sequence of a proteolytic fragment will also include a mass modifying label; see infra for a discussion of labels useful in qMS.

Embodiments of the Second Aspect of the Invention

A composition of the second aspect of the invention comprises one or more of the polypeptides of the first aspect of the invention. When the composition is for pharmaceutical use, it further comprises a pharmaceutically acceptable carrier, excipient and/or adjuvant, optionally sterile. It will typically be formulated as a vaccine for parenteral or sublingual administration.

Any suitable administration form is useful for the pharmaceutical composition, but one particularly relevant form is a powder, optionally formulated to be re-dissolved before use. Also, fast-dispersing tablets (optionally freeze dried) suitable for sublingual administration or buccal administration are of relevance.

The pharmaceutical composition may be a vaccine, e.g. a product for use in conducting immunotherapy, including but not limited to a vaccine for treating an allergic immune response to mites. The vaccine may be formulated for parenteral administration, such as by subcutaneous, intradermal, transcutaneous administration, e.g. formulated as a powder that optionally may be re-dissolved before use.

A pharmaceutical composition comprises in addition to the peptide combination, therapeutically inactive ingredients, such as pharmaceutically acceptable or physiologically acceptable excipient(s), carrier(s) and/or adjuvant(s), which are well-known to the person skilled in the art and may include, but are not limited to, solvents, emulsifiers, wetting agents, plasticizers, solubilizers (e.g. solubility enhancing agents), coloring substances, fillers, preservatives, anti-oxidants, anti-microbial agents, viscosity adjusting agents, buffering agents, pH adjusting agents, isotonicity adjusting agents, mucoadhesive substances, and the like. Examples of formulation strategies are well-known to the person skilled in the art.

In some embodiments, the peptide(s) may be formulated (e.g. mixed together) with immune-modifying agents like adjuvants usually applied in immunotherapy products.

In some embodiments, the pharmaceutical composition may be formulated for parenteral administration, such as formulated for injection, e.g. subcutaneous and/or intradermal injection. Therefore, in some embodiments, the pharmaceutical composition may be a liquid (i.e. formulated as a liquid), including a solution, a suspension, a dispersion, and a gelled liquid. A liquid pharmaceutical composition may be formed by dissolving a powder, granulate or lyophilizate of a peptide combination described herein in a suitable solvent and then administering to a subject. Suitable solvents may be any solvent having physiologically acceptable properties and able to dissolve the peptide combination in desired concentrations.

A desired concentration may depend on the aliquot to be administered (i.e. to be injected) and the desired single dose. It is emphasized that for the purpose of injection the aliquot is in the range of about 10 to 500 microliters, e.g. 50 to 300 microliters or less and a desired single dose is within range of 1 to 1000 nanomoles. Typically the concentration of each peptide is the same, such as in an equimolar concentration, but each peptide of the composition may also be present in different concentrations. Typically, the solvent is an aqueous solution, optionally mixed with other solvents. Thus, a solvent may comprise at least 60% w/w of water, e.g. at least 65% w/w, 70% w/w, 75% w/w, 80% w/w, 85% w/w, 90% w/w or 95% w/w, 99% w/w of water, such as distilled water, such as sterile water. In some embodiments, the solvent is sterile distilled water, e.g. water for injection. An aqueous solution may comprise other solvents than water, for example DMSO (dimethylsulfoxide), glycerol, ethanol, acetonitrile, vegetable or synthetic oils. The pH of the aqueous phase of the solvent may be in a physiological acceptable range, typically in the range of 3 to 9, such as in the range of pH 3 to 8, such as in the range of pH 4 to 8, such as in the range of pH 5 to 8, such as in the range of pH 6 to 8. Thus, the liquid formulation may comprise a pH controlling agent or buffering agent (e.g. citrate buffer, phosphate buffer, acetate buffer), optionally the pH may be adjusted with dilutions of strong base (e.g. sodium hydroxide or the like) and/or dilutions of strong acids (e.g. hydrochloric acid).

Typically, the liquid formulation is isotonic, and optionally sterile. Therefore, in some embodiments, the formulation comprises saline, such as isotonic saline. The liquid may contain additional excipients, such as another solvent, a solubilizing enhancing agent, ionic and non-ionic emulsifiers, a dispersant, a thickener, a preservative, an anti-microbial agent, and/or an antioxidant. Non-limiting illustrative examples of solvents include water, saline, DMSO, glycerol, ethanol, acetonitrile, vegetable or synthetic oils.

Typically, the freeze-dried composition may be dissolved before use, for example dissolved in an aqueous, optionally sterile, solution, for example a solution having a pH in the range of 3-9, such as a pH in the range of 3-8, such as a pH in the range of 4-8. A lyophilizate may contain additional ingredients, e.g. bulking agents and lyoprotectants, buffering, antioxidants, antimicrobial agents, solubilizers.

A freeze-dried composition may also be formulated into a solid dosage form that is administered for example by the oral route such as by oral mucosa. Thus, in some embodiments, the pharmaceutical composition may be formulated for oral administration, for example for sublingual administration. Therefore, the pharmaceutical composition may be a solid dosage form, such as a freeze-dried solid dosage form, typically a tablet, a capsule or sachet, which optionally may be formulated for fast disintegration. Pharmaceutical formulations and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel ad Soklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

Peptides may be prone to degradation when exposed to oxygen, for example when exposed to air or solvents containing air. Therefore, in some embodiments, the pharmaceutical composition comprises an inert gas, e.g. argon or nitrogen.

Embodiments Relating to the Third Aspect of the Invention

As set forth above, the third aspect relates to a method of treating allergy in a patient, where signs or symptoms of said allergy are elicited in the patient by exposure to house dust mites or storage mites and/or exposure to at least one protein allergen present in house dust mites or storage mites, the method comprising administering, to the patient, a therapeutically effective amount of a polypeptide of the first aspect of the invention, optionally two or more polypeptides of the first aspect of the invention or a composition of the second aspect of the invention.

As discussed above, the inventors have found that the polypeptides of SEQ ID NOs: 1-44 appear to be generally non-allergenic in many patients, thus rendering them highly safe as immunogens used in anti-allergy therapy. It cannot be excluded that occasional patients will be allergic (e.g. have raised IgE antibodies against one or more of the sequences of SEQ ID NOs: 1-44), but it is generally understood that it is advantageous that patients subjected to the immunogens according to the invention are non-allergic towards the protein from which the immunogen is derived, meaning that it is attempted to avoid to treat those patients having detectable IgE levels against the polypeptides of SEQ ID NOs: 1-44 with said polypeptides or a T cell-epitope-containing fragment thereof. Hence, in embodiments of the first aspect, the polypeptide used for the administration is one, wherein exposure of the patient to the polypeptide does not elicit signs or symptoms of allergy in the patient. Regarding signs or symptoms of allergy, cf. below for further discussion, but it is generally understood that this means signs or symptoms of IgE mediated allergy including that the patient has elicited IgE-antibodies against the polypeptide.

While true prophylaxis of allergy is not excluded when carrying out the method of the third aspect of the invention, it is expected that the method will find particular use in patients that have already experienced mite allergy or have raised IgE antibodies against a mite allergen. Therefore, all embodiments of the third aspect may entail or consist of treating the allergy by relieving or reducing an immune response triggered by exposure to the mites or the protein allergen. Also, treating the allergy can in all embodiments of the third aspect comprise or consist of relieving one or more signs/symptoms of an immune response triggered by exposure to the mites or the protein allergen. Moreover, treating the allergy may in all embodiments of the third aspect consist of or comprise induction of immunological tolerance against the mites or the protein allergen. And treating the allergy may in all embodiments of the third aspect comprise or consist of relieving one or more signs/symptom(s) associated with allergic rhinitis and/or allergic conjunctivitis and/or allergic asthma and/or allergic eczema (e.g. atopic dermatitis).

The signs/symptoms of allergy mentioned above are those typically associated with the allergies treated according to the present invention, typically signs/symptoms may include one or more of the following; itchy running nose, itchy watery eyes, itchy skin and shortness of breath and the patient may experience that the signs/symptoms will to some extent be relieved by treatment with antihistamines or steroids. In a clinical setting, the signs and symptoms may include detectable levels of IgE antibodies against one or more the mites of interest.

In the event that the treatment entails or consists of relieving one or more signs or symptoms associated with allergic rhinitis, the relief is typically
    reduction of the intensity of itchy nose and/or
    reduction of the number of sneezes within a given period (e.g. daily, weekly, monthly) and/or
    reduction of the intensity of blocked nose (congestion) and/or
    reduction of the amount of nasal fluid and/or
    reduction of the eosinophilic count in nasal fluid and/or
    reduction of specific IgE antibody level (titre) in nasal fluid or in serum and/or
    reduction of basophil histamine release in blood.

It is to be noted that a "sign" of allergy is an objectively observable characteristic of the disease, whereas a "symptom" is the patient's subjective experience(s) relative to the disease. Some signs can be symptoms and vice versa, but if a patient for instance experiences dizziness due to a disease, this can only be categorized as a symptom, because it is not objectively observable by anybody else than the patient. On the other hand, increasing levels of for example IgE-antibodies is a "sign", since it cannot be sensed by the patient but it can be objectively measured in an appropriate assay.

Where treating the allergy comprises or consists of relieving one or more signs or symptoms associated with allergic conjunctivitis, the relief typically comprises
    reducing the intensity of itchy eyes, redness in the white of the eyes and/or watery eyes; and/or reducing the eosinophilic count in conjunctival tissue scrapings; and/or reducing specific IgE antibody level (titer) in conjunctival tissue scrapings or in serum; and/or reducing basophil histamine release in blood.

Where treating the allergy comprises or consists of relieving one or more signs or symptoms associated with allergic asthma, the relief typically comprises reducing the intensity and/or number of coughs within a given period (e.g. daily, weekly, monthly); and/or reducing the intensity of wheezes; and/or improving being short of breath; and/or improving lung function; and/or reducing specific IgE antibody level (titre) in lung fluid or in serum; and/or reducing basophil histamine release in blood.

Where treating the allergy comprises or consists of relieving one or more signs or symptoms associated with atopic dermatitis, the relief typically comprises reducing itch intensity of the skin; and/or reducing eczema score; and/or reducing number of (peripheral) blood eosinophils.

In all embodiments of the third aspect of the invention, the method may comprise or consist of reducing the patient's need for concomitant treatment with corticosteroids or H1 antihistamines to reduce, relieve, or suppress one or more symptoms of an immune response associated with the allergy. In other words, these embodiments have the long term benefit of reducing the patient's need for medication.

As used herein, the term "immunological tolerance" refers to a) a decreased or reduced level of a specific immunological response (thought to be mediated at least in part by antigen-specific effector T lymphocytes, B lymphocytes, antibodies, or a combination thereof); b) a delay in the onset or progression of a specific immunological response; or c) a reduced risk of the onset or progression of a specific immunological response to mites. An increase, improvement, enhancement or induction of "tolerance" may refer to a decrease, reduction, inhibition, suppression, or limiting or controlling or clearing of specific immunological reactivity to an allergen as compared to reactivity to the allergen in a previous exposure to the same allergen. Thus, in certain embodiments, the method comprises inducing immunological tolerance in a subject to mites, e.g. to an allergen of mites discussed herein to suppress an allergic immune response to the allergen. Immunological tolerance in a subject to an allergen can also be reflected by reducing the occurrence, frequency, severity, progression, or duration of an allergic response of the subject to the allergen. Induction of immune tolerance (also referred to as desensitization), and the relative amount of immune tolerance, can be measured by methods disclosed herein or known to the skilled artisan. For example, induction of immune tolerance can be measured by the modulated lymphokine and/or cytokine level in a subject or animal before versus after administering a peptide combination described herein for the first time. A modulated cytokine level can be an increase of a cytokine level, for instance an increase of a lymphokine and/or cytokine level of at least 1.5, 2, 3, 4, 5, 6, 7, 8, 10, 20, 50 times or more relative to before administering the peptide combination for the first time. Alternatively, modulation can be a decrease of the level of a particular cytokine level, for instance a decrease of the lymphokine and/or cytokine level of at least 1.5, 2, 3, 4, 5, 6, 7, 8, 10, 20, 50 times or more relative to before administering a peptide combination for the first time. The lymphokines/cytokines chosen to be measured can be from any relevant lymphokines/cytokines, such as IL-2, IL-5, IL-4, IL-6, IL-10, IL-12, IL-13, IL-17, TNF-alfa, IFN-gamma, TGF-beta, MCP-1, RANK-L and FIt3L. Accordingly, the term "inducing immunological tolerance" may include eliciting, stimulating, promoting, increasing or enhancing immunological tolerance. Immunological tolerance may involve modulation of T cell activity, including but not limited to CD4+ T cells, CD8+ T cells, Th1 cells, Th2 cells and regulatory T cells (Tregs), and memory T cells, including inflammatory lymphokines/cytokines produced by T cells.

The patients subjected to the treatment of the third aspect of the invention typically present with an immune response clinically presented as atopic dermatitis, urticaria, contact dermatitis, allergic conjunctivitis, allergic rhinitis, allergic asthma, anapylaxis, and/or hay fever. In particular advantageous versions of any one of the embodiments of the third aspect of the invention, the treatment thus decreases, reduces, suppresses or inhibits atopic dermatitis, urticaria, contact dermatitis, allergic conjunctivitis, allergic rhinitis, allergic asthma, anaphylaxis, and/or hay fever.

Without being bound to any theory, it is believed that the method of the third aspect of the invention is capable of increasing an IgG antibody response in the patient to a protein allergen of the mites and/or of decreasing an IgE antibody response in the patient to a protein allergen of the mites and/or of decreasing a T cell response in the patient against a protein allergen of the mites, since each one of these physiological effects have a beneficial effect on the signs and symptoms of allergy. Hence, in advantageous versions of all embodiments of the third aspect of the invention, the method does provide for increasing an IgG antibody response in the patient to a protein allergen of the mites and/or for decreasing an IgE antibody response in the patient to a protein allergen of the mites and/or for decreasing a T cell response in the patient against a protein allergen of the mites.

It will be understood that the patients that are subjected to the method of the third aspect of the invention are typically sensitized to at least one protein allergen of the mites. It is to be understood that such patients may exhibit allergy signs or experience symptoms of allergy, but it is not excluded that "patients" that merely exhibit clinical signs of being sensitized against at least one protein allergy of the mites will also benefit from the treatment.

The allergy treated according to the invention is in all embodiments of the third aspect of the invention allergy towards house dust mites of the genus *Dermatophagoides* (for example selected from the group consisting of *Dermatophagoides pteronyssinus, Dermatophagoides farinae*) or of the genus *Euroglyphus* (for example *Euroglyphus maynei*), or wherein the mites are storage mites of the genus *Glycyphagus, Lepidoglyphus, Tyrophagus*, or *Blomia* (for example *Glycyphagus domesticus, Lepidoglyphus destructor, Tyrophagus putrescentiae*, or *Blomia tropicalis*).

Consequently, the protein allergen is in all embodiments of the third aspect of the invention selected from one or more protein allergens in the groups consisting of a group 1 allergen of mites (for example a group 1 allergen of a house dust mite (e.g. Der p 1, Der f 1, or Eur m 1, or a group 1 allergen of a storage mite, e.g. Gly d 1, Lep d 1, Typ p 1 and Blo t 1) and a group 2 allergen of mites (for example a group 2 allergen of a house dust mite, e.g. Der p 2, Der f 2 and Eur m 2, and a group 2 allergen of a storage mite, e.g. Gly d 2, Lep d 2, Typ p 2 and Blo t 2).

As mentioned above, a particular embodiment of the third aspect of the invention entails that a polypeptide of the first aspect or a composition of the second aspect does not elicit signs or symptoms of allergy. These signs and symptoms are in important embodiments selected from the group consisting of:

the presence in the patient of specific IgE antibodies that binds to the a polypeptide of the first aspect or a composition of the second aspect (e.g. the level of specific IgE is below the detection level when tested in an assay measuring specific IgE (e.g. ImmunoCAP® Specific IgE Blood Test), for example the level is below 0.7 kU/L, when tested by an ImmunoCAP® test;

serum histamine release induced by a polypeptide of the first aspect or a composition of the second aspect is below the detection level when tested in a basophil activation test (BAT)

a positive skin prick test with a polypeptide of the first aspect or a composition of the second aspect; and the signs or symptoms discussed in detail supra.

In certain embodiments of third aspect of the invention, a polypeptide of the first aspect or a composition of the second aspect is formulated together with a pharmaceutically and immunologically acceptable carrier, vehicle or excipient.

When exercising the method of the third aspect of the invention and any embodiment thereof, a polypeptide of the first aspect or a composition of the second aspect may further be formulated together with an immunological adjuvant. Also a polypeptide of the first aspect or a composition of the second aspect may be formulated with a suitable carrier, diluent, or vehicle.

It is particularly preferred that a polypeptide of the first aspect or a composition of the second aspect is administered by the parenteral route to the patient, such as via a route of administration selected from any one of subcutaneous, intradermal, epicutaneous, topical, sublingual, buccal, intranasal, respiratory and the intralymphatic route. In particular the sublingual and buccal routes are of interest.

A polypeptide of the first aspect or a composition of the second aspect may also be administered to a subject in need thereof by injection, such as by subcutaneous or intradermal administration, but may also include other routes of administration, such as epicutaneous, transcutaneous, topical, rectal, oral, intranasal, respiratory and intralymphatic route of administration.

Typically, the subject in need thereof is a human, a pet such as a dog or a cat, a domestic animal such as a horse, or a laboratory animal (a mouse, a guinea pig or a rabbit). The subject may be sensitized to mites (e.g. having specific IgE antibodies against an allergen of mites and/or having a T cell response against an allergen of mites). Therefore, a subject in need thereof may produce specific IgE antibodies or a T cell response against mite allergens.

A polypeptide of the first aspect or a composition of the second aspect may be formulated for injection or for sublingual administration (e.g. a solid dosage form such as a tablet, and in particular a freeze-dried tablet) or is formulated in a composition as described infra for the compositions of the invention.

Typically, a polypeptide of the first aspect or a composition of the second aspect is administered several times, i.e. repeatedly, such as in weekly, by-weekly, monthly or quarterly intervals.

As will be understood from the above, the allergy is, according to the third aspect of the invention and any embodiments thereof, preferably treated by immunotherapy. The patient in question need not be human, since many pets suffer from allergy towards the mites discussed above. As such, the patient may be human or a mammal, such as a cat, dog, and a horse.

A pharmacologically effective amount of a single dose of a polypeptide of the first aspect or a composition of the second aspect may be in the range of 1 to 1000 nanomole, for example 1 to 500 nanomole, for example 1 to 250 nanomole, for example 5 to 250 nanomole. Typically, a polypeptide or composition of the invention is administered as a liquid in a volume of about 50 to 150 microliter, such as by intradermal administration.

Embodiments of Diagnostic Aspects of the Invention

The fourth aspect of the invention relates to an in vitro method of determining whether T cells of a subject are responsive to one or more polypeptides of the first aspect or a composition of the second aspect. The method comprises contacting T cells obtained from the subject with said polypeptide(s) or composition(s) and determining whether the T cells are stimulated.

The fifth aspect of the invention relates to an in vitro method of diagnosing a subject for sensitization or allergy to house dust mites or storage mites, comprising contacting T cells obtained from the subject one or more polypeptides of the first aspect or a composition of the second aspect and determining whether the T cells are stimulated.

The sixth aspect of the invention relates to an in vitro method for determining whether a subject has, or is at risk of developing, an allergy to house dust mites or storage mites, comprising contacting T cells obtained from the subject with one or more polypeptides of the first aspect or a composition of the second aspect and determining whether the T cells are stimulated.

A number of assay formats are available for the purpose of determining T cell stimulation and are well known for the person skilled. For instance ELISPOT/Fluorospot, simple proliferation assays as well as the assay disclosed in Example 2 are all useful for the purpose of determining T cell responsiveness.

The seventh aspect of the invention relates to an in vitro method of diagnosing a subject for allergy or sensitivity to house dust mites or storage mites, comprising determining the presence of specific IgE against one or more polypeptides of the first aspect or a composition of the second aspect in a biological sample (e.g. serum, plasma or blood) obtained from the subject. Any conventional antibody based immune assay is useful for this purpose and include enzyme linked immune sorbent assays (ELISAs), radioimmune assays (RIAs), immunoblotting techniques, etc. but also cell based assays such as measurement of histamine release induced by an analyte in a basophil activation test (BAT).

The eighth aspect of the invention relates to a diagnostic kit comprising one or more polypeptides of the first aspect or a composition of the second aspect. Such a kit will normally also include necessary detection agents, visualisation means, carriers etc. that enable one or more of the above-described diagnostic assays.

OTHER ASPECTS OF THE INVENTION

The ninth aspect of the invention relates an isolated nucleic acid fragment, which comprises
i) a nucleotide sequence encoding a polypeptide according to the first aspect of the invention, or ii) a nucleotide sequence complementary to the nucleotide sequence in i)-v).

A tenth aspect of the invention relates to a vector comprising a nucleic acid sequence of the invention, such as a cloning vector or an expression vector.

Such a vector conventionally may include, in operable linkage and in the 5'-3' direction,
- an expression control region comprising an enhancer/promoter for driving expression of the nucleic acid fragment defined in option i) for the nucleic acid fragment of the invention,
- an optional signal peptide coding sequence,
- a nucleotide sequence defined in option i) for the nucleic acid of the invention, and
- an optional terminator.

The expression control region may drive expression in prokaryotic cell such as a bacterium, e.g. in E coli, but it may in certain instances be necessary to includes expression control regions suitable for eukaryotic cells and in certain cases this applies in particular to plant cells.

The vector may be capable of autonomous replication and/or it may be capable of being integrated into the genome of a host cell—the latter is of particular relevance when constructing cells and cell lines that are capable of stable expression of the nucleic acid fragment of the invention.

Suitable vectors are a virus, such as an attenuated virus, a bacteriophage, a plasmid, a minichromosome, and a cosmid.

It will be understood that the nucleic acid fragments of the invention may be used for both production purposes, so such vectors will typically be in the form of cloning vectors or expression vectors.

Such a vector of the invention often comprises in operable linkage and in the 5'-3' direction, an expression control region comprising an enhancer/promoter for driving expression of the nucleic acid, an optional signal peptide coding sequence, a nucleotide sequence of the invention, and optionally a terminator. Hence, such a vector constitutes an expression vector useful for effecting production in cells of a polypeptide of the invention. Since the polypeptides of the invention are of mite origin, recombinant production has to be effected in host cells that can express the coding nucleic acid. Bacterial host cells may be used in some cases. However, if the vector is to drive expression in eukaryotic cell, the expression control region should be adapted to this particular use.

For production purposes it is therefore often convenient that the expression control region drives expression in a prokaryotic cell such as a bacterium, e.g. in E. coli, or in a eukaryotic cell such as a fungal cell, a plant cell, an insect cell, or a mammalian cell.

Also, for production purposes, it is practical that the vector is capable of integrating the nucleic acid into the genome of a selected host cell—this is particularly useful if the vector is use in the production of stably transformed cells, where the progeny will also include the genetic information introduced via the vector. Alternatively, vectors incapable of being integrated into the genome of a piscine host cell are useful in early screening of production cells.

Polypeptides of the invention may as indicated be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found.

Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques. In addition to encoding the polypeptides of this invention, a vector of the present invention may encode polypeptide sequences such as a "tag" or immunogenicity enhancing peptide (e.g. an immunogenic carrier or a fusion partner that stimulates the immune system, such as a cytokine or active fragment thereof). Useful vectors encoding such fusion proteins include pIN vectors, vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration.

Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including polymerase chain reaction in connection with the compositions disclosed herein.

It may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression. The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQa and/or DQP3, β-Interferon, Interleukin-2, Interleukin-2 Receptor, MHC Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), αI-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/Heavy metals; MMTV (mouse mammary tumor virus)—Glucocorticoids; β-Interferon—poly(rl)x/poly(rc); Adenovirus 5 E2-EIA; Collagenase—Phorbol Ester (TPA); Stromelysin—Phorbol Ester (TPA); SV40—Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70-E1A/SV40 Large T Antigen; Proliferin—Phorbol Ester/TPA; Tumor Necrosis Factor—PMA; and Thyroid Stimulating Hormonea Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a mammalian cell is targeted, it is preferable to position the polynucleotide coding region adjacent to and under the control of a promoter that is capable of being expressed in a mammalian cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression.

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotic cells, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The eleventh aspect of the invention relates to a cell which is transformed so as to carry the vector of the invention—particularly preferred transformed cells are also capable of expressing the nucleic acid fragment of the invention in order to enable production of the polypeptides disclosed herein.

The transformed cell may hence be capable of replicating the nucleic acid fragment defined in option i) or ii) of the ninth aspect of the invention and/or capable of expressing said nucleic acid fragment.

Depending on the particular use of the transformed cell it can be of prokaryotic or eukaryotic origin cell. Preferred prokaryotic cells are bacteria selected from the group consisting of *Escherichia* (such as *E. coli*), *Bacillus* (e.g. *Bacillus subtilis*), *Salmonella*, and *Mycobacterium*, preferably non-pathogenic, e.g. *M. bovis* BCG. Preferred eukaryotic cells are fungal cells, insect cells, mammalian cells, and plant cells.

For production purposes, it is preferred that the cell is stably transformed by having the nucleic acid defined in option i) or ii) of the ninth aspect of the invention stably integrated into its genome.

Also for production purposes, it is preferred that the transformed cell secretes or carries on its surface the polypeptide disclosed herein—when the cell is a bacterium, it may be advantageous that secretion is into the periplasmic space or into the culture medium.

The twelfth aspect of the invention is a cell line derived from a transformed cell of the invention. In particular clonal cell lines are interesting.

The twelfth aspect of the invention relates to a method for the preparation of the polypeptide disclosed herein, comprising culturing a transformed cell or cell line of the invention under conditions that facilitate that the transformed cell expresses the nucleic acid fragment according to option i) of the ninth aspect of the invention and subsequently recovering said polypeptide, or preparing said polypeptide by means of solid or liquid phase peptide synthesis.

The twelfth aspect may be preceded by steps that include recombinant preparation of the cell or cell line of the invention, i.e. introduction of a vector of the invention into a host cell and propagation and selection of those transformed cells that effectively express the nucleic acid of the invention.

The thirteenth aspect of the invention relates to antibodies that specifically bind and recognize a polypeptide of the first aspect of the invention, in particular the polypeptides having the amino acid sequences set forth in SEQ ID NO: 1-44 and 261-332 (preferably SEQ ID NOs: 1-44 and 305-318).

As such, the antibody may be an isolated polyclonal antibody, which has been raised against the polypeptide of the first aspect of the invention. In this connection "isolated" is intended to mean that the polyclonal antibody is essentially free from antibody species that bind non-specifically to the polypeptide of the first aspect. Another way to phrase this is that the polyclonal antibody of the present invention is essentially free from antibody species that have $K_D$ values $>10^{-6}$ for binding to the polypeptide of the first aspect of the invention.

Polyclonal antibodies of the invention can be obtained from any mammalian species of convenience: the antibody can e.g. be isolated from a rabbit, mouse, rat, cat, dog, horse, cow, camel, llama, or even a human being.

Also, the antibody can be a monoclonal antibody or a fragment or analogue thereof, which specifically binds the polypeptide of the first aspect of the invention.

A "fragment or analogue" of a monoclonal antibody comprises at least the antigen-binding or variable regions of the monoclonal antibody. Examples of antibody fragments/analogues include Fab, Fab', F(ab)$_2$, F(ab')$_2$, F(ab)$_3$, Fv (typically the $V_L$ and $V_H$ domains of a single arm of an antibody), single-chain Fv (scFv), dsFv, Fd fragments (typically the $V_H$ and $C_H1$ domain), and dAb (typically a $V_H$ domain) fragments; $V_H$, $V_L$, VhH, and V-NAR domains; minibodies, diabodies, triabodies, tetrabodies, and kappa bodies (see, e.g., III et al., Protein Eng 1997; 10: 949-57); camel or llama IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO 2005/040219, and published U.S. Patent Applications 2005/0238646 and 2002/0161201, all of which are incorporated by reference herein.

The monoclonal antibody of the invention, the fragment, or the analogue thereof may also be presented in the form of a "derivative", wherein one or more of the amino acids of the monoclonal antibody, the fragment, or the analogue are chemically modified, e.g., by alkylation, PEGylation, acylation, ester formation or amide formation or the like, e.g., for linking the antibody to a second molecule. This includes, but is not limited to, PEGylated antibodies, cysteine-PEGylated antibodies, and variants thereof.

Monoclonal antibody are preferably those having high affinity for the polypeptide of the first aspect of the present invention. Typically, high affinities, expressed as a $K_D$ of less than $10^{-6}$ are preferred, and even lower $K_D$ values are preferred, such as less than $10^{-7}$, $10^{-8}$, $10^{-9}$, $10^{-10}$, $10^{-11}$, or $10^{-12}$.

The fourteenth aspect of the invention relates to methods of detecting, quantitatively or qualitatively, the presence in a sample of a polypeptide of the first aspect of the present invention. For example, the sample may be an allergen extract or an immunotherapy product comprising an allergen extract or a polypeptide of the first aspect. The method may be performed in order to characterise an allergen extract, either qualitatively or quantitatively. Any convenient detection method may be employed. For instance, many such methods (which are by nature qualitative or semi-quantitative) rely on the use of specifically binding antibodies. For instance, detection may entail contacting the sample with an antibody of the thirteenth aspect of the invention and detecting specific binding of material in said sample to said antibody. Such assays may have very simple formats and can e.g. be in the form of agglutination assays or immunoblots (dot blot analysis, quantitative dot blot, Western blot) of any format. To facilitate detection the antibody may be labelled with a radioactive isotope, a component of a ligand/receptor pair, a luminescent or fluorescent label, an enzyme, etc.

Possible formats for use in immune detection are for instance contacting the sample with a system comprising a solid phase with an antibody of the thirteenth aspect coupled thereto and comprising a labelled polypeptide (as described above) of the first aspect of the invention, where said labelled polypeptide specifically binds said antibody, and gauging the degree of competition exerted by material in the sample on the binding between said labelled polypeptide and said antibody; hence, this format is in the form of a competitive binding assay where the ability of the sample to outcompete a polypeptide of the first aspect is gauged, contacting the sample with a system comprising 1) a solid phase with a polypeptide of the first aspect coupled thereto and comprising 2) a labelled antibody of the thirteenth aspect, where said polypeptide specifically binds said labelled antibody, and gauging the degree of competition exerted by material in the sample on the binding between said polypeptide and said antibody;

also this is a competitive assay, but here the ability of the sample to attract labelled antibody is gauged.

The latter immune assays may be put into practice in a number of format known per se in the art: ELISAs, RIAs, etc.

A further possibility is to utilise the polypeptides of the first aspect in similar assay formats but with a view to identifying IgE antibodies in a sample. In such assays (e.g. RAST assays), possible presence of anti-polypeptide IgE is gauged by either indirect assays (competitive assays) or in assays that determine direct binding between polypeptide and antibody.

A further embodiment of the method of the fourteenth aspect of the invention relates to mass spectrometric identification or quantification of a polypeptide of the first aspect of the invention in a sample, for example in an allergen extract or an immunotherapeutic product comprising an allergen extract or a polypeptide of the first aspect. In essences, the polypeptide material of a sample is subjected to proteolytic treatment and the thus obtained material is subsequently subjected to quantitative MS, optionally using at least one polypeptide of the first aspect or a fragment of said polypeptide, which is obtainable by the same proteolytic treatment as the sample, but often produced synthetically. Thus, a further embodiment of the invention relates to a synthetically produced fragment of a polypeptide of the first aspect, which is identical to a fragment produced by proteolytic treatment of said polypeptide. Proteolytic treatment may be performed with trypsin or chymotrypsin or other enzymes known in the art. The synthetically produced fragment may be used in the mass spectrometric identification or quantification of said polypeptides. This method is in particular useful if the polypeptide tested has any one of SEQ ID NO: 1-44, and 261-332, but in particular of the naturally occurring polypeptides having SEQ ID NOs: 1-44 and 305-318.

Methods for qualitative determination for instance involve mass fingerprinting methods as those taught in Trauger A. et al. (2002), Spectroscopy. 16 (1): 15-28. For relevant teachings pertaining to quantitative determination, reference is made to Wells W et al. (2006), Journal of Proteome Research. 5 (3): 651-658, as well as to Bret, Cooper and J. Feng and W. Garrett (2010), Spectroscopy. 21 (9): 1534-1546, Haqqani A S et al. (2008), Methods Mol. Biol. 439: 241-56. These references are incorporated by reference herein.

If employing labelling of standard peptides for use in qMS, SILAC (stable isotope labeling by amino acids in cell culture), trypsin-catalyzed $^{18}O$ labelling, ICAT (isotope coded affinity tagging), and iTRAQ (isobaric tags for relative and absolute quantitation) are useful. "Semi-quantitative" mass spectrometry may be performed without labelling of samples, e.g. with MALDI analysis (in linear mode). The peak intensity, or the peak area, from individual proteins is correlated to the total amount of protein in the sample. Other types of "label-free" quantitative mass spectrometry uses the spectral counts (or peptide counts) of enzyme digested proteins as a means for determining relative protein amounts.

It is however preferred to employ labelled standard peptides in the qMS methods. Reference is generally made to the quantification methods taught in WO 2007/031080.

Sequences

The amino acid sequences of the polypeptides of the present invention are set forth in the sequence listing. For ease of reference, the sequences are provided as follows, together with the alternative designation used herein as well as their origin.

SEQ ID NO: 13; Cluster ID (L) 96; Cluster ID (A) 55
Protein name: A0001; Species: *Dermatophagoides farinae*
KKTKDCDVEK PIRECLKNGL LRYSDGQKIN QFPDSIEDLN RACEELKKSE TCARNFIDTC TETSYEKRSL

DSLLDGIQRV LKRLCRSQSK KEQLLQNVGC ANSVVQDTKL CLKNYRMLVF AANKLNDKSK IMRILCCKSR

KVAPCIGEAM KSKGNAVCSA KNIDYFREMH QNIKAEMTAV VCSDFERDQC ENVEVPAITE AEYKDQNIFN

PLRDLYKKVI LA

SEQ ID NO: 14; Cluster ID (L) 96; Cluster ID (A) 55
Protein name: A0001; Species: *Dermatophagoides pteronyssinus*
KKSPDCDIER PIRECLKDGL LRYSSGQKIN QFPDTIQDLN RACEELKKSE TCARTFIDTC TESSYEKRSL

DSLLDGIQRV MKRLCRSQTK KEKLLENVGC ANSVVQDTKQ CLKNYRMLVF AANKLDNKNK IMRILCCKSR

KVAPCIGEAM KAKGTAVCSA KNIDYFKDVH QNIKQEMTAV VCSDFERDQC ENVDVPNISE SEYKDQNIFN

PLRDLYKKVI LG

SEQ ID NO: 2; Cluster ID (L) 65; Cluster ID (A) 74
Protein name: A0003; Species: *Dermatophagoides farinae*
MAIDGKYQME SSEHFEEFVK EMGLDVDMTN VDLSKTSTME ICKDGDVYHI KSETAGIAHE IKFKVGEEFE

DDMNGHKFKN VVTMECDNKM VQKKTSADGG KVVNVVREFT DAGCTVKSTY NTVTWTRVYK RM

SEQ ID NO: 3; Cluster ID (L) 65; Cluster ID (A) 74
Protein name: A0003; Species: *Dermatophagoides pteronyssinus*
MAIDGKYQME SSEHFEEFVK EMGLDVDMTN VDLSKTSTME ICKDGDVYHI KSETAGIAHE IKFKVGEEFE

DDMNGHKFKN VVTMECDNKM VQKKTSADGG KVVNVVREFT DAGCTVKSTY NTVTWTRVYK RM

SEQ ID NO: 305
Protein name: A0003; Species: *Blomia tropicalis*
GKYQLESSEN FDEFLKELGV NFILRNLAKT SKPTIEITLD GDTYTIKTIT TLKTSVITFK IGEEFEESRM

DGKTVKTVIT QEGDKLIQVQ QGDKEVKIVR EFTETHLTTI CTVGEITSTR VYKRV

SEQ ID NO: 34; Cluster ID (L) 46; Cluster ID (A) 21
Protein name: A0006; Species: *Dermatophagoides farinae*
DSNSDTTFIF NGDGCEQNHL FQTRYRPQIQ QLASDVQRII DHVMSVNESG RTYRQLAEFV DRFGSRLTGT

KNLEDSIDYM IDLLRQEGHD NVHGESVQVP RWTRGNEWAR MIKPREKKLN ILGLGYSEGT NGQTIEAPIV

VVRNFTELEQ KSRLIPGKIV VYNFHYESYG KQAIYRHSGA SRAAEFGAVA AMIRSLTPFS IDSPHTGMQT

YDVNVTRIPA ISITAEDADL FQRFSDRNEE VIVQIYSENR NEKEQGISRN TVSDIRGEQY PDEIVLVSGH

IDSWDVGQGA LDDGAGSFIS WRALSVIKQL GLRPKRTMRS ILWTGEEFGL IGVYDYVKKH QNELKNYVLA

MESDIGTFTP KGITFSGRNS TSQCTLWEIL QLMHPINATT LTISTEGSDV QAFYENGVPI SSLDTANDKY

FYFHHTQGDT MTVEQSDDLD KCQALWTSIS YALAMLDDRL PR

SEQ ID NO: 35; Cluster ID (L) 46; Cluster ID (A) 21
Protein name: A0006; Species: *Dermatophagoides pteronyssinus*
DSNPGETSIF NGEGCANDQL FQTRIRPQIQ QLASNVQRII DHVMSANESG RTYRQLAEFV DRFGSRLTGT

KNLEDSIDYM IDLLKQEGHD NVHGEPVQVP KWTRGNEWAR MIKPRDKKLN ILGLGYSEGT NGQTIEAPIV

VVRNFTELEQ KAGLIPGKIV VYNFKYESYG KQAIYRHSGA SRAAKFGAVA AMIRSLTPFS IDSPHTGMQS

YDVNVTKIPA ISITTEDADL FQRFSDRNEE VIVQIYSENH NEKDKGISRN TVSDVRGEKY PNEIVLVSGH

IDSWDVGQGA SDDGAGAFIS WRALSVIKKL GLRPKRTLRS VLWTGEEFGL IGVYDYIKKH RNELKDYVIA

MESDIGTFTP RGITYSGKNS TSQCTLWEIL QLMHPINATT LTISTEGSDV QAFYENGVPI SSLDTANDKY

FYFHHTQGDT MTVEQPDDLD KCQALWTSVS YALAMLDDRL SR

SEQ ID NO: 30; Cluster ID (L) 61; Cluster ID (A) 30
Protein name: A0007; Species: *Dermatophagoides farinae*
MAKFNYLPVD VQEELRNTAN AIVSVGKGIL AADESTGTIG KRFADINVEN VEPNRRAYRQ LLFYSENIEQ

YISGVILFDE TVYQKDDNNT PFPELLKKKG IIPGIKVDTG VVTLQGTNGE STTQGLDNLT KRCQEYYNHG

CRFAKWRCVL KIGKDEPSAL AILENANVLA RYASCCQQAR IVPIVEPEIL PDGDHDLERC QKVTETVLAA

VYKALNDHHV YLEGSLLKPN MVTPGQSCPQ KASPQDIARA TVTALQRTVP AAVPGVVFLS GGQSEEEASV

-continued

NLNAINQYQG KKPWALSFSY GRALQASALR AWQGKPENIS AGQKEFLQRA KANSLSAQGQ YTGGVVGAAA

DQDLFIKDHQ Y

SEQ ID NO: 31; Cluster ID (L) 61; Cluster ID (A) 30
Protein name: A0007; Species: *Dermatophagoides pteronyssinus*
MAKFNYLPVD VQEELRNTAN AIVSVGKGIL AADESTGTIG KRFADINVEN VEQNRQAYRQ LLFYSEGIEQ

YISGVILFDE TVYQKDDKGV PFPELLKKKG IIPGIKVDTG VVTLQGTNGE STTQGLDNLT KRCQEYYNQG

CRFAKWRCVL KIGQDEPSSL AIVENANVLA RYASCCQQAR IVPIVEPEIL PDGDHNLERC QKVTETVLAA

VYKALNDHHV YLEGTLLKPN MVTPGQSCPQ KASPQEVAQA TVTALQRTVP AAVPGIVFLS GGQSEEEASV

NLNAINQYQG KKPWALSFSY GRALQASALR AWQGKPENIG AGQKELLQRA KANVLAHKGQ YVAGSIPSLA

SAKSNFVAQH KY

SEQ ID NO: 306
Protein name: A0007; Species: *Blomia tropicalis*
MSIIQNLPAD VQEELRKTAN AIVTPGKGIL AADESTGTIG KRFADINVEN VENNRRTYRD LLFSAPDEVN

NYISGVILFD ETVYQKNAAG VPFPQVLAKR GIIPGIKVDT GVVVLQGTNG ESTTQGLDNL TKRCQAYYEQ

GCRFAKWRCV LKIGDNEPSP LAILENANVL ARYASCCQQA RIVPIVEPEI LPDGAHDIER CQKVTEKVLA

AVYKALNDHN VFLEGTLLKP NMVTAGQSFA GPKPSPQEVA RATVTALQRT VPAAVPGIVF LSGGQSEEEA

SINLNAINQF EGKKPWALSF SYGRALQASV LRAWQGKDEL IAAGQKELVN RSKANSDASL GKYSGGIVGA

AGEQDLFIKD HQY

SEQ ID NO: 7; Cluster ID (L) 44; Cluster ID (A) 67
Protein name: A0008; Species: *Dermatophagoides farinae*
MSANTERTFI MLKPDAVQRG IVGEIIRRFE AKGFKLVAMK FMMASEDLLK KHYADLAARP FFPGLIKYMQ

MGPVVPMVWE GLNAVKTGRV MLGETNPAES KPGTIRGDLC IQTGRNIIHG SDSVETAKRE IDLWFRPEEL

VDYKPSQYEW VYEN

SEQ ID NO: 8; Cluster ID (L) 44; Cluster ID (A) 67
Protein name: A0008; Species: *Dermatophagoides pteronyssinus*
MSANTERTFI MLKPDAVQRG IVGEIIRRFE AKGFKLVAMK FMMASEDLLK KHYADLAARP FFPGLIKYMQ

MGPVVPMVWE GLNAVKTGRV MLGETNPAES KPGTIRGDLC IQTGRNIIHG SDSVETAKRE IDLWFRPEEL

VNYKPSQYEW VYEN

SEQ ID NO: 43; Cluster ID (L) 58; Cluster ID (A) 6
Protein name: A0009; Species: *Dermatophagoides farinae*
VVIKVENLPE RCDYSQCPKW DPNDINVHLV AHTHDDVGWL KTVEQYYYGL KNDIQRAGVQ YILDTVIEEL

IRNKQRRFIY VEIAFFWKWW QEQDEDQRMI VRELVRTGQL EFINGGWSMP DEAATHYNSL IDQSTWGLRQ

LNDTFGKCGH PKVTWQIDPF GHSREMANLY AQMGYDALFF ARQDYQDREN RMTNRKLEHV WQGSDDLGTA

GDIFTGMMFS GYGPIEFNWD ITNGPEDAVV DNPESEEYNV PDKIRRFVEK AKYFAQYYAT NHFMFPMGTD

FQYGDAHTWF KNLDKLIKAV NNAGKGVRAF YSTPSCYARA LYETNRTWTT KTDDFFPYAS DEHAYWTGYF

TSRPALKRME RMGNNLLQAC KQLDILAGND GRFEMNITRL REAMGVMQHH DAVTGTEKQH VAFNYAKMLD

SAMLQCRHVI SESYRKLFPT QTKEQHEFCP YLNISSCPST EMGESRTIHL YNPLGHRLVN RTIRVPVKDG

YYYQVRDQND HSIPAVLISI PEFVRKIPGR KSVATKELVF RVPIIESLGI RRFHMIATKE KQQDSAVEIQ

GEKFVGHKGQ RFQLKDGLII EFDSNGKIAT MIRNNQSISI SNEFRLFHGA DIGRHSGAYI FRPSEQKTFP

VTEKMEATLY VDQKFGIVQE VHQQFDSFVG QIIRLDKQGD YVEFDFVVGP IPVDDLGIKE IITRYNTNLA

NDETFFTDSN GRQMLRRRWN YRPSWKYEIE EPVSGNYYPV NSRIAIRDDR KSLQMTIMTD RSQGGSLSPE

QINGSVDLMV HRRLLHDDYF GVDEPLNEPG VDGHGIVIRG RHLLLLDTLE KAAEKHRPLA QEMFMEPIIS

FTSSMEKNQP IYKGLTKDLP GNVHLLTLEQ WHSKRYLLRL EHFYQRFEDP SLSNPATVSL RHLFQSFEIT

AVEELTLGAN QPISALKNRL QYRYIRPLNE QQSSIITDPI IEGENFDIHL EPMQIRTFLI DIKRN

-continued

SEQ ID NO: 44; Cluster ID (L) 58; Cluster ID (A) 6
Protein name: A0009; Species: *Dermatophagoides pteronyssinus*
```
VVIKVENLPE QCDYTQCPKW SKDDINVHLV AHTHDDVGWL KTVEQYYYGL KNDIQRAGVQ YILDTMIEEL

IRNKDRRFIY VEIAFFWKWW QEQNEEQRMI VKELVRTGQL EFINGGWSMP DEAATHYNSL IDQSTWGLRQ

LNDTFGRCGH PKVTWQIDPF GHSKEMANLY AQMGYDALFF ARQDYQDREN RMSNRTLEHV WQGSDDLGEI

GDIFTGMMFS GYGPIEFNWD ITNGPEDAVV DNPESEEYNV PDKIRRFVEK AKYFGQFYAT NHFMFPMGTD

FQYTDAHTWF KNLDKLINAV NKAGKGVRAF YSTPSCYAHA LYEQNRTWTT KTDDFFPYAS DEHAYWTGYF

TSRPAIKRME RIGNNLLQAC KQLDVLADNN GRFEMNLTKM REAMGVMQHH DAVTGTEKQH VAFNYAKMLD

SAMLQCRHII NESYKKLLPK SSTSEHEFCP YLNISSCPTT EMGESRIIYL YNPLGHRLIN HTVRLPIKNG

YYYRIQDQNN QSVPSVLVPI PEFVQKIPGR KSVATKELVF RVPVIEPLGI TTMYMYVDKN EQPNSAIEIK

GENPDDNDDK SKWLVLTKNL IVEFYSNGTI SRISIDKLHQ SISISNEFRL YHGAGGTGRH SGAYIFRPNE

QKTFPVTNKI KSTFFIDRKY HIVQEVHQQF DSSFVGQIIR MDKYNDNVEF DFVVGPIPVN DQIGKEIIAS

YKTDLENDET FYTDANGRQM LRRRWNYRPS WKYNVQEPIS GNYYPVNSRI AIRDEKQSLQ MTIMTDRSQG

GSLSPEQING SIDIMIHRRL LHDDYFGVGE ALNEPGVDGH GLVIRGKHLL LLNSIKQSAS EHRPLAQQMF

MEPIISFTSI ESNKQAEKQS NQYIGLNNDL PSNVHLLTLE QWHSKRYLLR LEHFYQSNED TELSKPVKLS

LRHLFKSFEI IAVEELTLGA NQPISSLKNR LHYRYNRPLE QRQQQQSSLL LDDPKIEGEN FDIHLSPMQI

RTFLIDIKRN
```

SEQ ID NO: 307
Protein name: A0009; Species: *Blomia tropicalis*
```
VVIKVENLPA RCDYTKCPKS DPNKINVHLV PHTHDDVGWL KTVEQYYYGS KTYYQKAGVQ YILDSVMNEL

IHNKERKFIY VETAFFWKWW MEQDYGMRNI VKELVETGQL EFINAGWSMN DEASTHYNSI IDQMSWGFYR

LQTTFGRCGV PKVAWQIDPF GHSKEQAALF ALMNFDALFF AREDWQEQSH RRKNRTLEHV WQASSDLGKS

ADLFTGMMNF GYGPPQGFNW DLVGGADEPV IDDPESDEYN VPRRVKELID LAKTYQKYYA TNNVMFPMGT

DFQYQDAHIY FKNMDKLIKY VNENSTEVNI FYSTPSCYAK SLKDSGKTFT AKNDDYFPYA SDPHSYWTGY

FTSRPAIKRF ERVGNNYLQV CKQMDTYTGH QATRDRHTTK LREIMGVMQH HDAVSGTEKQ HVAFNYAKHL

QSGIESCRKV ISEAYQLLQH PHTKTVQTFC DYLNISSCAI TESGQNFVVN IYNPLSKTLK NHPIRLPINS

DKYYNVVDDE GKSVYSELTF IPEYVQAIPE RTTNATTDLV FLASIPPLGY ASYFVQATTT KSPDSANAVT

VTKITNETRL SSGNFSVVFD STGALSKVEL PSGESIPFKN EFRYYNGAAD NIRASGAYIF RPKEQQTFPF

AKLVSANLLT RTSSGGIVHE VHQKFDSNVE QVIRVLPDSD SIEFEYVVGP IPVKDGIGKE VVLTYETDFK

NNKTFYTDAN GRQMMKRKWD YRPEFKMEVT EPISGNYYPI NSRIYLQDEK KGMQMTILND RSQGGTSPRD

GVIEIMVHRR LLHDDGFGVG EALNEPGVDN KGLIIRGRHL VQFSDIKTAA SKHRPKAQQL FMAPVLSFVP

DVSDYETYKR SHLTKYSALI NPLPEQIHLL TLERWMEGHF LLRLEHYFQT NEDAELSKPV TLNLKHMFKS

FKIFEAEELT LGGNQPIFET KHRMKFNYIP VENVTEPPEH SFDPTKLEVK LYPMQIRTFS VRV
```

SEQ ID NO: 41; Cluster ID (L) 10; Cluster ID (A) 7
Protein name: A0010; Species: *Dermatophagoides pteronyssinus*
```
LDSDPMKCNS IRNEDRIDCN PDPPISKEIC EQRGCCWNAG NNTDDGNLIS RALPHLGVPS CYYGENYIGY

KIEKIYIKDE DLSMTKLKRV RPSGFPKDIE NVNIEIHQLN DQVLRLKFID ANQKRYEVPT PKLNIPSVSK

SSNSRLYSTE ISGSHLIVRR RETNQSIFDI NLAQMVYSDQ LIHLTSKLPS KYIYGIGEHR EPFRKTTDWK

RYTQWTRDQV PISDHALYGS HPFYMMVENK TKLASGVFLF NSNAMDILTQ PSPAITFRTV GGILDFFIFF

GPKPEQVVQQ YHNLIGLPAM PPFWSLGYQQ CRYGYNNFTN LNQTYWRTRQ AGIPMDVQWT DIDMFDSYND

FTYNHKQFKE LPDFIRNVLH KNGQKFIPMF DCGISSGEKA HSYRPYDYGV ELDIFVKNSS KQIFNGKVWN

GKSTVWPDFS HPNATKYWSK MFEEYHKIIE FDGAWIDMNE PSNFYDGQID GCPKTEIENP QYVPGMTDDS

LTLRHKTLCM TARHYNDQLH YNLHNLYGFQ EAIATNEALK TTLNKRPFII SRSSAPGHGH WASHWDGDVI

SDWSSMRWTI PSILNFNLFG VPMIGADICG FNGDTTVELC RRWYQLGAFY SFVRNHNTDN AIDQDPVALG
```

-continued

ETVVRTARSA LTYRYAFLPY LYTLFYNVHQ NGGTVLRPMF FEFPDDDHLY DIETQFMWGD SMLIAPILYP

NQTENKVYLP KGTWHNMRQT FESQGQYFTI KDSLDDINYV FFRSGSIIPI QGPQNNTEMM KSKDFGLVVI

LDSKNPEPYA KGSLYLDSGD SLDPVKKGEY NFYNFEVKNN TLTIESQHLG YQTNQSIIIL EILGIDRKPT

SIIFDGKPYY QFIYTTNNML IIQTKLSIFN DNDKSKKIHY QFEWKFN

SEQ ID NO: 42; Cluster ID (L) 10; Cluster ID (A) 7
Protein name: A0010; Species: Dermatophagoides farinae
DSLKCSSIRN EDRIDCNPDP PISKNVCEQR GCCWKTAGND LKNLSSKVLP NLNVPYCYYG ENYIGYKIEK

HSKNLIQLKR NRSSGFARDI ENINIEIHEL NDKVIRLKFI DANKKRYEVP IPKLNLPSTT SSSSSNSRLY

SVELDGSHLI VRRRETNQSI FDINLAYMVY SDQLIHVTSR LPSKYIYGLG EHRAPFRKNT NWKRYTQWTR

DQYPVTDKAL YGNHPFYLTV EDESPKKSAS GVFLFNSNAM DIITQPSPAI TFRTIGGILD FFVFFGPKPE

DVISQYQNLI GLPAMPPFWS LGYQQCRYGY NNFTNLNTTY TRNRAVGIPM DVQWTDIDAF NSNNDFTYDH

KRFKELPDFI NNVLHPNGQK FIPMFDCGIS SGEPAGSYKP FDSGVELDVF VKNSSNKIFR GKVWNGKSTV

WPDFSHPNAT EYWMDMFAEY HKTIAFDGAW LDMNEPSNFY NGEEHGCPES EIENPQYVPG MTDDSLTLRH

KTLCMTARHY NDQLHYNLHN LYSLSMAMAT NAALTKLNKR PFIISRATAP GHGHWAYHWN GDILSDWSSM

RWTIPSILNF NMFGIPMVGA DICGFGGNTA EELCIRWYQL GAFYSFARNH NDIHSIDQDP AALGESVIRA

ARSSLQYRYR FLAHLYTLFY HVHKNGGTVL RPMFFEFPHD EHTYEIETQF MWGDSVLIAP ILYPNQTQHK

IYLPKGTWYN RKVSFESQGQ YITMNDSYDD IDYVFVRGGS IIPTQEPHDN TELMKTKDFL LIVALDNQTS

YAKGSLYWDS GDSLNPDKTG HYNFYNFDAV NNTLTIQSQW LGYQTTQNIN FINILGVPKL PTSFKLNGHV

SDPRIIRFNY DEQTNILTVE TKLPIYNQDS SSHDRIHYQF EWIME

SEQ ID NO: 308
Protein name: A0010; Species: Blomia tropicalis
QCMAIPPNSR IDCNPDPPIS AEVCQSRGCC WMPSSNESSE NMNLLKKNVL PPLNVPYCFF GSDYHGYNVS

NVQTINDNQK VINLQRIRDS GFVNDVKNVR IQIDELSSNV LRIKMIDSDS SRYEVPIPVL NLPKRNEVLE

SLNEKMYQVE MNSTDFMLTV YRAKTKAIVF NVNLGQLIYS NQFIQITNKL ASNFIFGIGE NRESFRKLTN

WKRYTLFARD QWPVPDRALY GSHPFYLATE SDNSSHGVFL FNSNAMDIIT QPMPAITYRT IGGILDFFLF

LGPTSENVIE QYHQLIGLPT MPAYWTLGFH LSRYGYRNLS NLEKTFRRTR KAEIPFDVQW TDIDMFDSNN

DFTYDRKRFD GLPKFIEHLH SINMRFVPMF DCGISSGEHP PQSYLPYKMG LEMNVFVRNG TNQPFEGKVW

NSKSTVWPDF THPNATKYWT RQFAEYHKTI QFDGAWIDMN EPSNFLDGAF NGCPTNSTLE TPQYTPGMVE

DSLTLNHKTL CMSARHSIGL HYNLHNLYGI SEAIVTKSAL ESVLKRRSFI LSRSTAPGHG HFAAHWDGDI

LSDWPSMKWS ISSILNFNIF GVPLIGADIC GFNGNTTIEL CARWHQLGAF YTFVRNHNTD NAIDQDPVAL

GPLVVKAAKN ALKLRYALLP YLYTQFYRVH RKGGTILRPL FFEFVHDQVV LEIETQFMWG SSIMVAPALS

INETETSVYF PSGTWFHSYN FTRINTIGKF LPQLASFDYP NVYFRAGSII PTLRPMLTTD ETHSGNFTLL

VALSNENGHA EGDLYLDSGD GLDTEVLGHY NLYSFKVEKK ILEIKSSHLG YSTEQMIDNV LILGIDKSPI

EIKINGRSMK SWSYSKNKIH INSLNLPLYD LKTIDKSKLI QIHYQIEWV

SEQ ID NO: 39; Cluster ID (L) 64; Cluster ID (A) 16
Protein name: A0011; Species: Dermatophagoides farinae
KKAPEGCFRA AVLDHVHQTN VRQLSDFAKI IELNFKVYED AAALAKKQGA DIIVFPEDGL IYNIASREKA

DEFASDIPDG ETNACTLETK SVYNRLACLA QKHEIFVVAD LIDRKSCEEL GISNTSDSCP ADKKFLFNTA

VLFDRQGKLL GRYHKMHLFG EMTMNIPPKP ELLVIDTELG RLGMQICFDM IFKTPGHFLA EQNKFDTMLF

PTWWFDEAPM LSSSQYQMAW AFGNNVTLLA SNIHRVELGS RGSGIYVGPH QTLATALYDD SVERLVLANV

PIKPRETDKS VCPLDSEIIE VPQQIPIPNS VKYHHLNMNL LDVTLVELSS KDSEFHICYK GVCCQIEYRL

AVKDQPRESW VDRVPLLANM LEYFTPEERY YLMVANRTRP GTYRWTEEIC AVVVCPSSRW NIGKVEKDCS

QFGSNQELNS RFVYAKLRGA FSESTAVYPS AVGPKNQLIN PENKWKYWKV NVPDKPEHFV ELGAKDNPES

KAIELSTLAL YGRNYDLDPT YKQKPVPINL

-continued

SEQ ID NO: 40; Cluster ID (L) 64; Cluster ID (A) 16
Protein name: A0011; Species: *Dermatophagoides pteronyssinus*
KSAPEGCFRA AVLDHVHQTD ARHLSNTAKI IDLNFKVYED AAALAKKQGA DIIVFPENGL IYSILSREKA

DEFASDIPDA EVNACTLDSK FVYNRLACLA QKHQMFVVAD LIDRKSCEEL GINNVSDSCP ADKKFLFNTA

VLFDRQGKLL GRYHKMHLFG EISMNPPPKP ELLVIDTELG RLGMQICFDM IFKTPGYLLA QENKFDTMLF

PTWWFDESPM LSSSQYQMAW AFGNNVTLLA SNIHRIEVGS RGSGIYVGPH RTLAAALYDD SVERLVLANV

PIKPKETDQS ACPLDSEIIE VPQQIPIPKS VKYHHQNLNL KDVTLLQLSS NESEVHLCHK GVCCQFEYRL

AMKDQPQESW VDRVPLLANM LHYLTPEERY YLLIANRTRP GAYPWSEEFC AVVVCPSSRW NFGKMQKDCS

KIGSNQELSS RFVHAKLRGK FSEDTAVYPS AVGSKNQLIY PENKWKFWKV NVPNEPEYFI ELGAKDNSES

RAMELGALVL YGRNYNRDPR YEQKALPIN

SEQ ID NO: 309
Protein name: A0011; Species: *Blomia tropicalis*
GCFRAAVLDH VHQSSRNGGG TKENIKLNLK LYETAAKTAK EQGADIIVFP ENGIVYGIGS RANALKYGEI

LPESKTSMCT DSYASSHPIA YQLACLAKEH QMFVAADMID VQTCQTKSCP IDKKYAFNTA VLFDRNGYLL

GKYHKMHPFG ELQFNVPPKD ELVVIETEIG RLSMQVCFDL IYNKPGVVLA SQDKIDTMLF PTWWFDELPF

LAASQYQMSW AFGNKINLLA SNIHLVAVGS KGSGIFAGGH GQFEVISEPD AKARILVATL PINARSDAQC

SMDSKKIEVP QMVPIPSNVI YNYQMMNLTE NTVKKLDPSM EAISACDGGV CCQLNYQMDQ SSIKSDEEYY

LIVTNRTRPG AYPWTEEYCG LVLCPHMTKL DTCKQISSNN PLQTKFLYAK LSGEFSSETH VYPSVIGSEH

KVLPKDGGLW TYEDEKTDVG AKKQKFFITF GNKEERKSYT ISTIGLYGRV YARDPPYEQK PL

SEQ ID NO: 22; Cluster ID (L) 103; Cluster ID (A) 19
Protein name: A0012; Species: *Dermatophagoides pteronyssinus*
QSRDRNNKPY RIVCYWGTWA FYRPGTGKFE AENVNPNLCT HLMYGFAKLQ NNKIALYDPD LDDGDEDWNS

GLNWGHGMIR RMVNLRTYNP HLTTMISIGG WNEGSDKYSM MVRDPSSRKI FIQSVLDLLA EFDLDGLDFD

WEYPSMKATG DNDRKPGRDE DKEDFITLLR ELHEAFQPHG YLLSSAVSAG KPTIDRAYNI PEVSKYLDFI

NLMSYDHGG WESHTGHNAP LNSYDNANEL DKEFTVTYSV DYWLSHGVDA KN

SEQ ID NO: 38; Cluster ID (L) 103; Cluster ID (A) 19
Protein name: A0012; Species: *Dermatophagoides farinae*
QSRDRNDKPY RIVCYWGTWA FYRPASGKFQ AENVNPNLCT HIMYGFAKLQ NNKIALYDPD LDDGDEDWNS

GLQWGHGMIR RMVNLRTYNP HLTTMISLGG WNEGSDKYSI MVRDPASRKI FIQSVLHLLA EFDLDGLDFD

WEYPAMQASG DSDRKPGRAE DKEDFVTLLR ELHEAFQPHG YVLSSAVSAG KPTIDRAYNI PEVSKYLDFI

NLMSYDHGG WESHTGHNAP LNSYKNANEL DKEFTVTYSV EYWLNHGVDP KKLVLGIPLY GRTFTLAGSE

HGIGAPTIGK GGESGTITRT IGMLGYNEIC TMIKQGWQLY RDEIERIPYA VHANQWIGYD DRESVNEKLN

LLMAKHLGGA MVWSIDTDDF VGNCVGVKYP LLRSISKKLN NVDGPDPDIK RYHYHTSTAK PHTDGTTSTH

HDHKTTTTKH HKTTQPHHKT TQPHHTQTIT TTTERPHGKF QCHQAGFFAD PENPRKFHQC VDFGGHLKDY

EFMCGEGTHY DEKLHICVR

SEQ ID NO: 310
Protein name: A0012; Species: *Blomia tropicalis*
DRNKLPHKVV CYWGTWAFYR PGSDKFEAE NINPNLCTHI NYGFAKLVGN KIALFDPDLD TGDEDWASGL

TWGHGMIRRL NELRKYNKNL STLISIGGWN EGSNKYSTMV STAGGRSEFV KSVIEFLQKY EFDGLDLDWE

YPGMSASGDA DRKPGREQDK ADYIELLKEL RQAFEPHGYI LSAAVSAGAP TIDRAYNVPE VSKHLHFINL

MAYDFHGGWD TKTAHNAPLY ALPGAEGIDK EFTVSYAVEY WISKGADPKK LVLGIPLYGR TFTLAGPNHD

IGAPVTGHGG QAGPITRLIG MLGYNEICSM VKNGWEIHWN DIQQIPYATH ASQWIGYDNE KSIEKKLDYV

HQKNLGGGMV WSIDTDDFSG HCGVKYPLLK TISRRLNNID GPDVVIPRTH ATTPHPDDHD HTTKRPDDPH

TDPHTEPHHD KTTSAPNPDG KFQCHSTGFF KDPSDPRKFH QCVDIGNGKL KDYEFNCPLG SHYDEQLHVCV

SEQ ID NO: 36; Cluster ID (L) 40; Cluster ID (A) 23
Protein name: A0013; Species: *Dermatophagoides farinae*
DTPANCTYED IKGLWLFEES TPINDRTEKC DNGRREYTKK IYVRLDFPNT AVDKFGNVGT WTLIYNQGFE

VIINYRKYFA FSAYERKSNS KVISYCHKTI PGWSHDLLGN NWACYIGHKV NDWNSSPLQK IGSEQFPIKE

HIEQPLYLKN IDLSHALSQN HVDQINSKQK SWKATVYPEM QSKTVEHLIK MAGGEKSRIM SRPKPIRATE

QQRHEARGLP ESFDWRNVDG INYVSPVRNQ GNCGSCYAFA SMAMLEARIR IATNNTAKPV FSPQEVVDCS

EYSQGCDGGF GYLIAGKYAQ DFGVVEESCY PYKAYTGKCK LDYNTTAKCQ QRTYTIKYNY LGGYFGACNE

EAMRIELVKN GPIAVGFEVY KDFMTYRRGI YSHDSDYETE QKVGVEFNPF VLTNHAVLIV GYGRDEKSGE

NYWIVKNSWG EQWGIDGGYF LIRRGTNECG IESIAMAATP IPN

SEQ ID NO: 37; Cluster ID (L) 40; Cluster ID (A) 23
Protein name:A0013;Species: *Dermatophagoides pteronyssinus*
DTPANCTYED IKGLWLFEET EPIKDRWEKC PEHQQQREKY SKKIFIRLDF PNVAVDKFGN IGEWTMIYNQ

GFEVKINYRK YFAFSAYERK SENNVLSYCH KTQPGWSHDV LGNNWACYVG HKVNNWNDDD VSKTTTVGAE

KFPVKQHSER ELYLQNINVE HILSQKHIDH LNSQQKSWKA IVYPDLQSKS IEHLIQMAGG RKSRIINRPK

PLRATEQQKQ LARSLPESFD WRNLNGIDYV SPVRDQGKCG SCYTFASMAM LESRIRIQTN NTFKPIFSTQ

EVVDCSEYSQ GCDGGFSYLI AGKYAQDFGV IDESCYPYKG VTGKCQNQQN FNQTNEKCKQ RTYTIDYKYV

GGYFGACNEE AMQIELVQNG PIAVGFEVYG DFFGYSEGIY SHQPSNESND QHQQIKAEFN PFEMTNHAVL

IVGYGKDKKT GEKYWIVKNS WGKQWGMDGY FWMRRGTDEC AIESLAMAAT PIPN

SEQ ID NO: 311
Protein name: A0013; Species: *Blomia tropicalis*
DTPANCTYED IRGEWEFHET ERIASRKEVC DDNSVSTTKH TVYLKLEFPN IATDQHGNVG HWTIIYNQGF

EVSINYRKYF AFSLYKQVGK QVTSYCDSTF PGWSHDVLGN NWACFKGRKV NRQQEKSFDE TMINNGKTHT

VQPFLLESVP VNHNLIQMNV NKINMKQSSW KAKFYPHLMN LNTEDLIRMA GGRGSAIVNR PSTVPASEEI

KEKVRQLPES FDWRNVNGIN YVSPVRDQGK CGSCYIFSSM AQLEARVRIA TNNSEQPIFS TQEVVDCSKY

SQGCDGGFPY LIAGKYGRDY GVIADECYPY KGKNGKCSLP YNSTGTKCMK RSYTLHYHYV GGYYGGCNEE

LMLLELVKNG PITVGFEVYD DFTSYSGGIY SHDKSKDQWR NGVHFNPFQL TNHAVLIVGY GVDKQSGEKY

WIVKNSWGKD WGLDGYFWIK RGNDECGIES LAVSVTPIP

SEQ ID NO: 32; Cluster ID (L) 33; Cluster ID (A) 25
Protein name: A0014; Species: *Dermatophagoides farinae*
IEQVHISLGT NATEMIVTWT EPQKHTDIDI DAVVYYGRAS SSFDQAAIAK SEHFKDDETK YTTFRALLTG

LESDTRYHYK IQLDDKESSI FAFKTLKLDE NWLPRFAIYG DLGYVNEQSL PYLKKDVEKN MFDVIFHIGD

IAYDLQDENG EVGNNFMRSI ESIASKIPYM TCPGNHERHS NFSHYDSRFS MIGDRSQPNH QDSLDKRINN

HFHSMEIGPA TIIMFSTEYY YYTYYGWEQI ERQYRFLEKE LIRANENRNK RPWIIAMGHR PLYCLKMGDS

SCDHQTMERP EIRQGIRMHD QGERQYGLED LFHKYGVDIQ FYGHEHFYAR MFPIYKYQMY KGKQSDNPYD

HADGPIHITT GSAGNKEIHP LFNHLKEWVA HHFYDYGYTR LIFENQYRIR LQQVSDDQHG KVLDEIEIIK

SSPQPHWMP

SEQ ID NO: 33; Cluster ID (L) 33; Cluster ID (A) 25
Protein name: A0014; Species: *Dermatophagoides pteronyssinus*
IEQVHIALGS NETEIIVTWT EPHKHDDKTS DAVVYYGQAK SSFDQKVKAI SEYFKDDKTK YTTYRALLTG

LLPGTEYHYR IQMDDLESSI FEFKTLKTGE ENWLPRFAIY GDLGYVNEQS LPYLKKDVEQ NLFDVIFHIG

DFAYDLNDEH GKVGHHFMRS IEPVASKVAY MTCPGNHERH DNFSHYDSRF SMIGDRSQPI HSDKLNKRLN

NHFHSMTIGP ATIILFSTEY YYYTKYGWQQ IEHQYRWLEQ ELKRANENRQ KHPWIIVMGH RPLYCLKMGD

DSCDHQTMER KEIRQGIRMH DEGERQYGLE DLFFKYGVDI QFYGHEHFYA RLFPIYKYKM YNGTKSKNPY

DHPGAPIHIT TGSAGNKELH PEFNHLNDWV AEHFYDYGYT RLMFEDKYRI RLQQISDDQH GKVLDEIEIV

KSSPQPHWMN VEHH

-continued

SEQ ID NO: 26; Cluster ID (L) 25; Cluster ID (A) 34
Protein name: A0015; Species: *Dermatophagoides farinae*
SPTSIRTFEE FKRQFNKQYQ SIEHEEIARK NFQETLRYVQ ANQDKAVINE YADLSAEEFA DGYLMNVQDV

QDLEAEMDAH KEYFDDPDCK LHGDFNPPKE FDLRPHLTPI KKQIKNCGCC WALSTISCVE TAYLAQKNVS

LQLSTQELVN CAKEHGCKKG TVLDGIEYIM ANGTTTEEAC PFISEESTCD QSKKPRYEIS NWCYFKPVED

DIRKNLVLRR TSVSVSMNIE NLKAFVHYDG SFVIRENSFP SIGNKSYHAV NIVGFGTKDD IDHWIVRNSW

GEKWGDKGYF YVERDINLWG IKDWAFTTIV

SEQ ID NO: 27; Cluster ID (L) 25; Cluster ID (A) 34
Protein name: A0015; Species: *Dermatophagoides pteronyssinus*
SPTGWNIRTF EQFKIQFNKH YDSIEQEEHA RENFLETLKY VDANPDKAVI NEFADLSAEE FADGYLMSEE

SMQDSEQQLK LLRAGYDYHD DPECLFDENL EAPKQVDLRP DLSPIMRQTL HCGCCWAISP ISSAESAYKA

RYNVSIQLSV QELVNCAVEH GCEIGKTAIA FNYLVTNGTT TQKAYPYTAK EGACNPPEKP RYTLENWCAY

IDPSIKNKNK PDLRKVLAQK RTSITVQISI KNVKAFAHHN GSFIIRENSF PDEGKPSGHA INIVGYGTKD

GVDYWIVRNS WSTGWGDKGY FYVERGVNWW GIEEYAFIAT F

SEQ ID NO: 312
Protein name: A0015; Species: *Blomia tropicalis*
IKTFEQFKKV FGKVYRNAEE EARREHHFKE QLKWVEEHNG IDGVEYAINE YSDMSEQEFS FHLSGGGLNF

TYMKMEAAKE PLINTYGSLP QNFDWRQKAR LTRIRQQGAC GSCWAFAAAG VAESLYSIQK QQSIELSEQE

LVDCTYNRYD SSYQCNGCGS GYSTEAFKYM IRTGLVEERN YPYNMRTQWC DPDVEGQRYH VSGYQQLRYQ

SSDEDVMYTI QQHGPVVIYM HGSNNYFRNL GNGVLRGVAY NDAYTDHAVI LVGWGTVQGV DYWIIRNSWG

TGWGNGGYGY VERGHNSLGI NNFVTYATL

SEQ ID NO: 28; Cluster ID (L) 43; Cluster ID (A) 39
Protein name: A0016; Species: *Dermatophagoides farinae*
MVKIGINGFG RIGRLVLRAA VKKGVEVVAV NDPFLDVKYM VYMFKFDSTH GRYQGEVKEE GGLLVVDGQK

IQVFQERNPA DIPWGKVGAD YVVESTGVFT TIEKAKAHLA GGAKKVVISA PSADAPMYVM GVNHDKYDPS

QQIISNASCT TNCLAPLAKV INDKFGIENG LMTTVHAVTA TQKTVDGPSG KMWRDGRGAG QNIIPASTGA

AKAVGKVIPE LNGKLTGMAL RVPVPDVSVV DLTVTLKNPA SYDEIKAAIK AAAESDHWKG ILEYTDEEVV

SSDFISDTHS SIFDAKAGIA LTPTFVKLIA WYDNEFGYSN RVIDLIKYVA SK

SEQ ID NO: 29; Cluster ID (L) 43; Cluster ID (A) 39
Protein name: A0016; Species: *Dermatophagoides pteronyssinus*
MVKIGINGFG RIGRLVLRAA IKKGVEVAAI NDPFLDVKYM VYMFKFDSTH GRYQGEVKEE GGLLVVDGQK

IQVFQERNPA EIPWGKVGAD YVVESTGVFT TIEKAKAHLA GGAKKVIISA PSADAPMYVM GVNHDKYDPK

QQIISNASCT TNCLAPLAKV INDKFGIENG LMTTVHAITA TQKTVDGPSG KLWRDGRGAG QNIIPASTGA

AKAVGKVIPE LNGKLTGMAL RVPVPDVSVV DLTVTLKNPA SYDEIKAAVK AAAESDHWKG ILEYTDEEVV

SSDFISDTHS SIFDAKAGIA LTPTFVKLIA WYDNEFGYSN RVVDLIKYVA SK

SEQ ID NO: 21; Cluster ID (L) 13; Cluster ID (A) 49
Protein name: A0017; Species: *Dermatophagoides farinae*
MSSSSGKKYD FSGKVALVTG SSSGIGAAIA VQFAQYGAKL TITGRDGAAL ESVAKKIEIE SGHQPLQIVG

DLLDQSLPAK LINETVSKFG RLDFLVNNAG GSTAHRELND EKLMEAFDKV FALNVRAVLQ LSQLAAIHLE

KSKGNIINIS SIVSMKPYGH VYSSSKAALD MITKTLAKEL GLKGVRVNSI NPGPVATGFL RSVGMSATAY

TDLADTMINH TLLKFLAQPD EIANLASFLA SDDARNMTGS IVVSDTGSLL V

SEQ ID NO: 25; Cluster ID (L) 13; Cluster ID (A) 49
Protein name: A0017; Species: *Dermatophagoides pteronyssinus*
MSSSSGKKYD FSGKVALVTG SSSGIGAAIA LQFAQYGAQV TITGRDAAAL ESVAKRIEAE SGHQPLQIVG

NLLDQSLPAK LIDGTISKYG RLDFLVNNAG FSTQHRDIHD EKLMEAFDQV YGLNVRAVVQ LSQLAATHLE

KSKGNIINIS SNLSMMPVHI IYSSSKAALD MITKTMAMEF GKKGVRVNSI NPGPVATQFM RSLGMPVTFL

KENEEFVKEL TLLKFVAQPV EIANLASFLA SDDARNMTGS IVVNDTGSLL APRVDFKKLD EIKKK

SEQ ID NO: 313
Protein name: A0017; Species: *Blomia tropicalis*
SLTNKKYDFS GKVALVTGSS SGIGAAIAIQ FAQYGAKVTI TGRNAENLDK IAKKIAEVSN GVEALQIIGD

LTIDDSLPKR LIDETVTKFG RLDFLVNNAG GATPQGTLAS PDLLKGFDDV FKLNVRSVIE LTQLAMPHLE

KTKGNIINIS SVASIKPYMV VYSSSKAALD MITKTSALEL GPKGIRVNSI NPGPVVTAFG RSMGVDPSHH

KKMFDSFEKQ MLMERVGQPE DIANLASFLA SDDAINITGS IMVNDSGCLL

SEQ ID NO: 5; Cluster ID (L) 97; Cluster ID (A) 71
Protein name: A0018; Species: *Dermatophagoides farinae*
MVKAVVVLKG EPNVTGTIFF EQQDNGPVKV SGTVQGLKSG LHGFHVHEFG DNTNGCTSAG AHYNPFNKTH

GAPADEERHV GDLGNVEAND AGIANVAIED SLISLTGERS IVGRSLVVHA DPDDLGRGGH ELSKTTGNAG

GRLACGVIGV TK

SEQ ID NO: 6; Cluster ID (L) 97; Cluster ID (A) 71
Protein name: A0018; Species: *Dermatophagoides pteronyssinus*
MVKAVVVLKG DPNVSGTIFF EQQDNGPVKV TGSVQGLKPG LHGFHVHEFG DNTNGCTSAG AHYNPLNKTH

GAPNDEERHV GDLGNIEAND KGVANVVIED SLISLTGEKS IVGRSLVVHA DPDDLGRGGH ELSKTTGNAG

GRLVCGVIGV TK

SEQ ID NO: 314
Protein name: A0018; Species: *Blomia tropicalis*
KAVVVLKGDS PVSGTIFFEQ KDNGPVSVTG TVNGLTAGDH GFHVHEFGDN TNGCTSAGAH FNPFGKTHGA

PADQERHVGD LGNVTADANG VANVNIQDSL ITLEGANTIV GRSLVVHADP DDLGRGGHEL SKTTGNAGGR

VACGVIGLTK

SEQ ID NO: 1; Cluster ID (L) 75; Cluster ID (A) 75
Protein name: A0019; Species: *Dermatophagoides farinae*
DGSHIVKAAR SQIGVPYSWG GGGIHGKSKG IGEGANIVGF DCSGLAQYSI YQGTHKTIAR TAAAQYNDNH

CHHVAYGSHQ PGDLVFFGNP IYHVGIVSAH GRMVNAPKPG TKVREENIWS YHISHVARCW

SEQ ID NO: 4; Cluster ID (L) 75; Cluster ID (A) 75
Protein name: A0019; Species: *Dermatophagoides pteronyssinus*
QVYCNGAAIV SAARSQIGVP YSWGGGGIHG KSRGIGEGAN TVGFDCSGLA QYSVYQGTHK VLARVASGQY

SDPKCHHVAY GSHQPGDLVF FGNPIHHVGI VSAHGRMINA PHTGTNVREE NIWSDHIANV ARCW

SEQ ID NO: 315
Protein name: A0019; Species: *Blomia tropicalis*
QAMAGGHEIV TAARSQLGVP YSWGGGNWAG KSKGIDSGAH TVGFDCSGLA QYAVYHGTHK KIARVASAQY

ADHQCHHVPY AQHLPGDLVF FNDGGSIHHV AIISGKNTMI HAPHTGDHVR EAAVYVKGRM STVQRCF

SEQ ID NO: 15; Cluster ID (L) 31; Cluster ID (A) 59
Protein name: A0020; Species: *Dermatophagoides farinae*
MSKPTFYFHP FSGPCRTVST VAKILNVEME MKKLDLLTQE HLKPEFLKVN PFHKIPTFVD TDGFTIDESR

VIAMYLLQSR KPDSFLYPNN DLKKRTQIDR WLHYDISFAT IISTPMYCKF RGKPVQDHQV EQGKETLKTL

DGVMASFGGK FLTGSDQITL ADIAMYFSCN TMEIYSEYFK FDDYPNLKSW YQRVAEALKQ YDTEGEIPKA

IEMIKQFAQQ RMAESAKQ

SEQ ID NO: 16; Cluster ID (L) 31; Cluster ID (A) 59
Protein name: A0020; Species: *Dermatophagoides pteronyssinus*
MSKPIFYYHP FSGPCRTVST VAKILNVDME MKKLDLLTKE HLNPEFLKVN PFHKVPTFVD SDGFVVDESR

VIAMYLVESR KPDSFLYPKN DLKKRIQIDR WLHYDINLST TISAPMFCVF RGHQVQDYQV EQGKETLKTL

DGVMQSFEGK FLTGADQFTL ADIAMYFSLN TMEVYPKYFK FDDYPNLKSW YHRVAEALKQ YDTEGTIPKA

IETMKQFIQQ RAAEAEKH

SEQ ID NO: 316
Protein name: A0019; Species: *Blomia tropicalis*
MSKPTLYYMW ESPPCCTVIA IARILNIELD MKHVDLTKKD QNNPEFKKIN PFAIVPTFVE TDGYTLWESR

AISTYLVQSR SPDSTLYPGS DLKKRSTIDK FLQYDLGTFN RAIYDVVSEI FKSGKLNEQN IPRLGEVLKT

LEETLAANNE SNGGPFITGD DQLTIADISM HFSWTLLSLL PERLIDQSSY PTIRAWNQAV IQALKPYNRD

QKFTEAQRRL KAFITMMIES AKN

```
SEQ ID NO: 19; Cluster ID (L) 105; Cluster ID (A) 50
Protein name: A0022; Species: Dermatophagoides farinae
EWRLVWQDEF NGNQLDLNQW SYEVGGNGWG NNELEFYTYN RTENARIENG NLVIDVRVEN YRERQFTSAR

LHTRQAWTYG RFEARARMPY GHNLWPAIWM MPQDSIYGIW AASGEIDIVE YRGDNPDRIE GTAHYGGTWP

NHIYSGSGPR SFSVNFSQDF HTFALEWDHK QLRWYMDNQQ YFTLDIDRML WSGKGVNPYT KNGQPFDQPF

HWMLNVAVGG NFFGPGPYVT PDQARQWPKH TLEIDYVRVY QQ

SEQ ID NO: 20; Cluster ID (L) 105; Cluster ID (A) 50
Protein name: A0022; Species: Dermatophagoides pteronyssinus
NWQMVWQDEF NGGHLDQNHW EFETGGGGWG NNELEFYTAN RSQNVRVENG HLVIDVRVES YGGRDFTSGR

IHSKQAWAYG KFEARARLPS GHHLWPAIWM FPRDSKYGPW AASGEIDIME YRGDVHDKIE GTIHYGGQWP

NNIYTGSGPH HFNVDFSKDF HNFAVEWDTK EIRWYMDGNK YFSVNIDRNM WSGKGNNPYN KNGQPFDQPF

RWILNVAVGG NFFGPGPYVT PDQARHWQKH TMEIDYVRVY QWR

SEQ ID NO: 317
Protein name: A0022; Species: Blomia tropicalis
NWQLVWSDEF NGNGLDENNW NYQTGCSQQN DELECYTSHR HENVRVENGH LVIEARPEEY QGHHFTSGRL

HGKKAWAYGK FEARAKMPSG HHLWPAIWMM PRDSKYGGWA ASGEIDILEL RGDKPHEIVG TIHYGGSWPN

NIYHGSGERY YQQDFSQDYH TFAVEWDQKE IRWYVDGQHY HTENIDRNMW SGRGNNPYHK NGEPFDQPFY

WILNVAVGGN FFGPGPYVSP AEARNWHKRT MEVDYVRVYQ WR

SEQ ID NO: 23; Cluster ID (L) 8; Cluster ID (A) 42
Protein name: A0023; Species: Dermatophagoides farinae
SPAQRPSLRG VTIRNAPFLE EIDGKFKGFI PDLMDAIAEK AGFDYTLYLS PDGRYGNADK EGNVTGMIGE

VYNKKADFAA ADLTMTEARE NYITFTEPFM INQLAALIRR EDAEGMNTLE DLVNAGKTQP NHKPIILGTL

RNGATNHFLS KSDDPLAKKM YEQIKANDQS ATTSISKGIE RVDKQGGYAF IMESSSAEHE IANNCKLTML

LDWRNLYPRK YAFALPKDSQ YLQHFNNAIK QLNTEDKIAE LRRKYWSNNC SNTQTKNTGA

SEQ ID NO: 24; Cluster ID (L) 8; Cluster ID (A) 42
Protein name: A0023; Species: Dermatophagoides pteronyssinus
DPVQQRPTLR GVTVRVGPFV KENNGKFEGF IPDLVQAISE KVGFDYTLYL SPDGRYGNVI SDGNVTGMIG

EVYNKKADFA AADLTMTEAR ENYITFTEPF MINQLAALIR REDAEGLNTL EDLAKAQETF PKRKRIVLGT

LRNGATNYFL SKSDDPLAKK IYEQIKADDQ SVVKSISEGV ERVDKQGGYA FIMESASAEH EIANNCKLTM

LLDWRNLFPR KYAFALPKDS PYLEHFNNAI KQLNSEGKIA ELRRKYWANN CAENKTKDDK N

SEQ ID NO: 11; Cluster ID (L) 36; Cluster ID (A) 65
Protein name: A0024; Species: Dermatophagoides farinae
MSISAHGGGL VNGIAGMENK FTVFTSGKPV SGLTVAFEGP TKPEINFNST KDGSVDVGYT PKAGGQYKIH

IKYEGKEIVG SPFKCNISGD EATHRKLTEK VKVGGPNINA GKVNQDNQLT IDCKEAGITG GISFAMEGPA

KVEVSFRNNN DGTITVIYKP PTPGDYKLHL KFNDIHLPGS PYPIVVAA

SEQ ID NO: 12; Cluster ID (L) 36; Cluster ID (A) 65
Protein name: A0024; Species: Dermatophagoides pteronyssinus
MSISAHGGGL VNGIAGMENK FTVFTSGKPV SGLTVAFEGP TKPEINFNST KDGSVDVGYI PKAGGQYKIH

IKYEGKEIVG SPFKCNISGD ESTHRKLTEK VKVGGPNIST GKVNQDNQLT IDCKEAGITG GISFAMEGPA

KVEVSFRNNN DGTITVIYKP PTPGDYKLHL KFNDIHLPGS PYPIVVSA

SEQ ID NO: 318
Protein name: A0024; Species: Blomia tropicalis
MSISAHGGGL INGIAGMENK FTVFTSGKPV SGLTVAFEGP TKPDINFNSA KDGSVDVSYT PKAGGMYKIH

IKYDGKEIIG SPFKTNITGD EATHRKLTEK VKVGGPNVST GKANADNELT IDCKEAGITG GISFAMEGPA

KVEVSFRNNN DGTITVVYKP PQNGDYKLHL KFNDIHLPGS PFPIVVS

SEQ ID NO: 17; Cluster ID (L) 104; Cluster ID (A) NA
Protein name: A0025; Species: Dermatophagoides farinae
ESLFIYDDYS CGSYGHDVNE LIEQFQLFKK NEHNQNESIE IIGHFLKKIR EYRVEAIKVM LETDRKLLTL

NNSQIILNIQ YQKKKIRCEN LKHLSELLTM HLLAYKQGMF DFAEEIDPDV NFDRQFKNFL DRSSEVMNIN
```

-continued

EFSDIEKKWS NSSAKKLLKN DIDGLITALD DLREDFLKNI ILPEFDAQSR YDLYFSIQDQ INIRSTLKLF

GTIKMFMKEL LDDLNQPDFE ILY

SEQ ID NO: 18; Cluster ID (L) 104; Cluster ID (A) NA
Protein name: A0025; Species: *Dermatophagoides pteronyssinus*
QSLFVDYNDY SCGSSQNETN ELIQEFKIFK KNINGNENFK KINDFIEKAR LFRDNAAKQM LEIDQQLLTL

NVIQISQRIK LENNKIQCEK LTKFSELLSM QLLAYEVGMF EFAEEIDPNI DFDRKMKNFL DETSRLFNLA

EFEKLEKKFR NATSIEKLKN YIDGELVALN DYINEFLKDI IMSEFTVQSR YYLNFSIEDQ VQIDSTLMTF

SALKILLNDL KDYLEHLDN

SEQ ID NO: 9; Cluster ID (L) 102; Cluster ID (A) 62
Protein name: NA; Species: *Dermatophagoides farinae*
NRVSVGVYYE TICSGCRTHF INAIVPLRQQ LGEYVDIDLV PFGNAHIYSN GPQCQHGALE CYGNAFQACS

LDMNGFDTGF KLVECMFRSS YYSNPQYSAK RCAQQLNLNY DQLHSCATGQ KGFELIKVMA RKTPRHNYVP

WTTVESRTVD VNVDLVKYIC DNYLNNVPAC N

SEQ ID NO: 10; Cluster ID (L) 102; Cluster ID (A) 62
Protein name: NA; Species: *Dermatophagoides pteronyssinus*
TQRVTVGVYY ETICPGCRSH FIQAIVPLKN QLGQYVNIDL VPFGNAHFYS NGPQCQHGQL ECYGNAFQAC

SLDMNGFETA FKLVECMFRS NYFSNPEYSS KQCSQQLNLD YQQLDSCANG QKGLQLIREM ANKTPSHQYV

PWTTVQGRFV DGNVDLVDYI CENYLNGVPA CN

Each of the above amino acid sequences (SEQ ID NOs: 1-44 and 305-318) can according to the present invention be modified by substituting each cysteine residue with at least either a serine residue, an alanine residue or a 2-aminobutyric acid (also known as α-butyric acid and homoalanine) residue. The sequences of the thus modified variants of SEQ ID NOs: 1-44 and 305-318 are set forth in SEQ ID NOs: 261-304 and 319-332.

In embodiments of SEQ ID NOs: 261-304 and 319-332, all cysteine residues in an amino acid sequence are substituted with serine residues. In other embodiments of SEQ ID NOs: 261-304 and 319-332, all cysteine residues in an amino acid sequence are substituted with an alanine residue. In other embodiments of SEQ ID NOs: 261-304 and 319-332, all cysteine residues in an amino acid sequence are substituted with 2-aminobutyric acid residues. Further, in a group of embodiments of SEQ ID NOs: 261-304 and 319-332, more than 1 of serine, alanine and 2-aminobutyric acid substitutions can be present in the same amino acid sequence and in some embodiments all 3 substitutions are present in the same amino acid sequence.

SEQ ID NOs: 45-260 refer to 15-mer peptides of the invention that are fragments of proteins of SEQ ID NOs: 1-44:

| SEQ ID NO: | Source Protein ID | Species | Peptide ID # | Start pos | Sequence |
|---|---|---|---|---|---|
| 45 | A0001 | Der f/p | 2344 | 131 | IMRIL<u>CC</u>KSRKVAP<u>C</u> |
| 46 | A0007 | Der f/p | 1800 | 4 | FNYLPVDVQEELRNT |
| 47 | A0007 | Der f/p | 1805 | 94 | ELLKKGIIPGIKVD |
| 48 | A0007 | Der f/p | 1804 | 69 | EQYISGVILFDETVY |
| 49 | A0007 | Der f/p | 1806 | 99 | KGIIPGIKVDTGVVT |
| 50 | A0008 | Der f/p | 1360 | 9 | FIMLKPDAVQRGIVG |
| 51 | A0008 | Der f/p | 1361 | 19 | RGIVGEIIRRFEAKG |
| 52 | A0008 | Der f/p | 1362 | 24 | EIIRRFEAKGFKLVA |
| 53 | A0008 | Der f/p | 1363 | 29 | FEAKGFKLVAMKFMM |
| 54 | A0008 | Der f/p | 1364 | 34 | FKLVAMKFMMASEDL |
| 55 | A0008 | Der f/p | 1365 | 40 | KFMMASEDLLKKHYA |
| 56 | A0008 | Der f/p | 1366 | 49 | LKKHYADLAARPFFP |
| 57 | A0008 | Der f/p | 1368 | 79 | WEGLNAVKTGRVMLG |
| 58 | A0009 | Der f | 1710 | 387 | ITRLREAMGVMQHHD |
| 59 | A0009 | Der f/p | 1711 | 405 | GTEKQHVAFNYAKML |

-continued

| SEQ ID NO: | Source Protein ID | Species | Peptide ID # | Start pos | Sequence |
|---|---|---|---|---|---|
| 60 | A0009 | Der f/p | 1712 | 410 | HVAFNYAKMLDSAML |
| 61 | A0009 | Der f | 1714 | 422 | AMLQCRHVISESYRK |
| 62 | A0009 | Der p | 1715 | 427 | RHIINESYKKLLPKS |
| 63 | A0009 | Der f | 1716 | 447 | EFCPYLNISSCPSTE |
| 64 | A0009 | Der p | 1718 | 470 | LYNPLGHRLINHTVR |
| 65 | A0009 | Der f | 1722 | 507 | LISIPEFVRKIPGRK |
| 66 | A0009 | Der f | 1742 | 647 | IVQEVHQQFDSFVGQ |
| 67 | A0009 | Der f | 1757 | 778 | LMVHRRLLHDDYFGV |
| 68 | A0009 | Der f | 1758 | 802 | DGHGIVIRGRHLLLL |
| 69 | A0009 | Der p | 1767 | 842 | EPIISFTSIESNKQA |
| 70 | A0009 | Der f | 1776 | 872 | HSKRYLLRLEHFYQR |
| 71 | A0009 | Der f | 1777 | 878 | LLRLEHFYQRFEDPS |
| 72 | A0009 | Der p | 1778 | 885 | KRYLLRLEHFYQSNE |
| 73 | A0009 | Der f | 1775 | 888 | TLEQWHSKRYLLRLE |
| 74 | A0009 | Der f | 1779 | 897 | TVSLRHLFQSFEITA |
| 75 | A0009 | Der p | 1782 | 910 | SLRHLFKSFEIIAVE |
| 76 | A0009 | Der p | 1783 | 915 | FKSFEIIAVEELTLG |
| 77 | A0009 | Der p | 1786 | 930 | ANQPISSLKNRLHYR |
| 78 | A0009 | Der p | 1785 | 990 | ELTLGANQPISSLKN |
| 79 | A0010 | Der f | 305 | 38 | GNDLKNLSSKVLPNL |
| 80 | A0010 | Der f | 307 | 43 | NLSSKVLPNLNVPYC |
| 81 | A0010 | Der p | 306 | 44 | DDGNLISRALPHLGV |
| 82 | A0010 | Der f | 309 | 63 | YIGYKIEKHSKNLIQ |
| 83 | A0010 | Der p | 312 | 81 | DLSMTKLKRVRPSGF |
| 84 | A0010 | Der p | 313 | 106 | IHQLNDQVLRLKFID |
| 85 | A0010 | Der p | 314 | 111 | DQVLRLKFIDANQKR |
| 86 | A0010 | Der f | 315 | 138 | RLYSVELDGSHLIVR |
| 87 | A0010 | Der f | 316 | 158 | QSIFDINLAYMVYSD |
| 88 | A0010 | Der f | 318 | 168 | MVYSDQLIHVTSRLP |
| 89 | A0010 | Der f | 321 | 193 | RAPFRKNTNWKRYTQ |
| 90 | A0010 | Der p | 324 | 241 | TKLASGVFLFNSNAM |
| 91 | A0010 | Der p | 325 | 246 | GVFLFNSNAMDILTQ |
| 92 | A0010 | Der p | 330 | 281 | GPKPEQVVQQYHNLI |
| 93 | A0010 | Der p | 331 | 286 | QVVQQYHNLIGLPAM |
| 94 | A0010 | Der f | 334 | 313 | FTNLNTTYTRNRAVG |
| 95 | A0010 | Der f | 335 | 348 | TTYTRNRAVGIPMDV |
| 96 | A0010 | Der p | 337 | 361 | LPDFIRNVLHKNGQK |
| 97 | A0010 | Der f | 340 | 428 | NATEYWMDMFAEYHK |

-continued

| SEQ ID NO: | Source Protein ID | Species | Peptide ID # | Start pos | Sequence |
|---|---|---|---|---|---|
| 98 | A0010 | Der f | 341 | 433 | WMDMFAEYHKTIAFD |
| 99 | A0010 | Der f | 342 | 438 | AEYHKTIAFDGAWLD |
| 100 | A0010 | Der f/p | 343 | 487 | TLRHKTLCMTARHYN |
| 101 | A0010 | Der f/p | 344 | 498 | RHYNDQLHYNLHNLY |
| 102 | A0010 | Der f | 346 | 508 | QLHYNLHNLYGFQEA |
| 103 | A0010 | Der f | 345 | 508 | QLHYNLHNLYSLSMA |
| 104 | A0010 | Der f | 347 | 508 | LHNLYSLSMAMATNA |
| 105 | A0010 | Der f | 348 | 513 | SLSMAMATNAALTKL |
| 106 | A0010 | Der f | 350 | 522 | AALTKLNKRPFIISR |
| 107 | A0010 | Der p | 349 | 526 | NEALKTTLNKRPFII |
| 108 | A0010 | Der f | 351 | 528 | NKRPFIISRATAPGH |
| 109 | A0010 | Der f | 352 | 548 | HWNGDILSDWSSMRW |
| 110 | A0010 | Der f | 353 | 553 | ILSDWSSMRWTIPSI |
| 111 | A0010 | Der f | 354 | 558 | SSMRWTIPSILNFNM |
| 112 | A0010 | Der p | 355 | 571 | PSILNFNLFGVPMIG |
| 113 | A0010 | Der f | 356 | 593 | LCIRWYQLGAFYSFA |
| 114 | A0010 | Der f | 357 | 598 | YQLGAFYSFARNHND |
| 115 | A0010 | Der p | 358 | 608 | AFYSFVRNHNTDNAI |
| 116 | A0010 | Der f | 359 | 623 | LGESVIRAARSSLQY |
| 117 | A0010 | Der f | 360 | 628 | IRAARSSLQYRYRFL |
| 118 | A0010 | Der f | 361 | 633 | SSLQYRYRFLAHLYT |
| 119 | A0010 | Der f | 362 | 638 | RYRFLAHLYTLFYHV |
| 120 | A0010 | Der f | 363 | 643 | AHLYTLFYHVHKNGG |
| 121 | A0010 | Der p | 364 | 681 | DIETQFMWGDSMLIA |
| 122 | A0010 | Der p | 365 | 686 | FMWGDSMLIAPILYP |
| 123 | A0010 | Der f | 366 | 728 | YDDIDYVFVRGGSII |
| 124 | A0010 | Der p | 367 | 736 | DINYVFFRSGSIIPI |
| 125 | A0010 | Der p | 368 | 741 | FFRSGSIIPIQGPQN |
| 126 | A0010 | Der f | 375 | 816 | TQNINFINILGVPKL |
| 127 | A0010 | Der p | 373 | 816 | SQHLGYQTNQSIIIL |
| 128 | A0010 | Der p | 374 | 821 | YQTNQSIIILEILGI |
| 129 | A0010 | Der f | 377 | 822 | INILGVPKLPTSFKL |
| 130 | A0010 | Der p | 378 | 841 | SIIFDGKPYYQFIYT |
| 131 | A0010 | Der f | 380 | 843 | PRIIRFNYDEQTNIL |
| 132 | A0010 | Der p | 379 | 846 | GKPYYQFIYTTNNML |
| 133 | A0010 | Der p | 381 | 851 | QFIYTTNNMLIIQTK |
| 134 | A0010 | Der p | 382 | 856 | TNNMLIIQTKLSIFN |
| 135 | A0010 | Der p | 383 | 861 | IIQTKLSIFNDNDKS |

-continued

| SEQ ID NO: | Source Protein ID | Species | Peptide ID # | Start pos | Sequence |
|---|---|---|---|---|---|
| 136 | A0010 | Der p | 384 | 873 | DKSKKIHYQFEWKFN |
| 137 | A0010 | Der f | 369 | 885 | HDNTELMKTKDFLLI |
| 138 | A0010 | Der p | 332 | 887 | YHNLIGLPAMPPFWS |
| 139 | A0011 | Der f | 1859 | 32 | ELNFKVYEDAAALAK |
| 140 | A0011 | Der f | 1860 | 57 | EDGLIYNIASREKAD |
| 141 | A0011 | Der f | 1861 | 102 | KHEIFVVADLIDRKS |
| 142 | A0011 | Der f/p | 1862 | 132 | DKKFLFNTAVLFDRQ |
| 143 | A0011 | Der f/p | 1863 | 137 | FNTAVLFDRQGKLLG |
| 144 | A0011 | Der f | 1865 | 152 | RYHKMHLFGEMTMNI |
| 145 | A0011 | Der f/p | 1866 | 167 | PPKPELLVIDTELGR |
| 146 | A0011 | Der f/p | 1867 | 172 | LLVIDTELGRLGMQI |
| 147 | A0011 | Der f | 1868 | 185 | LGMQICFDMIFKTPG |
| 148 | A0011 | Der f | 1870 | 212 | TWWFDEAPMLSSSQY |
| 149 | A0011 | Der f/p | 1871 | 222 | ssSQYQMAWAFGNNV |
| 150 | A0011 | Der f | 1880 | 427 | ELNSRFVYAKLRGAF |
| 151 | A0011 | Der f | 1881 | 432 | FVYAKLRGAFSESTA |
| 152 | A0011 | Der f | 1882 | 437 | LRGAFSESTAVYPSA |
| 153 | A0012 | Der f | 2421 | 17 | GTWAFYRPASGKFQA |
| 154 | A0012 | Der f | 2422 | 37 | NLCTHIMYGFAKLQN |
| 155 | A0012 | Der f | 2423 | 42 | IMYGFAKLQNNKIAL |
| 156 | A0012 | Der f | 2424 | 72 | LQWGHGMIRRMVNLR |
| 157 | A0012 | Der f/p | 2425 | 74 | GMIRRMVNLRTYNPH |
| 158 | A0012 | Der f/p | 2426 | 82 | MVNLRTYNPHLTTMI |
| 159 | A0012 | Der f | 2428 | 107 | KYSIMVRDPASRKIF |
| 160 | A0012 | Der f | 2429 | 117 | SRKIFIQSVLHLLAE |
| 161 | A0012 | Der f | 2430 | 122 | IQSVLHLLAEFDLDG |
| 162 | A0012 | Der f | 2431 | 161 | KEDFVTLLRELHEAF |
| 163 | A0012 | Der f | 2432 | 177 | QPHGYVLSSAVSAGK |
| 164 | A0012 | Der f/p | 2433 | 202 | EVSKYLDFINLMSYD |
| 165 | A0012 | Der f/p | 2434 | 207 | LDFINLMSYDYHGGW |
| 166 | A0012 | Der f | 2435 | 242 | KEFTVTYSVEYWLNH |
| 167 | A0012 | Der f | 2436 | 257 | GVDPKKLVLGIPLYG |
| 168 | A0012 | Der f | 2437 | 269 | LYGRTFTLAGSEHGI |
| 169 | A0012 | Der f | 2441 | 347 | EKLNLLMAKHLGGAM |
| 170 | A0012 | Der f | 2442 | 372 | GNCVGVKYPLLRSIS |
| 171 | A0012 | Der f | 2443 | 377 | VKYPLLRSISKKLNN |
| 172 | A0012 | Der f | 2445 | 457 | HGKFQCHQAGFFADP |
| 173 | A0013 | Der f | 1096 | 13 | GLWLFEESTPINDRT |

-continued

| SEQ ID NO: | Source Protein ID | Species | Peptide ID # | Start pos | Sequence |
|---|---|---|---|---|---|
| 174 | A0013 | Der f | 1097 | 38 | TKKIYVRLDFPNTAV |
| 175 | A0013 | Der f | 1099 | 63 | LIYNQGFEVIINYRK |
| 176 | A0013 | Der f | 1100 | 68 | GFEVIINYRKYFAFS |
| 177 | A0013 | Der f/p | 1101 | 73 | INYRKYFAFSAYERK |
| 178 | A0013 | Der f | 1102 | 78 | YFAFSAYERKSNSKV |
| 179 | A0013 | Der f | 1113 | 253 | AMLEARIRIATNNTA |
| 180 | A0013 | Der f | 1115 | 287 | DGGFGYLIAGKYAQD |
| 181 | A0013 | Der f | 1116 | 333 | TYTIKYNYLGGYFGA |
| 182 | A0013 | Der f | 1117 | 353 | MRIELVKNGPIAVGF |
| 183 | A0013 | Der f | 1118 | 363 | IAVGFEVYKDFMTYR |
| 184 | A0013 | Der f | 1119 | 368 | EVYKDFMTYRRGIYS |
| 185 | A0014 | Der p | 1006 | 31 | DAVVYYGQAKSSFDQ |
| 186 | A0014 | Der f/p | 1009 | 110 | GDLGYVNEQSLPYLK |
| 187 | A0014 | Der p | 1012 | 155 | HFMRSIEPVASKVAY |
| 188 | A0014 | Der p | 1013 | 186 | YDSRFSMIGDRSQPI |
| 189 | A0014 | Der p | 1014 | 211 | NHFHSMTIGPATIIL |
| 190 | A0014 | Der p | 1015 | 221 | ATIILFSTEYYYYTK |
| 191 | A0014 | Der p | 1016 | 261 | KHPWIIVMGHRPLYC |
| 192 | A0014 | Der p | 1017 | 306 | QYGLEDLFFKYGVDI |
| 193 | A0014 | Der p | 1018 | 311 | DLFFKYGVDIQFYGH |
| 194 | A0014 | Der p | 1019 | 326 | EHFYARLFPIYKYKM |
| 195 | A0014 | Der p | 1020 | 331 | RLFPIYKYKMYNGTK |
| 196 | A0014 | Der p | 1021 | 336 | YKYKMYNGTKSKNPY |
| 197 | A0014 | Der p | 1022 | 371 | PEFNHLNDWVAEHFY |
| 198 | A0014 | Der p | 1023 | 381 | AEHFYDYGYTRLMFE |
| 199 | A0014 | Der p | 1024 | 386 | DYGYTRLMFEDKYRI |
| 200 | A0014 | Der p | 1025 | 391 | RLMFEDKYRIRLQQI |
| 201 | A0016 | Der f/p | 1353 | 3 | KIGINGFGRIGRLVL |
| 202 | A0017 | Der f/p | 404 | 9 | YDFSGKVALVTGSSS |
| 203 | A0017 | Der f | 406 | 29 | IAVQFAQYGAKLTIT |
| 204 | A0017 | Der f | 407 | 69 | VGDLLDQSLPAKLIN |
| 205 | A0017 | Der f | 412 | 124 | NVRAVLQLSQLAAIH |
| 206 | A0017 | Der f | 413 | 129 | LQLSQLAAIHLEKSK |
| 207 | A0017 | Der f | 421 | 179 | ELGLKGVRVNSINPG |
| 208 | A0017 | Der f | 425 | 219 | NHTLLKFLAQPDEIA |
| 209 | A0017 | Der f | 428 | 247 | MTGSIVVSDTGSLLV |
| 210 | A0018 | Der f | 2351 | 3 | KAVVVLKGEPNVTGT |
| 211 | A0018 | Der p | 2352 | 93 | VANVVIEDSLISLTG |

-continued

| SEQ ID NO: | Source Protein ID | Species | Peptide ID # | Start pos | Sequence |
|---|---|---|---|---|---|
| 212 | A0018 | Der f | 2353 | 98 | IEDSLISLTGERSIV |
| 213 | A0018 | Der f | 2354 | 103 | ISLTGERSIVGRSLV |
| 214 | A0018 | Der p | 2355 | 108 | EKSIVGRSLVVHADP |
| 215 | A0019 | Der p | 2065 | 3 | YCNGAAIVSAARSQI |
| 216 | A0019 | Der p | 2066 | 8 | AIVSAARSQIGVPYS |
| 217 | A0019 | Der p | 2067 | 53 | SVYQGTHKVLARVAS |
| 218 | A0019 | Der p | 2068 | 86 | GDLVFFGNPIHHVGI |
| 219 | A0019 | Der p | 2069 | 93 | NPIHHVGIVSAHGRM |
| 220 | A0019 | Der p | 2070 | 98 | VGIVSAHGRMINAPH |
| 221 | A0020 | Der f | 968 | 42 | LKPEFLKVNPFHKIP |
| 222 | A0020 | Der f | 969 | 47 | LKVNPFHKIPTFVDT |
| 223 | A0020 | Der f | 970 | 52 | FHKIPTFVDTDGFTI |
| 224 | A0020 | Der f | 971 | 62 | DGFTIDESRVIAMYL |
| 225 | A0020 | Der f | 978 | 157 | QITLADIAMYFSCNT |
| 226 | A0020 | Der f | 979 | 162 | DIAMYFSCNTMEIYS |
| 227 | A0022 | Der p | 2481 | 168 | DTKEIRWYMDGNKYF |
| 228 | A0022 | Der p | 2485 | 238 | QKHTMEIDYVRVYQW |
| 229 | A0023 | Der f | 178 | 7 | SLRGVTIRNAPFLEE |
| 230 | A0023 | Der f/p | 179 | 87 | EARENYITFTEPFMI |
| 231 | A0023 | Der f/p | 180 | 92 | YITFTEPFMINQLAA |
| 232 | A0023 | Der f/p | 181 | 97 | EPFMINQLAALIRRE |
| 233 | A0023 | Der f | 182 | 132 | HKPIILGTLRNGATN |
| 234 | A0023 | Der f | 183 | 137 | LGTLRNGATNHFLSK |
| 235 | A0023 | Der f | 184 | 187 | GYAFIMESSSAEHEI |
| 236 | A0023 | Der f | 185 | 207 | LTMLLDWRNLYPRKY |
| 237 | A0023 | Der f | 186 | 212 | DWRNLYPRKYAFALP |
| 238 | A0023 | Der f | 187 | 217 | YPRKYAFALPKDSQY |
| 239 | A0023 | Der f | 188 | 228 | KDSQYLQHFNNAIKQ |
| 240 | A0023 | Der f | 189 | 232 | LQHFNNAIKQLNTED |
| 241 | A0024 | Der f/p | 1057 | 19 | NKFTVFTSGKPVSGL |
| 242 | A0024 | Der f/p | 1058 | 129 | TGGISFAMEGPAKVE |
| 243 | A0024 | Der f/p | 1059 | 154 | ITVIYKPPTPGDYKL |
| 244 | A0024 | Der f/p | 1060 | 164 | GDYKLHLKFNDIHLP |
| 245 | A0025 | Der f | 2455 | 49 | IREYRVEAIKVMLET |
| 246 | A0025 | Der f | 2456 | 54 | VEAIKVMLETDRKLL |
| 247 | A0025 | Der f | 2457 | 64 | DRKLLTLNNSQIILN |
| 248 | A0025 | Der f | 2459 | 74 | QIILNIQYQKKKIRC |
| 249 | A0025 | Der f | 2462 | 94 | LSELLTMHLLAYKQG |

-continued

| SEQ ID NO: | Source Protein ID | Species | Peptide ID # | Start pos | Sequence |
|---|---|---|---|---|---|
| 250 | A0025 | Der p | 2480 | 148 | GPHHFNVDFSKDFHN |
| 251 | A0025 | Der f/p | 2465 | 149 | WSNSSAKKLLKNDID |
| 252 | A0025 | Der f/p | 2471 | 204 | RSTLKLFGTIKMFMK |
| 253 | A0025 | Der f/p | 2472 | 209 | LFGTIKMFMKELLDD |
| 254 | Cluster 102 | Der f | | 18 | THEINAIVPLRQQLG |
| 255 | Cluster 102 | Der f | | 21 | AIVPLRQQLGEYVDI |
| 256 | Cluster 102 | Der f | | 33 | EYVDIDLVPFGNAHI |
| 257 | Cluster 102 | Der f | | 118 | TGQKGFELIKVMARK |
| 258 | Cluster 102 | Der f | | 123 | FELIKVMARKTPRHN |
| 259 | Cluster 102 | Der f | | 138 | YVPWTTVESRTVDVN |
| 260 | Cluster 102 | Der f | | 153 | VDLVKYICDNYLNNV |

"Der f" denotes the species Dermatophagoides farinae
"Der p" denotes the species Dermatophagoides pteronyssinus
"Der f/p" denotes both species.

In each of the above sequences SEQ ID NOs: 45, 61, 63, 80, 100, 113, 147, 154, 170, 172, 191, 215, 225, 226, 248, and 260, cysteine residues (underlined and in bold typeface) may be substituted with serine, alanine or 2-aminobutyric acid; in different embodiments of SEQ ID NOs: 45 and 63, all cysteine residues may be so substituted, either exclusively with serine residues, exclusively with alanine residues, exclusively with 2-aminobutyric acid residues, or with a combination thereof.

REFERENCES

Bret, Cooper and J. Feng and W. Garrett (2010), Spectroscopy. 21 (9): 1534-1546.
Goodman R. et al, Clin Transl Allergy. 2014; 4(Suppl 2): P12
Haqqani A S et al. (2008), Methods Mol. Biol. 439: 241-56.
Henmar H et al., Clin Exp Immunol 2008; 153(3):316-23.
Ishihama Y, Oda Y, Tabata T, Sato T, Nagasu T, Rappsilber J, Mann M. Exponentially modified protein abundance index (emPAI) for estimation of absolute protein amount in proteomics by the number of sequenced peptides per protein. Mol Cell Proteomics 2005; 4:1265-72.
Trauger A. et al. (2002), Spectroscopy. 16 (1): 15-28.
Wells W et al. (2006), Journal of Proteome Research. 5 (3): 651-658.

Example 1

This example includes a description of the identification of mite proteins extractable from mite fecal particles and/or mite bodies within a short extraction time upon being treated with neutral buffered aqueous solutions. Contrary to the relative long and more violent extraction conditions usually applied in the preparation of allergen extracts applicable for allergy immunotherapy, the present extraction conditions avoided mechanical manipulation, the extraction time was kept as short as 10 minutes and the extraction media was isotonic phosphate buffer with physiological pH. Using this extraction approach, there was identified HDM proteins releasable immediately and concurrently with known allergens, only. The short extraction time and mild extraction conditions were chosen to mimic the extraction of proteins/allergens potentially taken place on the respiratory mucosal surface in subjects exposed to mites. The identification of co-eluting proteins were then conducted using LC-MS/MS and transcriptomes of the two HDM species Der f and Der p. Homologous proteins to the Der f/Der p sequence were identified using transcriptomes of four other mite/storage mite species; Blomia tropicalis (Blo t), Glycyphagus domesticus (Gly d), Lepidoglyphus destructor (Lep d) and Tyrophagus putrescentiae (Tyr p).

Preparation of Extracts:

10% (w/v) extracts were made using mite cultures of two different house dust mite species (Der p and Der f) and separately on the body fraction and the fecal fraction of the culture. In details, a sample of about 0.5 g was taken from each of the culture fractions and suspended in 5 ml of Phosphate buffer (PBS pH 7.2: 137 mM NaCl, 2.7 mM KCl, 8.2 mM $Na_2HPO_4$, 1.5 mM $KH_2PO_4$), and then gently rotated for 10 minutes at room temperature. Larger particles were removed by filtering through a PD10 PE bed-filter followed by removal of smaller particles through a 5 μm (Millex)+a 0.8 μm (Millex) filter. Filtered samples were kept on ice.

LC-MS/MS:

The four extraction samples were evaporated and 50 μg of each of the dried samples was re-suspended in 5 μl water. The samples were then denatured (6 M urea, 0.3 M $NH_4HCO_3$), reduced (9 mM DTT, 56° C. for 15 min), alkylated (17 mM Iodoacetamide), and finally trypsin-digested (5 µg trypsin at 37° C., over night). Resulting peptides were then separated and analysed by liquid chromatography tandem mass spectrometry (LC-MS/MS).

Reverse phase liquid chromatography (Ultimate 3000 RSLC nano, Thermo) was performed using C18 pre- and analytical columns at a flow rate of 300 nl/min. The applied gradient consisted of a 220 min linear increase of solvent B from 4% to 55%, where solvent A=0.05% v/v formic acid and solvent B=80% v/v acetonitrile/0.04% v/v formic acid.

Peptides eluting from the LC were sprayed directly into an ESI-QTOF mass spectrometer (MaXis, Bruker). Spectra were acquired in the mass range 50-2200 m/z at 2 Hz and MS/MS sequencing at a spectral rate of 4-16 Hz.

Data Analysis:

Data processing (compound finding and charge deconvolution) was performed using DataAnalysis 4.2 (Bruker). Proteins were identified by searching the MS/MS spectral data against a database (see section below) using MASCOT 2.2 (Matrix Science) and X! Tandem search engines at the following parameters: Enzyme=trypsin, Max missed cleavages=2, Fixed modifications=carbamidomethyl (C), Variable modifications=oxidation (M), Peptide mass tolerance=10 ppm, Fragment mass tolerance ≤0.1 Da. False discovery rate (FDR) was <2% (average of 0.54%).

Database:

The database used for protein identification was compiled based on in-house transcriptomes of the two HDM species Der f and Der p as well as in-house transcriptomes of four other mite/storage mite species; *Blomia tropicalis* (Blo t), *Glycyphagus domesticus* (Gly d), *Lepidoglyphus destructor* (Lep d) and *Tyrophagus putrescentiae* (Tyr p), prepared as follows:

RNA-sequencing of all mite species was performed by UCSD using an Illumina HiSeq 2000. Sequences were assembled into transcripts including isoforms and homologs with Trinity. All transcriptomes were translated into amino acid sequences in all six reading frames. For each of the transcriptome sequences, the longest translated continuous amino acid sequence without an occurring stop codon was included in the compiled transcriptome database for the MASCOT search. A minimum length of 60 amino acids was required. Additional translated sequences from other reading frames were included if the length of the respective sequence was longer than 80% of the previously identified longest translated continuous amino acid sequence.

In addition to these transcript-derived sequences, Swissprot and Trembl sequences from the Acari subclass were also included in the database, as well as all previously identified allergens from Der f and Der p (extracted from allergen.org and allergome.org), and proteins commonly found in proteomics experiments, adding up to a database of a total of 409,187 sequences. Application of an 80% homology filter to respective species of extract origin yielded a total of 87 conserved protein groups and 438 proteins, with each group consisting of 1, 2, or more proteins. A total of 492 sequences were included in the final analysis. These sequences were clustered at a 40% identity threshold using the epitope cluster analysis tool available at IEDB into 96 clusters. Each of the 96 sequence clusters were aligned separately using the MEGA software tool (using ClustalW). Clusters corresponding to known allergens were removed from consideration, leaving a set of remaining clusters, herein named "L" clusters.

In another set of analysis, proteins were identified by conservation analysis of each translated sequence against three arachnid proteomes (*Ixodes scapularis, Metaseiulus occidentalis, Stegodyphus mimosarum*) derived from de novo sequence assembly. Each sequence was aligned against each proteome to identify proteins and known allergens that had >70% sequence identity over at least 50% of the length of the proteome transcript. Similar analyses were performed for each of the sequences against 1,130 proteins of the aero, bacteria, contact and venom or salivary categories from the Allergen Online Database version 15 (Goodman R. et al, Clin Transl Allergy. 2014; 4(Suppl 2): P12). Identified proteins in the samples were clustered according to a sequence homology cut off of ≥67% (historically cut off distinguishing iso-allergens from two distinct allergen groups), and a representative sequence for each cluster was selected. These clusters were named "A" clusters.

The section headed "Amino Acid Sequences" supra shows representative sequences of 22 proteins found in "L" and "A" clusters (either the Der p or the Der f sequence) and of their homologous sequences detected in either Der p, Der f and Blo t (if detected). Other homologous sequences are also found in the transcriptomes of other mites (Gly d, Lep d and Tyr p), but not reported by their sequence.

Table 1 below shows for each protein ID, the percent amino acid sequence identity between Der f and Der p homologous proteins (column 4), calculated by sequence alignment between the protein first detected in the "L" and "A" clusters (species indicated in column 2) and the homologous sequences from the other house dust mite species (species indicated in column 3); the percent amino acid sequence identity between the house dust mite protein and the homologous sequences found in humans (column 5), calculated by sequence alignment between the protein first detected in the "L" and "A" clusters (species indicated in column 2) and the human homolog protein; the percent amino acid sequence identity between the house dust mite protein and the closest homologous sequences found in Blo t by mass spectrometry (column 6), calculated by sequence alignment between the protein first detected in the "L" and "A" clusters (species indicated in column 2) and the Blo t homolog protein.

TABLE 1

| Protein ID | First detected in | Homolog species | % sequence identity between f/p | % sequence identity to human homolog | % sequence identity of closest homolog of Blo t |
|---|---|---|---|---|---|
| A0001 | Der f | Der p | 87% | No significant similarity | Not identified |
| A0003 | Der f | Der p | 83% | 38% | 46% |
| A0007 | Der f | Der p | 90% | 66% | 81% |
| A0009 | Der p | Der f | 80% | 43% | 57% |
| A0010 | Der f | Der p | 73% | 40% | 54% |
| A0011 | Der f | Der p | 84% | 30% | 48% |
| A0012 | Der f | Der p | 92% | 38% | 65% |
| A0013 | Der f | Der p | 72% | 52% | 61% |

TABLE 1-continued

| Protein ID | First detected in | Homolog species | % sequence identity between f/p | % sequence identity to human homolog | % sequence identity of closest homolog of Blo t |
|---|---|---|---|---|---|
| A0014 | Der p | Der f | 80% | 45% | Not identified |
| A0015 | Der p | Der f | 56% | 28% | 32% |
| A0016 | Der f | Der p | 97% | 74% | Not identified |
| A0017 | Der f | Der p | 76% | 35% | 66% |
| A0018 | Der f | Der p | 91% | 67% | 82% |
| A0019 | Der p | Der f | 80% | <33% | 62% |
| A0020 | Der f | Der p | 83% | 30% | 44% |
| A0022 | Der p | Der f | 73% | No significant similarity | 73% |
| A0023 | Der f | Der p | 80% | 33% | Not identified |
| A0024 | Der f | Der p | 97% | 41% | 90% |
| A0025 | Der f | Der p | 48% | No significant similarity | Not identified |

Example 2

This example includes a description of the immunogenicity of the proteins selected in Example 1. Immunogenicity was tested with respect to the ability of the protein or fragments of the proteins (peptides) to
- stimulate reactivity of T cells obtained from mite allergic donors;
- activate basophilic cells obtained from mite allergic donors; and/or
- react with specific IgE and IgG antibodies of plasma from mite allergic donors.

Peptide Library:

Each sequence of an "L" cluster was aligned separately using the MEGA software tool with ClustalW. Fifteen-mer peptides overlapping by 10 amino acids were generated and the last 15-mer peptide was added when the sequence length was not divisible by 5, 14,783 unique peptides remained.

Promiscuous HLA Class II Binding Predictions and Pool Generation:

HLA class II binding predictions optimized for global coverage were performed for the seven class II alleles (HLA-DRB1*03:01, HLA-DRB1*07:01, HLA-DRB1*15:01, HLA-DRB3*01:01, HLA-DRB3*02:02, HLA-DRB4*01:01 and HLA-DRB5*01:01) using the standalone version of the IEDB class II binding prediction tool. The median consensus percentile rank was estimated from the consensus percentile ranks for the seven alleles. Further, peptides with more than ten overlapping amino acids, which appeared because several occurrences of some sequence regions were repeated multiple times in the same sequence, were eliminated (e.g. "TLSDYNIQKESTLHLVLRLRG-GMQIFVKTLTG" was repeated seven times in one sequence.) Variant peptides were also removed, retaining the better peptide based on the median consensus percentile rank and conservation among the sequences within its respective cluster. Peptides with median consensus percentile rank ≤10.0 and conserved in ≥35% of sequences in the same cluster were finally selected, also including additional selected peptides chosen to maximize DRB1 allele coverage, for a grand total of 2,589 peptides.

Peptide Synthesis:

Peptides were purchased from Mimotopes (Clayton, Victoria, Australia) or A and A (San Diego, Calif.) as crude material on a small (1-mg) scale. Individual peptides were resuspended in DMSO at a final concentration of 40 mg/mL. Peptide "megapools" of 30-65 peptides/pool were generated. Following lyophilization, each pool was reconstituted in DMSO so that each peptide was present at a concentration of 4 mg/mL. To facilitate deconvolution of positive megapools, each megapool was further broken down in 2-6 "mesopools" (259 mesopools in total), each containing 8-14 peptides. Each mesopool was then deconvoluted to identify individual positive peptides. To avoid dimerization and polymerization of peptides by intra- and intermolecular disulfide bond formation between cysteine residues, this amino acid were in some instances substituted by a serine residue in the peptides. Such peptides are herein marked with an asterisk (*).

Expression of Recombinant Proteins:

Small scale recombinant proteins (>75% purity, endotoxin level<10 EU/mg) were expressed in $E.\ coli$ and/or in insect cells as a custom service by GenScript (NJ, USA) using codon optimized DNA constructs. Selected proteins were further expressed in a human embryonic kidney (HEK293) suspension cell line (Freestyle™ 293 Expression System, Thermo Fisher, MA, USA), according to the manufacturer's instructions. Briefly: 30 µg transfection grade, codon optimized plasmids encoding the protein of interest (made as a custom service by Genscript, NJ, USA), was mixed with 60 µl 293Fectin™, and incubated for 25 min. This mixture was added to 30 ml suspension culture of HEK293 cells with a cell density of $1.10^6$ cell/ml. The culture was incubated in 125 ml disposable, polycarbonate, Erlenmeyer flasks with vent caps (Corning, N.Y.) in a 37° C. incubator having a humidified atmosphere with 8% $CO_2$ and orbital shaking at 125 rpm for 2-5 days before harvesting. Recombinant proteins secreted into the medium were harvested by sedimentation of the HEK293 cells at 100 g for 5 min. The cell supernatants were subsequently sterilized through a low protein binding Millex-GP 0.45 um filter (Millipore, MA, USA).

Study Population:

PBMCs from European HDM-allergic individuals were recruited in the Copenhagen region (defined by clinical history of allergy to house dust mite and specific IgE to group 1 and group 2 major allergens from Der p and/or Der f and with measured specific IgE (CAP) >0.7 kU/L towards Der p/f 1 or Der p/f 2. In addition, PBMCs from 10 US HDM-allergic individuals were recruited in San Diego (defined by Der p extract IgE titers greater than 0.35 kUA/L). PBMCs were isolated from whole blood by density gradient centrifugation according to manufacturers' instructions (Ficoll-Hypaque, Amersham Biosciences, Uppsala, Sweden). Der p- and Der f-specific extract IgE titers were determined using the ImmunoCAP system (Thermo Fisher, Uppsala, Sweden). In a separate series of experiments, pooled plasma from 10 European and 10 American HDM atopic individuals from the San Diego region, respectively, was utilized to run 2D immunoblots to elucidate IgE and IgG reactivity towards the proteins, which had at least one peptide with positive T cell response.

T Cell Reactivity of Protein:

T cells reactivity was determined by establishment of HDM specific T-cell lines according to standard methods. In short, PMBCs from HDM allergic donors were cultured for 2-3 weeks in the presence of house dust mite allergen extract. The responses to proteins having SEQ ID NOs 1-44 were assessed by IL-5/IFNg FluoroSPOT (Mabtech FS-0108-10) according manufacturer protocol, (after 2 weeks) or proliferation in a standard 72 h T cell proliferation assay, as described in Henmar H et al., Clin Exp Immunol 2008; 153(3):316-23. (after 3 weeks). In addition these established T cell lines were used for further characterization and epitope mapping.

T Cell Reactivity of Peptides:

HDM-specific T cells were expanded in vitro. Briefly, PBMCs from HDM-allergic individuals were stimulated with HDM extract (5 μg/mL) and expanded over 14-17 days with IL-2 (added every 3 days). Cells were harvested on day 14, restimulated with HDM extract (5 μg/mL), individual peptides (10 μg/mL) or peptide pools (5 μg/mL) and screened for IFN-A/IL-5-production by ELISPOT. Criteria for positivity were 100 or 20 spot forming cells (SFCs) per $10^6$ PBMCs for peptide pools or single peptides, respectively, p<0.05, and a stimulation index >2.

Basophil Activation:

Basophil Activation Test (BAT) was used as a predictive in vitro assay for indication of safety/immediate hypersensitivity reactions. The BAT assay is a widely used diagnostic test that is also used for evaluation of allergenicity of allergen derived components. In short: whole blood from HDM allergic donors was stimulated for 1 h with the proteins, and the increased expression of activation markers on the surface of basophils were measured by flow cytometry. The BAT test was carried out using different concentrations of the proteins and the allergens Der p 2 and Der p 1 was used as controls and tested in the same concentration rates.

Determination of IgE and IgG Reactivity:

Briefly, extracts of Der p and Der f were mixed 1:1 and 300 μg of extract proteins was run on 2D gels (3-10 pH range, 12% 138 (vol/vol) acrylamide) at Applied Biomics. The 2D-immunoblots of the labeled extracts were incubated with either (1) pooled plasma (diluted 1:20) from 10 HDM allergic donors recruited in San Diego or (2) pooled sera from 10 HDM allergic donors recruited in Europe (diluted 1:33). Blots were incubated with goat anti-human IgE and mouse anti-human IgG (Sigma-Aldrich), and HDM donor antibody reactivity visualized using Cy2-conjugated donkey anti-goat IgG and Cy5-conjugated donkey anti-mouse IgG antibodies (Biotium). In total 237 IgE and/or IgG-reactive protein spots were picked and analyzed by mass spectrometry by searching the MS spectra against a transcriptome sequence database. Using this database, the most likely protein of a given spot was identified. The antibody reactivity of each spot was then determined by visual inspection of the 2D-gel images. We took into account both the reactivities of the San Diego and European pools. If any spot in a given protein was antibody reactive with either cohort, the protein was considered reactive for that antibody. Then, the protein sequences from the proteomic analysis were aligned with the bioinformatically determined peptide clusters.

Table 2 shows the results obtained for the selection of 22 proteins (either the Der p of Der f protein were tested). Notably, a number of the proteins produced a T cell response in many of the tested donors, but none or a low fraction of donors had IgE reactivity towards the proteins.

TABLE 2

| SEQ ID NO: | Cluster ID (L) | Cluster ID (A) | Protein ID name | Species | aa length | % T cell responding donors to protein | % responding donors in BAT Assay | IgG reactivity | IgE reactivity |
|---|---|---|---|---|---|---|---|---|---|
| 13 | 96 | 55 | A0001 | Der f | 222 | 6 of 29 | 0 of 16 | | |
| 14 | 96 | 55 | A0001 | Der p | 222 | | | + | + |
| 2 | 65 | 74 | A0003 | Der f | 132 | | | | |
| 3 | 65 | 74 | A0003 | Der p | 132 | 1 of 29 | 0 of 16 | − | − |
| 34 | 46 | 21 | A0006 | Der f | 462 | | | | |
| 35 | 46 | 21 | A0006 | Der p | 462 | | | + | − |
| 30 | 61 | 30 | A0007 | Der f | 361 | | | | |
| 31 | 61 | 30 | A0007 | Der p | 362 | 6 of 27 | 0 of 8 | + | + |
| 7 | 44 | 67 | A0008 | Der f | 154 | | | | |
| 8 | 44 | 67 | A0008 | Der p | 154 | | | − | − |
| 43 | 58 | 6 | A0009 | Der f | 975 | | | | |
| 44 | 58 | 6 | A0009 | Der p | 990 | 7 of 24 | | + | + |
| 41 | 10 | 7 | A0010 | Der f | 887 | | | | |
| 42 | 10 | 7 | A0010 | Der p | 885 | | | + | − |
| 39 | 64 | 16 | A0011 | Der f | 520 | | | | |
| 40 | 64 | 16 | A0011 | Der p | 520 | 15 of 27 | 0 of 8 | − | − |
| 22 | 103 | 19 | A0012 | Der f | 509 | | | | |
| 38 | 103 | 19 | A0012 | Der p | 262 | 11 of 27 | 0 of 8 | + | − |
| 36 | 40 | 23 | A0013 | Der f | 463 | | | | |
| 37 | 40 | 23 | A0013 | Der p | 474 | 4 of 27 | 0 of 8 | − | − |
| 32 | 33 | 25 | A0014 | Der f | 429 | | | | |
| 33 | 33 | 25 | A0014 | Der p | 434 | 10 of 27 | 1 of 8* | − | − |
| 26 | 25 | 34 | A0015 | Der f | 310 | | | | |
| 27 | 25 | 34 | A0015 | Der p | 321 | 1 of 24 | | + | + |
| 28 | 43 | 39 | A0016 | Der f | 332 | | | | |
| 29 | 43 | 39 | A0016 | Der p | 332 | 2 of 27 | 1 of 8* | + | + |
| 21 | 13 | 49 | A0017 | Der f | 261 | | | | |
| 25 | 13 | 49 | A0017 | Der p | 275 | 3 of 26 | 1 of 8* | − | − |
| 5 | 97 | 71 | A0018 | Der f | 152 | | | | |
| 6 | 97 | 71 | A0018 | Der p | 152 | 0 of 27 | 1 of 8* | − | − |

TABLE 2-continued

| SEQ ID NO: | Cluster ID (L) | Cluster ID (A) | Protein ID name | Species | aa length | % T cell responding donors to protein | % responding donors in BAT Assay | IgG reactivity | IgE reactivity |
|---|---|---|---|---|---|---|---|---|---|
| 1 | 75 | 75 | A0019 | Der f | 130 | | | | |
| 4 | 75 | 75 | A0019 | Der p | 134 | 8 of 24 | | − | − |
| 15 | 31 | 59 | A0020 | Der f | 228 | | | | |
| 16 | 31 | 59 | A0020 | Der p | 228 | 3 of 24 | | + | + |
| 19 | 105 | 50 | A0022 | Der f | 252 | | | | |
| 20 | 105 | 50 | A0022 | Der p | 253 | 6 of 24 | | + | + |
| 23 | 8 | 42 | A0023 | Der f | 270 | | | | |
| 24 | 8 | 42 | A0023 | Der p | 271 | 3 of 24 | | − | − |
| 11 | 36 | 65 | A0024 | Der f | 188 | | | | |
| 12 | 36 | 65 | A0024 | Der p | 188 | 5 of 24 | | − | − |
| 17 | 104 | NA | A0025 | Der f | 233 | | | | |
| 18 | 104 | NA | A0025 | Der p | 233 | 0 of 24 | | − | − |
| 9 | 102 | 62 | NA | Der f | 171 | | | | |
| 10 | 102 | 62 | NA | Der p | 172 | | | + | − |

Table 3 shows the percentage of donors that produced a response against a peptide together with information about the source protein of the peptide (i.e. the protein with 100% sequence alignment over the peptide sequence). For example peptide with ID No: 2344 derives from protein A0001 and has 100% sequence alignment with the sequence of A0001 of Der f as well as the Der p within the stretch of consecutive amino acid residues from position 131 to 145, while peptide with ID NO: 1714 derives specifically from the Der f sequence of protein A0009 and peptide with ID NO: 1715 derives specifically from the Der p sequence of protein A0009. The peptides in the table are identical to the 15-mer peptides having SEQ ID NOs: 45-260 that are detailed in the section supra headed "Amino Acid Sequences".

TABLE 3

| SEQ ID NO | Peptide ID # | Source protein | SFC/ donor | % responder | SEQ ID NO | Peptide ID # | Source protein | SFC/ donor | % responder |
|---|---|---|---|---|---|---|---|---|---|
| 45 | 2344 | A0001 | 4 | 5% | 153 | 2421 | A0012 | 3 | 5% |
| 46 | 1800 | A0007 | 7 | 5% | 154 | 2422 | A0012 | 5 | 5% |
| 47 | 1805 | A0007 | 12 | 5% | 155 | 2423 | A0012 | 15 | 10% |
| 48 | 1804 | A0007 | 326 | 20% | 156 | 2424 | A0012 | 227 | 20% |
| 49 | 1806 | A0007 | 83 | 10% | 157 | 2425 | A0012 | 227 | 20% |
| 50 | 1360 | A0008 | 7 | 5% | 158 | 2426 | A0012 | 136 | 20% |
| 51 | 1361 | A0008 | 5 | 5% | 159 | 2428 | A0012 | 19 | 10% |
| 52 | 1362 | A0008 | 40 | 5% | 160 | 2429 | A0012 | 3 | 5% |
| 53 | 1363 | A0008 | 7 | 5% | 161 | 2430 | A0012 | 5 | 5% |
| 54 | 1364 | A0008 | 6 | 5% | 162 | 2431 | A0012 | 4 | 5% |
| 55 | 1365 | A0008 | 5 | 5% | 163 | 2432 | A0012 | 3 | 5% |
| 56 | 1366 | A0008 | 8 | 5% | 164 | 2433 | A0012 | 10 | 10% |
| 57 | 1368 | A0008 | 5 | 5% | 165 | 2434 | A0012 | 4 | 5% |
| 58 | 1710 | A0009 | 8 | 5% | 166 | 2435 | A0012 | 16 | 10% |
| 59 | 1711 | A0009 | 80 | 5% | 167 | 2436 | A0012 | 69 | 10% |
| 60 | 1712 | A0009 | 75 | 5% | 168 | 2437 | A0012 | 78 | 10% |
| 61 | 1714 | A0009 | 5 | 5% | 169 | 2441 | A0012 | 8 | 5% |
| 62 | 1715 | A0009 | 4 | 5% | 170 | 2442 | A0012 | 3 | 5% |
| 63 | 1716 | A0009 | 7 | 10% | 171 | 2443 | A0012 | 8 | 5% |
| 64 | 1718 | A0009 | 6 | 5% | 172 | 2445 | A0012 | 7 | 10% |
| 65 | 1722 | A0009 | 6 | 5% | 173 | 1096 | A0013 | 145 | 20% |
| 66 | 1742 | A0009 | 6 | 5% | 174 | 1097 | A0013 | 12 | 5% |
| 67 | 1757 | A0009 | 2 | 5% | 175 | 1099 | A0013 | 12 | 5% |
| 68 | 1758 | A0009 | 24 | 5% | 176 | 1100 | A0013 | 17 | 5% |
| 69 | 1767 | A0009 | 112 | 5% | 177 | 1101 | A0013 | 122 | 10% |
| 70 | 1776 | A0009 | 5 | 5% | 178 | 1102 | A0013 | 42 | 10% |
| 71 | 1777 | A0009 | 8 | 5% | 179 | 1113 | A0013 | 5 | 5% |
| 72 | 1778 | A0009 | 4 | 5% | 180 | 1115 | A0013 | 29 | 10% |
| 73 | 1775 | A0009 | 4 | 5% | 181 | 1116 | A0013 | 40 | 10% |
| 74 | 1779 | A0009 | 25 | 5% | 182 | 1117 | A0013 | 175 | 10% |
| 75 | 1782 | A0009 | 6 | 5% | 183 | 1118 | A0013 | 163 | 20% |
| 76 | 1783 | A0009 | 8 | 5% | 184 | 1119 | A0013 | 16 | 10% |
| 77 | 1786 | A0009 | 4 | 5% | 185 | 1006 | A0014 | 15 | 5% |
| 78 | 1785 | A0009 | 6 | 5% | 186 | 1009 | A0014 | 64 | 5% |
| 79 | 305 | A0010 | 5 | 5% | 187 | 1012 | A0014 | 25 | 10% |
| 80 | 307 | A0010 | 4 | 5% | 188 | 1013 | A0014 | 24 | 10% |
| 81 | 306 | A0010 | 8 | 5% | 189 | 1014 | A0014 | 24 | 10% |
| 82 | 309 | A0010 | 4 | 5% | 190 | 1015 | A0014 | 22 | 10% |
| 83 | 312 | A0010 | 4 | 5% | 191 | 1016 | A0014 | 93 | 20% |
| 84 | 313 | A0010 | 3 | 5% | 192 | 1017 | A0014 | 9 | 5% |
| 85 | 314 | A0010 | 222 | 20% | 193 | 1018 | A0014 | 19 | 5% |

TABLE 3-continued

| SEQ ID NO | Peptide ID # | Source protein | SFC/donor | % responder | SEQ ID NO | Peptide ID # | Source protein | SFC/donor | % responder |
|---|---|---|---|---|---|---|---|---|---|
| 86 | 315 | A0010 | 3 | 5% | 194 | 1019 | A0014 | 146 | 15% |
| 87 | 316 | A0010 | 69 | 20% | 195 | 1020 | A0014 | 31 | 10% |
| 88 | 318 | A0010 | 3 | 5% | 196 | 1021 | A0014 | 17 | 5% |
| 89 | 321 | A0010 | 9 | 5% | 197 | 1022 | A0014 | 21 | 10% |
| 90 | 324 | A0010 | 11 | 5% | 198 | 1023 | A0014 | 23 | 10% |
| 91 | 325 | A0010 | 9 | 5% | 199 | 1024 | A0014 | 11 | 5% |
| 92 | 330 | A0010 | 1 | 5% | 200 | 1025 | A0014 | 15 | 5% |
| 93 | 331 | A0010 | 11 | 10% | 201 | 1353 | A0016 | 8 | 5% |
| 94 | 334 | A0010 | 94 | 15% | 202 | 404 | A0017 | 4 | 5% |
| 95 | 335 | A0010 | 77 | 15% | 203 | 406 | A0017 | 2 | 5% |
| 96 | 337 | A0010 | 5 | 10% | 204 | 407 | A0017 | 4 | 5% |
| 97 | 340 | A0010 | 227 | 25% | 205 | 412 | A0017 | 44 | 5% |
| 98 | 341 | A0010 | 8 | 5% | 206 | 413 | A0017 | 83 | 10% |
| 99 | 342 | A0010 | 24 | 15% | 207 | 421 | A0017 | 6 | 5% |
| 100 | 343 | A0010 | 12 | 10% | 208 | 425 | A0017 | 38 | 5% |
| 101 | 344 | A0010 | 10 | 5% | 209 | 428 | A0017 | 7 | 5% |
| 102 | 346 | A0010 | 14 | 10% | 210 | 2351 | A0018 | 9 | 5% |
| 103 | 345 | A0010 | 69 | 5% | 211 | 2352 | A0018 | 10 | 5% |
| 104 | 347 | A0010 | 29 | 10% | 212 | 2353 | A0018 | 6 | 5% |
| 105 | 348 | A0010 | 9 | 5% | 213 | 2354 | A0018 | 9 | 5% |
| 106 | 350 | A0010 | 14 | 10% | 214 | 2355 | A0018 | 9 | 5% |
| 107 | 349 | A0010 | 9 | 5% | 215 | 2065 | A0019 | 203 | 30% |
| 108 | 351 | A0010 | 146 | 5% | 216 | 2066 | A0019 | 366 | 25% |
| 109 | 352 | A0010 | 88 | 25% | 217 | 2067 | A0019 | 229 | 30% |
| 110 | 353 | A0010 | 36 | 30% | 218 | 2068 | A0019 | 239 | 15% |
| 111 | 354 | A0010 | 19 | 10% | 219 | 2069 | A0019 | 78 | 5% |
| 112 | 355 | A0010 | 4 | 5% | 220 | 2070 | A0019 | 162 | 10% |
| 113 | 356 | A0010 | 40 | 15% | 221 | 968 | A0020 | 38 | 20% |
| 114 | 357 | A0010 | 35 | 15% | 222 | 969 | A0020 | 13 | 5% |
| 115 | 358 | A0010 | 15 | 20% | 223 | 970 | A0020 | 117 | 15% |
| 116 | 359 | A0010 | 30 | 15% | 224 | 971 | A0020 | 35 | 10% |
| 117 | 360 | A0010 | 20 | 20% | 225 | 978 | A0020 | 14 | 10% |
| 118 | 361 | A0010 | 37 | 20% | 226 | 979 | A0020 | 20 | 15% |
| 119 | 362 | A0010 | 158 | 10% | 227 | 2481 | A0022 | 26 | 10% |
| 120 | 363 | A0010 | 8 | 5% | 228 | 2485 | A0022 | 20 | 5% |
| 121 | 364 | A0010 | 8 | 5% | 229 | 178 | A0023 | 11 | 5% |
| 122 | 365 | A0010 | 2 | 5% | 230 | 179 | A0023 | 16 | 5% |
| 123 | 366 | A0010 | 149 | 30% | 231 | 180 | A0023 | 15 | 5% |
| 124 | 367 | A0010 | 20 | 10% | 232 | 181 | A0023 | 5 | 5% |
| 125 | 368 | A0010 | 5 | 5% | 233 | 182 | A0023 | 5 | 5% |
| 126 | 375 | A0010 | 72 | 15% | 234 | 183 | A0023 | 8 | 5% |
| 127 | 373 | A0010 | 7 | 10% | 235 | 184 | A0023 | 10 | 5% |
| 128 | 374 | A0010 | 10 | 10% | 236 | 185 | A0023 | 11 | 5% |
| 129 | 377 | A0010 | 24 | 20% | 237 | 186 | A0023 | 10 | 5% |
| 130 | 378 | A0010 | 55 | 5% | 238 | 187 | A0023 | 8 | 5% |
| 131 | 380 | A0010 | 160 | 25% | 239 | 188 | A0023 | 119 | 15% |
| 132 | 379 | A0010 | 44 | 15% | 240 | 189 | A0023 | 15 | 10% |
| 133 | 381 | A0010 | 47 | 5% | 241 | 1057 | A0024 | 16 | 5% |
| 134 | 382 | A0010 | 4 | 5% | 242 | 1058 | A0024 | 11 | 5% |
| 135 | 383 | A0010 | 3 | 5% | 243 | 1059 | A0024 | 16 | 5% |
| 136 | 384 | A0010 | 2 | 5% | 244 | 1060 | A0024 | 8 | 5% |
| 137 | 369 | A0010 | 41 | 10% | 245 | 2455 | A0025 | 10 | 5% |
| 138 | 332 | A0010 | 3 | 5% | 246 | 2456 | A0025 | 13 | 10% |
| 139 | 1859 | A0011 | 16 | 10% | 247 | 2457 | A0025 | 18 | 10% |
| 140 | 1860 | A0011 | 55 | 5% | 248 | 2459 | A0025 | 6 | 5% |
| 141 | 1861 | A0011 | 7 | 5% | 249 | 2462 | A0025 | 14 | 10% |
| 142 | 1862 | A0011 | 22 | 10% | 250 | 2480 | A0025 | 55 | 10% |
| 143 | 1863 | A0011 | 11 | 10% | 251 | 2465 | A0025 | 6 | 5% |
| 144 | 1865 | A0011 | 10 | 10% | 252 | 2471 | A0025 | 14 | 10% |
| 145 | 1866 | A0011 | 228 | 30% | 253 | 2472 | A0025 | 9 | 5% |
| 146 | 1867 | A0011 | 54 | 20% | 254 | | Cluster 102 | 88 | 10% |
| 147 | 1868 | A0011 | 28 | 20% | 255 | | Cluster 102 | 72 | 10% |
| 148 | 1870 | A0011 | 21 | 10% | 256 | | Cluster 102 | 417 | 15% |
| 149 | 1871 | A0011 | 12 | 10% | 257 | | Cluster 102 | 604 | 15% |
| 150 | 1880 | A0011 | 21 | 5% | 258 | | Cluster 102 | 316 | 15% |
| 151 | 1881 | A0011 | 9 | 5% | 259 | | Cluster 102 | 52 | 20% |
| 152 | 1882 | A0011 | 5 | 5% | 260 | | Cluster 102 | 50 | 10% |

Example 3

This example relates to the further testing of immunogenicity of the proteins identified in Example 1. Their ability to react with IgE antibodies in HDM allergic individuals, to stimulate in vitro T cell proliferation of HDM allergic individuals and non-allergics, and to stimulate ex vivo cytokine production of HDM allergic individuals and non-allergics. The following tests were used:

Basophil Activation Test (BAT) was used as a predictive in vitro assay for indication of safety/immediate hypersensitivity reactions. BAT test was carried out using blood from HDM allergic individuals (n=14), and by use of different concentrations of test proteins or the major house dust mite allergens (Der p 1, Der f 1, Der p 2 or Der f 2, e.g. a concentration of 1, 10, 100 or 1000 ng/ml.

In vitro T cell reactivity determined in T cell lines obtained from HDM allergic individuals (n=30) and non-allergics (n=8): Determined by establishment of HDM specific T-cell lines according to standard methods. In short, PMBCs from HDM allergic donors were cultured for 3 weeks in the presence of house dust mite allergen extract. The responses to proteins at a concentration of 0.5 ug/ml or 2 ug/ml of the test protein or the major house dust mite allergens (Der p 1, Der f 1, Der p 2 or Der f 2) were assessed by proliferation in a standard 72 h T cell proliferation assay, as described in Henmar H et al., *Clin Exp Immunol* 2008; 153(3):316-23. T cell reactivity was.

Ex vivo stimulation of PBMC cells obtained from mite allergic patients (n=16) and non-allergics (n=6): Determined by measuring the production of the cytokines; IFN-gamma, IL-9, IL-10, IL-17 and IL-31 following stimulation with test protein in concentration up to 10 ug/ml. Freshly isolated PBMC $5 \times 10^6$/ml were cultured with a test protein for 5 days and cell supernatant were harvested and stored at $-80°$ C. Cytokines of the supernatants were measured using ProcartaPlex Multiplex Immunoassays with MAGPIX Multiplex Reader according manufactory protocol.

TABLE 4

| Test protein | # of individuals of 14 with positive BAT test | | | | % responders of in-vitro T cell proliferation test | |
|---|---|---|---|---|---|---|
| | 1 ng/ml | 10 ng/ml | 100 ng/ml | 1000 ng/ml | Allergic | Non-allergics |
| A001 | 0 | 0 | 1 | 2 | 17 | 0 |
| A003 | 0 | 0 | 0 | 1 | 3 | 0 |
| A007 | 0 | 0 | 0 | 0 | 21 | 38 |
| A009 | 0 | 0 | 0 | 3 | 36 | 63 |
| A010 | 0 | 0 | 0 | 1 | 100* | 14 |
| A011 | 0 | 0 | 0 | 1 | 64 | 13 |
| A012 | 0 | 0 | 0 | 0 | 39 | 13 |
| A013 | 0 | 0 | 0 | 0 | 18 | 13 |
| A014 | 0 | 0 | 0 | 0 | 43 | 0 |
| A015 | 0 | 0 | 0 | 0 | 4 | 0 |
| A016 | 0 | 0 | 0 | 0 | 7 | 0 |
| A017 | 0 | 0 | 0 | 0 | 7 | 0 |
| A018 | 0 | 0 | 0 | 0 | 0 | 0 |
| A019 | 2 | 2 | 2 | 4 | 39 | 13 |
| A020 | 0 | 1 | 1 | 1 | 18 | 25 |
| A022 | 0 | 0 | 3 | 5 | 29 | 0 |
| A023 | 1 | 1 | 1 | 1 | 21 | 0 |
| A024 | 2 | 2 | 3 | 3 | 21 | 0 |
| A025 | 1 | 1 | 1 | 5 | 0 | 0 |
| A026 | 1 | 1 | 1 | 2 | 54 | 71 |
| Derf1 | 10 | 10 | 10 | 10 | 70 | 0 |
| Derf2 | 13 | 13 | 13 | 13 | 67 | 14 |
| Derp1 | 7 | 10 | 10 | 10 | 73 | 13 |
| Derp2 | 13 | 13 | 13 | 13 | 57 | 0 |

*A010 were only tested in T-cell lines from 3 allergic donors, all responsive.

Comments: Overall, the test proteins identified in Example 1, did only provide a positive BAT test in none or a very few mite allergic individuals, whereas they stimulated T cell proliferation in a larger percentage of the mite allergic individuals. In contrast, the major allergens produce both positive BAT test and stimulates T cell proliferation in a significant larger fraction of the mite allergic individuals.

TABLE 5

| Test protein | % HDM allergic individuals with cytokine production in ex-vivo T cell assay | | | | | | | % non-allergic individuals with cytokine production in ex-vivo T cell assay | | | | | | |
|---|---|---|---|---|---|---|---|---|---|---|---|---|---|---|
| | IL-5 | IL-9 | IL-13 | INF-g | IL-10 | IL-17 | IL-31 | IL-5 | IL-9 | IL-13 | INF-g | IL-10 | IL-17 | IL-31 |
| A001 | 6 | 0 | 6 | 6 | 75 | 25 | 0 | 0 | 0 | 0 | 0 | 100 | 50 | 0 |
| A003 | 6 | 0 | 13 | 0 | 19 | 13 | 0 | 0 | 0 | 0 | 0 | 17 | 17 | 0 |
| A007 | 6 | 6 | 19 | 31 | 44 | 38 | 0 | 0 | 0 | 0 | 33 | 83 | 67 | 0 |
| A009 | 0 | 0 | 6 | 19 | 94 | 19 | 0 | 0 | 0 | 0 | 50 | 100 | 33 | 0 |
| A010 | 31 | 13 | 44 | 0 | 38 | 13 | 6 | 0 | 0 | 0 | 0 | 0 | 0 | 0 |
| A011 | 25 | 6 | 19 | 0 | 13 | 6 | 6 | 0 | 0 | 0 | 17 | 0 | 0 | 0 |
| A012 | 69 | 25 | 44 | 0 | 19 | 19 | 0 | 0 | 0 | 0 | 17 | 67 | 33 | 0 |
| A013 | 50 | 25 | 38 | 0 | 38 | 6 | 0 | 0 | 0 | 0 | 0 | 0 | 0 | 0 |
| A014 | 6 | 0 | 6 | 13 | 25 | 31 | 0 | 0 | 0 | 0 | 33 | 33 | 33 | 0 |
| A015 | 6 | 0 | 6 | 25 | 75 | 44 | 6 | 0 | 0 | 0 | 33 | 67 | 50 | 0 |
| A016 | 6 | 0 | 13 | 6 | 25 | 13 | 0 | 0 | 0 | 0 | 0 | 0 | 17 | 0 |
| A017 | 0 | 0 | 0 | 6 | 25 | 13 | 0 | 0 | 0 | 0 | 0 | 33 | 17 | 0 |
| A018 | 0 | 6 | 13 | 19 | 56 | 44 | 6 | 0 | 0 | 17 | 33 | 67 | 83 | 0 |
| A019 | 38 | 56 | 56 | 50 | 75 | 100 | 13 | 0 | 0 | 0 | 100 | 100 | 100 | 17 |
| A020 | 6 | 0 | 6 | 0 | 25 | 6 | 0 | 0 | 0 | 0 | 17 | 0 | 0 | 0 |
| A022 | 31 | 6 | 13 | 0 | 6 | 0 | 0 | 0 | 0 | 0 | 17 | 0 | 0 | 0 |
| A023 | 13 | 13 | 13 | 0 | 6 | 0 | 0 | 0 | 0 | 0 | 0 | 0 | 0 | 0 |
| A024 | 13 | 6 | 6 | 0 | 25 | 6 | 0 | 0 | 0 | 0 | 0 | 17 | 0 | 0 |
| A025 | 13 | 6 | 13 | 0 | 6 | 0 | 0 | 0 | 0 | 0 | 0 | 0 | 0 | 0 |
| A026 | 44 | 25 | 44 | 0 | 38 | 0 | 0 | 0 | 0 | 0 | 0 | 50 | 17 | 0 |
| Derf1 | 75 | 19 | 56 | 0 | 50 | 6 | 0 | 0 | 0 | 0 | 0 | 33 | 17 | 0 |
| Derf2 | 63 | 50 | 69 | 6 | 81 | 13 | 6 | 0 | 0 | 0 | 17 | 33 | 67 | 0 |

TABLE 5-continued

| Test protein | % HDM allergic individuals with cytokine production in ex-vivo T cell assay | | | | | | | % non-allergic individuals with cytokine production in ex-vivo T cell assay | | | | | | |
|---|---|---|---|---|---|---|---|---|---|---|---|---|---|---|
| | IL-5 | IL-9 | IL-13 | INF-g | IL-10 | IL-17 | IL-31 | IL-5 | IL-9 | IL-13 | INF-g | IL-10 | IL-17 | IL-31 |
| Derp1 | 50 | 6 | 50 | 0 | 50 | 6 | 0 | 0 | 0 | 0 | 0 | 17 | 17 | 0 |
| Derp2 | 56 | 31 | 50 | 0 | 56 | 0 | 6 | 0 | 0 | 0 | 0 | 17 | 0 | 0 |

Example 4

This example relates to the abundance of the proteins in house dust mite extracts relatively to the abundance of known allergens of house dust mite extracts.

The abundance was determined as follows: MS/MS spectra were searched (via MASCOT search engine, Matrix Science) against an in-house allergen database that included the protein sequences of all novel proteins A0001-A0025 as well as all known HDM allergens group 1-35. The sum of the relative and semi-quantitative Exponentially Modified Protein Abundance Index (emPAI) scores (Ishihama Y et al. 2005) of all hits were set to 100%, and the relative percentage (molar %) of each protein was calculated. The abundance of the known HDM allergens is shown as one pooled result.

Table 6 shows the relative abundance of the novel proteins and known HDM allergens

TABLE 6

| Protein | Der p bodies Mild extraction (10 min) | Der p fecals Mild extraction (10 min) | Der p full extract | Der f bodies, Mild extraction (10 min) | Der f fecals Mild extraction (10 min) | Der f full extract |
|---|---|---|---|---|---|---|
| HDM allergens | 64.2 | 88.5 | 50.1 | 50.8 | 47.3 | 51.2 |
| A0001 | 5.0 | 0.5 | 4.5 | 8.0 | 11.6 | 9.2 |
| A0003 | 3.9 | <0.0 | 17.8 | 19.0 | 11.9 | 13.5 |
| A0006 | 0.6 | 0.5 | 0.7 | 1.2 | 0.6 | 0.7 |
| A0007 | 1.3 | 0.3 | 2.1 | 4.5 | 2.4 | 3.5 |
| A0008 | 2.0 | 0.8 | 4.8 | 4.2 | 3.4 | 4.7 |
| A0009 | 1.0 | 0.3 | 0.6 | 2.3 | 0.6 | 0.4 |
| A00010 | 0.8 | 0.5 | 0.6 | 2.0 | 0.3 | 1.1 |
| A00011 | <0.0 | <0.0 | 0.2 | 0.4 | <0.0 | 0.4 |
| A00012 | <0.0 | <0.0 | <0.0 | <0.0 | <0.0 | 0.2 |
| A00013 | <0.0 | <0.0 | <0.0 | 0.4 | 1.0 | <0.0 |
| A00014 | 4.0 | 0.5 | 0.7 | 0.8 | <0.0 | 0.9 |
| A00015 | 2.5 | 0.3 | 1.4 | <0.0 | <0.0 | <0.0 |
| A00016 | 0.4 | <0.0 | 2.4 | 0.6 | 4.2 | 4.8 |
| A00017 | <0.0 | <0.0 | <0.0 | <0.0 | 1.2 | 0.4 |
| A00018 | 3.7 | 0.9 | 4.1 | 4.8 | 11.3 | 2.6 |
| A00019 | 6.3 | 5.3 | 1.8 | <0.0 | <0.0 | <0.0 |
| A00020 | <0.0 | 0.5 | 1.5 | <0.0 | 1.3 | 0.9 |
| A00022 | 4.2 | 1.0 | 1.3 | <0.0 | <0.0 | <0.0 |
| A00023 | <0.0 | <0.0 | <0.0 | <0.0 | 1.1 | 0.8 |
| A00024 | <0.0 | <0.0 | 5.3 | 1.0 | 1.8 | 2.9 |
| A00025 | <0.0 | <0.0 | <0.0 | <0.0 | <0.0 | 1.9 |

The invention claimed is:

1. A method of treating allergy in a patient, where signs and/or symptoms of said allergy are elicited in the patient by exposure to house dust mites or storage mites and/or exposure to at least one protein allergen present in house dust mites or storage mites, the method comprising administering, to the patient, a therapeutically effective amount of a polypeptide consisting of
   (a) an amino acid sequence of SEQ ID NO: 41 or 42, or
   (b) an amino acid sequence consisting of at least or exactly 12 contiguous amino acid residues from the amino acid sequence of SEQ ID NO: 41 or 42.

2. The method according to claim 1, wherein exposure of the patient to the polypeptide does not elicit signs or symptoms of allergy in the patient.

3. The method according to claim 1, wherein treating the allergy comprises or consists of relieving or reducing an immune response triggered by exposure to the mites or the protein allergen.

4. The method according to claim 1, wherein the mites are house dust mites of the genus *Dermatophagoides* or of the genus *Euroglyphus* (for example *Euroglyphus maynei*), or wherein the mites are storage mites of the genus *Glycyphagus, Lepidoglyphus, Tyrophagus,* or *Blomia*.

5. An in vitro method for stimulating T cells in a sample obtained from a subject, said method comprising
   providing a blood sample obtained from the subject
   contacting T cells obtained from the blood sample with a polypeptide consisting of
   (a) an amino acid sequence of SEQ ID NOs: 41 or 42 or
   (b) an amino acid sequence consisting of at least or exactly 12 contiguous amino acid residues from the amino acid sequence of (a) and
   measuring T cells stimulated to produce cytokines selected from the group consisting of IL-4, IL-5, IL-13 and IL-10 by use of ELISPOT or FLOUROSPOT.

6. The method according to claim 1, wherein the at least or exactly 12 contiguous amino acid residues of option (b) constitute at least or exactly or at most 15 amino acid residues.

7. The method according to claim 1, wherein the consecutive amino acids of option (b) comprise a Th2 cell epitope.

8. The method according to claim 1, wherein the amino acid sequence consists of at least or exactly 12 contiguous amino acids selected from the group consisting of any one of SEQ ID NOs: 79, 80, 82, 86-89, 94, 95, 97-106, 108, 111, 113-114, 116-120, 123, 126, 129, 131, 137 and 138.

9. The method according to claim 1, wherein the amino acid sequence consists of at least or exactly 12 contiguous amino acids selected from the group consisting of any one of SEQ ID NOs: 81, 83-85, 90-93, 96, 100, 101, 107, 112, 115, 121, 122, 124, 125, 127, 128, 130 and 132-136.

10. The method according to claim 5, wherein the amino acid sequence consists of at least or exactly 12 contiguous amino acids selected from the group consisting of any one of SEQ ID NOs: 79, 80, 82, 86-89, 94, 95, 97-106, 108, 111, 113-114, 116-120, 123, 126, 129, 131, 137 and 138.

11. The method according to claim 5, wherein the amino acid sequence consists of at least or exactly 12 contiguous amino acids selected from the group consisting of any one of SEQ ID NOs: 81, 83-85, 90-93, 96, 100, 101, 107, 112, 115, 121, 122, 124, 125, 127, 128, 130 and 132-136.

* * * * *

SEQUENCE LISTING

<160> NUMBER OF SEQ ID NOS: 332

<210> SEQ ID NO 1
<211> LENGTH: 130
<212> TYPE: PRT
<213> ORGANISM: Dermatophagoides farinae

<400> SEQUENCE: 1

Asp Gly Ser His Ile Val Lys Ala Ala Arg Ser Gln Ile Gly Val Pro
1               5                   10                  15

Tyr Ser Trp Gly Gly Gly Ile His Gly Lys Ser Lys Gly Ile Gly
            20                  25                  30

Glu Gly Ala Asn Ile Val Gly Phe Asp Cys Ser Gly Leu Ala Gln Tyr
        35                  40                  45

Ser Ile Tyr Gln Gly Thr His Lys Thr Ile Ala Arg Thr Ala Ala Ala
    50                  55                  60

```
Gln Tyr Asn Asp Asn His Cys His Val Ala Tyr Gly Ser His Gln
 65                  70                  75                  80

Pro Gly Asp Leu Val Phe Phe Gly Asn Pro Ile Tyr Val Gly Ile
                 85                  90                  95

Val Ser Ala His Gly Arg Met Val Asn Ala Pro Lys Pro Gly Thr Lys
            100                 105                 110

Val Arg Glu Glu Asn Ile Trp Ser Tyr His Ile Ser His Val Ala Arg
        115                 120                 125

Cys Trp
    130

<210> SEQ ID NO 2
<211> LENGTH: 132
<212> TYPE: PRT
<213> ORGANISM: Dermatophagoides farinae

<400> SEQUENCE: 2

Met Ala Ile Asp Gly Lys Tyr Gln Met Glu Ser Ser Glu His Phe Glu
  1               5                  10                  15

Glu Phe Val Lys Glu Met Gly Leu Asp Val Asp Met Thr Asn Val Asp
                 20                  25                  30

Leu Ser Lys Thr Ser Thr Met Glu Ile Cys Lys Asp Gly Asp Val Tyr
             35                  40                  45

His Ile Lys Ser Glu Thr Ala Gly Ile Ala His Glu Ile Lys Phe Lys
         50                  55                  60

Val Gly Glu Glu Phe Glu Asp Asp Met Asn Gly His Lys Phe Lys Asn
 65                  70                  75                  80

Val Val Thr Met Glu Cys Asp Asn Lys Met Val Gln Lys Lys Thr Ser
                 85                  90                  95

Ala Asp Gly Gly Lys Val Val Asn Val Val Arg Glu Phe Thr Asp Ala
            100                 105                 110

Gly Cys Thr Val Lys Ser Thr Tyr Asn Thr Val Thr Trp Thr Arg Val
        115                 120                 125

Tyr Lys Arg Met
    130

<210> SEQ ID NO 3
<211> LENGTH: 132
<212> TYPE: PRT
<213> ORGANISM: Dermatophagoides pteronyssinus

<400> SEQUENCE: 3

Met Ala Ile Asp Gly Lys Tyr Gln Met Glu Ser Ser Glu His Phe Glu
  1               5                  10                  15

Glu Phe Val Lys Glu Met Gly Leu Asp Val Asp Met Thr Asn Val Asp
                 20                  25                  30

Leu Ser Lys Thr Ser Thr Met Glu Ile Cys Lys Asp Gly Asp Val Tyr
             35                  40                  45

His Ile Lys Ser Glu Thr Ala Gly Ile Ala His Glu Ile Lys Phe Lys
         50                  55                  60

Val Gly Glu Glu Phe Glu Asp Asp Met Asn Gly His Lys Phe Lys Asn
 65                  70                  75                  80

Val Val Thr Met Glu Cys Asp Asn Lys Met Val Gln Lys Lys Thr Ser
                 85                  90                  95

Ala Asp Gly Gly Lys Val Val Asn Val Val Arg Glu Phe Thr Asp Ala
            100                 105                 110
```

```
Gly Cys Thr Val Lys Ser Thr Tyr Asn Thr Val Thr Trp Thr Arg Val
            115                 120                 125

Tyr Lys Arg Met
    130

<210> SEQ ID NO 4
<211> LENGTH: 134
<212> TYPE: PRT
<213> ORGANISM: Dermatophagoides pteronyssinus

<400> SEQUENCE: 4

Gln Val Tyr Cys Asn Gly Ala Ala Ile Val Ser Ala Ala Arg Ser Gln
1               5                   10                  15

Ile Gly Val Pro Tyr Ser Trp Gly Gly Gly Ile His Gly Lys Ser
            20                  25                  30

Arg Gly Ile Gly Glu Gly Ala Asn Thr Val Gly Phe Asp Cys Ser Gly
            35                  40                  45

Leu Ala Gln Tyr Ser Val Tyr Gln Gly Thr His Lys Val Leu Ala Arg
        50                  55                  60

Val Ala Ser Gly Gln Tyr Ser Asp Pro Lys Cys His His Val Ala Tyr
65                  70                  75                  80

Gly Ser His Gln Pro Gly Asp Leu Val Phe Phe Gly Asn Pro Ile His
                85                  90                  95

His Val Gly Ile Val Ser Ala His Gly Arg Met Ile Asn Ala Pro His
            100                 105                 110

Thr Gly Thr Asn Val Arg Glu Glu Asn Ile Trp Ser Asp His Ile Ala
            115                 120                 125

Asn Val Ala Arg Cys Trp
        130

<210> SEQ ID NO 5
<211> LENGTH: 152
<212> TYPE: PRT
<213> ORGANISM: Dermatophagoides farinae

<400> SEQUENCE: 5

Met Val Lys Ala Val Val Leu Lys Gly Glu Pro Asn Val Thr Gly
1               5                   10                  15

Thr Ile Phe Phe Glu Gln Gln Asp Asn Gly Pro Val Lys Val Ser Gly
            20                  25                  30

Thr Val Gln Gly Leu Lys Ser Gly Leu His Gly Phe His Val His Glu
            35                  40                  45

Phe Gly Asp Asn Thr Asn Gly Cys Thr Ser Ala Gly Ala His Tyr Asn
        50                  55                  60

Pro Phe Asn Lys Thr His Gly Ala Pro Ala Asp Glu Glu Arg His Val
65                  70                  75                  80

Gly Asp Leu Gly Asn Val Glu Ala Asn Asp Ala Gly Ile Ala Asn Val
                85                  90                  95

Ala Ile Glu Asp Ser Leu Ile Ser Leu Thr Gly Glu Arg Ser Ile Val
            100                 105                 110

Gly Arg Ser Leu Val Val His Ala Asp Pro Asp Leu Gly Arg Gly
            115                 120                 125

Gly His Glu Leu Ser Lys Thr Thr Gly Asn Ala Gly Gly Arg Leu Ala
        130                 135                 140

Cys Gly Val Ile Gly Val Thr Lys
145                 150
```

<210> SEQ ID NO 6
<211> LENGTH: 152
<212> TYPE: PRT
<213> ORGANISM: Dermatophagoides pteronyssinus

<400> SEQUENCE: 6

Met Val Lys Ala Val Val Leu Lys Gly Asp Pro Asn Val Ser Gly
1               5                   10                  15

Thr Ile Phe Phe Glu Gln Gln Asp Asn Gly Pro Val Lys Val Thr Gly
            20                  25                  30

Ser Val Gln Gly Leu Lys Pro Gly Leu His Gly Phe His Val His Glu
        35                  40                  45

Phe Gly Asp Asn Thr Asn Gly Cys Thr Ser Ala Gly Ala His Tyr Asn
    50                  55                  60

Pro Leu Asn Lys Thr His Gly Ala Pro Asn Asp Glu Glu Arg His Val
65                  70                  75                  80

Gly Asp Leu Gly Asn Ile Glu Ala Asn Asp Lys Gly Val Ala Asn Val
                85                  90                  95

Val Ile Glu Asp Ser Leu Ile Ser Leu Thr Gly Glu Lys Ser Ile Val
            100                 105                 110

Gly Arg Ser Leu Val Val His Ala Asp Pro Asp Leu Gly Arg Gly
        115                 120                 125

Gly His Glu Leu Ser Lys Thr Thr Gly Asn Ala Gly Gly Arg Leu Val
    130                 135                 140

Cys Gly Val Ile Gly Val Thr Lys
145                 150

<210> SEQ ID NO 7
<211> LENGTH: 154
<212> TYPE: PRT
<213> ORGANISM: Dermatophagoides farinae

<400> SEQUENCE: 7

Met Ser Ala Asn Thr Glu Arg Thr Phe Ile Met Leu Lys Pro Asp Ala
1               5                   10                  15

Val Gln Arg Gly Ile Val Gly Glu Ile Ile Arg Arg Phe Glu Ala Lys
            20                  25                  30

Gly Phe Lys Leu Val Ala Met Lys Phe Met Met Ala Ser Glu Asp Leu
        35                  40                  45

Leu Lys Lys His Tyr Ala Asp Leu Ala Ala Arg Pro Phe Phe Pro Gly
    50                  55                  60

Leu Ile Lys Tyr Met Gln Met Gly Pro Val Val Pro Met Val Trp Glu
65                  70                  75                  80

Gly Leu Asn Ala Val Lys Thr Gly Arg Val Met Leu Gly Glu Thr Asn
                85                  90                  95

Pro Ala Glu Ser Lys Pro Gly Thr Ile Arg Gly Asp Leu Cys Ile Gln
            100                 105                 110

Thr Gly Arg Asn Ile Ile His Gly Ser Asp Ser Val Glu Thr Ala Lys
        115                 120                 125

Arg Glu Ile Asp Leu Trp Phe Arg Pro Glu Glu Leu Val Asp Tyr Lys
    130                 135                 140

Pro Ser Gln Tyr Glu Trp Val Tyr Glu Asn
145                 150

<210> SEQ ID NO 8
<211> LENGTH: 154

```
<212> TYPE: PRT
<213> ORGANISM: Dermatophagoides pteronyssinus

<400> SEQUENCE: 8

Met Ser Ala Asn Thr Glu Arg Thr Phe Ile Met Leu Lys Pro Asp Ala
1               5                   10                  15

Val Gln Arg Gly Ile Val Gly Glu Ile Ile Arg Arg Phe Glu Ala Lys
            20                  25                  30

Gly Phe Lys Leu Val Ala Met Lys Phe Met Met Ala Ser Glu Asp Leu
        35                  40                  45

Leu Lys Lys His Tyr Ala Asp Leu Ala Ala Arg Pro Phe Phe Pro Gly
    50                  55                  60

Leu Ile Lys Tyr Met Gln Met Gly Pro Val Val Pro Met Val Trp Glu
65                  70                  75                  80

Gly Leu Asn Ala Val Lys Thr Gly Arg Val Met Leu Gly Glu Thr Asn
                85                  90                  95

Pro Ala Glu Ser Lys Pro Gly Thr Ile Arg Gly Asp Leu Cys Ile Gln
            100                 105                 110

Thr Gly Arg Asn Ile Ile His Gly Ser Asp Ser Val Glu Thr Ala Lys
        115                 120                 125

Arg Glu Ile Asp Leu Trp Phe Arg Pro Glu Glu Leu Val Asn Tyr Lys
    130                 135                 140

Pro Ser Gln Tyr Glu Trp Val Tyr Glu Asn
145                 150

<210> SEQ ID NO 9
<211> LENGTH: 171
<212> TYPE: PRT
<213> ORGANISM: Dermatophagoides farinae

<400> SEQUENCE: 9

Asn Arg Val Ser Val Gly Val Tyr Tyr Glu Thr Ile Cys Ser Gly Cys
1               5                   10                  15

Arg Thr His Phe Ile Asn Ala Ile Val Pro Leu Arg Gln Gln Leu Gly
            20                  25                  30

Glu Tyr Val Asp Ile Asp Leu Val Pro Phe Gly Asn Ala His Ile Tyr
        35                  40                  45

Ser Asn Gly Pro Gln Cys Gln His Gly Ala Leu Glu Cys Tyr Gly Asn
    50                  55                  60

Ala Phe Gln Ala Cys Ser Leu Asp Met Asn Gly Phe Asp Thr Gly Phe
65                  70                  75                  80

Lys Leu Val Glu Cys Met Phe Arg Ser Ser Tyr Tyr Ser Asn Pro Gln
                85                  90                  95

Tyr Ser Ala Lys Arg Cys Ala Gln Gln Leu Asn Leu Asn Tyr Asp Gln
            100                 105                 110

Leu His Ser Cys Ala Thr Gly Gln Lys Gly Phe Glu Leu Ile Lys Val
        115                 120                 125

Met Ala Arg Lys Thr Pro Arg His Asn Tyr Val Pro Trp Thr Thr Val
    130                 135                 140

Glu Ser Arg Thr Val Asp Val Asn Val Asp Leu Val Lys Tyr Ile Cys
145                 150                 155                 160

Asp Asn Tyr Leu Asn Asn Val Pro Ala Cys Asn
                165                 170

<210> SEQ ID NO 10
<211> LENGTH: 172
```

```
<212> TYPE: PRT
<213> ORGANISM: Dermatophagoides pteronyssinus

<400> SEQUENCE: 10

Thr Gln Arg Val Thr Val Gly Val Tyr Tyr Glu Thr Ile Cys Pro Gly
1               5                   10                  15

Cys Arg Ser His Phe Ile Gln Ala Ile Val Pro Leu Lys Asn Gln Leu
            20                  25                  30

Gly Gln Tyr Val Asn Ile Asp Leu Val Pro Phe Gly Asn Ala His Phe
        35                  40                  45

Tyr Ser Asn Gly Pro Gln Cys Gln His Gly Gln Leu Glu Cys Tyr Gly
    50                  55                  60

Asn Ala Phe Gln Ala Cys Ser Leu Asp Met Asn Gly Phe Glu Thr Ala
65                  70                  75                  80

Phe Lys Leu Val Glu Cys Met Phe Arg Ser Asn Tyr Phe Ser Asn Pro
                85                  90                  95

Glu Tyr Ser Ser Lys Gln Cys Ser Gln Gln Leu Asn Leu Asp Tyr Gln
            100                 105                 110

Gln Leu Asp Ser Cys Ala Asn Gly Gln Lys Gly Leu Gln Leu Ile Arg
        115                 120                 125

Glu Met Ala Asn Lys Thr Pro Ser His Gln Tyr Val Pro Trp Thr Thr
130                 135                 140

Val Gln Gly Arg Phe Val Asp Gly Asn Val Asp Leu Val Asp Tyr Ile
145                 150                 155                 160

Cys Glu Asn Tyr Leu Asn Gly Val Pro Ala Cys Asn
                165                 170

<210> SEQ ID NO 11
<211> LENGTH: 188
<212> TYPE: PRT
<213> ORGANISM: Dermatophagoides farinae

<400> SEQUENCE: 11

Met Ser Ile Ser Ala His Gly Gly Leu Val Asn Gly Ile Ala Gly
1               5                   10                  15

Met Glu Asn Lys Phe Thr Val Phe Thr Ser Gly Lys Pro Val Ser Gly
            20                  25                  30

Leu Thr Val Ala Phe Glu Gly Pro Thr Lys Pro Glu Ile Asn Phe Asn
        35                  40                  45

Ser Thr Lys Asp Gly Ser Val Asp Val Gly Tyr Thr Pro Lys Ala Gly
    50                  55                  60

Gly Gln Tyr Lys Ile His Ile Lys Tyr Glu Gly Lys Glu Ile Val Gly
65                  70                  75                  80

Ser Pro Phe Lys Cys Asn Ile Ser Gly Asp Glu Ala Thr His Arg Lys
                85                  90                  95

Leu Thr Glu Lys Val Lys Val Gly Pro Asn Ile Asn Ala Gly Lys
            100                 105                 110

Val Asn Gln Asp Asn Gln Leu Thr Ile Asp Cys Lys Glu Ala Gly Ile
        115                 120                 125

Thr Gly Gly Ile Ser Phe Ala Met Glu Gly Pro Ala Lys Val Glu Val
130                 135                 140

Ser Phe Arg Asn Asn Asn Asp Gly Thr Ile Thr Val Ile Tyr Lys Pro
145                 150                 155                 160

Pro Thr Pro Gly Asp Tyr Lys Leu His Leu Lys Phe Asn Asp Ile His
                165                 170                 175
```

```
Leu Pro Gly Ser Pro Tyr Pro Ile Val Val Ala Ala
            180                 185

<210> SEQ ID NO 12
<211> LENGTH: 188
<212> TYPE: PRT
<213> ORGANISM: Dermatophagoides pteronyssinus

<400> SEQUENCE: 12

Met Ser Ile Ser Ala His Gly Gly Leu Val Asn Gly Ile Ala Gly
1               5                   10                  15

Met Glu Asn Lys Phe Thr Val Phe Thr Ser Gly Lys Pro Val Ser Gly
            20                  25                  30

Leu Thr Val Ala Phe Glu Gly Pro Thr Lys Pro Glu Ile Asn Phe Asn
            35                  40                  45

Ser Thr Lys Asp Gly Ser Val Asp Val Gly Tyr Ile Pro Lys Ala Gly
        50                  55                  60

Gly Gln Tyr Lys Ile His Ile Lys Tyr Glu Gly Lys Glu Ile Val Gly
65                  70                  75                  80

Ser Pro Phe Lys Cys Asn Ile Ser Gly Asp Glu Ser Thr His Arg Lys
                85                  90                  95

Leu Thr Glu Lys Val Lys Val Gly Gly Pro Asn Ile Ser Thr Gly Lys
            100                 105                 110

Val Asn Gln Asp Asn Gln Leu Thr Ile Asp Cys Lys Glu Ala Gly Ile
            115                 120                 125

Thr Gly Gly Ile Ser Phe Ala Met Glu Gly Pro Ala Lys Val Glu Val
        130                 135                 140

Ser Phe Arg Asn Asn Asn Asp Gly Thr Ile Thr Val Ile Tyr Lys Pro
145                 150                 155                 160

Pro Thr Pro Gly Asp Tyr Lys Leu His Leu Lys Phe Asn Asp Ile His
                165                 170                 175

Leu Pro Gly Ser Pro Tyr Pro Ile Val Val Ser Ala
            180                 185

<210> SEQ ID NO 13
<211> LENGTH: 222
<212> TYPE: PRT
<213> ORGANISM: Dermatophagoides farinae

<400> SEQUENCE: 13

Lys Lys Thr Lys Asp Cys Asp Val Glu Lys Pro Ile Arg Glu Cys Leu
1               5                   10                  15

Lys Asn Gly Leu Leu Arg Tyr Ser Asp Gly Gln Lys Ile Asn Gln Phe
            20                  25                  30

Pro Asp Ser Ile Glu Asp Leu Asn Arg Ala Cys Glu Glu Leu Lys Lys
            35                  40                  45

Ser Glu Thr Cys Ala Arg Asn Phe Ile Asp Thr Cys Thr Glu Thr Ser
        50                  55                  60

Tyr Glu Lys Arg Ser Leu Asp Ser Leu Leu Asp Gly Ile Gln Arg Val
65                  70                  75                  80

Leu Lys Arg Leu Cys Arg Ser Gln Ser Lys Glu Gln Leu Leu Gln
            85                  90                  95

Asn Val Gly Cys Ala Asn Ser Val Val Gln Asp Thr Lys Leu Cys Leu
            100                 105                 110

Lys Asn Tyr Arg Met Leu Val Phe Ala Ala Asn Lys Leu Asn Asp Lys
            115                 120                 125
```

```
Ser Lys Ile Met Arg Ile Leu Cys Cys Lys Ser Arg Lys Val Ala Pro
    130                 135                 140

Cys Ile Gly Glu Ala Met Lys Ser Lys Gly Asn Ala Val Cys Ser Ala
145                 150                 155                 160

Lys Asn Ile Asp Tyr Phe Arg Glu Met His Gln Asn Ile Lys Ala Glu
                165                 170                 175

Met Thr Ala Val Val Cys Ser Asp Phe Glu Arg Asp Gln Cys Glu Asn
                180                 185                 190

Val Glu Val Pro Ala Ile Thr Glu Ala Glu Tyr Lys Asp Gln Asn Ile
            195                 200                 205

Phe Asn Pro Leu Arg Asp Leu Tyr Lys Lys Val Ile Leu Ala
    210                 215                 220
```

<210> SEQ ID NO 14
<211> LENGTH: 222
<212> TYPE: PRT
<213> ORGANISM: Dermatophagoides pteronyssinus

<400> SEQUENCE: 14

```
Lys Lys Ser Pro Asp Cys Asp Ile Glu Arg Pro Ile Arg Glu Cys Leu
1               5                   10                  15

Lys Asp Gly Leu Leu Arg Tyr Ser Ser Gly Gln Lys Ile Asn Gln Phe
                20                  25                  30

Pro Asp Thr Ile Gln Asp Leu Asn Arg Ala Cys Glu Glu Leu Lys Lys
            35                  40                  45

Ser Glu Thr Cys Ala Arg Thr Phe Ile Asp Thr Cys Thr Glu Ser Ser
    50                  55                  60

Tyr Glu Lys Arg Ser Leu Asp Ser Leu Leu Asp Gly Ile Gln Arg Val
65                  70                  75                  80

Met Lys Arg Leu Cys Arg Ser Gln Thr Lys Glu Lys Leu Leu Glu
                85                  90                  95

Asn Val Gly Cys Ala Asn Ser Val Val Gln Asp Thr Lys Gln Cys Leu
            100                 105                 110

Lys Asn Tyr Arg Met Leu Val Phe Ala Ala Asn Lys Leu Asp Asn Lys
        115                 120                 125

Asn Lys Ile Met Arg Ile Leu Cys Cys Lys Ser Arg Lys Val Ala Pro
    130                 135                 140

Cys Ile Gly Glu Ala Met Lys Ala Lys Gly Thr Ala Val Cys Ser Ala
145                 150                 155                 160

Lys Asn Ile Asp Tyr Phe Lys Asp Val His Gln Asn Ile Lys Gln Glu
                165                 170                 175

Met Thr Ala Val Val Cys Ser Asp Phe Glu Arg Asp Gln Cys Glu Asn
                180                 185                 190

Val Asp Val Pro Asn Ile Ser Glu Ser Glu Tyr Lys Asp Gln Asn Ile
            195                 200                 205

Phe Asn Pro Leu Arg Asp Leu Tyr Lys Lys Val Ile Leu Gly
    210                 215                 220
```

<210> SEQ ID NO 15
<211> LENGTH: 228
<212> TYPE: PRT
<213> ORGANISM: Dermatophagoides farinae

<400> SEQUENCE: 15

```
Met Ser Lys Pro Thr Phe Tyr Phe His Pro Phe Ser Gly Pro Cys Arg
1               5                   10                  15
```

```
Thr Val Ser Thr Val Ala Lys Ile Leu Asn Val Glu Met Glu Met Lys
            20                  25                  30

Lys Leu Asp Leu Leu Thr Gln Glu His Leu Lys Pro Glu Phe Leu Lys
        35                  40                  45

Val Asn Pro Phe His Lys Ile Pro Thr Phe Val Asp Thr Asp Gly Phe
    50                  55                  60

Thr Ile Asp Glu Ser Arg Val Ile Ala Met Tyr Leu Leu Gln Ser Arg
65                  70                  75                  80

Lys Pro Asp Ser Phe Leu Tyr Pro Asn Asn Asp Leu Lys Lys Arg Thr
                85                  90                  95

Gln Ile Asp Arg Trp Leu His Tyr Asp Ile Ser Phe Ala Thr Ile Ile
                100                 105                 110

Ser Thr Pro Met Tyr Cys Lys Phe Arg Gly Lys Pro Val Gln Asp His
            115                 120                 125

Gln Val Glu Gln Gly Lys Glu Thr Leu Lys Thr Leu Asp Gly Val Met
        130                 135                 140

Ala Ser Phe Gly Gly Lys Phe Leu Thr Gly Ser Asp Gln Ile Thr Leu
145                 150                 155                 160

Ala Asp Ile Ala Met Tyr Phe Ser Cys Asn Thr Met Glu Ile Tyr Ser
                165                 170                 175

Glu Tyr Phe Lys Phe Asp Asp Tyr Pro Asn Leu Lys Ser Trp Tyr Gln
                180                 185                 190

Arg Val Ala Glu Ala Leu Lys Gln Tyr Asp Thr Glu Gly Glu Ile Pro
            195                 200                 205

Lys Ala Ile Glu Met Ile Lys Gln Phe Ala Gln Arg Met Ala Glu
    210                 215                 220

Ser Ala Lys Gln
225

<210> SEQ ID NO 16
<211> LENGTH: 228
<212> TYPE: PRT
<213> ORGANISM: Dermatophagoides pteronyssinus

<400> SEQUENCE: 16

Met Ser Lys Pro Ile Phe Tyr Tyr His Pro Phe Ser Gly Pro Cys Arg
1               5                   10                  15

Thr Val Ser Thr Val Ala Lys Ile Leu Asn Val Asp Met Glu Met Lys
            20                  25                  30

Lys Leu Asp Leu Leu Thr Lys Glu His Leu Asn Pro Glu Phe Leu Lys
        35                  40                  45

Val Asn Pro Phe His Lys Val Pro Thr Phe Val Asp Ser Asp Gly Phe
    50                  55                  60

Val Val Asp Glu Ser Arg Val Ile Ala Met Tyr Leu Val Glu Ser Arg
65                  70                  75                  80

Lys Pro Asp Ser Phe Leu Tyr Pro Lys Asn Asp Leu Lys Lys Arg Ile
                85                  90                  95

Gln Ile Asp Arg Trp Leu His Tyr Asp Ile Asn Leu Ser Thr Thr Ile
                100                 105                 110

Ser Ala Pro Met Phe Cys Val Phe Arg Gly His Gln Val Gln Asp Tyr
            115                 120                 125

Gln Val Glu Gln Gly Lys Glu Thr Leu Lys Thr Leu Asp Gly Val Met
        130                 135                 140

Gln Ser Phe Glu Gly Lys Phe Leu Thr Gly Ala Asp Gln Phe Thr Leu
145                 150                 155                 160
```

```
Ala Asp Ile Ala Met Tyr Phe Ser Leu Asn Thr Met Glu Val Tyr Pro
            165                 170                 175

Lys Tyr Phe Lys Phe Asp Asp Tyr Pro Asn Leu Lys Ser Trp Tyr His
            180                 185                 190

Arg Val Ala Glu Ala Leu Lys Gln Tyr Asp Thr Glu Gly Thr Ile Pro
            195                 200                 205

Lys Ala Ile Glu Thr Met Lys Gln Phe Ile Gln Gln Arg Ala Ala Glu
            210                 215                 220

Ala Glu Lys His
225

<210> SEQ ID NO 17
<211> LENGTH: 233
<212> TYPE: PRT
<213> ORGANISM: Dermatophagoides farinae

<400> SEQUENCE: 17

Glu Ser Leu Phe Ile Tyr Asp Asp Tyr Ser Cys Gly Ser Tyr Gly His
1               5                   10                  15

Asp Val Asn Glu Leu Ile Glu Gln Phe Gln Leu Phe Lys Lys Asn Glu
            20                  25                  30

His Asn Gln Asn Glu Ser Ile Glu Ile Ile Gly His Phe Leu Lys Lys
        35                  40                  45

Ile Arg Glu Tyr Arg Val Glu Ala Ile Lys Val Met Leu Glu Thr Asp
50                  55                  60

Arg Lys Leu Leu Thr Leu Asn Asn Ser Gln Ile Ile Leu Asn Ile Gln
65                  70                  75                  80

Tyr Gln Lys Lys Lys Ile Arg Cys Glu Asn Leu Lys His Leu Ser Glu
                85                  90                  95

Leu Leu Thr Met His Leu Leu Ala Tyr Lys Gln Gly Met Phe Asp Phe
            100                 105                 110

Ala Glu Glu Ile Asp Pro Asp Val Asn Phe Asp Arg Gln Phe Lys Asn
        115                 120                 125

Phe Leu Asp Arg Ser Ser Glu Val Met Asn Ile Asn Glu Phe Ser Asp
130                 135                 140

Ile Glu Lys Lys Trp Ser Asn Ser Ser Ala Lys Lys Leu Leu Lys Asn
145                 150                 155                 160

Asp Ile Asp Gly Leu Ile Thr Ala Leu Asp Asp Leu Arg Glu Asp Phe
                165                 170                 175

Leu Lys Asn Ile Ile Leu Pro Glu Phe Asp Ala Gln Ser Arg Tyr Asp
            180                 185                 190

Leu Tyr Phe Ser Ile Gln Asp Gln Ile Asn Ile Arg Ser Thr Leu Lys
        195                 200                 205

Leu Phe Gly Thr Ile Lys Met Phe Met Lys Glu Leu Leu Asp Asp Leu
210                 215                 220

Asn Gln Pro Asp Phe Glu Ile Leu Tyr
225                 230

<210> SEQ ID NO 18
<211> LENGTH: 229
<212> TYPE: PRT
<213> ORGANISM: Dermatophagoides pteronyssinus

<400> SEQUENCE: 18

Gln Ser Leu Phe Val Asp Tyr Asn Asp Tyr Ser Cys Gly Ser Ser Gln
1               5                   10                  15
```

Asn Glu Thr Asn Glu Leu Ile Gln Glu Phe Lys Ile Phe Lys Lys Asn
              20                  25                  30

Ile Asn Gly Asn Glu Asn Phe Lys Lys Ile Asn Asp Phe Ile Glu Lys
          35                  40                  45

Ala Arg Leu Phe Arg Asp Asn Ala Ala Lys Gln Met Leu Glu Ile Asp
 50                  55                  60

Gln Gln Leu Leu Thr Leu Asn Val Ile Gln Ile Ser Gln Arg Ile Lys
 65                  70                  75                  80

Leu Glu Asn Asn Lys Ile Gln Cys Glu Lys Leu Thr Lys Phe Ser Glu
              85                  90                  95

Leu Leu Ser Met Gln Leu Leu Ala Tyr Glu Val Gly Met Phe Glu Phe
             100                 105                 110

Ala Glu Glu Ile Asp Pro Asn Ile Asp Phe Asp Arg Lys Met Lys Asn
             115                 120                 125

Phe Leu Asp Glu Thr Ser Arg Leu Phe Asn Leu Ala Glu Phe Glu Lys
130                 135                 140

Leu Glu Lys Lys Phe Arg Asn Ala Thr Ser Ile Glu Lys Leu Lys Asn
145                 150                 155                 160

Tyr Ile Asp Gly Glu Leu Val Ala Leu Asn Asp Tyr Ile Asn Glu Phe
             165                 170                 175

Leu Lys Asp Ile Ile Met Ser Glu Phe Thr Val Gln Ser Arg Tyr Tyr
             180                 185                 190

Leu Asn Phe Ser Ile Glu Asp Gln Val Gln Ile Asp Ser Thr Leu Met
             195                 200                 205

Thr Phe Ser Ala Leu Lys Ile Leu Leu Asn Asp Leu Lys Asp Tyr Leu
210                 215                 220

Glu His Leu Asp Asn
225

<210> SEQ ID NO 19
<211> LENGTH: 252
<212> TYPE: PRT
<213> ORGANISM: Dermatophagoides farinae

<400> SEQUENCE: 19

Glu Trp Arg Leu Val Trp Gln Asp Glu Phe Asn Gly Asn Gln Leu Asp
1               5                  10                  15

Leu Asn Gln Trp Ser Tyr Glu Val Gly Gly Asn Gly Trp Gly Asn Asn
              20                  25                  30

Glu Leu Glu Phe Tyr Thr Tyr Asn Arg Thr Glu Asn Ala Arg Ile Glu
          35                  40                  45

Asn Gly Asn Leu Val Ile Asp Val Arg Val Glu Asn Tyr Arg Glu Arg
 50                  55                  60

Gln Phe Thr Ser Ala Arg Leu His Thr Arg Gln Ala Trp Thr Tyr Gly
 65                  70                  75                  80

Arg Phe Glu Ala Arg Ala Arg Met Pro Tyr Gly His Asn Leu Trp Pro
              85                  90                  95

Ala Ile Trp Met Met Pro Gln Asp Ser Ile Tyr Gly Ile Trp Ala Ala
             100                 105                 110

Ser Gly Glu Ile Asp Ile Val Glu Tyr Arg Gly Asp Asn Pro Asp Arg
             115                 120                 125

Ile Glu Gly Thr Ala His Tyr Gly Gly Thr Trp Pro Asn His Ile Tyr
130                 135                 140

Ser Gly Ser Gly Pro Arg Ser Phe Ser Val Asn Phe Ser Gln Asp Phe

```
              145                 150                 155                 160
His Thr Phe Ala Leu Glu Trp Asp His Lys Gln Leu Arg Trp Tyr Met
                165                 170                 175

Asp Asn Gln Gln Tyr Phe Thr Leu Asp Ile Asp Arg Met Leu Trp Ser
                180                 185                 190

Gly Lys Gly Val Asn Pro Tyr Thr Lys Asn Gly Gln Pro Phe Asp Gln
                195                 200                 205

Pro Phe His Trp Met Leu Asn Val Ala Val Gly Asn Phe Phe Gly
210                 215                 220

Pro Gly Pro Tyr Val Thr Pro Asp Gln Ala Arg Gln Trp Pro Lys His
225                 230                 235                 240

Thr Leu Glu Ile Asp Tyr Val Arg Val Tyr Gln Gln
                245                 250

<210> SEQ ID NO 20
<211> LENGTH: 253
<212> TYPE: PRT
<213> ORGANISM: Dermatophagoides pteronyssinus

<400> SEQUENCE: 20

Asn Trp Gln Met Val Trp Gln Asp Glu Phe Asn Gly Gly His Leu Asp
1               5                   10                  15

Gln Asn His Trp Glu Phe Glu Thr Gly Gly Gly Trp Gly Asn Asn
                20                  25                  30

Glu Leu Glu Phe Tyr Thr Ala Asn Arg Ser Gln Asn Val Arg Val Glu
            35                  40                  45

Asn Gly His Leu Val Ile Asp Val Arg Val Glu Ser Tyr Gly Gly Arg
        50                  55                  60

Asp Phe Thr Ser Gly Arg Ile His Ser Lys Gln Ala Trp Ala Tyr Gly
65                  70                  75                  80

Lys Phe Glu Ala Arg Ala Arg Leu Pro Ser Gly His His Leu Trp Pro
                85                  90                  95

Ala Ile Trp Met Phe Pro Arg Asp Ser Lys Tyr Gly Pro Trp Ala Ala
                100                 105                 110

Ser Gly Glu Ile Asp Ile Met Glu Tyr Arg Gly Asp Val His Asp Lys
            115                 120                 125

Ile Glu Gly Thr Ile His Tyr Gly Gly Gln Trp Pro Asn Asn Ile Tyr
        130                 135                 140

Thr Gly Ser Gly Pro His His Phe Asn Val Asp Phe Ser Lys Asp Phe
145                 150                 155                 160

His Asn Phe Ala Val Glu Trp Asp Thr Lys Glu Ile Arg Trp Tyr Met
                165                 170                 175

Asp Gly Asn Lys Tyr Phe Ser Val Asn Ile Asp Arg Asn Met Trp Ser
                180                 185                 190

Gly Lys Gly Asn Asn Pro Tyr Asn Lys Asn Gly Gln Pro Phe Asp Gln
                195                 200                 205

Pro Phe Arg Trp Ile Leu Asn Val Ala Val Gly Gly Asn Phe Phe Gly
            210                 215                 220

Pro Gly Pro Tyr Val Thr Pro Asp Gln Ala Arg His Trp Gln Lys His
225                 230                 235                 240

Thr Met Glu Ile Asp Tyr Val Arg Val Tyr Gln Trp Arg
                245                 250

<210> SEQ ID NO 21
<211> LENGTH: 261
```

```
<212> TYPE: PRT
<213> ORGANISM: Dermatophagoides farinae

<400> SEQUENCE: 21

Met Ser Ser Ser Gly Lys Lys Tyr Asp Phe Ser Gly Lys Val Ala
1               5                   10                  15

Leu Val Thr Gly Ser Ser Gly Ile Gly Ala Ala Ile Ala Val Gln
                20                  25                  30

Phe Ala Gln Tyr Gly Ala Lys Leu Thr Ile Thr Gly Arg Asp Gly Ala
            35                  40                  45

Ala Leu Glu Ser Val Ala Lys Lys Ile Glu Ile Glu Ser Gly His Gln
        50                  55                  60

Pro Leu Gln Ile Val Gly Asp Leu Leu Asp Gln Ser Leu Pro Ala Lys
65                  70                  75                  80

Leu Ile Asn Glu Thr Val Ser Lys Phe Gly Arg Leu Asp Phe Leu Val
                85                  90                  95

Asn Asn Ala Gly Gly Ser Thr Ala His Arg Glu Leu Asn Asp Glu Lys
            100                 105                 110

Leu Met Glu Ala Phe Asp Lys Val Phe Ala Leu Asn Val Arg Ala Val
        115                 120                 125

Leu Gln Leu Ser Gln Leu Ala Ala Ile His Leu Glu Lys Ser Lys Gly
    130                 135                 140

Asn Ile Ile Asn Ile Ser Ser Ile Val Ser Met Lys Pro Tyr Gly His
145                 150                 155                 160

Val Tyr Ser Ser Lys Ala Ala Leu Asp Met Ile Thr Lys Thr Leu
                165                 170                 175

Ala Lys Glu Leu Gly Leu Lys Gly Val Arg Val Asn Ser Ile Asn Pro
            180                 185                 190

Gly Pro Val Ala Thr Gly Phe Leu Arg Ser Val Gly Met Ser Ala Thr
        195                 200                 205

Ala Tyr Thr Asp Leu Ala Asp Thr Met Ile Asn His Thr Leu Leu Lys
    210                 215                 220

Phe Leu Ala Gln Pro Asp Glu Ile Ala Asn Leu Ala Ser Phe Leu Ala
225                 230                 235                 240

Ser Asp Asp Ala Arg Asn Met Thr Gly Ser Ile Val Val Ser Asp Thr
                245                 250                 255

Gly Ser Leu Leu Val
            260

<210> SEQ ID NO 22
<211> LENGTH: 262
<212> TYPE: PRT
<213> ORGANISM: Dermatophagoides pteronyssinus

<400> SEQUENCE: 22

Gln Ser Arg Asp Arg Asn Asn Lys Pro Tyr Arg Ile Val Cys Tyr Trp
1               5                   10                  15

Gly Thr Trp Ala Phe Tyr Arg Pro Gly Thr Gly Lys Phe Glu Ala Glu
                20                  25                  30

Asn Val Asn Pro Asn Leu Cys Thr His Leu Met Tyr Gly Phe Ala Lys
            35                  40                  45

Leu Gln Asn Asn Lys Ile Ala Leu Tyr Asp Pro Asp Leu Asp Asp Gly
        50                  55                  60

Asp Glu Asp Trp Asn Ser Gly Leu Asn Trp Gly His Gly Met Ile Arg
65                  70                  75                  80
```

```
Arg Met Val Asn Leu Arg Thr Tyr Asn Pro His Leu Thr Thr Met Ile
                85                  90                  95

Ser Ile Gly Gly Trp Asn Glu Gly Ser Asp Lys Tyr Ser Met Met Val
            100                 105                 110

Arg Asp Pro Ser Ser Arg Lys Ile Phe Ile Gln Ser Val Leu Asp Leu
            115                 120                 125

Leu Ala Glu Phe Asp Leu Asp Gly Leu Asp Phe Asp Trp Glu Tyr Pro
130                 135                 140

Ser Met Lys Ala Thr Gly Asp Asn Asp Arg Lys Pro Gly Arg Asp Glu
145                 150                 155                 160

Asp Lys Glu Asp Phe Ile Thr Leu Leu Arg Glu Leu His Glu Ala Phe
                165                 170                 175

Gln Pro His Gly Tyr Leu Leu Ser Ser Ala Val Ser Ala Gly Lys Pro
            180                 185                 190

Thr Ile Asp Arg Ala Tyr Asn Ile Pro Glu Val Ser Lys Tyr Leu Asp
            195                 200                 205

Phe Ile Asn Leu Met Ser Tyr Asp Tyr His Gly Gly Trp Glu Ser His
            210                 215                 220

Thr Gly His Asn Ala Pro Leu Asn Ser Tyr Asp Asn Ala Asn Glu Leu
225                 230                 235                 240

Asp Lys Glu Phe Thr Val Thr Tyr Ser Val Asp Tyr Trp Leu Ser His
                245                 250                 255

Gly Val Asp Ala Lys Asn
            260

<210> SEQ ID NO 23
<211> LENGTH: 270
<212> TYPE: PRT
<213> ORGANISM: Dermatophagoides farinae

<400> SEQUENCE: 23

Ser Pro Ala Gln Arg Pro Ser Leu Arg Gly Val Thr Ile Arg Asn Ala
1               5                   10                  15

Pro Phe Leu Glu Glu Ile Asp Gly Lys Phe Lys Gly Phe Ile Pro Asp
            20                  25                  30

Leu Met Asp Ala Ile Ala Glu Lys Ala Gly Phe Asp Tyr Thr Leu Tyr
            35                  40                  45

Leu Ser Pro Asp Gly Arg Tyr Gly Asn Ala Asp Lys Glu Gly Asn Val
        50                  55                  60

Thr Gly Met Ile Gly Glu Val Tyr Asn Lys Lys Ala Asp Phe Ala Ala
65                  70                  75                  80

Ala Asp Leu Thr Met Thr Glu Ala Arg Glu Asn Tyr Ile Thr Phe Thr
                85                  90                  95

Glu Pro Phe Met Ile Asn Gln Leu Ala Ala Leu Ile Arg Arg Glu Asp
            100                 105                 110

Ala Glu Gly Met Asn Thr Leu Glu Asp Leu Val Asn Ala Gly Lys Thr
            115                 120                 125

Gln Pro Asn His Lys Pro Ile Ile Leu Gly Thr Leu Arg Asn Gly Ala
130                 135                 140

Thr Asn His Phe Leu Ser Lys Ser Asp Asp Pro Leu Ala Lys Lys Met
145                 150                 155                 160

Tyr Glu Gln Ile Lys Ala Asn Asp Gln Ser Ala Thr Thr Ser Ile Ser
                165                 170                 175

Lys Gly Ile Glu Arg Val Asp Lys Gln Gly Gly Tyr Ala Phe Ile Met
            180                 185                 190
```

```
Glu Ser Ser Ser Ala Glu His Glu Ile Ala Asn Asn Cys Lys Leu Thr
            195                 200                 205

Met Leu Leu Asp Trp Arg Asn Leu Tyr Pro Arg Lys Tyr Ala Phe Ala
    210                 215                 220

Leu Pro Lys Asp Ser Gln Tyr Leu Gln His Phe Asn Asn Ala Ile Lys
225                 230                 235                 240

Gln Leu Asn Thr Glu Asp Lys Ile Ala Glu Leu Arg Arg Lys Tyr Trp
                245                 250                 255

Ser Asn Asn Cys Ser Asn Thr Gln Thr Lys Asn Thr Gly Ala
                260                 265                 270

<210> SEQ ID NO 24
<211> LENGTH: 271
<212> TYPE: PRT
<213> ORGANISM: Dermatophagoides pteronyssinus

<400> SEQUENCE: 24

Asp Pro Val Gln Gln Arg Pro Thr Leu Arg Gly Val Thr Val Arg Val
1               5                   10                  15

Gly Pro Phe Val Lys Glu Asn Asn Gly Lys Phe Glu Gly Phe Ile Pro
            20                  25                  30

Asp Leu Val Gln Ala Ile Ser Glu Lys Val Gly Phe Asp Tyr Thr Leu
        35                  40                  45

Tyr Leu Ser Pro Asp Gly Arg Tyr Gly Asn Val Ile Ser Asp Gly Asn
    50                  55                  60

Val Thr Gly Met Ile Gly Glu Val Tyr Asn Lys Lys Ala Asp Phe Ala
65                  70                  75                  80

Ala Ala Asp Leu Thr Met Thr Glu Ala Arg Glu Asn Tyr Ile Thr Phe
                85                  90                  95

Thr Glu Pro Phe Met Ile Asn Gln Leu Ala Ala Leu Ile Arg Arg Glu
            100                 105                 110

Asp Ala Glu Gly Leu Asn Thr Leu Glu Asp Leu Ala Lys Ala Gln Glu
        115                 120                 125

Thr Phe Pro Lys Arg Lys Arg Ile Val Leu Gly Thr Leu Arg Asn Gly
    130                 135                 140

Ala Thr Asn Tyr Phe Leu Ser Lys Ser Asp Asp Pro Leu Ala Lys Lys
145                 150                 155                 160

Ile Tyr Glu Gln Ile Lys Ala Asp Asp Gln Ser Val Val Lys Ser Ile
                165                 170                 175

Ser Glu Gly Val Glu Arg Val Asp Lys Gln Gly Gly Tyr Ala Phe Ile
            180                 185                 190

Met Glu Ser Ala Ser Ala Glu His Glu Ile Ala Asn Asn Cys Lys Leu
        195                 200                 205

Thr Met Leu Leu Asp Trp Arg Asn Leu Phe Pro Arg Lys Tyr Ala Phe
    210                 215                 220

Ala Leu Pro Lys Asp Ser Pro Tyr Leu Glu His Phe Asn Asn Ala Ile
225                 230                 235                 240

Lys Gln Leu Asn Ser Glu Gly Lys Ile Ala Glu Leu Arg Arg Lys Tyr
                245                 250                 255

Trp Ala Asn Asn Cys Ala Glu Asn Lys Thr Lys Asp Asp Lys Asn
            260                 265                 270

<210> SEQ ID NO 25
<211> LENGTH: 275
<212> TYPE: PRT
```

<213> ORGANISM: Dermatophagoides pteronyssinus

<400> SEQUENCE: 25

```
Met Ser Ser Ser Ser Gly Lys Lys Tyr Asp Phe Ser Gly Lys Val Ala
1               5                   10                  15
Leu Val Thr Gly Ser Ser Gly Ile Gly Ala Ala Ile Ala Leu Gln
            20                  25                  30
Phe Ala Gln Tyr Gly Ala Gln Val Thr Ile Thr Gly Arg Asp Ala Ala
        35                  40                  45
Ala Leu Glu Ser Val Ala Lys Arg Ile Glu Ala Glu Ser Gly His Gln
    50                  55                  60
Pro Leu Gln Ile Val Gly Asn Leu Leu Asp Gln Ser Leu Pro Ala Lys
65                  70                  75                  80
Leu Ile Asp Gly Thr Ile Ser Lys Tyr Gly Arg Leu Asp Phe Leu Val
                85                  90                  95
Asn Asn Ala Gly Phe Ser Thr Gln His Arg Asp Ile His Asp Glu Lys
            100                 105                 110
Leu Met Glu Ala Phe Asp Gln Val Tyr Gly Leu Asn Val Arg Ala Val
        115                 120                 125
Val Gln Leu Ser Gln Leu Ala Ala Thr His Leu Glu Lys Ser Lys Gly
    130                 135                 140
Asn Ile Ile Asn Ile Ser Ser Asn Leu Ser Met Met Pro Val His Ile
145                 150                 155                 160
Ile Tyr Ser Ser Ser Lys Ala Ala Leu Asp Met Ile Thr Lys Thr Met
                165                 170                 175
Ala Met Glu Phe Gly Lys Lys Gly Val Arg Val Asn Ser Ile Asn Pro
            180                 185                 190
Gly Pro Val Ala Thr Gln Phe Met Arg Ser Leu Gly Met Pro Val Thr
        195                 200                 205
Phe Leu Lys Glu Asn Glu Glu Phe Val Lys Glu Leu Thr Leu Leu Lys
    210                 215                 220
Phe Val Ala Gln Pro Val Glu Ile Ala Asn Leu Ala Ser Phe Leu Ala
225                 230                 235                 240
Ser Asp Asp Ala Arg Asn Met Thr Gly Ser Ile Val Val Asn Asp Thr
                245                 250                 255
Gly Ser Leu Leu Ala Pro Arg Asp Phe Lys Lys Leu Asp Glu Ile
            260                 265                 270
Lys Lys Lys
    275
```

<210> SEQ ID NO 26
<211> LENGTH: 310
<212> TYPE: PRT
<213> ORGANISM: Dermatophagoides farinae

<400> SEQUENCE: 26

```
Ser Pro Thr Ser Ile Arg Thr Phe Glu Glu Phe Lys Arg Gln Phe Asn
1               5                   10                  15
Lys Gln Tyr Gln Ser Ile Glu His Glu Glu Ile Ala Arg Lys Asn Phe
            20                  25                  30
Gln Glu Thr Leu Arg Tyr Val Gln Ala Asn Gln Asp Lys Ala Val Ile
        35                  40                  45
Asn Glu Tyr Ala Asp Leu Ser Ala Glu Glu Phe Ala Asp Gly Tyr Leu
    50                  55                  60
Met Asn Val Gln Asp Val Gln Asp Leu Glu Ala Glu Met Asp Ala His
```

```
                65                  70                  75                  80
Lys Glu Tyr Phe Asp Asp Pro Asp Cys Lys Leu His Gly Asp Phe Asn
                    85                  90                  95

Pro Pro Lys Glu Phe Asp Leu Arg Pro His Leu Thr Pro Ile Lys Lys
                100                 105                 110

Gln Ile Lys Asn Cys Gly Cys Cys Trp Ala Leu Ser Thr Ile Ser Cys
            115                 120                 125

Val Glu Thr Ala Tyr Leu Ala Gln Lys Asn Val Ser Leu Gln Leu Ser
    130                 135                 140

Thr Gln Glu Leu Val Asn Cys Ala Lys Glu His Gly Cys Lys Lys Gly
145                 150                 155                 160

Thr Val Leu Asp Gly Ile Glu Tyr Ile Met Ala Asn Gly Thr Thr Thr
                165                 170                 175

Glu Glu Ala Cys Pro Phe Ile Ser Glu Glu Ser Thr Cys Asp Gln Ser
                180                 185                 190

Lys Lys Pro Arg Tyr Glu Ile Ser Asn Trp Cys Tyr Phe Lys Pro Val
            195                 200                 205

Glu Asp Asp Ile Arg Lys Asn Leu Val Leu Arg Thr Ser Val Ser
    210                 215                 220

Val Ser Met Asn Ile Glu Asn Leu Lys Ala Phe Val His Tyr Asp Gly
225                 230                 235                 240

Ser Phe Val Ile Arg Glu Asn Ser Phe Pro Ser Ile Gly Asn Lys Ser
                245                 250                 255

Tyr His Ala Val Asn Ile Val Gly Phe Gly Thr Lys Asp Asp Ile Asp
            260                 265                 270

His Trp Ile Val Arg Asn Ser Trp Gly Glu Lys Trp Gly Asp Lys Gly
        275                 280                 285

Tyr Phe Tyr Val Glu Arg Asp Ile Asn Leu Trp Gly Ile Lys Asp Trp
    290                 295                 300

Ala Phe Thr Thr Ile Val
305                 310

<210> SEQ ID NO 27
<211> LENGTH: 321
<212> TYPE: PRT
<213> ORGANISM: Dermatophagoides pteronyssinus

<400> SEQUENCE: 27

Ser Pro Thr Gly Trp Asn Ile Arg Thr Phe Glu Gln Phe Lys Ile Gln
1               5                   10                  15

Phe Asn Lys His Tyr Asp Ser Ile Glu Gln Glu His Ala Arg Glu
                20                  25                  30

Asn Phe Leu Glu Thr Leu Lys Tyr Val Asp Ala Asn Pro Asp Lys Ala
            35                  40                  45

Val Ile Asn Glu Phe Ala Asp Leu Ser Ala Glu Glu Phe Ala Asp Gly
    50                  55                  60

Tyr Leu Met Ser Glu Glu Ser Met Gln Asp Ser Glu Gln Gln Leu Lys
65                  70                  75                  80

Leu Leu Arg Ala Gly Tyr Asp Tyr His Asp Asp Pro Glu Cys Leu Phe
                85                  90                  95

Asp Glu Asn Leu Glu Ala Pro Lys Gln Val Asp Leu Arg Pro Asp Leu
            100                 105                 110

Ser Pro Ile Met Arg Gln Thr Leu His Cys Gly Cys Cys Trp Ala Ile
        115                 120                 125
```

Ser Pro Ile Ser Ser Ala Glu Ser Ala Tyr Lys Ala Arg Tyr Asn Val
            130                 135                 140

Ser Ile Gln Leu Ser Val Gln Glu Leu Val Asn Cys Ala Val Glu His
145                 150                 155                 160

Gly Cys Glu Ile Gly Lys Thr Ala Ile Ala Phe Asn Tyr Leu Val Thr
                165                 170                 175

Asn Gly Thr Thr Thr Gln Lys Ala Tyr Pro Tyr Thr Ala Lys Glu Gly
            180                 185                 190

Ala Cys Asn Pro Pro Glu Lys Pro Arg Tyr Thr Leu Glu Asn Trp Cys
            195                 200                 205

Ala Tyr Ile Asp Pro Ser Ile Lys Asn Lys Asn Lys Pro Asp Leu Arg
210                 215                 220

Lys Val Leu Ala Gln Lys Arg Thr Ser Ile Thr Val Gln Ile Ser Ile
225                 230                 235                 240

Lys Asn Val Lys Ala Phe Ala His His Asn Gly Ser Phe Ile Ile Arg
                245                 250                 255

Glu Asn Ser Phe Pro Asp Glu Gly Lys Pro Ser Gly His Ala Ile Asn
            260                 265                 270

Ile Val Gly Tyr Gly Thr Lys Asp Gly Val Asp Tyr Trp Ile Val Arg
            275                 280                 285

Asn Ser Trp Ser Thr Gly Trp Gly Asp Lys Gly Tyr Phe Tyr Val Glu
290                 295                 300

Arg Gly Val Asn Trp Trp Gly Ile Glu Glu Tyr Ala Phe Ile Ala Thr
305                 310                 315                 320

Phe

<210> SEQ ID NO 28
<211> LENGTH: 332
<212> TYPE: PRT
<213> ORGANISM: Dermatophagoides farinae
<400> SEQUENCE: 28

Met Val Lys Ile Gly Ile Asn Gly Phe Gly Arg Ile Gly Arg Leu Val
1               5                   10                  15

Leu Arg Ala Ala Val Lys Lys Gly Val Glu Val Ala Val Asn Asp
            20                  25                  30

Pro Phe Leu Asp Val Lys Tyr Met Val Tyr Met Phe Lys Phe Asp Ser
                35                  40                  45

Thr His Gly Arg Tyr Gln Gly Glu Val Lys Glu Gly Gly Leu Leu
            50                  55                  60

Val Val Asp Gly Gln Lys Ile Gln Val Phe Gln Glu Arg Asn Pro Ala
65                  70                  75                  80

Asp Ile Pro Trp Gly Lys Val Gly Ala Asp Tyr Val Val Glu Ser Thr
                85                  90                  95

Gly Val Phe Thr Thr Ile Glu Lys Ala Lys Ala His Leu Ala Gly Gly
                100                 105                 110

Ala Lys Lys Val Val Ile Ser Ala Pro Ser Ala Asp Ala Pro Met Tyr
            115                 120                 125

Val Met Gly Val Asn His Asp Lys Tyr Asp Pro Ser Gln Gln Ile Ile
130                 135                 140

Ser Asn Ala Ser Cys Thr Thr Asn Cys Leu Ala Pro Leu Ala Lys Val
145                 150                 155                 160

Ile Asn Asp Lys Phe Gly Ile Glu Asn Gly Leu Met Thr Thr Val His
                165                 170                 175

Ala Val Thr Ala Thr Gln Lys Thr Val Asp Gly Pro Ser Gly Lys Met
            180                 185                 190

Trp Arg Asp Gly Arg Gly Ala Gly Gln Asn Ile Ile Pro Ala Ser Thr
            195                 200                 205

Gly Ala Ala Lys Ala Val Gly Lys Val Ile Pro Glu Leu Asn Gly Lys
            210                 215                 220

Leu Thr Gly Met Ala Leu Arg Val Pro Val Pro Asp Val Ser Val Val
225                 230                 235                 240

Asp Leu Thr Val Thr Leu Lys Asn Pro Ala Ser Tyr Asp Glu Ile Lys
            245                 250                 255

Ala Ala Ile Lys Ala Ala Ala Glu Ser Asp His Trp Lys Gly Ile Leu
            260                 265                 270

Glu Tyr Thr Asp Glu Glu Val Val Ser Ser Asp Phe Ile Ser Asp Thr
            275                 280                 285

His Ser Ser Ile Phe Asp Ala Lys Ala Gly Ile Ala Leu Thr Pro Thr
            290                 295                 300

Phe Val Lys Leu Ile Ala Trp Tyr Asp Asn Glu Phe Gly Tyr Ser Asn
305                 310                 315                 320

Arg Val Ile Asp Leu Ile Lys Tyr Val Ala Ser Lys
            325                 330

<210> SEQ ID NO 29
<211> LENGTH: 332
<212> TYPE: PRT
<213> ORGANISM: Dermatophagoides pteronyssinus

<400> SEQUENCE: 29

Met Val Lys Ile Gly Ile Asn Gly Phe Gly Arg Ile Gly Arg Leu Val
1               5                   10                  15

Leu Arg Ala Ala Ile Lys Lys Gly Val Glu Val Ala Ala Ile Asn Asp
            20                  25                  30

Pro Phe Leu Asp Val Lys Tyr Met Val Tyr Met Phe Lys Phe Asp Ser
            35                  40                  45

Thr His Gly Arg Tyr Gln Gly Glu Val Lys Glu Glu Gly Gly Leu Leu
        50                  55                  60

Val Val Asp Gly Gln Lys Ile Gln Val Phe Gln Glu Arg Asn Pro Ala
65                  70                  75                  80

Glu Ile Pro Trp Gly Lys Val Gly Ala Asp Tyr Val Val Glu Ser Thr
            85                  90                  95

Gly Val Phe Thr Thr Ile Glu Lys Ala Lys Ala His Leu Ala Gly Gly
            100                 105                 110

Ala Lys Lys Val Ile Ile Ser Ala Pro Ser Ala Asp Ala Pro Met Tyr
            115                 120                 125

Val Met Gly Val Asn His Asp Lys Tyr Asp Pro Lys Gln Gln Ile Ile
            130                 135                 140

Ser Asn Ala Ser Cys Thr Thr Asn Cys Leu Ala Pro Leu Ala Lys Val
145                 150                 155                 160

Ile Asn Asp Lys Phe Gly Ile Glu Asn Gly Leu Met Thr Thr Val His
            165                 170                 175

Ala Ile Thr Ala Thr Gln Lys Thr Val Asp Gly Pro Ser Gly Lys Leu
            180                 185                 190

Trp Arg Asp Gly Arg Gly Ala Gly Gln Asn Ile Ile Pro Ala Ser Thr
            195                 200                 205

Gly Ala Ala Lys Ala Val Gly Lys Val Ile Pro Glu Leu Asn Gly Lys
            210                 215                 220

```
Leu Thr Gly Met Ala Leu Arg Val Pro Val Pro Asp Val Ser Val Val
225                 230                 235                 240

Asp Leu Thr Val Thr Leu Lys Asn Pro Ala Ser Tyr Asp Glu Ile Lys
                245                 250                 255

Ala Ala Val Lys Ala Ala Glu Ser Asp His Trp Lys Gly Ile Leu
            260                 265                 270

Glu Tyr Thr Asp Glu Glu Val Val Ser Ser Asp Phe Ile Ser Asp Thr
            275                 280                 285

His Ser Ser Ile Phe Asp Ala Lys Ala Gly Ile Ala Leu Thr Pro Thr
            290                 295                 300

Phe Val Lys Leu Ile Ala Trp Tyr Asp Asn Glu Phe Gly Tyr Ser Asn
305                 310                 315                 320

Arg Val Val Asp Leu Ile Lys Tyr Val Ala Ser Lys
                325                 330
```

<210> SEQ ID NO 30
<211> LENGTH: 361
<212> TYPE: PRT
<213> ORGANISM: Dermatophagoides farinae

<400> SEQUENCE: 30

```
Met Ala Lys Phe Asn Tyr Leu Pro Val Asp Val Gln Glu Glu Leu Arg
1               5                   10                  15

Asn Thr Ala Asn Ala Ile Val Ser Val Gly Lys Gly Ile Leu Ala Ala
                20                  25                  30

Asp Glu Ser Thr Gly Thr Ile Gly Lys Arg Phe Ala Asp Ile Asn Val
            35                  40                  45

Glu Asn Val Glu Pro Asn Arg Arg Ala Tyr Arg Gln Leu Leu Phe Tyr
        50                  55                  60

Ser Glu Asn Ile Glu Gln Tyr Ile Ser Gly Val Ile Leu Phe Asp Glu
65                  70                  75                  80

Thr Val Tyr Gln Lys Asp Asp Asn Thr Pro Phe Pro Glu Leu Leu
                85                  90                  95

Lys Lys Lys Gly Ile Ile Pro Gly Ile Lys Val Asp Thr Gly Val Val
                100                 105                 110

Thr Leu Gln Gly Thr Asn Gly Glu Ser Thr Thr Gln Gly Leu Asp Asn
            115                 120                 125

Leu Thr Lys Arg Cys Gln Glu Tyr Tyr Asn His Gly Cys Arg Phe Ala
            130                 135                 140

Lys Trp Arg Cys Val Leu Lys Ile Gly Lys Asp Glu Pro Ser Ala Leu
145                 150                 155                 160

Ala Ile Leu Glu Asn Ala Asn Val Leu Ala Arg Tyr Ala Ser Cys Cys
                165                 170                 175

Gln Gln Ala Arg Ile Val Pro Ile Val Glu Pro Glu Ile Leu Pro Asp
            180                 185                 190

Gly Asp His Asp Leu Glu Arg Cys Gln Lys Val Thr Glu Thr Val Leu
            195                 200                 205

Ala Ala Val Tyr Lys Ala Leu Asn Asp His His Val Tyr Leu Glu Gly
            210                 215                 220

Ser Leu Leu Lys Pro Asn Met Val Thr Pro Gly Gln Ser Cys Pro Gln
225                 230                 235                 240

Lys Ala Ser Pro Gln Asp Ile Ala Arg Ala Thr Val Thr Ala Leu Gln
                245                 250                 255

Arg Thr Val Pro Ala Ala Val Pro Gly Val Val Phe Leu Ser Gly Gly
```

```
            260                 265                 270
Gln Ser Glu Glu Ala Ser Val Asn Leu Asn Ala Ile Asn Gln Tyr
        275                 280                 285
Gln Gly Lys Lys Pro Trp Ala Leu Ser Phe Ser Tyr Gly Arg Ala Leu
        290                 295                 300
Gln Ala Ser Ala Leu Arg Ala Trp Gln Gly Lys Pro Glu Asn Ile Ser
305                 310                 315                 320
Ala Gly Gln Lys Glu Phe Leu Gln Arg Ala Lys Ala Asn Ser Leu Ser
                325                 330                 335
Ala Gln Gly Gln Tyr Thr Gly Gly Val Val Gly Ala Ala Ala Asp Gln
                340                 345                 350
Asp Leu Phe Ile Lys Asp His Gln Tyr
                355                 360

<210> SEQ ID NO 31
<211> LENGTH: 362
<212> TYPE: PRT
<213> ORGANISM: Dermatophagoides pteronyssinus

<400> SEQUENCE: 31

Met Ala Lys Phe Asn Tyr Leu Pro Val Asp Val Gln Glu Glu Leu Arg
1               5                   10                  15
Asn Thr Ala Asn Ala Ile Val Ser Val Gly Lys Gly Ile Leu Ala Ala
                20                  25                  30
Asp Glu Ser Thr Gly Thr Ile Gly Lys Arg Phe Ala Asp Ile Asn Val
            35                  40                  45
Glu Asn Val Glu Gln Asn Arg Gln Ala Tyr Arg Gln Leu Leu Phe Tyr
        50                  55                  60
Ser Glu Gly Ile Glu Gln Tyr Ile Ser Gly Val Ile Leu Phe Asp Glu
65                  70                  75                  80
Thr Val Tyr Gln Lys Asp Asp Lys Gly Val Pro Phe Pro Glu Leu Leu
                85                  90                  95
Lys Lys Lys Gly Ile Ile Pro Gly Ile Lys Val Asp Thr Gly Val Val
                100                 105                 110
Thr Leu Gln Gly Thr Asn Gly Glu Ser Thr Thr Gln Gly Leu Asp Asn
            115                 120                 125
Leu Thr Lys Arg Cys Gln Glu Tyr Tyr Asn Gln Gly Cys Arg Phe Ala
130                 135                 140
Lys Trp Arg Cys Val Leu Lys Ile Gly Gln Asp Glu Pro Ser Ser Leu
145                 150                 155                 160
Ala Ile Val Glu Asn Ala Asn Val Leu Ala Arg Tyr Ala Ser Cys Cys
                165                 170                 175
Gln Gln Ala Arg Ile Val Pro Ile Val Glu Pro Glu Ile Leu Pro Asp
            180                 185                 190
Gly Asp His Asn Leu Glu Arg Cys Gln Lys Val Thr Glu Thr Val Leu
        195                 200                 205
Ala Ala Val Tyr Lys Ala Leu Asn Asp His His Val Tyr Leu Glu Gly
    210                 215                 220
Thr Leu Leu Lys Pro Asn Met Val Thr Pro Gly Gln Ser Cys Pro Gln
225                 230                 235                 240
Lys Ala Ser Pro Gln Glu Val Ala Gln Ala Thr Val Thr Ala Leu Gln
                245                 250                 255
Arg Thr Val Pro Ala Ala Val Pro Gly Ile Val Phe Leu Ser Gly Gly
            260                 265                 270
```

```
Gln Ser Glu Glu Ala Ser Val Asn Leu Asn Ala Ile Asn Gln Tyr
            275                 280                 285

Gln Gly Lys Lys Pro Trp Ala Leu Ser Phe Ser Tyr Gly Arg Ala Leu
        290                 295                 300

Gln Ala Ser Ala Leu Arg Ala Trp Gln Gly Lys Pro Glu Asn Ile Gly
305                 310                 315                 320

Ala Gly Gln Lys Glu Leu Leu Gln Arg Ala Lys Ala Asn Val Leu Ala
                325                 330                 335

His Lys Gly Gln Tyr Val Ala Gly Ser Ile Pro Ser Leu Ala Ser Ala
            340                 345                 350

Lys Ser Asn Phe Val Ala Gln His Lys Tyr
        355                 360
```

<210> SEQ ID NO 32
<211> LENGTH: 429
<212> TYPE: PRT
<213> ORGANISM: Dermatophagoides farinae

<400> SEQUENCE: 32

```
Ile Glu Gln Val His Ile Ser Leu Gly Thr Asn Ala Thr Glu Met Ile
1               5                   10                  15

Val Thr Trp Thr Glu Pro Gln Lys His Thr Asp Ile Asp Ile Asp Ala
                20                  25                  30

Val Val Tyr Tyr Gly Arg Ala Ser Ser Phe Asp Gln Ala Ala Ile
                35                  40                  45

Ala Lys Ser Glu His Phe Lys Asp Asp Glu Thr Lys Tyr Thr Thr Phe
        50                  55                  60

Arg Ala Leu Leu Thr Gly Leu Glu Ser Asp Thr Arg Tyr His Tyr Lys
65                  70                  75                  80

Ile Gln Leu Asp Asp Lys Glu Ser Ile Phe Ala Phe Lys Thr Leu
                85                  90                  95

Lys Leu Asp Glu Asn Trp Leu Pro Arg Phe Ala Ile Tyr Gly Asp Leu
            100                 105                 110

Gly Tyr Val Asn Glu Gln Ser Leu Pro Tyr Leu Lys Lys Asp Val Glu
        115                 120                 125

Lys Asn Met Phe Asp Val Ile Phe His Ile Gly Asp Ile Ala Tyr Asp
    130                 135                 140

Leu Gln Asp Glu Asn Gly Glu Val Gly Asn Asn Phe Met Arg Ser Ile
145                 150                 155                 160

Glu Ser Ile Ala Ser Lys Ile Pro Tyr Met Thr Cys Pro Gly Asn His
                165                 170                 175

Glu Arg His Ser Asn Phe Ser His Tyr Asp Ser Arg Phe Ser Met Ile
            180                 185                 190

Gly Asp Arg Ser Gln Pro Asn His Gln Asp Ser Leu Asp Lys Arg Ile
        195                 200                 205

Asn Asn His Phe His Ser Met Glu Ile Gly Pro Ala Thr Ile Ile Met
    210                 215                 220

Phe Ser Thr Glu Tyr Tyr Tyr Thr Tyr Tyr Gly Trp Glu Gln Ile
225                 230                 235                 240

Glu Arg Gln Tyr Arg Phe Leu Glu Lys Glu Leu Ile Arg Ala Asn Glu
                245                 250                 255

Asn Arg Asn Lys Arg Pro Trp Ile Ile Ala Met Gly His Arg Pro Leu
            260                 265                 270

Tyr Cys Leu Lys Met Gly Asp Ser Ser Cys Asp His Gln Thr Met Glu
        275                 280                 285
```

```
Arg Pro Glu Ile Arg Gln Gly Ile Arg Met His Asp Gln Gly Glu Arg
        290                 295                 300

Gln Tyr Gly Leu Glu Asp Leu Phe His Lys Tyr Gly Val Asp Ile Gln
305                 310                 315                 320

Phe Tyr Gly His Glu His Phe Tyr Ala Arg Met Phe Pro Ile Tyr Lys
                325                 330                 335

Tyr Gln Met Tyr Lys Gly Lys Gln Ser Asp Asn Pro Tyr Asp His Ala
            340                 345                 350

Asp Gly Pro Ile His Ile Thr Thr Gly Ser Ala Gly Asn Lys Glu Ile
        355                 360                 365

His Pro Leu Phe Asn His Leu Lys Glu Trp Val Ala His His Phe Tyr
370                 375                 380

Asp Tyr Gly Tyr Thr Arg Leu Ile Phe Glu Asn Gln Tyr Arg Ile Arg
385                 390                 395                 400

Leu Gln Gln Val Ser Asp Asp Gln His Gly Lys Val Leu Asp Glu Ile
                405                 410                 415

Glu Ile Ile Lys Ser Ser Pro Gln Pro His Trp Met Pro
            420                 425

<210> SEQ ID NO 33
<211> LENGTH: 434
<212> TYPE: PRT
<213> ORGANISM: Dermatophagoides pteronyssinus

<400> SEQUENCE: 33

Ile Glu Gln Val His Ile Ala Leu Gly Ser Asn Glu Thr Glu Ile Ile
1               5                   10                  15

Val Thr Trp Thr Glu Pro His Lys His Asp Asp Lys Thr Ser Asp Ala
            20                  25                  30

Val Val Tyr Tyr Gly Gln Ala Lys Ser Ser Phe Asp Gln Lys Val Lys
        35                  40                  45

Ala Ile Ser Glu Tyr Phe Lys Asp Asp Lys Thr Lys Tyr Thr Thr Tyr
50                  55                  60

Arg Ala Leu Leu Thr Gly Leu Leu Pro Gly Thr Glu Tyr His Tyr Arg
65                  70                  75                  80

Ile Gln Met Asp Asp Leu Glu Ser Ser Ile Phe Glu Phe Lys Thr Leu
                85                  90                  95

Lys Thr Gly Glu Glu Asn Trp Leu Pro Arg Phe Ala Ile Tyr Gly Asp
            100                 105                 110

Leu Gly Tyr Val Asn Glu Gln Ser Leu Pro Tyr Leu Lys Lys Asp Val
        115                 120                 125

Glu Gln Asn Leu Phe Asp Val Ile Phe His Ile Gly Asp Phe Ala Tyr
130                 135                 140

Asp Leu Asn Asp Glu His Gly Lys Val Gly His His Phe Met Arg Ser
145                 150                 155                 160

Ile Glu Pro Val Ala Ser Lys Val Ala Tyr Met Thr Cys Pro Gly Asn
                165                 170                 175

His Glu Arg His Asp Asn Phe Ser His Tyr Asp Ser Arg Phe Ser Met
            180                 185                 190

Ile Gly Asp Arg Ser Gln Pro Ile His Ser Asp Lys Leu Asn Lys Arg
        195                 200                 205

Leu Asn Asn His Phe His Ser Met Thr Ile Gly Pro Ala Thr Ile Ile
210                 215                 220

Leu Phe Ser Thr Glu Tyr Tyr Tyr Tyr Thr Lys Tyr Gly Trp Gln Gln
```

```
                    225                 230                 235                 240
Ile Glu His Gln Tyr Arg Trp Leu Glu Gln Glu Leu Lys Arg Ala Asn
                245                 250                 255
Glu Asn Arg Gln Lys His Pro Trp Ile Ile Val Met Gly His Arg Pro
                260                 265                 270
Leu Tyr Cys Leu Lys Met Gly Asp Asp Ser Cys Asp His Gln Thr Met
                275                 280                 285
Glu Arg Lys Glu Ile Arg Gln Gly Ile Arg Met His Asp Glu Gly Glu
            290                 295                 300
Arg Gln Tyr Gly Leu Glu Asp Leu Phe Phe Lys Tyr Gly Val Asp Ile
305                 310                 315                 320
Gln Phe Tyr Gly His Glu His Phe Tyr Ala Arg Leu Phe Pro Ile Tyr
                325                 330                 335
Lys Tyr Lys Met Tyr Asn Gly Thr Lys Ser Lys Asn Pro Tyr Asp His
                340                 345                 350
Pro Gly Ala Pro Ile His Ile Thr Thr Gly Ser Ala Gly Asn Lys Glu
                355                 360                 365
Leu His Pro Glu Phe Asn His Leu Asn Asp Trp Val Ala Glu His Phe
            370                 375                 380
Tyr Asp Tyr Gly Tyr Thr Arg Leu Met Phe Glu Asp Lys Tyr Arg Ile
385                 390                 395                 400
Arg Leu Gln Gln Ile Ser Asp Asp Gln His Gly Lys Val Leu Asp Glu
                405                 410                 415
Ile Glu Ile Val Lys Ser Ser Pro Gln Pro His Trp Met Asn Val Glu
                420                 425                 430
His His

<210> SEQ ID NO 34
<211> LENGTH: 462
<212> TYPE: PRT
<213> ORGANISM: Dermatophagoides farinae

<400> SEQUENCE: 34

Asp Ser Asn Ser Asp Thr Thr Phe Ile Phe Asn Gly Asp Gly Cys Glu
1               5                   10                  15
Gln Asn His Leu Phe Gln Thr Arg Tyr Arg Pro Gln Ile Gln Gln Leu
                20                  25                  30
Ala Ser Asp Val Gln Arg Ile Ile Asp His Val Met Ser Val Asn Glu
            35                  40                  45
Ser Gly Arg Thr Tyr Arg Gln Leu Ala Glu Phe Val Asp Arg Phe Gly
        50                  55                  60
Ser Arg Leu Thr Gly Thr Lys Asn Leu Glu Asp Ser Ile Asp Tyr Met
65                  70                  75                  80
Ile Asp Leu Leu Arg Gln Glu Gly His Asp Asn Val His Gly Glu Ser
                85                  90                  95
Val Gln Val Pro Arg Trp Thr Gly Asn Glu Trp Ala Arg Met Ile
                100                 105                 110
Lys Pro Arg Glu Lys Lys Leu Asn Ile Leu Gly Leu Gly Tyr Ser Glu
                115                 120                 125
Gly Thr Asn Gly Gln Thr Ile Glu Ala Pro Ile Val Val Arg Asn
            130                 135                 140
Phe Thr Glu Leu Glu Gln Lys Ser Arg Leu Ile Pro Gly Lys Ile Val
145                 150                 155                 160
Val Tyr Asn Phe His Tyr Glu Ser Tyr Gly Lys Gln Ala Ile Tyr Arg
```

His Ser Gly Ala Ser Arg Ala Ala Glu Phe Gly Ala Val Ala Ala Met
                165                 170                 175
Ile Arg Ser Leu Thr Pro Phe Ser Ile Asp Ser Pro His Thr Gly Met
    180                 185                 190
Gln Thr Tyr Asp Val Asn Val Thr Arg Ile Pro Ala Ile Ser Ile Thr
195                 200                 205
Ala Glu Asp Ala Asp Leu Phe Gln Arg Phe Ser Asp Arg Asn Glu Glu
        210                 215                 220
Val Ile Val Gln Ile Tyr Ser Glu Asn Arg Asn Glu Lys Glu Gln Gly
225                 230                 235                 240
Ile Ser Arg Asn Thr Val Ser Asp Ile Arg Gly Glu Gln Tyr Pro Asp
            245                 250                 255
Glu Ile Val Leu Val Ser Gly His Ile Asp Ser Trp Asp Val Gly Gln
                260                 265                 270
Gly Ala Leu Asp Asp Gly Ala Gly Ser Phe Ile Ser Trp Arg Ala Leu
    275                 280                 285
Ser Val Ile Lys Gln Leu Gly Leu Arg Pro Lys Arg Thr Met Arg Ser
290                 295                 300
Ile Leu Trp Thr Gly Glu Glu Phe Gly Leu Ile Gly Val Tyr Asp Tyr
305                 310                 315                 320
Val Lys Lys His Gln Asn Glu Leu Lys Asn Tyr Val Leu Ala Met Glu
            325                 330                 335
Ser Asp Ile Gly Thr Phe Thr Pro Lys Gly Ile Thr Phe Ser Gly Arg
                340                 345                 350
Asn Ser Thr Ser Gln Cys Thr Leu Trp Glu Ile Leu Gln Leu Met His
    355                 360                 365
Pro Ile Asn Ala Thr Thr Leu Thr Ile Ser Thr Glu Gly Ser Asp Val
370                 375                 380
Gln Ala Phe Tyr Glu Asn Gly Val Pro Ile Ser Ser Leu Asp Thr Ala
385                 390                 395                 400
Asn Asp Lys Tyr Phe Tyr Phe His His Thr Gln Gly Asp Thr Met Thr
            405                 410                 415
Val Glu Gln Ser Asp Asp Leu Asp Lys Cys Gln Ala Leu Trp Thr Ser
                420                 425                 430
Ile Ser Tyr Ala Leu Ala Met Leu Asp Asp Arg Leu Pro Arg
    435                 440                 445

<210> SEQ ID NO 35
<211> LENGTH: 462
<212> TYPE: PRT
<213> ORGANISM: Dermatophagoides pteronyssinus

<400> SEQUENCE: 35

Asp Ser Asn Pro Gly Glu Thr Ser Ile Phe Asn Gly Glu Gly Cys Ala
1               5                   10                  15
Asn Asp Gln Leu Phe Gln Thr Arg Ile Arg Pro Gln Ile Gln Gln Leu
                20                  25                  30
Ala Ser Asn Val Gln Arg Ile Ile Asp His Val Met Ser Ala Asn Glu
            35                  40                  45
Ser Gly Arg Thr Tyr Arg Gln Leu Ala Glu Phe Val Asp Arg Phe Gly
        50                  55                  60
Ser Arg Leu Thr Gly Thr Lys Asn Leu Glu Asp Ser Ile Asp Tyr Met
65                  70                  75                  80

```
Ile Asp Leu Leu Lys Gln Glu Gly His Asp Asn Val His Gly Glu Pro
             85                  90                  95

Val Gln Val Pro Lys Trp Thr Arg Gly Asn Glu Trp Ala Arg Met Ile
        100                 105                 110

Lys Pro Arg Asp Lys Lys Leu Asn Ile Leu Gly Leu Gly Tyr Ser Glu
        115                 120                 125

Gly Thr Asn Gly Gln Thr Ile Glu Ala Pro Ile Val Val Arg Asn
        130                 135                 140

Phe Thr Glu Leu Glu Gln Lys Ala Gly Leu Ile Pro Gly Lys Ile Val
145                 150                 155                 160

Val Tyr Asn Phe Lys Tyr Glu Ser Tyr Gly Lys Gln Ala Ile Tyr Arg
                165                 170                 175

His Ser Gly Ala Ser Arg Ala Ala Lys Phe Gly Ala Val Ala Ala Met
                180                 185                 190

Ile Arg Ser Leu Thr Pro Phe Ser Ile Asp Ser Pro His Thr Gly Met
            195                 200                 205

Gln Ser Tyr Asp Val Asn Val Thr Lys Ile Pro Ala Ile Ser Ile Thr
    210                 215                 220

Thr Glu Asp Ala Asp Leu Phe Gln Arg Phe Ser Asp Arg Asn Glu Glu
225                 230                 235                 240

Val Ile Val Gln Ile Tyr Ser Glu Asn His Asn Glu Lys Asp Lys Gly
                245                 250                 255

Ile Ser Arg Asn Thr Val Ser Asp Val Arg Gly Glu Lys Tyr Pro Asn
                260                 265                 270

Glu Ile Val Leu Val Ser Gly His Ile Asp Ser Trp Asp Val Gly Gln
            275                 280                 285

Gly Ala Ser Asp Asp Gly Ala Gly Ala Phe Ile Ser Trp Arg Ala Leu
    290                 295                 300

Ser Val Ile Lys Lys Leu Gly Leu Arg Pro Lys Arg Thr Leu Arg Ser
305                 310                 315                 320

Val Leu Trp Thr Gly Glu Glu Phe Gly Leu Ile Gly Val Tyr Asp Tyr
                325                 330                 335

Ile Lys Lys His Arg Asn Glu Leu Lys Asp Tyr Val Ile Ala Met Glu
                340                 345                 350

Ser Asp Ile Gly Thr Phe Thr Pro Arg Gly Ile Thr Tyr Ser Gly Lys
            355                 360                 365

Asn Ser Thr Ser Gln Cys Thr Leu Trp Glu Ile Leu Gln Leu Met His
    370                 375                 380

Pro Ile Asn Ala Thr Thr Leu Thr Ile Ser Thr Glu Gly Ser Asp Val
385                 390                 395                 400

Gln Ala Phe Tyr Glu Asn Gly Val Pro Ile Ser Ser Leu Asp Thr Ala
                405                 410                 415

Asn Asp Lys Tyr Phe Tyr Phe His His Thr Gln Gly Asp Thr Met Thr
                420                 425                 430

Val Glu Gln Pro Asp Asp Leu Asp Lys Cys Gln Ala Leu Trp Thr Ser
            435                 440                 445

Val Ser Tyr Ala Leu Ala Met Leu Asp Asp Arg Leu Ser Arg
    450                 455                 460

<210> SEQ ID NO 36
<211> LENGTH: 463
<212> TYPE: PRT
<213> ORGANISM: Dermatophagoides farinae

<400> SEQUENCE: 36
```

```
Asp Thr Pro Ala Asn Cys Thr Tyr Glu Asp Ile Lys Gly Leu Trp Leu
1               5                   10                  15

Phe Glu Glu Ser Thr Pro Ile Asn Asp Arg Thr Glu Lys Cys Asp Asn
            20                  25                  30

Gly Arg Arg Glu Tyr Thr Lys Lys Ile Tyr Val Arg Leu Asp Phe Pro
        35                  40                  45

Asn Thr Ala Val Asp Lys Phe Gly Asn Val Gly Thr Trp Thr Leu Ile
    50                  55                  60

Tyr Asn Gln Gly Phe Glu Val Ile Ile Asn Tyr Arg Lys Tyr Phe Ala
65                  70                  75                  80

Phe Ser Ala Tyr Glu Arg Lys Ser Asn Ser Lys Val Ile Ser Tyr Cys
                85                  90                  95

His Lys Thr Ile Pro Gly Trp Ser His Asp Leu Leu Gly Asn Asn Trp
            100                 105                 110

Ala Cys Tyr Ile Gly His Lys Val Asn Asp Trp Asn Ser Ser Pro Leu
        115                 120                 125

Gln Lys Ile Gly Ser Glu Gln Phe Pro Ile Lys Glu His Ile Glu Gln
    130                 135                 140

Pro Leu Tyr Leu Lys Asn Ile Asp Leu Ser His Ala Leu Ser Gln Asn
145                 150                 155                 160

His Val Asp Gln Ile Asn Ser Lys Gln Lys Ser Trp Lys Ala Thr Val
                165                 170                 175

Tyr Pro Glu Met Gln Ser Lys Thr Val Glu His Leu Ile Lys Met Ala
            180                 185                 190

Gly Gly Glu Lys Ser Arg Ile Met Ser Arg Pro Lys Pro Ile Arg Ala
        195                 200                 205

Thr Glu Gln Gln Arg His Glu Ala Arg Gly Leu Pro Glu Ser Phe Asp
    210                 215                 220

Trp Arg Asn Val Asp Gly Ile Asn Tyr Val Ser Pro Val Arg Asn Gln
225                 230                 235                 240

Gly Asn Cys Gly Ser Cys Tyr Ala Phe Ala Ser Met Ala Met Leu Glu
                245                 250                 255

Ala Arg Ile Arg Ile Ala Thr Asn Asn Thr Ala Lys Pro Val Phe Ser
            260                 265                 270

Pro Gln Glu Val Val Asp Cys Ser Glu Tyr Ser Gln Gly Cys Asp Gly
        275                 280                 285

Gly Phe Gly Tyr Leu Ile Ala Gly Lys Tyr Ala Gln Asp Phe Gly Val
    290                 295                 300

Val Glu Glu Ser Cys Tyr Pro Tyr Lys Ala Tyr Thr Gly Lys Cys Lys
305                 310                 315                 320

Leu Asp Tyr Asn Thr Thr Ala Lys Cys Gln Gln Arg Thr Tyr Thr Ile
                325                 330                 335

Lys Tyr Asn Tyr Leu Gly Gly Tyr Phe Gly Ala Cys Asn Glu Glu Ala
            340                 345                 350

Met Arg Ile Glu Leu Val Lys Asn Gly Pro Ile Ala Val Gly Phe Glu
        355                 360                 365

Val Tyr Lys Asp Phe Met Thr Tyr Arg Arg Gly Ile Tyr Ser His Asp
    370                 375                 380

Ser Asp Tyr Glu Thr Glu Gln Lys Val Gly Val Glu Phe Asn Pro Phe
385                 390                 395                 400

Val Leu Thr Asn His Ala Val Leu Ile Val Gly Tyr Gly Arg Asp Glu
                405                 410                 415
```

```
Lys Ser Gly Glu Asn Tyr Trp Ile Val Lys Asn Ser Trp Gly Glu Gln
                420                 425                 430

Trp Gly Ile Asp Gly Gly Tyr Phe Leu Ile Arg Arg Gly Thr Asn Glu
            435                 440                 445

Cys Gly Ile Glu Ser Ile Ala Met Ala Ala Thr Pro Ile Pro Asn
        450                 455                 460

<210> SEQ ID NO 37
<211> LENGTH: 474
<212> TYPE: PRT
<213> ORGANISM: Dermatophagoides pteronyssinus

<400> SEQUENCE: 37

Asp Thr Pro Ala Asn Cys Thr Tyr Glu Asp Ile Lys Gly Leu Trp Leu
1               5                   10                  15

Phe Glu Glu Thr Glu Pro Ile Lys Asp Arg Trp Glu Lys Cys Pro Glu
                20                  25                  30

His Gln Gln Gln Arg Glu Lys Tyr Ser Lys Lys Ile Phe Ile Arg Leu
            35                  40                  45

Asp Phe Pro Asn Val Ala Val Asp Lys Phe Gly Asn Ile Gly Glu Trp
        50                  55                  60

Thr Met Ile Tyr Asn Gln Gly Phe Glu Val Lys Ile Asn Tyr Arg Lys
65                  70                  75                  80

Tyr Phe Ala Phe Ser Ala Tyr Glu Arg Lys Ser Glu Asn Asn Val Leu
                85                  90                  95

Ser Tyr Cys His Lys Thr Gln Pro Gly Trp Ser His Asp Val Leu Gly
                100                 105                 110

Asn Asn Trp Ala Cys Tyr Val Gly His Lys Val Asn Asn Trp Asn Asp
            115                 120                 125

Asp Asp Val Ser Lys Thr Thr Val Gly Ala Glu Lys Phe Pro Val
        130                 135                 140

Lys Gln His Ser Glu Arg Glu Leu Tyr Leu Gln Asn Ile Asn Val Glu
145                 150                 155                 160

His Ile Leu Ser Gln Lys His Ile Asp His Leu Asn Ser Gln Gln Lys
                165                 170                 175

Ser Trp Lys Ala Ile Val Tyr Pro Asp Leu Gln Ser Lys Ser Ile Glu
            180                 185                 190

His Leu Ile Gln Met Ala Gly Gly Arg Lys Ser Arg Ile Ile Asn Arg
        195                 200                 205

Pro Lys Pro Leu Arg Ala Thr Glu Gln Gln Lys Gln Leu Ala Arg Ser
    210                 215                 220

Leu Pro Glu Ser Phe Asp Trp Arg Asn Leu Asn Gly Ile Asp Tyr Val
225                 230                 235                 240

Ser Pro Val Arg Asp Gln Gly Lys Cys Gly Ser Cys Tyr Thr Phe Ala
                245                 250                 255

Ser Met Ala Met Leu Glu Ser Arg Ile Arg Ile Gln Thr Asn Asn Thr
            260                 265                 270

Phe Lys Pro Ile Phe Ser Thr Gln Glu Val Val Asp Cys Ser Glu Tyr
        275                 280                 285

Ser Gln Gly Cys Asp Gly Gly Phe Ser Tyr Leu Ile Ala Gly Lys Tyr
    290                 295                 300

Ala Gln Asp Phe Gly Val Ile Asp Glu Ser Cys Tyr Pro Tyr Lys Gly
305                 310                 315                 320

Val Thr Gly Lys Cys Gln Asn Gln Gln Asn Phe Asn Gln Thr Asn Glu
                325                 330                 335
```

```
Lys Cys Lys Gln Arg Thr Tyr Thr Ile Asp Tyr Lys Tyr Val Gly Gly
                340                 345                 350

Tyr Phe Gly Ala Cys Asn Glu Glu Ala Met Gln Ile Glu Leu Val Gln
            355                 360                 365

Asn Gly Pro Ile Ala Val Gly Phe Glu Val Tyr Gly Asp Phe Phe Gly
        370                 375                 380

Tyr Ser Glu Gly Ile Tyr Ser His Gln Pro Ser Asn Glu Ser Asn Asp
385                 390                 395                 400

Gln His Gln Gln Ile Lys Ala Glu Phe Asn Pro Phe Glu Met Thr Asn
                405                 410                 415

His Ala Val Leu Ile Val Gly Tyr Gly Lys Asp Lys Lys Thr Gly Glu
            420                 425                 430

Lys Tyr Trp Ile Val Lys Asn Ser Trp Gly Lys Gln Trp Gly Met Asp
        435                 440                 445

Gly Tyr Phe Trp Met Arg Gly Thr Asp Glu Cys Ala Ile Glu Ser
    450                 455                 460

Leu Ala Met Ala Ala Thr Pro Ile Pro Asn
465                 470

<210> SEQ ID NO 38
<211> LENGTH: 509
<212> TYPE: PRT
<213> ORGANISM: Dermatophagoides farinae

<400> SEQUENCE: 38

Gln Ser Arg Asp Arg Asn Asp Lys Pro Tyr Arg Ile Val Cys Tyr Trp
1               5                   10                  15

Gly Thr Trp Ala Phe Tyr Arg Pro Ala Ser Gly Lys Phe Gln Ala Glu
            20                  25                  30

Asn Val Asn Pro Asn Leu Cys Thr His Ile Met Tyr Gly Phe Ala Lys
        35                  40                  45

Leu Gln Asn Asn Lys Ile Ala Leu Tyr Asp Pro Asp Leu Asp Asp Gly
    50                  55                  60

Asp Glu Asp Trp Asn Ser Gly Leu Gln Trp Gly His Gly Met Ile Arg
65              70                  75                  80

Arg Met Val Asn Leu Arg Thr Tyr Asn Pro His Leu Thr Thr Met Ile
                85                  90                  95

Ser Leu Gly Gly Trp Asn Glu Gly Ser Asp Lys Tyr Ser Ile Met Val
            100                 105                 110

Arg Asp Pro Ala Ser Arg Lys Ile Phe Ile Gln Ser Val Leu His Leu
        115                 120                 125

Leu Ala Glu Phe Asp Leu Asp Gly Leu Asp Phe Asp Trp Glu Tyr Pro
    130                 135                 140

Ala Met Gln Ala Ser Gly Asp Ser Asp Arg Lys Pro Gly Arg Ala Glu
145                 150                 155                 160

Asp Lys Glu Asp Phe Val Thr Leu Leu Arg Glu Leu His Glu Ala Phe
                165                 170                 175

Gln Pro His Gly Tyr Val Leu Ser Ser Ala Val Ser Ala Gly Lys Pro
            180                 185                 190

Thr Ile Asp Arg Ala Tyr Asn Ile Pro Glu Val Ser Lys Tyr Leu Asp
        195                 200                 205

Phe Ile Asn Leu Met Ser Tyr Asp Tyr His Gly Gly Trp Glu Ser His
    210                 215                 220

Thr Gly His Asn Ala Pro Leu Asn Ser Tyr Lys Asn Ala Asn Glu Leu
```

```
                225                 230                 235                 240
Asp Lys Glu Phe Thr Val Thr Tyr Ser Val Glu Tyr Trp Leu Asn His
                    245                 250                 255

Gly Val Asp Pro Lys Leu Val Leu Gly Ile Pro Leu Tyr Gly Arg
                260                 265                 270

Thr Phe Thr Leu Ala Gly Ser Glu His Gly Ile Gly Ala Pro Thr Ile
                    275                 280                 285

Gly Lys Gly Gly Glu Ser Gly Thr Ile Thr Arg Thr Ile Gly Met Leu
                290                 295                 300

Gly Tyr Asn Glu Ile Cys Thr Met Ile Lys Gln Gly Trp Gln Leu Tyr
305                 310                 315                 320

Arg Asp Glu Ile Glu Arg Ile Pro Tyr Ala Val His Ala Asn Gln Trp
                    325                 330                 335

Ile Gly Tyr Asp Asp Arg Glu Ser Val Asn Glu Lys Leu Asn Leu Leu
                    340                 345                 350

Met Ala Lys His Leu Gly Gly Ala Met Val Trp Ser Ile Asp Thr Asp
                    355                 360                 365

Asp Phe Val Gly Asn Cys Val Gly Val Lys Tyr Pro Leu Leu Arg Ser
                370                 375                 380

Ile Ser Lys Lys Leu Asn Asn Val Asp Gly Pro Asp Pro Asp Ile Lys
385                 390                 395                 400

Arg Tyr His Tyr His Thr Ser Thr Ala Lys Pro His Thr Asp Gly Thr
                    405                 410                 415

Thr Ser Thr His His Asp His Lys Thr Thr Thr Thr Lys His His Lys
                    420                 425                 430

Thr Thr Gln Pro His His Lys Thr Thr Gln Pro His His Thr Gln Thr
                    435                 440                 445

Ile Thr Thr Thr Thr Glu Arg Pro His Gly Lys Phe Gln Cys His Gln
                450                 455                 460

Ala Gly Phe Phe Ala Asp Pro Glu Asn Pro Arg Lys Phe His Gln Cys
465                 470                 475                 480

Val Asp Phe Gly Gly His Leu Lys Asp Tyr Glu Phe Met Cys Gly Glu
                    485                 490                 495

Gly Thr His Tyr Asp Glu Lys Leu His Ile Cys Val Arg
                    500                 505

<210> SEQ ID NO 39
<211> LENGTH: 520
<212> TYPE: PRT
<213> ORGANISM: Dermatophagoides farinae

<400> SEQUENCE: 39

Lys Lys Ala Pro Glu Gly Cys Phe Arg Ala Ala Val Leu Asp His Val
1               5                   10                  15

His Gln Thr Asn Val Arg Gln Leu Ser Asp Phe Ala Lys Ile Ile Glu
                20                  25                  30

Leu Asn Phe Lys Val Tyr Glu Asp Ala Ala Ala Leu Ala Lys Lys Gln
            35                  40                  45

Gly Ala Asp Ile Ile Val Phe Pro Glu Asp Gly Leu Ile Tyr Asn Ile
        50                  55                  60

Ala Ser Arg Glu Lys Ala Asp Glu Phe Ala Ser Asp Ile Pro Asp Gly
65                  70                  75                  80

Glu Thr Asn Ala Cys Thr Leu Glu Thr Lys Ser Val Tyr Asn Arg Leu
                85                  90                  95
```

```
Ala Cys Leu Ala Gln Lys His Glu Ile Phe Val Val Ala Asp Leu Ile
            100                 105                 110

Asp Arg Lys Ser Cys Glu Glu Leu Gly Ile Ser Asn Thr Ser Asp Ser
            115                 120                 125

Cys Pro Ala Asp Lys Lys Phe Leu Phe Asn Thr Ala Val Leu Phe Asp
        130                 135                 140

Arg Gln Gly Lys Leu Leu Gly Arg Tyr His Lys Met His Leu Phe Gly
145                 150                 155                 160

Glu Met Thr Met Asn Ile Pro Pro Lys Pro Glu Leu Leu Val Ile Asp
                    165                 170                 175

Thr Glu Leu Gly Arg Leu Gly Met Gln Ile Cys Phe Asp Met Ile Phe
            180                 185                 190

Lys Thr Pro Gly His Phe Leu Ala Glu Gln Asn Lys Phe Asp Thr Met
            195                 200                 205

Leu Phe Pro Thr Trp Trp Phe Asp Glu Ala Pro Met Leu Ser Ser Ser
        210                 215                 220

Gln Tyr Gln Met Ala Trp Ala Phe Gly Asn Asn Val Thr Leu Leu Ala
225                 230                 235                 240

Ser Asn Ile His Arg Val Glu Leu Gly Ser Arg Gly Ser Gly Ile Tyr
                    245                 250                 255

Val Gly Pro His Gln Thr Leu Ala Thr Ala Leu Tyr Asp Asp Ser Val
            260                 265                 270

Glu Arg Leu Val Leu Ala Asn Val Pro Ile Lys Pro Arg Glu Thr Asp
            275                 280                 285

Lys Ser Val Cys Pro Leu Asp Ser Glu Ile Ile Glu Val Pro Gln Gln
        290                 295                 300

Ile Pro Ile Pro Asn Ser Val Lys Tyr His His Leu Asn Met Asn Leu
305                 310                 315                 320

Leu Asp Val Thr Leu Val Glu Leu Ser Ser Lys Asp Ser Glu Phe His
                    325                 330                 335

Ile Cys Tyr Lys Gly Val Cys Cys Gln Ile Glu Tyr Arg Leu Ala Val
            340                 345                 350

Lys Asp Gln Pro Arg Glu Ser Trp Val Asp Arg Val Pro Leu Leu Ala
            355                 360                 365

Asn Met Leu Glu Tyr Phe Thr Pro Glu Glu Arg Tyr Tyr Leu Met Val
        370                 375                 380

Ala Asn Arg Thr Arg Pro Gly Thr Tyr Arg Trp Thr Glu Glu Ile Cys
385                 390                 395                 400

Ala Val Val Val Cys Pro Ser Ser Arg Trp Asn Ile Gly Lys Val Glu
                    405                 410                 415

Lys Asp Cys Ser Gln Phe Gly Ser Asn Gln Glu Leu Asn Ser Arg Phe
            420                 425                 430

Val Tyr Ala Lys Leu Arg Gly Ala Phe Ser Glu Ser Thr Ala Val Tyr
            435                 440                 445

Pro Ser Ala Val Gly Pro Lys Asn Gln Leu Ile Asn Pro Glu Asn Lys
        450                 455                 460

Trp Lys Tyr Trp Lys Val Asn Val Pro Asp Lys Pro Glu His Phe Val
465                 470                 475                 480

Glu Leu Gly Ala Lys Asp Asn Pro Glu Ser Lys Ala Ile Glu Leu Ser
                    485                 490                 495

Thr Leu Ala Leu Tyr Gly Arg Asn Tyr Asp Leu Asp Pro Thr Tyr Lys
            500                 505                 510

Gln Lys Pro Val Pro Ile Asn Leu
```

<210> SEQ ID NO 40
<211> LENGTH: 519
<212> TYPE: PRT
<213> ORGANISM: Dermatophagoides pteronyssinus

<400> SEQUENCE: 40

```
Lys Ser Ala Pro Glu Gly Cys Phe Arg Ala Ala Val Leu Asp His Val
1               5                   10                  15

His Gln Thr Asp Ala Arg His Leu Ser Asn Thr Ala Lys Ile Ile Asp
            20                  25                  30

Leu Asn Phe Lys Val Tyr Glu Asp Ala Ala Leu Ala Lys Lys Gln
        35                  40                  45

Gly Ala Asp Ile Ile Val Phe Pro Glu Asn Gly Leu Ile Tyr Ser Ile
    50                  55                  60

Leu Ser Arg Glu Lys Ala Asp Glu Phe Ala Ser Asp Ile Pro Asp Ala
65                  70                  75                  80

Glu Val Asn Ala Cys Thr Leu Asp Ser Lys Phe Val Tyr Asn Arg Leu
                85                  90                  95

Ala Cys Leu Ala Gln Lys His Gln Met Phe Val Val Ala Asp Leu Ile
            100                 105                 110

Asp Arg Lys Ser Cys Glu Glu Leu Gly Ile Asn Asn Val Ser Asp Ser
        115                 120                 125

Cys Pro Ala Asp Lys Lys Phe Leu Phe Asn Thr Ala Val Leu Phe Asp
    130                 135                 140

Arg Gln Gly Lys Leu Leu Gly Arg Tyr His Lys Met His Leu Phe Gly
145                 150                 155                 160

Glu Ile Ser Met Asn Pro Pro Lys Pro Glu Leu Leu Val Ile Asp
                165                 170                 175

Thr Glu Leu Gly Arg Leu Gly Met Gln Ile Cys Phe Asp Met Ile Phe
            180                 185                 190

Lys Thr Pro Gly Tyr Leu Leu Ala Gln Glu Asn Lys Phe Asp Thr Met
        195                 200                 205

Leu Phe Pro Thr Trp Trp Phe Asp Glu Ser Pro Met Leu Ser Ser Ser
    210                 215                 220

Gln Tyr Gln Met Ala Trp Ala Phe Gly Asn Asn Val Thr Leu Leu Ala
225                 230                 235                 240

Ser Asn Ile His Arg Ile Glu Val Gly Ser Arg Gly Ser Gly Ile Tyr
                245                 250                 255

Val Gly Pro His Arg Thr Leu Ala Ala Ala Leu Tyr Asp Asp Ser Val
            260                 265                 270

Glu Arg Leu Val Leu Ala Asn Val Pro Ile Lys Pro Lys Glu Thr Asp
        275                 280                 285

Gln Ser Ala Cys Pro Leu Asp Ser Glu Ile Ile Glu Val Pro Gln Gln
    290                 295                 300

Ile Pro Ile Pro Lys Ser Val Lys Tyr His His Gln Asn Leu Asn Leu
305                 310                 315                 320

Lys Asp Val Thr Leu Leu Gln Leu Ser Ser Asn Glu Ser Glu Val His
                325                 330                 335

Leu Cys His Lys Gly Val Cys Cys Gln Phe Glu Tyr Arg Leu Ala Met
            340                 345                 350

Lys Asp Gln Pro Gln Glu Ser Trp Val Asp Arg Val Pro Leu Leu Ala
        355                 360                 365
```

```
Asn Met Leu His Tyr Leu Thr Pro Glu Glu Arg Tyr Tyr Leu Ile
    370                 375                 380
Ala Asn Arg Thr Arg Pro Gly Ala Tyr Pro Trp Ser Glu Glu Phe Cys
385                 390                 395                 400
Ala Val Val Val Cys Pro Ser Ser Arg Trp Asn Phe Gly Lys Met Gln
                405                 410                 415
Lys Asp Cys Ser Lys Ile Gly Ser Asn Gln Glu Leu Ser Ser Arg Phe
            420                 425                 430
Val His Ala Lys Leu Arg Gly Lys Phe Ser Glu Asp Thr Ala Val Tyr
        435                 440                 445
Pro Ser Ala Val Gly Ser Lys Asn Gln Leu Ile Tyr Pro Glu Asn Lys
    450                 455                 460
Trp Lys Phe Trp Lys Val Asn Val Pro Asn Glu Pro Glu Tyr Phe Ile
465                 470                 475                 480
Glu Leu Gly Ala Lys Asp Asn Ser Glu Ser Arg Ala Met Glu Leu Gly
                485                 490                 495
Ala Leu Val Leu Tyr Gly Arg Asn Tyr Asn Arg Asp Pro Arg Tyr Glu
            500                 505                 510
Gln Lys Ala Leu Pro Ile Asn
        515

<210> SEQ ID NO 41
<211> LENGTH: 887
<212> TYPE: PRT
<213> ORGANISM: Dermatophagoides pteronyssinus

<400> SEQUENCE: 41

Leu Asp Ser Asp Pro Met Lys Cys Asn Ser Ile Arg Asn Glu Asp Arg
1               5                   10                  15
Ile Asp Cys Asn Pro Asp Pro Pro Ile Ser Lys Glu Ile Cys Glu Gln
                20                  25                  30
Arg Gly Cys Cys Trp Asn Ala Gly Asn Asn Thr Asp Asp Gly Asn Leu
            35                  40                  45
Ile Ser Arg Ala Leu Pro His Leu Gly Val Pro Ser Cys Tyr Tyr Gly
        50                  55                  60
Glu Asn Tyr Ile Gly Tyr Lys Ile Glu Lys Ile Tyr Ile Lys Asp Glu
65                  70                  75                  80
Asp Leu Ser Met Thr Lys Leu Lys Arg Val Arg Pro Ser Gly Phe Pro
                85                  90                  95
Lys Asp Ile Glu Asn Val Asn Ile Glu Ile His Gln Leu Asn Asp Gln
            100                 105                 110
Val Leu Arg Leu Lys Phe Ile Asp Ala Asn Gln Lys Arg Tyr Glu Val
        115                 120                 125
Pro Thr Pro Lys Leu Asn Ile Pro Ser Val Ser Lys Ser Ser Asn Ser
    130                 135                 140
Arg Leu Tyr Ser Thr Glu Ile Ser Gly Ser His Leu Ile Val Arg Arg
145                 150                 155                 160
Arg Glu Thr Asn Gln Ser Ile Phe Asp Ile Asn Leu Ala Gln Met Val
                165                 170                 175
Tyr Ser Asp Gln Leu Ile His Leu Thr Ser Lys Leu Pro Ser Lys Tyr
            180                 185                 190
Ile Tyr Gly Ile Gly Glu His Arg Glu Pro Phe Arg Lys Thr Thr Asp
        195                 200                 205
Trp Lys Arg Tyr Thr Gln Trp Thr Arg Asp Gln Val Pro Ile Ser Asp
    210                 215                 220
```

```
His Ala Leu Tyr Gly Ser His Pro Phe Tyr Met Met Val Glu Asn Lys
225                 230                 235                 240

Thr Lys Leu Ala Ser Gly Val Phe Leu Phe Asn Ser Asn Ala Met Asp
                245                 250                 255

Ile Leu Thr Gln Pro Ser Pro Ala Ile Thr Phe Arg Thr Val Gly Gly
            260                 265                 270

Ile Leu Asp Phe Phe Ile Phe Phe Gly Pro Lys Pro Glu Gln Val Val
        275                 280                 285

Gln Gln Tyr His Asn Leu Ile Gly Leu Pro Ala Met Pro Pro Phe Trp
    290                 295                 300

Ser Leu Gly Tyr Gln Gln Cys Arg Tyr Gly Tyr Asn Asn Phe Thr Asn
305                 310                 315                 320

Leu Asn Gln Thr Tyr Trp Arg Thr Arg Gln Ala Gly Ile Pro Met Asp
                325                 330                 335

Val Gln Trp Thr Asp Ile Asp Met Phe Asp Ser Tyr Asn Asp Phe Thr
            340                 345                 350

Tyr Asn His Lys Gln Phe Lys Glu Leu Pro Asp Phe Ile Arg Asn Val
        355                 360                 365

Leu His Lys Asn Gly Gln Lys Phe Ile Pro Met Phe Asp Cys Gly Ile
    370                 375                 380

Ser Ser Gly Glu Lys Ala His Ser Tyr Arg Pro Tyr Asp Tyr Gly Val
385                 390                 395                 400

Glu Leu Asp Ile Phe Val Lys Asn Ser Ser Lys Gln Ile Phe Asn Gly
                405                 410                 415

Lys Val Trp Asn Gly Lys Ser Thr Val Trp Pro Asp Phe Ser His Pro
            420                 425                 430

Asn Ala Thr Lys Tyr Trp Ser Lys Met Phe Glu Glu Tyr His Lys Ile
        435                 440                 445

Ile Glu Phe Asp Gly Ala Trp Ile Asp Met Asn Glu Pro Ser Asn Phe
    450                 455                 460

Tyr Asp Gly Gln Ile Asp Gly Cys Pro Lys Thr Glu Ile Glu Asn Pro
465                 470                 475                 480

Gln Tyr Val Pro Gly Met Thr Asp Asp Ser Leu Thr Leu Arg His Lys
                485                 490                 495

Thr Leu Cys Met Thr Ala Arg His Tyr Asn Asp Gln Leu His Tyr Asn
            500                 505                 510

Leu His Asn Leu Tyr Gly Phe Gln Glu Ala Ile Ala Thr Asn Glu Ala
        515                 520                 525

Leu Lys Thr Thr Leu Asn Lys Arg Pro Phe Ile Ile Ser Arg Ser Ser
    530                 535                 540

Ala Pro Gly His Gly His Trp Ala Ser His Trp Asp Gly Asp Val Ile
545                 550                 555                 560

Ser Asp Trp Ser Ser Met Arg Trp Thr Ile Pro Ser Ile Leu Asn Phe
                565                 570                 575

Asn Leu Phe Gly Val Pro Met Ile Gly Ala Asp Ile Cys Gly Phe Asn
            580                 585                 590

Gly Asp Thr Thr Val Glu Leu Cys Arg Arg Trp Tyr Gln Leu Gly Ala
        595                 600                 605

Phe Tyr Ser Phe Val Arg Asn His Asn Thr Asp Asn Ala Ile Asp Gln
    610                 615                 620

Asp Pro Val Ala Leu Gly Glu Thr Val Val Arg Thr Ala Arg Ser Ala
625                 630                 635                 640
```

-continued

```
Leu Thr Tyr Arg Tyr Ala Phe Leu Pro Tyr Leu Tyr Thr Leu Phe Tyr
            645                 650                 655

Asn Val His Gln Asn Gly Gly Thr Val Leu Arg Pro Met Phe Phe Glu
        660                 665                 670

Phe Pro Asp Asp His Leu Tyr Asp Ile Glu Thr Gln Phe Met Trp
    675                 680                 685

Gly Asp Ser Met Leu Ile Ala Pro Ile Leu Tyr Pro Asn Gln Thr Glu
690                 695                 700

Asn Lys Val Tyr Leu Pro Lys Gly Thr Trp His Asn Met Arg Gln Thr
705                 710                 715                 720

Phe Glu Ser Gln Gly Gln Tyr Phe Thr Ile Lys Asp Ser Leu Asp Asp
                725                 730                 735

Ile Asn Tyr Val Phe Phe Arg Ser Gly Ser Ile Ile Pro Ile Gln Gly
            740                 745                 750

Pro Gln Asn Asn Thr Glu Met Met Lys Ser Lys Asp Phe Gly Leu Val
        755                 760                 765

Val Ile Leu Asp Ser Lys Asn Pro Glu Pro Tyr Ala Lys Gly Ser Leu
    770                 775                 780

Tyr Leu Asp Ser Gly Asp Ser Leu Asp Pro Val Lys Lys Gly Glu Tyr
785                 790                 795                 800

Asn Phe Tyr Asn Phe Glu Val Lys Asn Asn Thr Leu Thr Ile Glu Ser
                805                 810                 815

Gln His Leu Gly Tyr Gln Thr Asn Gln Ser Ile Ile Leu Glu Ile
            820                 825                 830

Leu Gly Ile Asp Arg Lys Pro Thr Ser Ile Ile Phe Asp Gly Lys Pro
835                 840                 845

Tyr Tyr Gln Phe Ile Tyr Thr Thr Asn Asn Met Leu Ile Ile Gln Thr
850                 855                 860

Lys Leu Ser Ile Phe Asn Asp Asn Asp Lys Ser Lys Lys Ile His Tyr
865                 870                 875                 880

Gln Phe Glu Trp Lys Phe Asn
                885

<210> SEQ ID NO 42
<211> LENGTH: 885
<212> TYPE: PRT
<213> ORGANISM: Dermatophagoides farinae

<400> SEQUENCE: 42

Asp Ser Leu Lys Cys Ser Ser Ile Arg Asn Glu Asp Arg Ile Asp Cys
1               5                  10                  15

Asn Pro Asp Pro Pro Ile Ser Lys Asn Val Cys Glu Gln Arg Gly Cys
            20                  25                  30

Cys Trp Lys Thr Ala Gly Asn Asp Leu Lys Asn Leu Ser Ser Lys Val
        35                  40                  45

Leu Pro Asn Leu Asn Val Pro Tyr Cys Tyr Tyr Gly Glu Asn Tyr Ile
    50                  55                  60

Gly Tyr Lys Ile Glu Lys His Ser Lys Asn Leu Ile Gln Leu Lys Arg
65                  70                  75                  80

Asn Arg Ser Ser Gly Phe Ala Arg Asp Ile Glu Asn Ile Asn Ile Glu
                85                  90                  95

Ile His Glu Leu Asn Asp Lys Val Ile Arg Leu Lys Phe Ile Asp Ala
            100                 105                 110

Asn Lys Lys Arg Tyr Glu Val Pro Ile Pro Lys Leu Asn Leu Pro Ser
        115                 120                 125
```

```
Thr Thr Ser Ser Ser Ser Asn Ser Arg Leu Tyr Ser Val Glu Leu
    130                 135                 140

Asp Gly Ser His Leu Ile Val Arg Arg Glu Thr Asn Gln Ser Ile
145                 150                 155                 160

Phe Asp Ile Asn Leu Ala Tyr Met Val Tyr Ser Asp Gln Leu Ile His
                165                 170                 175

Val Thr Ser Arg Leu Pro Ser Lys Tyr Ile Tyr Gly Leu Gly Glu His
            180                 185                 190

Arg Ala Pro Phe Arg Lys Asn Thr Asn Trp Lys Arg Tyr Thr Gln Trp
        195                 200                 205

Thr Arg Asp Gln Tyr Pro Val Thr Asp Lys Ala Leu Tyr Gly Asn His
    210                 215                 220

Pro Phe Tyr Leu Thr Val Glu Asp Glu Ser Pro Lys Lys Ser Ala Ser
225                 230                 235                 240

Gly Val Phe Leu Phe Asn Ser Asn Ala Met Asp Ile Ile Thr Gln Pro
                245                 250                 255

Ser Pro Ala Ile Thr Phe Arg Thr Ile Gly Gly Ile Leu Asp Phe Phe
            260                 265                 270

Val Phe Phe Gly Pro Lys Pro Glu Asp Val Ile Ser Gln Tyr Gln Asn
        275                 280                 285

Leu Ile Gly Leu Pro Ala Met Pro Pro Phe Trp Ser Leu Gly Tyr Gln
    290                 295                 300

Gln Cys Arg Tyr Gly Tyr Asn Asn Phe Thr Asn Leu Asn Thr Thr Tyr
305                 310                 315                 320

Thr Arg Asn Arg Ala Val Gly Ile Pro Met Asp Val Gln Trp Thr Asp
                325                 330                 335

Ile Asp Ala Phe Asn Ser Asn Asn Asp Phe Thr Tyr Asp His Lys Arg
            340                 345                 350

Phe Lys Glu Leu Pro Asp Phe Ile Asn Asn Val Leu His Pro Asn Gly
        355                 360                 365

Gln Lys Phe Ile Pro Met Phe Asp Cys Gly Ile Ser Ser Gly Glu Pro
    370                 375                 380

Ala Gly Ser Tyr Lys Pro Phe Asp Ser Gly Val Glu Leu Asp Val Phe
385                 390                 395                 400

Val Lys Asn Ser Ser Asn Lys Ile Phe Arg Gly Lys Val Trp Asn Gly
                405                 410                 415

Lys Ser Thr Val Trp Pro Asp Phe Ser His Pro Asn Ala Thr Glu Tyr
            420                 425                 430

Trp Met Asp Met Phe Ala Glu Tyr His Lys Thr Ile Ala Phe Asp Gly
        435                 440                 445

Ala Trp Leu Asp Met Asn Glu Pro Ser Asn Phe Tyr Asn Gly Glu Glu
450                 455                 460

His Gly Cys Pro Glu Ser Glu Ile Glu Asn Pro Gln Tyr Val Pro Gly
465                 470                 475                 480

Met Thr Asp Asp Ser Leu Thr Leu Arg His Lys Thr Leu Cys Met Thr
                485                 490                 495

Ala Arg His Tyr Asn Asp Gln Leu His Tyr Asn Leu His Asn Leu Tyr
            500                 505                 510

Ser Leu Ser Met Ala Met Ala Thr Asn Ala Ala Leu Thr Lys Leu Asn
        515                 520                 525

Lys Arg Pro Phe Ile Ile Ser Arg Ala Thr Ala Pro Gly His Gly His
    530                 535                 540
```

```
Trp Ala Tyr His Trp Asn Gly Asp Ile Leu Ser Asp Trp Ser Ser Met
545                 550                 555                 560

Arg Trp Thr Ile Pro Ser Ile Leu Asn Phe Asn Met Phe Gly Ile Pro
                565                 570                 575

Met Val Gly Ala Asp Ile Cys Gly Phe Gly Gly Asn Thr Ala Glu Glu
            580                 585                 590

Leu Cys Ile Arg Trp Tyr Gln Leu Gly Ala Phe Tyr Ser Phe Ala Arg
            595                 600                 605

Asn His Asn Asp Ile His Ser Ile Asp Gln Asp Pro Ala Ala Leu Gly
        610                 615                 620

Glu Ser Val Ile Arg Ala Ala Arg Ser Ser Leu Gln Tyr Arg Tyr Arg
625                 630                 635                 640

Phe Leu Ala His Leu Tyr Thr Leu Phe Tyr His Val His Lys Asn Gly
                645                 650                 655

Gly Thr Val Leu Arg Pro Met Phe Phe Glu Phe Pro His Asp Glu His
                660                 665                 670

Thr Tyr Glu Ile Glu Thr Gln Phe Met Trp Gly Asp Ser Val Leu Ile
            675                 680                 685

Ala Pro Ile Leu Tyr Pro Asn Gln Thr Gln His Lys Ile Tyr Leu Pro
        690                 695                 700

Lys Gly Thr Trp Tyr Asn Arg Lys Val Ser Phe Glu Ser Gln Gly Gln
705                 710                 715                 720

Tyr Ile Thr Met Asn Asp Ser Tyr Asp Ile Asp Tyr Val Phe Val
                725                 730                 735

Arg Gly Gly Ser Ile Ile Pro Thr Gln Glu Pro His Asp Asn Thr Glu
            740                 745                 750

Leu Met Lys Thr Lys Asp Phe Leu Leu Ile Val Ala Leu Asp Asn Gln
            755                 760                 765

Thr Ser Tyr Ala Lys Gly Ser Leu Tyr Trp Asp Ser Gly Asp Ser Leu
        770                 775                 780

Asn Pro Asp Lys Thr Gly His Tyr Asn Phe Tyr Asn Phe Asp Ala Val
785                 790                 795                 800

Asn Asn Thr Leu Thr Ile Gln Ser Gln Trp Leu Gly Tyr Gln Thr Thr
                805                 810                 815

Gln Asn Ile Asn Phe Ile Asn Ile Leu Gly Val Pro Lys Leu Pro Thr
            820                 825                 830

Ser Phe Lys Leu Asn Gly His Val Ser Asp Pro Arg Ile Ile Arg Phe
        835                 840                 845

Asn Tyr Asp Glu Gln Thr Asn Ile Leu Thr Val Glu Thr Lys Leu Pro
850                 855                 860

Ile Tyr Asn Gln Asp Ser Ser Ser His Asp Arg Ile His Tyr Gln Phe
865                 870                 875                 880

Glu Trp Ile Met Glu
                885

<210> SEQ ID NO 43
<211> LENGTH: 975
<212> TYPE: PRT
<213> ORGANISM: Dermatophagoides farinae

<400> SEQUENCE: 43

Val Val Ile Lys Val Glu Asn Leu Pro Glu Arg Cys Asp Tyr Ser Gln
1               5                   10                  15

Cys Pro Lys Trp Asp Pro Asn Asp Ile Asn Val His Leu Val Ala His
            20                  25                  30
```

```
Thr His Asp Asp Val Gly Trp Leu Lys Thr Val Glu Gln Tyr Tyr Tyr
         35                  40                  45

Gly Leu Lys Asn Asp Ile Gln Arg Ala Gly Val Gln Tyr Ile Leu Asp
 50                  55                  60

Thr Val Ile Glu Glu Leu Ile Arg Asn Lys Gln Arg Arg Phe Ile Tyr
 65                  70                  75                  80

Val Glu Ile Ala Phe Phe Trp Lys Trp Trp Gln Glu Gln Asp Glu Asp
                 85                  90                  95

Gln Arg Met Ile Val Arg Glu Leu Val Arg Thr Gly Gln Leu Glu Phe
                100                 105                 110

Ile Asn Gly Gly Trp Ser Met Pro Asp Glu Ala Ala Thr His Tyr Asn
                115                 120                 125

Ser Leu Ile Asp Gln Ser Thr Trp Gly Leu Arg Gln Leu Asn Asp Thr
        130                 135                 140

Phe Gly Lys Cys Gly His Pro Lys Val Thr Trp Gln Ile Asp Pro Phe
145                 150                 155                 160

Gly His Ser Arg Glu Met Ala Asn Leu Tyr Ala Gln Met Gly Tyr Asp
                165                 170                 175

Ala Leu Phe Phe Ala Arg Gln Asp Tyr Gln Asp Arg Glu Asn Arg Met
                180                 185                 190

Thr Asn Arg Lys Leu Glu His Val Trp Gln Gly Ser Asp Asp Leu Gly
        195                 200                 205

Thr Ala Gly Asp Ile Phe Thr Gly Met Met Phe Ser Gly Tyr Gly Pro
        210                 215                 220

Ile Glu Phe Asn Trp Asp Ile Thr Asn Gly Pro Glu Asp Ala Val Val
225                 230                 235                 240

Asp Asn Pro Glu Ser Glu Glu Tyr Asn Val Pro Asp Lys Ile Arg Arg
                245                 250                 255

Phe Val Glu Lys Ala Lys Tyr Phe Ala Gln Tyr Tyr Ala Thr Asn His
                260                 265                 270

Phe Met Phe Pro Met Gly Thr Asp Phe Gln Tyr Gly Asp Ala His Thr
        275                 280                 285

Trp Phe Lys Asn Leu Asp Lys Leu Ile Lys Ala Val Asn Asn Ala Gly
        290                 295                 300

Lys Gly Val Arg Ala Phe Tyr Ser Thr Pro Ser Cys Tyr Ala Arg Ala
305                 310                 315                 320

Leu Tyr Glu Thr Asn Arg Thr Trp Thr Thr Lys Thr Asp Asp Phe Phe
                325                 330                 335

Pro Tyr Ala Ser Asp Glu His Ala Tyr Trp Thr Gly Tyr Phe Thr Ser
                340                 345                 350

Arg Pro Ala Leu Lys Arg Met Glu Arg Met Gly Asn Asn Leu Leu Gln
        355                 360                 365

Ala Cys Lys Gln Leu Asp Ile Leu Ala Gly Asn Asp Gly Arg Phe Glu
        370                 375                 380

Met Asn Ile Thr Arg Leu Arg Glu Ala Met Gly Val Met Gln His His
385                 390                 395                 400

Asp Ala Val Thr Gly Thr Glu Lys Gln His Val Ala Phe Asn Tyr Ala
                405                 410                 415

Lys Met Leu Asp Ser Ala Met Leu Gln Cys Arg His Val Ile Ser Glu
                420                 425                 430

Ser Tyr Arg Lys Leu Phe Pro Thr Gln Thr Lys Glu Gln His Glu Phe
        435                 440                 445
```

```
Cys Pro Tyr Leu Asn Ile Ser Ser Cys Pro Ser Thr Glu Met Gly Glu
    450                 455                 460

Ser Arg Thr Ile His Leu Tyr Asn Pro Leu Gly His Arg Leu Val Asn
465                 470                 475                 480

Arg Thr Ile Arg Val Pro Val Lys Asp Gly Tyr Tyr Gln Val Arg
                485                 490                 495

Asp Gln Asn Asp His Ser Ile Pro Ala Val Leu Ile Ser Ile Pro Glu
            500                 505                 510

Phe Val Arg Lys Ile Pro Gly Arg Lys Ser Val Ala Thr Lys Glu Leu
                515                 520                 525

Val Phe Arg Val Pro Ile Ile Glu Ser Leu Gly Ile Arg Arg Phe His
530                 535                 540

Met Ile Ala Thr Lys Glu Lys Gln Gln Asp Ser Ala Val Glu Ile Gln
545                 550                 555                 560

Gly Glu Lys Phe Val Gly His Lys Gly Gln Arg Phe Gln Leu Lys Asp
                565                 570                 575

Gly Leu Ile Ile Glu Phe Asp Ser Asn Gly Lys Ile Ala Thr Met Ile
                580                 585                 590

Arg Asn Asn Gln Ser Ile Ser Ile Ser Asn Glu Phe Arg Leu Phe His
            595                 600                 605

Gly Ala Asp Ile Gly Arg His Ser Gly Ala Tyr Ile Phe Arg Pro Ser
610                 615                 620

Glu Gln Lys Thr Phe Pro Val Thr Glu Lys Met Glu Ala Thr Leu Tyr
625                 630                 635                 640

Val Asp Gln Lys Phe Gly Ile Val Gln Glu Val His Gln Gln Phe Asp
                645                 650                 655

Ser Phe Val Gly Gln Ile Ile Arg Leu Asp Lys Gln Gly Asp Tyr Val
                660                 665                 670

Glu Phe Asp Phe Val Val Gly Pro Ile Pro Val Asp Asp Leu Ile Gly
            675                 680                 685

Lys Glu Ile Ile Thr Arg Tyr Asn Thr Asn Leu Ala Asn Asp Glu Thr
            690                 695                 700

Phe Phe Thr Asp Ser Asn Gly Arg Gln Met Leu Arg Arg Arg Trp Asn
705                 710                 715                 720

Tyr Arg Pro Ser Trp Lys Tyr Glu Ile Glu Glu Pro Val Ser Gly Asn
                725                 730                 735

Tyr Tyr Pro Val Asn Ser Arg Ile Ala Ile Arg Asp Asp Arg Lys Ser
                740                 745                 750

Leu Gln Met Thr Ile Met Thr Asp Arg Ser Gln Gly Gly Ser Leu Ser
            755                 760                 765

Pro Glu Gln Ile Asn Gly Ser Val Asp Leu Met Val His Arg Arg Leu
770                 775                 780

Leu His Asp Asp Tyr Phe Gly Val Asp Glu Pro Leu Asn Glu Pro Gly
785                 790                 795                 800

Val Asp Gly His Gly Ile Val Ile Arg Gly Arg His Leu Leu Leu Leu
                805                 810                 815

Asp Thr Leu Glu Lys Ala Ala Glu Lys His Arg Pro Leu Ala Gln Glu
            820                 825                 830

Met Phe Met Glu Pro Ile Ile Ser Phe Thr Ser Ser Met Glu Lys Asn
            835                 840                 845

Gln Pro Ile Tyr Lys Gly Leu Thr Lys Asp Leu Pro Gly Asn Val His
850                 855                 860

Leu Leu Thr Leu Glu Gln Trp His Ser Lys Arg Tyr Leu Leu Arg Leu
```

```
                865                 870                 875                 880
Glu His Phe Tyr Gln Arg Phe Glu Asp Pro Ser Leu Ser Asn Pro Ala
                    885                 890                 895

Thr Val Ser Leu Arg His Leu Phe Gln Ser Phe Glu Ile Thr Ala Val
                900                 905                 910

Glu Glu Leu Thr Leu Gly Ala Asn Gln Pro Ile Ser Ala Leu Lys Asn
                915                 920                 925

Arg Leu Gln Tyr Arg Tyr Ile Arg Pro Leu Asn Glu Gln Gln Ser Ser
                930                 935                 940

Ile Ile Thr Asp Pro Ile Ile Glu Gly Glu Asn Phe Asp Ile His Leu
945                 950                 955                 960

Glu Pro Met Gln Ile Arg Thr Phe Leu Ile Asp Ile Lys Arg Asn
                965                 970                 975

<210> SEQ ID NO 44
<211> LENGTH: 990
<212> TYPE: PRT
<213> ORGANISM: Dermatophagoides pteronyssinus

<400> SEQUENCE: 44

Val Val Ile Lys Val Glu Asn Leu Pro Glu Gln Cys Asp Tyr Thr Gln
1               5                   10                  15

Cys Pro Lys Trp Ser Lys Asp Asp Ile Asn Val His Leu Val Ala His
                20                  25                  30

Thr His Asp Asp Val Gly Trp Leu Lys Thr Val Glu Gln Tyr Tyr Tyr
                35                  40                  45

Gly Leu Lys Asn Asp Ile Gln Arg Ala Gly Val Gln Tyr Ile Leu Asp
                50                  55                  60

Thr Met Ile Glu Glu Leu Ile Arg Asn Lys Asp Arg Arg Phe Ile Tyr
65              70                  75                  80

Val Glu Ile Ala Phe Phe Trp Lys Trp Trp Gln Glu Gln Asn Glu Glu
                    85                  90                  95

Gln Arg Met Ile Val Lys Glu Leu Val Arg Thr Gly Gln Leu Glu Phe
                100                 105                 110

Ile Asn Gly Gly Trp Ser Met Pro Asp Glu Ala Ala Thr His Tyr Asn
                115                 120                 125

Ser Leu Ile Asp Gln Ser Thr Trp Gly Leu Arg Gln Leu Asn Asp Thr
                130                 135                 140

Phe Gly Arg Cys Gly His Pro Lys Val Thr Trp Gln Ile Asp Pro Phe
145                 150                 155                 160

Gly His Ser Lys Glu Met Ala Asn Leu Tyr Ala Gln Met Gly Tyr Asp
                    165                 170                 175

Ala Leu Phe Phe Ala Arg Gln Asp Tyr Gln Asp Arg Glu Asn Arg Met
                    180                 185                 190

Ser Asn Arg Thr Leu Glu His Val Trp Gln Gly Ser Asp Asp Leu Gly
                195                 200                 205

Glu Ile Gly Asp Ile Phe Thr Gly Met Met Phe Ser Gly Tyr Gly Pro
                210                 215                 220

Ile Glu Phe Asn Trp Asp Ile Thr Asn Gly Pro Glu Asp Ala Val Val
225                 230                 235                 240

Asp Asn Pro Glu Ser Glu Tyr Asn Val Pro Asp Lys Ile Arg Arg
                    245                 250                 255

Phe Val Glu Lys Ala Lys Tyr Phe Gly Gln Phe Tyr Ala Thr Asn His
                260                 265                 270
```

```
Phe Met Phe Pro Met Gly Thr Asp Phe Gln Tyr Thr Asp Ala His Thr
            275                 280                 285

Trp Phe Lys Asn Leu Asp Lys Leu Ile Asn Ala Val Asn Lys Ala Gly
        290                 295                 300

Lys Gly Val Arg Ala Phe Tyr Ser Thr Pro Ser Cys Tyr Ala His Ala
305                 310                 315                 320

Leu Tyr Glu Gln Asn Arg Thr Trp Thr Thr Lys Thr Asp Asp Phe Phe
                325                 330                 335

Pro Tyr Ala Ser Asp Glu His Ala Tyr Trp Thr Gly Tyr Phe Thr Ser
                340                 345                 350

Arg Pro Ala Ile Lys Arg Met Glu Arg Ile Gly Asn Asn Leu Leu Gln
            355                 360                 365

Ala Cys Lys Gln Leu Asp Val Leu Ala Asp Asn Asn Gly Arg Phe Glu
370                 375                 380

Met Asn Leu Thr Lys Met Arg Glu Ala Met Gly Val Met Gln His His
385                 390                 395                 400

Asp Ala Val Thr Gly Thr Glu Lys Gln His Val Ala Phe Asn Tyr Ala
                405                 410                 415

Lys Met Leu Asp Ser Ala Met Leu Gln Cys Arg His Ile Ile Asn Glu
            420                 425                 430

Ser Tyr Lys Lys Leu Leu Pro Lys Ser Ser Thr Ser Glu His Glu Phe
            435                 440                 445

Cys Pro Tyr Leu Asn Ile Ser Ser Cys Pro Thr Thr Glu Met Gly Glu
        450                 455                 460

Ser Arg Ile Ile Tyr Leu Tyr Asn Pro Leu Gly His Arg Leu Ile Asn
465                 470                 475                 480

His Thr Val Arg Leu Pro Ile Lys Asn Gly Tyr Tyr Arg Ile Gln
                485                 490                 495

Asp Gln Asn Asn Gln Ser Val Pro Ser Val Leu Val Pro Ile Pro Glu
                500                 505                 510

Phe Val Gln Lys Ile Pro Gly Arg Lys Ser Val Ala Thr Lys Glu Leu
            515                 520                 525

Val Phe Arg Val Pro Val Ile Glu Pro Leu Gly Ile Thr Thr Met Tyr
        530                 535                 540

Met Tyr Val Asp Lys Asn Glu Gln Pro Asn Ser Ala Ile Glu Ile Lys
545                 550                 555                 560

Gly Glu Asn Pro Asp Asn Asp Asp Lys Ser Lys Trp Leu Val Leu
                565                 570                 575

Thr Lys Asn Leu Ile Val Glu Phe Tyr Ser Asn Gly Thr Ile Ser Arg
            580                 585                 590

Ile Ser Ile Asp Lys Leu His Gln Ser Ile Ser Ile Ser Asn Glu Phe
            595                 600                 605

Arg Leu Tyr His Gly Ala Gly Gly Thr Gly Arg His Ser Gly Ala Tyr
            610                 615                 620

Ile Phe Arg Pro Asn Glu Gln Lys Thr Phe Pro Val Thr Asn Lys Ile
625                 630                 635                 640

Lys Ser Thr Phe Phe Ile Asp Arg Lys Tyr His Ile Val Gln Glu Val
                645                 650                 655

His Gln Gln Phe Asp Ser Ser Phe Val Gly Gln Ile Ile Arg Met Asp
                660                 665                 670

Lys Tyr Asn Asp Asn Val Glu Phe Asp Phe Val Val Gly Pro Ile Pro
            675                 680                 685

Val Asn Asp Gln Ile Gly Lys Glu Ile Ile Ala Ser Tyr Lys Thr Asp
```

```
                    690             695             700
Leu Glu Asn Asp Glu Thr Phe Tyr Thr Asp Ala Asn Gly Arg Gln Met
705                 710             715                 720

Leu Arg Arg Arg Trp Asn Tyr Arg Pro Ser Trp Lys Tyr Asn Val Gln
                725             730                 735

Glu Pro Ile Ser Gly Asn Tyr Tyr Pro Val Asn Ser Arg Ile Ala Ile
            740             745                 750

Arg Asp Glu Lys Gln Ser Leu Gln Met Thr Ile Met Thr Asp Arg Ser
                755             760             765

Gln Gly Gly Ser Leu Ser Pro Glu Gln Ile Asn Gly Ser Ile Asp Ile
            770             775             780

Met Ile His Arg Arg Leu Leu His Asp Asp Tyr Phe Gly Val Gly Glu
785             790              795             800

Ala Leu Asn Glu Pro Gly Val Asp Gly His Gly Leu Val Ile Arg Gly
                805             810             815

Lys His Leu Leu Leu Asn Ser Ile Lys Gln Ser Ala Ser Glu His
                820             825             830

Arg Pro Leu Ala Gln Gln Met Phe Met Glu Pro Ile Ile Ser Phe Thr
            835             840             845

Ser Ile Glu Ser Asn Lys Gln Ala Glu Lys Gln Ser Asn Gln Tyr Ile
            850             855             860

Gly Leu Asn Asn Asp Leu Pro Ser Asn Val His Leu Leu Thr Leu Glu
865             870             875             880

Gln Trp His Ser Lys Arg Tyr Leu Leu Arg Leu Glu His Phe Tyr Gln
                885             890             895

Ser Asn Glu Asp Thr Glu Leu Ser Lys Pro Val Lys Leu Ser Leu Arg
            900             905             910

His Leu Phe Lys Ser Phe Glu Ile Ile Ala Val Glu Leu Thr Leu
                915             920             925

Gly Ala Asn Gln Pro Ile Ser Ser Leu Lys Asn Arg Leu His Tyr Arg
            930             935             940

Tyr Asn Arg Pro Leu Glu Gln Arg Gln Gln Gln Ser Ser Leu Leu
945             950             955             960

Leu Asp Asp Pro Lys Ile Glu Gly Glu Asn Phe Asp Ile His Leu Ser
                965             970             975

Pro Met Gln Ile Arg Thr Phe Leu Ile Asp Ile Lys Arg Asn
                980             985             990

<210> SEQ ID NO 45
<211> LENGTH: 15
<212> TYPE: PRT
<213> ORGANISM: Artificial sequence
<220> FEATURE:
<223> OTHER INFORMATION: Immunogenic fragment

<400> SEQUENCE: 45

Ile Met Arg Ile Leu Cys Cys Lys Ser Arg Lys Val Ala Pro Cys
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: Immunogenic fragment

<400> SEQUENCE: 46
```

```
Phe Asn Tyr Leu Pro Val Asp Val Gln Glu Leu Arg Asn Thr
1               5                   10                  15
```

<210> SEQ ID NO 47
<211> LENGTH: 15
<212> TYPE: PRT
<213> ORGANISM: Artificial sequence
<220> FEATURE:
<223> OTHER INFORMATION: Immunogenic fragment

<400> SEQUENCE: 47

```
Glu Leu Leu Lys Lys Lys Gly Ile Ile Pro Gly Ile Lys Val Asp
1               5                   10                  15
```

<210> SEQ ID NO 48
<211> LENGTH: 15
<212> TYPE: PRT
<213> ORGANISM: Artificial sequence
<220> FEATURE:
<223> OTHER INFORMATION: Immunogenic fragment

<400> SEQUENCE: 48

```
Glu Gln Tyr Ile Ser Gly Val Ile Leu Phe Asp Glu Thr Val Tyr
1               5                   10                  15
```

<210> SEQ ID NO 49
<211> LENGTH: 15
<212> TYPE: PRT
<213> ORGANISM: Artificial sequence
<220> FEATURE:
<223> OTHER INFORMATION: Immunogenic fragment

<400> SEQUENCE: 49

```
Lys Gly Ile Ile Pro Gly Ile Lys Val Asp Thr Gly Val Val Thr
1               5                   10                  15
```

<210> SEQ ID NO 50
<211> LENGTH: 15
<212> TYPE: PRT
<213> ORGANISM: Artificial sequence
<220> FEATURE:
<223> OTHER INFORMATION: Immunogenic fragment

<400> SEQUENCE: 50

```
Phe Ile Met Leu Lys Pro Asp Ala Val Gln Arg Gly Ile Val Gly
1               5                   10                  15
```

<210> SEQ ID NO 51
<211> LENGTH: 15
<212> TYPE: PRT
<213> ORGANISM: Artificial sequence
<220> FEATURE:
<223> OTHER INFORMATION: Immunogenic fragment

<400> SEQUENCE: 51

```
Arg Gly Ile Val Gly Glu Ile Ile Arg Arg Phe Glu Ala Lys Gly
1               5                   10                  15
```

<210> SEQ ID NO 52
<211> LENGTH: 15
<212> TYPE: PRT
<213> ORGANISM: Artificial sequence
<220> FEATURE:
<223> OTHER INFORMATION: Immunogenic fragment

<400> SEQUENCE: 52

```
Glu Ile Ile Arg Arg Phe Glu Ala Lys Gly Phe Lys Leu Val Ala
```

-continued

```
<210> SEQ ID NO 53
<211> LENGTH: 15
<212> TYPE: PRT
<213> ORGANISM: Artificial sequence
<220> FEATURE:
<223> OTHER INFORMATION: Immunogenic fragment

<400> SEQUENCE: 53

Phe Glu Ala Lys Gly Phe Lys Leu Val Ala Met Lys Phe Met Met
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: Immunogenic fragment

<400> SEQUENCE: 54

Phe Lys Leu Val Ala Met Lys Phe Met Met Ala Ser Glu Asp Leu
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: Immunogenic fragment

<400> SEQUENCE: 55

Lys Phe Met Met Ala Ser Glu Asp Leu Leu Lys Lys His Tyr Ala
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: Immunogenic fragment

<400> SEQUENCE: 56

Leu Lys Lys His Tyr Ala Asp Leu Ala Ala Arg Pro Phe Phe Pro
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: Immunogenic fragment

<400> SEQUENCE: 57

Trp Glu Gly Leu Asn Ala Val Lys Thr Gly Arg Val Met Leu Gly
1               5                   10                  15

<210> SEQ ID NO 58
<211> LENGTH: 15
<212> TYPE: PRT
<213> ORGANISM: Artificial sequence
<220> FEATURE:
<223> OTHER INFORMATION: Immunogenic fragment

<400> SEQUENCE: 58

Ile Thr Arg Leu Arg Glu Ala Met Gly Val Met Gln His His Asp
1               5                   10                  15
```

```
<210> SEQ ID NO 59
<211> LENGTH: 15
<212> TYPE: PRT
<213> ORGANISM: Artificial sequence
<220> FEATURE:
<223> OTHER INFORMATION: Immunogenic fragment

<400> SEQUENCE: 59

Gly Thr Glu Lys Gln His Val Ala Phe Asn Tyr Ala Lys Met Leu
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: Immunogenic fragment

<400> SEQUENCE: 60

His Val Ala Phe Asn Tyr Ala Lys Met Leu Asp Ser Ala Met Leu
1               5                   10                  15

<210> SEQ ID NO 61
<211> LENGTH: 15
<212> TYPE: PRT
<213> ORGANISM: Artificial sequence
<220> FEATURE:
<223> OTHER INFORMATION: Immunogenic fragment

<400> SEQUENCE: 61

Ala Met Leu Gln Cys Arg His Val Ile Ser Glu Ser Tyr Arg Lys
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: Immunogenic fragment

<400> SEQUENCE: 62

Arg His Ile Ile Asn Glu Ser Tyr Lys Lys Leu Leu Pro Lys Ser
1               5                   10                  15

<210> SEQ ID NO 63
<211> LENGTH: 15
<212> TYPE: PRT
<213> ORGANISM: Artificial sequence
<220> FEATURE:
<223> OTHER INFORMATION: Immunogenic fragment

<400> SEQUENCE: 63

Glu Phe Cys Pro Tyr Leu Asn Ile Ser Ser Cys Pro Ser Thr Glu
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: Immunogenic fragment

<400> SEQUENCE: 64

Leu Tyr Asn Pro Leu Gly His Arg Leu Ile Asn His Thr Val Arg
1               5                   10                  15
```

```
<210> SEQ ID NO 65
<211> LENGTH: 15
<212> TYPE: PRT
<213> ORGANISM: Artificial sequence
<220> FEATURE:
<223> OTHER INFORMATION: Immunogenic fragment

<400> SEQUENCE: 65

Leu Ile Ser Ile Pro Glu Phe Val Arg Lys Ile Pro Gly Arg Lys
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Immunogenic fragment

<400> SEQUENCE: 66

Ile Val Gln Glu Val His Gln Gln Phe Asp Ser Phe Val Gly Gln
1               5                   10                  15

<210> SEQ ID NO 67
<211> LENGTH: 15
<212> TYPE: PRT
<213> ORGANISM: Artificial sequence
<220> FEATURE:
<223> OTHER INFORMATION: Immunogenic fragment

<400> SEQUENCE: 67

Leu Met Val His Arg Arg Leu Leu His Asp Asp Tyr Phe Gly Val
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Immunogenic fragment

<400> SEQUENCE: 68

Asp Gly His Gly Ile Val Ile Arg Gly Arg His Leu Leu Leu Leu
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: Immunogenic fragment

<400> SEQUENCE: 69

Glu Pro Ile Ile Ser Phe Thr Ser Ile Glu Ser Asn Lys Gln Ala
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: Immunogenic fragment

<400> SEQUENCE: 70

His Ser Lys Arg Tyr Leu Leu Arg Leu Glu His Phe Tyr Gln Arg
1               5                   10                  15
```

-continued

```
<210> SEQ ID NO 71
<211> LENGTH: 15
<212> TYPE: PRT
<213> ORGANISM: Artificial sequence
<220> FEATURE:
<223> OTHER INFORMATION: Immunogenic fragment

<400> SEQUENCE: 71

Leu Leu Arg Leu Glu His Phe Tyr Gln Arg Phe Glu Asp Pro Ser
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: Immunogenic fragment

<400> SEQUENCE: 72

Lys Arg Tyr Leu Leu Arg Leu Glu His Phe Tyr Gln Ser Asn Glu
1               5                   10                  15

<210> SEQ ID NO 73
<211> LENGTH: 15
<212> TYPE: PRT
<213> ORGANISM: Artificial sequence
<220> FEATURE:
<223> OTHER INFORMATION: Immunogenic fragment

<400> SEQUENCE: 73

Thr Leu Glu Gln Trp His Ser Lys Arg Tyr Leu Leu Arg Leu Glu
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Immunogenic fragment

<400> SEQUENCE: 74

Thr Val Ser Leu Arg His Leu Phe Gln Ser Phe Glu Ile Thr Ala
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Immunogenic fragment

<400> SEQUENCE: 75

Ser Leu Arg His Leu Phe Lys Ser Phe Glu Ile Ile Ala Val Glu
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: Immunogenic fragment

<400> SEQUENCE: 76

Phe Lys Ser Phe Glu Ile Ile Ala Val Glu Glu Leu Thr Leu Gly
1               5                   10                  15

<210> SEQ ID NO 77
```

```
<211> LENGTH: 15
<212> TYPE: PRT
<213> ORGANISM: Artificial sequence
<220> FEATURE:
<223> OTHER INFORMATION: Immunogenic fragment

<400> SEQUENCE: 77

Ala Asn Gln Pro Ile Ser Ser Leu Lys Asn Arg Leu His Tyr Arg
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: Immunogenic fragment

<400> SEQUENCE: 78

Glu Leu Thr Leu Gly Ala Asn Gln Pro Ile Ser Ser Leu Lys Asn
1               5                   10                  15

<210> SEQ ID NO 79
<211> LENGTH: 15
<212> TYPE: PRT
<213> ORGANISM: Artificial sequence
<220> FEATURE:
<223> OTHER INFORMATION: Immunogenic fragment

<400> SEQUENCE: 79

Gly Asn Asp Leu Lys Asn Leu Ser Ser Lys Val Leu Pro Asn Leu
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: Immunogenic fragment

<400> SEQUENCE: 80

Asn Leu Ser Ser Lys Val Leu Pro Asn Leu Asn Val Pro Tyr Cys
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Immunogenic fragment

<400> SEQUENCE: 81

Asp Asp Gly Asn Leu Ile Ser Arg Ala Leu Pro His Leu Gly Val
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: Immunogenic fragment

<400> SEQUENCE: 82

Tyr Ile Gly Tyr Lys Ile Glu Lys His Ser Lys Asn Leu Ile Gln
1               5                   10                  15

<210> SEQ ID NO 83
<211> LENGTH: 15
```

```
<212> TYPE: PRT
<213> ORGANISM: Artificial sequence
<220> FEATURE:
<223> OTHER INFORMATION: Immunogenic fragment

<400> SEQUENCE: 83

Asp Leu Ser Met Thr Lys Leu Lys Arg Val Arg Pro Ser Gly Phe
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: Immunogenic fragment

<400> SEQUENCE: 84

Ile His Gln Leu Asn Asp Gln Val Leu Arg Leu Lys Phe Ile Asp
1               5                   10                  15

<210> SEQ ID NO 85
<211> LENGTH: 15
<212> TYPE: PRT
<213> ORGANISM: Artificial sequence
<220> FEATURE:
<223> OTHER INFORMATION: Immunogenic fragment

<400> SEQUENCE: 85

Asp Gln Val Leu Arg Leu Lys Phe Ile Asp Ala Asn Gln Lys Arg
1               5                   10                  15

<210> SEQ ID NO 86
<211> LENGTH: 15
<212> TYPE: PRT
<213> ORGANISM: Artificial sequence
<220> FEATURE:
<223> OTHER INFORMATION: Immunogenic fragment

<400> SEQUENCE: 86

Arg Leu Tyr Ser Val Glu Leu Asp Gly Ser His Leu Ile Val Arg
1               5                   10                  15

<210> SEQ ID NO 87
<211> LENGTH: 15
<212> TYPE: PRT
<213> ORGANISM: Artificial sequence
<220> FEATURE:
<223> OTHER INFORMATION: Immunogenic fragment

<400> SEQUENCE: 87

Gln Ser Ile Phe Asp Ile Asn Leu Ala Tyr Met Val Tyr Ser Asp
1               5                   10                  15

<210> SEQ ID NO 88
<211> LENGTH: 15
<212> TYPE: PRT
<213> ORGANISM: Artificial sequence
<220> FEATURE:
<223> OTHER INFORMATION: Immunogenic fragment

<400> SEQUENCE: 88

Met Val Tyr Ser Asp Gln Leu Ile His Val Thr Ser Arg Leu Pro
1               5                   10                  15

<210> SEQ ID NO 89
<211> LENGTH: 15
<212> TYPE: PRT
```

```
<213> ORGANISM: Artificial sequence
<220> FEATURE:
<223> OTHER INFORMATION: Immunogenic fragment

<400> SEQUENCE: 89

Arg Ala Pro Phe Arg Lys Asn Thr Asn Trp Lys Arg Tyr Thr Gln
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: Immunogenic fragment

<400> SEQUENCE: 90

Thr Lys Leu Ala Ser Gly Val Phe Leu Phe Asn Ser Asn Ala Met
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: Immunogenic fragment

<400> SEQUENCE: 91

Gly Val Phe Leu Phe Asn Ser Asn Ala Met Asp Ile Leu Thr Gln
1               5                   10                  15

<210> SEQ ID NO 92
<211> LENGTH: 15
<212> TYPE: PRT
<213> ORGANISM: Artificial sequence
<220> FEATURE:
<223> OTHER INFORMATION: Immunogenic fragment

<400> SEQUENCE: 92

Gly Pro Lys Pro Glu Gln Val Val Gln Gln Tyr His Asn Leu Ile
1               5                   10                  15

<210> SEQ ID NO 93
<211> LENGTH: 15
<212> TYPE: PRT
<213> ORGANISM: Artificial sequence
<220> FEATURE:
<223> OTHER INFORMATION: Immunogenic fragment

<400> SEQUENCE: 93

Gln Val Val Gln Gln Tyr His Asn Leu Ile Gly Leu Pro Ala Met
1               5                   10                  15

<210> SEQ ID NO 94
<211> LENGTH: 15
<212> TYPE: PRT
<213> ORGANISM: Artificial sequence
<220> FEATURE:
<223> OTHER INFORMATION: Immunogenic fragment

<400> SEQUENCE: 94

Phe Thr Asn Leu Asn Thr Thr Tyr Thr Arg Asn Arg Ala Val Gly
1               5                   10                  15

<210> SEQ ID NO 95
<211> LENGTH: 15
<212> TYPE: PRT
<213> ORGANISM: Artificial sequence
```

```
<220> FEATURE:
<223> OTHER INFORMATION: Immunogenic fragment

<400> SEQUENCE: 95

Thr Thr Tyr Thr Arg Asn Arg Ala Val Gly Ile Pro Met Asp Val
1               5                   10                  15

<210> SEQ ID NO 96
<211> LENGTH: 15
<212> TYPE: PRT
<213> ORGANISM: Artificial sequence
<220> FEATURE:
<223> OTHER INFORMATION: Immunogenic fragment

<400> SEQUENCE: 96

Leu Pro Asp Phe Ile Arg Asn Val Leu His Lys Asn Gly Gln Lys
1               5                   10                  15

<210> SEQ ID NO 97
<211> LENGTH: 15
<212> TYPE: PRT
<213> ORGANISM: Artificial sequence
<220> FEATURE:
<223> OTHER INFORMATION: Immunogenic fragment

<400> SEQUENCE: 97

Asn Ala Thr Glu Tyr Trp Met Asp Met Phe Ala Glu Tyr His Lys
1               5                   10                  15

<210> SEQ ID NO 98
<211> LENGTH: 15
<212> TYPE: PRT
<213> ORGANISM: Artificial sequence
<220> FEATURE:
<223> OTHER INFORMATION: Immunogenic fragment

<400> SEQUENCE: 98

Trp Met Asp Met Phe Ala Glu Tyr His Lys Thr Ile Ala Phe Asp
1               5                   10                  15

<210> SEQ ID NO 99
<211> LENGTH: 15
<212> TYPE: PRT
<213> ORGANISM: Artificial sequence
<220> FEATURE:
<223> OTHER INFORMATION: Immunogenic fragment

<400> SEQUENCE: 99

Ala Glu Tyr His Lys Thr Ile Ala Phe Asp Gly Ala Trp Leu Asp
1               5                   10                  15

<210> SEQ ID NO 100
<211> LENGTH: 15
<212> TYPE: PRT
<213> ORGANISM: Artificial sequence
<220> FEATURE:
<223> OTHER INFORMATION: Immunogenic fragment

<400> SEQUENCE: 100

Thr Leu Arg His Lys Thr Leu Cys Met Thr Ala Arg His Tyr Asn
1               5                   10                  15

<210> SEQ ID NO 101
<211> LENGTH: 15
<212> TYPE: PRT
<213> ORGANISM: Artificial sequence
<220> FEATURE:
```

<223> OTHER INFORMATION: Immunogenic fragment

<400> SEQUENCE: 101

Arg His Tyr Asn Asp Gln Leu His Tyr Asn Leu His Asn Leu Tyr
1               5                   10                  15

<210> SEQ ID NO 102
<211> LENGTH: 15
<212> TYPE: PRT
<213> ORGANISM: Artificial sequence
<220> FEATURE:
<223> OTHER INFORMATION: Immunogenic fragment

<400> SEQUENCE: 102

Gln Leu His Tyr Asn Leu His Asn Leu Tyr Gly Phe Gln Glu Ala
1               5                   10                  15

<210> SEQ ID NO 103
<211> LENGTH: 15
<212> TYPE: PRT
<213> ORGANISM: Artificial sequence
<220> FEATURE:
<223> OTHER INFORMATION: Immunogenic fragment

<400> SEQUENCE: 103

Gln Leu His Tyr Asn Leu His Asn Leu Tyr Ser Leu Ser Met Ala
1               5                   10                  15

<210> SEQ ID NO 104
<211> LENGTH: 15
<212> TYPE: PRT
<213> ORGANISM: Artificial sequence
<220> FEATURE:
<223> OTHER INFORMATION: Immunogenic fragment

<400> SEQUENCE: 104

Leu His Asn Leu Tyr Ser Leu Ser Met Ala Met Ala Thr Asn Ala
1               5                   10                  15

<210> SEQ ID NO 105
<211> LENGTH: 15
<212> TYPE: PRT
<213> ORGANISM: Artificial sequence
<220> FEATURE:
<223> OTHER INFORMATION: Immunogenic fragment

<400> SEQUENCE: 105

Ser Leu Ser Met Ala Met Ala Thr Asn Ala Ala Leu Thr Lys Leu
1               5                   10                  15

<210> SEQ ID NO 106
<211> LENGTH: 15
<212> TYPE: PRT
<213> ORGANISM: Artificial sequence
<220> FEATURE:
<223> OTHER INFORMATION: Immunogenic fragment

<400> SEQUENCE: 106

Ala Ala Leu Thr Lys Leu Asn Lys Arg Pro Phe Ile Ile Ser Arg
1               5                   10                  15

<210> SEQ ID NO 107
<211> LENGTH: 15
<212> TYPE: PRT
<213> ORGANISM: Artificial sequence
<220> FEATURE:
<223> OTHER INFORMATION: Immunogenic fragment

```
<400> SEQUENCE: 107

Asn Glu Ala Leu Lys Thr Thr Leu Asn Lys Arg Pro Phe Ile Ile
1               5                   10                  15

<210> SEQ ID NO 108
<211> LENGTH: 15
<212> TYPE: PRT
<213> ORGANISM: Artificial sequence
<220> FEATURE:
<223> OTHER INFORMATION: Immunogenic fragment

<400> SEQUENCE: 108

Asn Lys Arg Pro Phe Ile Ile Ser Arg Ala Thr Ala Pro Gly His
1               5                   10                  15

<210> SEQ ID NO 109
<211> LENGTH: 15
<212> TYPE: PRT
<213> ORGANISM: Artificial sequence
<220> FEATURE:
<223> OTHER INFORMATION: Immunogenic fragment

<400> SEQUENCE: 109

His Trp Asn Gly Asp Ile Leu Ser Asp Trp Ser Ser Met Arg Trp
1               5                   10                  15

<210> SEQ ID NO 110
<211> LENGTH: 15
<212> TYPE: PRT
<213> ORGANISM: Artificial sequence
<220> FEATURE:
<223> OTHER INFORMATION: Immunogenic fragment

<400> SEQUENCE: 110

Ile Leu Ser Asp Trp Ser Ser Met Arg Trp Thr Ile Pro Ser Ile
1               5                   10                  15

<210> SEQ ID NO 111
<211> LENGTH: 15
<212> TYPE: PRT
<213> ORGANISM: Artificial sequence
<220> FEATURE:
<223> OTHER INFORMATION: Immunogenic fragment

<400> SEQUENCE: 111

Ser Ser Met Arg Trp Thr Ile Pro Ser Ile Leu Asn Phe Asn Met
1               5                   10                  15

<210> SEQ ID NO 112
<211> LENGTH: 15
<212> TYPE: PRT
<213> ORGANISM: Artificial sequence
<220> FEATURE:
<223> OTHER INFORMATION: Immunogenic fragment

<400> SEQUENCE: 112

Pro Ser Ile Leu Asn Phe Asn Leu Phe Gly Val Pro Met Ile Gly
1               5                   10                  15

<210> SEQ ID NO 113
<211> LENGTH: 15
<212> TYPE: PRT
<213> ORGANISM: Artificial sequence
<220> FEATURE:
<223> OTHER INFORMATION: Immunogenic fragment
```

```
<400> SEQUENCE: 113

Leu Cys Ile Arg Trp Tyr Gln Leu Gly Ala Phe Tyr Ser Phe Ala
1               5                   10                  15

<210> SEQ ID NO 114
<211> LENGTH: 15
<212> TYPE: PRT
<213> ORGANISM: Artificial sequence
<220> FEATURE:
<223> OTHER INFORMATION: Immunogenic fragment

<400> SEQUENCE: 114

Tyr Gln Leu Gly Ala Phe Tyr Ser Phe Ala Arg Asn His Asn Asp
1               5                   10                  15

<210> SEQ ID NO 115
<211> LENGTH: 15
<212> TYPE: PRT
<213> ORGANISM: Artificial sequence
<220> FEATURE:
<223> OTHER INFORMATION: Immunogenic fragment

<400> SEQUENCE: 115

Ala Phe Tyr Ser Phe Val Arg Asn His Asn Thr Asp Asn Ala Ile
1               5                   10                  15

<210> SEQ ID NO 116
<211> LENGTH: 15
<212> TYPE: PRT
<213> ORGANISM: Artificial sequence
<220> FEATURE:
<223> OTHER INFORMATION: Immunogenic fragment

<400> SEQUENCE: 116

Leu Gly Glu Ser Val Ile Arg Ala Ala Arg Ser Ser Leu Gln Tyr
1               5                   10                  15

<210> SEQ ID NO 117
<211> LENGTH: 15
<212> TYPE: PRT
<213> ORGANISM: Artificial sequence
<220> FEATURE:
<223> OTHER INFORMATION: Immunogenic fragment

<400> SEQUENCE: 117

Ile Arg Ala Ala Arg Ser Ser Leu Gln Tyr Arg Tyr Arg Phe Leu
1               5                   10                  15

<210> SEQ ID NO 118
<211> LENGTH: 15
<212> TYPE: PRT
<213> ORGANISM: Artificial sequence
<220> FEATURE:
<223> OTHER INFORMATION: Immunogenic fragment

<400> SEQUENCE: 118

Ser Ser Leu Gln Tyr Arg Tyr Arg Phe Leu Ala His Leu Tyr Thr
1               5                   10                  15

<210> SEQ ID NO 119
<211> LENGTH: 15
<212> TYPE: PRT
<213> ORGANISM: Artificial sequence
<220> FEATURE:
<223> OTHER INFORMATION: Immunogenic fragment

<400> SEQUENCE: 119
```

Arg Tyr Arg Phe Leu Ala His Leu Tyr Thr Leu Phe Tyr His Val
1               5                   10                  15

<210> SEQ ID NO 120
<211> LENGTH: 15
<212> TYPE: PRT
<213> ORGANISM: Artificial sequence
<220> FEATURE:
<223> OTHER INFORMATION: Immunogenic fragment

<400> SEQUENCE: 120

Ala His Leu Tyr Thr Leu Phe Tyr His Val His Lys Asn Gly Gly
1               5                   10                  15

<210> SEQ ID NO 121
<211> LENGTH: 15
<212> TYPE: PRT
<213> ORGANISM: Artificial sequence
<220> FEATURE:
<223> OTHER INFORMATION: Immunogenic fragment

<400> SEQUENCE: 121

Asp Ile Glu Thr Gln Phe Met Trp Gly Asp Ser Met Leu Ile Ala
1               5                   10                  15

<210> SEQ ID NO 122
<211> LENGTH: 15
<212> TYPE: PRT
<213> ORGANISM: Artificial sequence
<220> FEATURE:
<223> OTHER INFORMATION: Immunogenic fragment

<400> SEQUENCE: 122

Phe Met Trp Gly Asp Ser Met Leu Ile Ala Pro Ile Leu Tyr Pro
1               5                   10                  15

<210> SEQ ID NO 123
<211> LENGTH: 15
<212> TYPE: PRT
<213> ORGANISM: Artificial sequence
<220> FEATURE:
<223> OTHER INFORMATION: Immunogenic fragment

<400> SEQUENCE: 123

Tyr Asp Asp Ile Asp Tyr Val Phe Val Arg Gly Gly Ser Ile Ile
1               5                   10                  15

<210> SEQ ID NO 124
<211> LENGTH: 15
<212> TYPE: PRT
<213> ORGANISM: Artificial sequence
<220> FEATURE:
<223> OTHER INFORMATION: Immunogenic fragment

<400> SEQUENCE: 124

Asp Ile Asn Tyr Val Phe Phe Arg Ser Gly Ser Ile Ile Pro Ile
1               5                   10                  15

<210> SEQ ID NO 125
<211> LENGTH: 15
<212> TYPE: PRT
<213> ORGANISM: Artificial sequence
<220> FEATURE:
<223> OTHER INFORMATION: Immunogenic fragment

<400> SEQUENCE: 125

Phe Phe Arg Ser Gly Ser Ile Ile Pro Ile Gln Gly Pro Gln Asn
1               5                   10                  15

<210> SEQ ID NO 126
<211> LENGTH: 15
<212> TYPE: PRT
<213> ORGANISM: Artificial sequence
<220> FEATURE:
<223> OTHER INFORMATION: Immunogenic fragment

<400> SEQUENCE: 126

Thr Gln Asn Ile Asn Phe Ile Asn Ile Leu Gly Val Pro Lys Leu
1               5                   10                  15

<210> SEQ ID NO 127
<211> LENGTH: 15
<212> TYPE: PRT
<213> ORGANISM: Artificial sequence
<220> FEATURE:
<223> OTHER INFORMATION: Immunogenic fragment

<400> SEQUENCE: 127

Ser Gln His Leu Gly Tyr Gln Thr Asn Gln Ser Ile Ile Ile Leu
1               5                   10                  15

<210> SEQ ID NO 128
<211> LENGTH: 15
<212> TYPE: PRT
<213> ORGANISM: Artificial sequence
<220> FEATURE:
<223> OTHER INFORMATION: Immunogenic fragment

<400> SEQUENCE: 128

Tyr Gln Thr Asn Gln Ser Ile Ile Ile Leu Glu Ile Leu Gly Ile
1               5                   10                  15

<210> SEQ ID NO 129
<211> LENGTH: 15
<212> TYPE: PRT
<213> ORGANISM: Artificial sequence
<220> FEATURE:
<223> OTHER INFORMATION: Immunogenic fragment

<400> SEQUENCE: 129

Ile Asn Ile Leu Gly Val Pro Lys Leu Pro Thr Ser Phe Lys Leu
1               5                   10                  15

<210> SEQ ID NO 130
<211> LENGTH: 15
<212> TYPE: PRT
<213> ORGANISM: Artificial sequence
<220> FEATURE:
<223> OTHER INFORMATION: Immunogenic fragment

<400> SEQUENCE: 130

Ser Ile Ile Phe Asp Gly Lys Pro Tyr Tyr Gln Phe Ile Tyr Thr
1               5                   10                  15

<210> SEQ ID NO 131
<211> LENGTH: 15
<212> TYPE: PRT
<213> ORGANISM: Artificial sequence
<220> FEATURE:
<223> OTHER INFORMATION: Immunogenic fragment

<400> SEQUENCE: 131

Pro Arg Ile Ile Arg Phe Asn Tyr Asp Glu Gln Thr Asn Ile Leu

```
                1               5                  10                  15

<210> SEQ ID NO 132
<211> LENGTH: 15
<212> TYPE: PRT
<213> ORGANISM: Artificial sequence
<220> FEATURE:
<223> OTHER INFORMATION: Immunogenic fragment

<400> SEQUENCE: 132

Gly Lys Pro Tyr Tyr Gln Phe Ile Tyr Thr Thr Asn Asn Met Leu
1               5                  10                  15

<210> SEQ ID NO 133
<211> LENGTH: 15
<212> TYPE: PRT
<213> ORGANISM: Artificial sequence
<220> FEATURE:
<223> OTHER INFORMATION: Immunogenic fragment

<400> SEQUENCE: 133

Gln Phe Ile Tyr Thr Thr Asn Asn Met Leu Ile Ile Gln Thr Lys
1               5                  10                  15

<210> SEQ ID NO 134
<211> LENGTH: 15
<212> TYPE: PRT
<213> ORGANISM: Artificial sequence
<220> FEATURE:
<223> OTHER INFORMATION: Immunogenic fragment

<400> SEQUENCE: 134

Thr Asn Asn Met Leu Ile Ile Gln Thr Lys Leu Ser Ile Phe Asn
1               5                  10                  15

<210> SEQ ID NO 135
<211> LENGTH: 15
<212> TYPE: PRT
<213> ORGANISM: Artificial sequence
<220> FEATURE:
<223> OTHER INFORMATION: Immunogenic fragment

<400> SEQUENCE: 135

Ile Ile Gln Thr Lys Leu Ser Ile Phe Asn Asp Asn Asp Lys Ser
1               5                  10                  15

<210> SEQ ID NO 136
<211> LENGTH: 15
<212> TYPE: PRT
<213> ORGANISM: Artificial sequence
<220> FEATURE:
<223> OTHER INFORMATION: Immunogenic fragment

<400> SEQUENCE: 136

Asp Lys Ser Lys Lys Ile His Tyr Gln Phe Glu Trp Lys Phe Asn
1               5                  10                  15

<210> SEQ ID NO 137
<211> LENGTH: 15
<212> TYPE: PRT
<213> ORGANISM: Artificial sequence
<220> FEATURE:
<223> OTHER INFORMATION: Immunogenic fragment

<400> SEQUENCE: 137

His Asp Asn Thr Glu Leu Met Lys Thr Lys Asp Phe Leu Leu Ile
1               5                  10                  15
```

<210> SEQ ID NO 138
<211> LENGTH: 15
<212> TYPE: PRT
<213> ORGANISM: Artificial sequence
<220> FEATURE:
<223> OTHER INFORMATION: Immunogenic fragment

<400> SEQUENCE: 138

Tyr His Asn Leu Ile Gly Leu Pro Ala Met Pro Pro Phe Trp Ser
1               5                   10                  15

<210> SEQ ID NO 139
<211> LENGTH: 15
<212> TYPE: PRT
<213> ORGANISM: Artificial sequence
<220> FEATURE:
<223> OTHER INFORMATION: Immunogenic fragment

<400> SEQUENCE: 139

Glu Leu Asn Phe Lys Val Tyr Glu Asp Ala Ala Ala Leu Ala Lys
1               5                   10                  15

<210> SEQ ID NO 140
<211> LENGTH: 15
<212> TYPE: PRT
<213> ORGANISM: Artificial sequence
<220> FEATURE:
<223> OTHER INFORMATION: Immunogenic fragment

<400> SEQUENCE: 140

Glu Asp Gly Leu Ile Tyr Asn Ile Ala Ser Arg Glu Lys Ala Asp
1               5                   10                  15

<210> SEQ ID NO 141
<211> LENGTH: 15
<212> TYPE: PRT
<213> ORGANISM: Artificial sequence
<220> FEATURE:
<223> OTHER INFORMATION: Immunogenic fragment

<400> SEQUENCE: 141

Lys His Glu Ile Phe Val Val Ala Asp Leu Ile Asp Arg Lys Ser
1               5                   10                  15

<210> SEQ ID NO 142
<211> LENGTH: 15
<212> TYPE: PRT
<213> ORGANISM: Artificial sequence
<220> FEATURE:
<223> OTHER INFORMATION: Immunogenic fragment

<400> SEQUENCE: 142

Asp Lys Lys Phe Leu Phe Asn Thr Ala Val Leu Phe Asp Arg Gln
1               5                   10                  15

<210> SEQ ID NO 143
<211> LENGTH: 15
<212> TYPE: PRT
<213> ORGANISM: Artificial sequence
<220> FEATURE:
<223> OTHER INFORMATION: Immunogenic fragment

<400> SEQUENCE: 143

Phe Asn Thr Ala Val Leu Phe Asp Arg Gln Gly Lys Leu Leu Gly
1               5                   10                  15

<210> SEQ ID NO 144
<211> LENGTH: 15
<212> TYPE: PRT
<213> ORGANISM: Artificial sequence
<220> FEATURE:
<223> OTHER INFORMATION: Immunogenic fragment

<400> SEQUENCE: 144

Arg Tyr His Lys Met His Leu Phe Gly Glu Met Thr Met Asn Ile
1               5                   10                  15

<210> SEQ ID NO 145
<211> LENGTH: 15
<212> TYPE: PRT
<213> ORGANISM: Artificial sequence
<220> FEATURE:
<223> OTHER INFORMATION: Immunogenic fragment

<400> SEQUENCE: 145

Pro Pro Lys Pro Glu Leu Leu Val Ile Asp Thr Glu Leu Gly Arg
1               5                   10                  15

<210> SEQ ID NO 146
<211> LENGTH: 15
<212> TYPE: PRT
<213> ORGANISM: Artificial sequence
<220> FEATURE:
<223> OTHER INFORMATION: Immunogenic fragment

<400> SEQUENCE: 146

Leu Leu Val Ile Asp Thr Glu Leu Gly Arg Leu Gly Met Gln Ile
1               5                   10                  15

<210> SEQ ID NO 147
<211> LENGTH: 15
<212> TYPE: PRT
<213> ORGANISM: Artificial sequence
<220> FEATURE:
<223> OTHER INFORMATION: Immunogenic fragment

<400> SEQUENCE: 147

Leu Gly Met Gln Ile Cys Phe Asp Met Ile Phe Lys Thr Pro Gly
1               5                   10                  15

<210> SEQ ID NO 148
<211> LENGTH: 15
<212> TYPE: PRT
<213> ORGANISM: Artificial sequence
<220> FEATURE:
<223> OTHER INFORMATION: Immunogenic fragment

<400> SEQUENCE: 148

Thr Trp Trp Phe Asp Glu Ala Pro Met Leu Ser Ser Ser Gln Tyr
1               5                   10                  15

<210> SEQ ID NO 149
<211> LENGTH: 15
<212> TYPE: PRT
<213> ORGANISM: Artificial sequence
<220> FEATURE:
<223> OTHER INFORMATION: Immunogenic fragment

<400> SEQUENCE: 149

Ser Ser Ser Gln Tyr Gln Met Ala Trp Ala Phe Gly Asn Asn Val
1               5                   10                  15

```
<210> SEQ ID NO 150
<211> LENGTH: 15
<212> TYPE: PRT
<213> ORGANISM: Artificial sequence
<220> FEATURE:
<223> OTHER INFORMATION: Immunogenic fragment

<400> SEQUENCE: 150

Glu Leu Asn Ser Arg Phe Val Tyr Ala Lys Leu Arg Gly Ala Phe
1               5                   10                  15

<210> SEQ ID NO 151
<211> LENGTH: 15
<212> TYPE: PRT
<213> ORGANISM: Artificial sequence
<220> FEATURE:
<223> OTHER INFORMATION: Immunogenic fragment

<400> SEQUENCE: 151

Phe Val Tyr Ala Lys Leu Arg Gly Ala Phe Ser Glu Ser Thr Ala
1               5                   10                  15

<210> SEQ ID NO 152
<211> LENGTH: 15
<212> TYPE: PRT
<213> ORGANISM: Artificial sequence
<220> FEATURE:
<223> OTHER INFORMATION: Immunogenic fragment

<400> SEQUENCE: 152

Leu Arg Gly Ala Phe Ser Glu Ser Thr Ala Val Tyr Pro Ser Ala
1               5                   10                  15

<210> SEQ ID NO 153
<211> LENGTH: 15
<212> TYPE: PRT
<213> ORGANISM: Artificial sequence
<220> FEATURE:
<223> OTHER INFORMATION: Immunogenic fragment

<400> SEQUENCE: 153

Gly Thr Trp Ala Phe Tyr Arg Pro Ala Ser Gly Lys Phe Gln Ala
1               5                   10                  15

<210> SEQ ID NO 154
<211> LENGTH: 15
<212> TYPE: PRT
<213> ORGANISM: Artificial sequence
<220> FEATURE:
<223> OTHER INFORMATION: Immunogenic fragment

<400> SEQUENCE: 154

Asn Leu Cys Thr His Ile Met Tyr Gly Phe Ala Lys Leu Gln Asn
1               5                   10                  15

<210> SEQ ID NO 155
<211> LENGTH: 15
<212> TYPE: PRT
<213> ORGANISM: Artificial sequence
<220> FEATURE:
<223> OTHER INFORMATION: Immunogenic fragment

<400> SEQUENCE: 155

Ile Met Tyr Gly Phe Ala Lys Leu Gln Asn Asn Lys Ile Ala Leu
1               5                   10                  15

<210> SEQ ID NO 156
```

<211> LENGTH: 15
<212> TYPE: PRT
<213> ORGANISM: Artificial sequence
<220> FEATURE:
<223> OTHER INFORMATION: Immunogenic fragment

<400> SEQUENCE: 156

Leu Gln Trp Gly His Gly Met Ile Arg Arg Met Val Asn Leu Arg
1               5                   10                  15

<210> SEQ ID NO 157
<211> LENGTH: 15
<212> TYPE: PRT
<213> ORGANISM: Artificial sequence
<220> FEATURE:
<223> OTHER INFORMATION: Immunogenic fragment

<400> SEQUENCE: 157

Gly Met Ile Arg Arg Met Val Asn Leu Arg Thr Tyr Asn Pro His
1               5                   10                  15

<210> SEQ ID NO 158
<211> LENGTH: 15
<212> TYPE: PRT
<213> ORGANISM: Artificial sequence
<220> FEATURE:
<223> OTHER INFORMATION: Immunogenic fragment

<400> SEQUENCE: 158

Met Val Asn Leu Arg Thr Tyr Asn Pro His Leu Thr Thr Met Ile
1               5                   10                  15

<210> SEQ ID NO 159
<211> LENGTH: 15
<212> TYPE: PRT
<213> ORGANISM: Artificial sequence
<220> FEATURE:
<223> OTHER INFORMATION: Immunogenic fragment

<400> SEQUENCE: 159

Lys Tyr Ser Ile Met Val Arg Asp Pro Ala Ser Arg Lys Ile Phe
1               5                   10                  15

<210> SEQ ID NO 160
<211> LENGTH: 15
<212> TYPE: PRT
<213> ORGANISM: Artificial sequence
<220> FEATURE:
<223> OTHER INFORMATION: Immunogenic fragment

<400> SEQUENCE: 160

Ser Arg Lys Ile Phe Ile Gln Ser Val Leu His Leu Leu Ala Glu
1               5                   10                  15

<210> SEQ ID NO 161
<211> LENGTH: 15
<212> TYPE: PRT
<213> ORGANISM: Artificial sequence
<220> FEATURE:
<223> OTHER INFORMATION: Immunogenic fragment

<400> SEQUENCE: 161

Ile Gln Ser Val Leu His Leu Leu Ala Glu Phe Asp Leu Asp Gly
1               5                   10                  15

<210> SEQ ID NO 162
<211> LENGTH: 15

```
<212> TYPE: PRT
<213> ORGANISM: Artificial sequence
<220> FEATURE:
<223> OTHER INFORMATION: Immunogenic fragment

<400> SEQUENCE: 162

Lys Glu Asp Phe Val Thr Leu Leu Arg Glu Leu His Glu Ala Phe
1               5                   10                  15

<210> SEQ ID NO 163
<211> LENGTH: 15
<212> TYPE: PRT
<213> ORGANISM: Artificial sequence
<220> FEATURE:
<223> OTHER INFORMATION: Immunogenic fragment

<400> SEQUENCE: 163

Gln Pro His Gly Tyr Val Leu Ser Ser Ala Val Ser Ala Gly Lys
1               5                   10                  15

<210> SEQ ID NO 164
<211> LENGTH: 15
<212> TYPE: PRT
<213> ORGANISM: Artificial sequence
<220> FEATURE:
<223> OTHER INFORMATION: Immunogenic fragment

<400> SEQUENCE: 164

Glu Val Ser Lys Tyr Leu Asp Phe Ile Asn Leu Met Ser Tyr Asp
1               5                   10                  15

<210> SEQ ID NO 165
<211> LENGTH: 15
<212> TYPE: PRT
<213> ORGANISM: Artificial sequence
<220> FEATURE:
<223> OTHER INFORMATION: Immunogenic fragment

<400> SEQUENCE: 165

Leu Asp Phe Ile Asn Leu Met Ser Tyr Asp Tyr His Gly Gly Trp
1               5                   10                  15

<210> SEQ ID NO 166
<211> LENGTH: 15
<212> TYPE: PRT
<213> ORGANISM: Artificial sequence
<220> FEATURE:
<223> OTHER INFORMATION: Immunogenic fragment

<400> SEQUENCE: 166

Lys Glu Phe Thr Val Thr Tyr Ser Val Glu Tyr Trp Leu Asn His
1               5                   10                  15

<210> SEQ ID NO 167
<211> LENGTH: 15
<212> TYPE: PRT
<213> ORGANISM: Artificial sequence
<220> FEATURE:
<223> OTHER INFORMATION: Immunogenic fragment

<400> SEQUENCE: 167

Gly Val Asp Pro Lys Lys Leu Val Leu Gly Ile Pro Leu Tyr Gly
1               5                   10                  15

<210> SEQ ID NO 168
<211> LENGTH: 15
<212> TYPE: PRT
```

```
<213> ORGANISM: Artificial sequence
<220> FEATURE:
<223> OTHER INFORMATION: Immunogenic fragment

<400> SEQUENCE: 168

Leu Tyr Gly Arg Thr Phe Thr Leu Ala Gly Ser Glu His Gly Ile
1               5                   10                  15

<210> SEQ ID NO 169
<211> LENGTH: 15
<212> TYPE: PRT
<213> ORGANISM: Artificial sequence
<220> FEATURE:
<223> OTHER INFORMATION: Immunogenic fragment

<400> SEQUENCE: 169

Glu Lys Leu Asn Leu Leu Met Ala Lys His Leu Gly Gly Ala Met
1               5                   10                  15

<210> SEQ ID NO 170
<211> LENGTH: 15
<212> TYPE: PRT
<213> ORGANISM: Artificial sequence
<220> FEATURE:
<223> OTHER INFORMATION: Immunogenic fragment

<400> SEQUENCE: 170

Gly Asn Cys Val Gly Val Lys Tyr Pro Leu Leu Arg Ser Ile Ser
1               5                   10                  15

<210> SEQ ID NO 171
<211> LENGTH: 15
<212> TYPE: PRT
<213> ORGANISM: Artificial sequence
<220> FEATURE:
<223> OTHER INFORMATION: Immunogenic fragment

<400> SEQUENCE: 171

Val Lys Tyr Pro Leu Leu Arg Ser Ile Ser Lys Lys Leu Asn Asn
1               5                   10                  15

<210> SEQ ID NO 172
<211> LENGTH: 15
<212> TYPE: PRT
<213> ORGANISM: Artificial sequence
<220> FEATURE:
<223> OTHER INFORMATION: Immunogenic fragment

<400> SEQUENCE: 172

His Gly Lys Phe Gln Cys His Gln Ala Gly Phe Phe Ala Asp Pro
1               5                   10                  15

<210> SEQ ID NO 173
<211> LENGTH: 15
<212> TYPE: PRT
<213> ORGANISM: Artificial sequence
<220> FEATURE:
<223> OTHER INFORMATION: Immunogenic fragment

<400> SEQUENCE: 173

Gly Leu Trp Leu Phe Glu Glu Ser Thr Pro Ile Asn Asp Arg Thr
1               5                   10                  15

<210> SEQ ID NO 174
<211> LENGTH: 15
<212> TYPE: PRT
<213> ORGANISM: Artificial sequence
```

```
<220> FEATURE:
<223> OTHER INFORMATION: Immunogenic fragment

<400> SEQUENCE: 174

Thr Lys Lys Ile Tyr Val Arg Leu Asp Phe Pro Asn Thr Ala Val
1               5                   10                  15

<210> SEQ ID NO 175
<211> LENGTH: 15
<212> TYPE: PRT
<213> ORGANISM: Artificial sequence
<220> FEATURE:
<223> OTHER INFORMATION: Immunogenic fragment

<400> SEQUENCE: 175

Leu Ile Tyr Asn Gln Gly Phe Glu Val Ile Ile Asn Tyr Arg Lys
1               5                   10                  15

<210> SEQ ID NO 176
<211> LENGTH: 15
<212> TYPE: PRT
<213> ORGANISM: Artificial sequence
<220> FEATURE:
<223> OTHER INFORMATION: Immunogenic fragment

<400> SEQUENCE: 176

Gly Phe Glu Val Ile Ile Asn Tyr Arg Lys Tyr Phe Ala Phe Ser
1               5                   10                  15

<210> SEQ ID NO 177
<211> LENGTH: 15
<212> TYPE: PRT
<213> ORGANISM: Artificial sequence
<220> FEATURE:
<223> OTHER INFORMATION: Immunogenic fragment

<400> SEQUENCE: 177

Ile Asn Tyr Arg Lys Tyr Phe Ala Phe Ser Ala Tyr Glu Arg Lys
1               5                   10                  15

<210> SEQ ID NO 178
<211> LENGTH: 15
<212> TYPE: PRT
<213> ORGANISM: Artificial sequence
<220> FEATURE:
<223> OTHER INFORMATION: Immunogenic fragment

<400> SEQUENCE: 178

Tyr Phe Ala Phe Ser Ala Tyr Glu Arg Lys Ser Asn Ser Lys Val
1               5                   10                  15

<210> SEQ ID NO 179
<211> LENGTH: 15
<212> TYPE: PRT
<213> ORGANISM: Artificial sequence
<220> FEATURE:
<223> OTHER INFORMATION: Immunogenic fragment

<400> SEQUENCE: 179

Ala Met Leu Glu Ala Arg Ile Arg Ile Ala Thr Asn Asn Thr Ala
1               5                   10                  15

<210> SEQ ID NO 180
<211> LENGTH: 15
<212> TYPE: PRT
<213> ORGANISM: Artificial sequence
<220> FEATURE:
```

```
<223> OTHER INFORMATION: Immunogenic fragment

<400> SEQUENCE: 180

Asp Gly Gly Phe Gly Tyr Leu Ile Ala Gly Lys Tyr Ala Gln Asp
1               5                   10                  15

<210> SEQ ID NO 181
<211> LENGTH: 15
<212> TYPE: PRT
<213> ORGANISM: Artificial sequence
<220> FEATURE:
<223> OTHER INFORMATION: Immunogenic fragment

<400> SEQUENCE: 181

Thr Tyr Thr Ile Lys Tyr Asn Tyr Leu Gly Gly Tyr Phe Gly Ala
1               5                   10                  15

<210> SEQ ID NO 182
<211> LENGTH: 15
<212> TYPE: PRT
<213> ORGANISM: Artificial sequence
<220> FEATURE:
<223> OTHER INFORMATION: Immunogenic fragment

<400> SEQUENCE: 182

Met Arg Ile Glu Leu Val Lys Asn Gly Pro Ile Ala Val Gly Phe
1               5                   10                  15

<210> SEQ ID NO 183
<211> LENGTH: 15
<212> TYPE: PRT
<213> ORGANISM: Artificial sequence
<220> FEATURE:
<223> OTHER INFORMATION: Immunogenic fragment

<400> SEQUENCE: 183

Ile Ala Val Gly Phe Glu Val Tyr Lys Asp Phe Met Thr Tyr Arg
1               5                   10                  15

<210> SEQ ID NO 184
<211> LENGTH: 15
<212> TYPE: PRT
<213> ORGANISM: Artificial sequence
<220> FEATURE:
<223> OTHER INFORMATION: Immunogenic fragment

<400> SEQUENCE: 184

Glu Val Tyr Lys Asp Phe Met Thr Tyr Arg Arg Gly Ile Tyr Ser
1               5                   10                  15

<210> SEQ ID NO 185
<211> LENGTH: 15
<212> TYPE: PRT
<213> ORGANISM: Artificial sequence
<220> FEATURE:
<223> OTHER INFORMATION: Immunogenic fragment

<400> SEQUENCE: 185

Asp Ala Val Val Tyr Tyr Gly Gln Ala Lys Ser Ser Phe Asp Gln
1               5                   10                  15

<210> SEQ ID NO 186
<211> LENGTH: 15
<212> TYPE: PRT
<213> ORGANISM: Artificial sequence
<220> FEATURE:
<223> OTHER INFORMATION: Immunogenic fragment
```

```
<400> SEQUENCE: 186

Gly Asp Leu Gly Tyr Val Asn Glu Gln Ser Leu Pro Tyr Leu Lys
1               5                   10                  15

<210> SEQ ID NO 187
<211> LENGTH: 15
<212> TYPE: PRT
<213> ORGANISM: Artificial sequence
<220> FEATURE:
<223> OTHER INFORMATION: Immunogenic fragment

<400> SEQUENCE: 187

His Phe Met Arg Ser Ile Glu Pro Val Ala Ser Lys Val Ala Tyr
1               5                   10                  15

<210> SEQ ID NO 188
<211> LENGTH: 15
<212> TYPE: PRT
<213> ORGANISM: Artificial sequence
<220> FEATURE:
<223> OTHER INFORMATION: Immunogenic fragment

<400> SEQUENCE: 188

Tyr Asp Ser Arg Phe Ser Met Ile Gly Asp Arg Ser Gln Pro Ile
1               5                   10                  15

<210> SEQ ID NO 189
<211> LENGTH: 15
<212> TYPE: PRT
<213> ORGANISM: Artificial sequence
<220> FEATURE:
<223> OTHER INFORMATION: Immunogenic fragment

<400> SEQUENCE: 189

Asn His Phe His Ser Met Thr Ile Gly Pro Ala Thr Ile Ile Leu
1               5                   10                  15

<210> SEQ ID NO 190
<211> LENGTH: 15
<212> TYPE: PRT
<213> ORGANISM: Artificial sequence
<220> FEATURE:
<223> OTHER INFORMATION: Immunogenic fragment

<400> SEQUENCE: 190

Ala Thr Ile Ile Leu Phe Ser Thr Glu Tyr Tyr Tyr Tyr Thr Lys
1               5                   10                  15

<210> SEQ ID NO 191
<211> LENGTH: 15
<212> TYPE: PRT
<213> ORGANISM: Artificial sequence
<220> FEATURE:
<223> OTHER INFORMATION: Immunogenic fragment

<400> SEQUENCE: 191

Lys His Pro Trp Ile Ile Val Met Gly His Arg Pro Leu Tyr Cys
1               5                   10                  15

<210> SEQ ID NO 192
<211> LENGTH: 15
<212> TYPE: PRT
<213> ORGANISM: Artificial sequence
<220> FEATURE:
<223> OTHER INFORMATION: Immunogenic fragment
```

<400> SEQUENCE: 192

Gln Tyr Gly Leu Glu Asp Leu Phe Phe Lys Tyr Gly Val Asp Ile
1               5                   10                  15

<210> SEQ ID NO 193
<211> LENGTH: 15
<212> TYPE: PRT
<213> ORGANISM: Artificial sequence
<220> FEATURE:
<223> OTHER INFORMATION: Immunogenic fragment

<400> SEQUENCE: 193

Asp Leu Phe Phe Lys Tyr Gly Val Asp Ile Gln Phe Tyr Gly His
1               5                   10                  15

<210> SEQ ID NO 194
<211> LENGTH: 15
<212> TYPE: PRT
<213> ORGANISM: Artificial sequence
<220> FEATURE:
<223> OTHER INFORMATION: Immunogenic fragment

<400> SEQUENCE: 194

Glu His Phe Tyr Ala Arg Leu Phe Pro Ile Tyr Lys Tyr Lys Met
1               5                   10                  15

<210> SEQ ID NO 195
<211> LENGTH: 15
<212> TYPE: PRT
<213> ORGANISM: Artificial sequence
<220> FEATURE:
<223> OTHER INFORMATION: Immunogenic fragment

<400> SEQUENCE: 195

Arg Leu Phe Pro Ile Tyr Lys Tyr Lys Met Tyr Asn Gly Thr Lys
1               5                   10                  15

<210> SEQ ID NO 196
<211> LENGTH: 15
<212> TYPE: PRT
<213> ORGANISM: Artificial sequence
<220> FEATURE:
<223> OTHER INFORMATION: Immunogenic fragment

<400> SEQUENCE: 196

Tyr Lys Tyr Lys Met Tyr Asn Gly Thr Lys Ser Lys Asn Pro Tyr
1               5                   10                  15

<210> SEQ ID NO 197
<211> LENGTH: 15
<212> TYPE: PRT
<213> ORGANISM: Artificial sequence
<220> FEATURE:
<223> OTHER INFORMATION: Immunogenic fragment

<400> SEQUENCE: 197

Pro Glu Phe Asn His Leu Asn Asp Trp Val Ala Glu His Phe Tyr
1               5                   10                  15

<210> SEQ ID NO 198
<211> LENGTH: 15
<212> TYPE: PRT
<213> ORGANISM: Artificial sequence
<220> FEATURE:
<223> OTHER INFORMATION: Immunogenic fragment

<400> SEQUENCE: 198

Ala Glu His Phe Tyr Asp Tyr Gly Tyr Thr Arg Leu Met Phe Glu
1               5                   10                  15

<210> SEQ ID NO 199
<211> LENGTH: 15
<212> TYPE: PRT
<213> ORGANISM: Artificial sequence
<220> FEATURE:
<223> OTHER INFORMATION: Immunogenic fragment

<400> SEQUENCE: 199

Asp Tyr Gly Tyr Thr Arg Leu Met Phe Glu Asp Lys Tyr Arg Ile
1               5                   10                  15

<210> SEQ ID NO 200
<211> LENGTH: 15
<212> TYPE: PRT
<213> ORGANISM: Artificial sequence
<220> FEATURE:
<223> OTHER INFORMATION: Immunogenic fragment

<400> SEQUENCE: 200

Arg Leu Met Phe Glu Asp Lys Tyr Arg Ile Arg Leu Gln Gln Ile
1               5                   10                  15

<210> SEQ ID NO 201
<211> LENGTH: 15
<212> TYPE: PRT
<213> ORGANISM: Artificial sequence
<220> FEATURE:
<223> OTHER INFORMATION: Immunogenic fragment

<400> SEQUENCE: 201

Lys Ile Gly Ile Asn Gly Phe Gly Arg Ile Gly Arg Leu Val Leu
1               5                   10                  15

<210> SEQ ID NO 202
<211> LENGTH: 15
<212> TYPE: PRT
<213> ORGANISM: Artificial sequence
<220> FEATURE:
<223> OTHER INFORMATION: Immunogenic fragment

<400> SEQUENCE: 202

Tyr Asp Phe Ser Gly Lys Val Ala Leu Val Thr Gly Ser Ser Ser
1               5                   10                  15

<210> SEQ ID NO 203
<211> LENGTH: 15
<212> TYPE: PRT
<213> ORGANISM: Artificial sequence
<220> FEATURE:
<223> OTHER INFORMATION: Immunogenic fragment

<400> SEQUENCE: 203

Ile Ala Val Gln Phe Ala Gln Tyr Gly Ala Lys Leu Thr Ile Thr
1               5                   10                  15

<210> SEQ ID NO 204
<211> LENGTH: 15
<212> TYPE: PRT
<213> ORGANISM: Artificial sequence
<220> FEATURE:
<223> OTHER INFORMATION: Immunogenic fragment

<400> SEQUENCE: 204

```
Val Gly Asp Leu Leu Asp Gln Ser Leu Pro Ala Lys Leu Ile Asn
1               5                   10                  15
```

<210> SEQ ID NO 205
<211> LENGTH: 15
<212> TYPE: PRT
<213> ORGANISM: Artificial sequence
<220> FEATURE:
<223> OTHER INFORMATION: Immunogenic fragment

<400> SEQUENCE: 205

```
Asn Val Arg Ala Val Leu Gln Leu Ser Gln Leu Ala Ala Ile His
1               5                   10                  15
```

<210> SEQ ID NO 206
<211> LENGTH: 15
<212> TYPE: PRT
<213> ORGANISM: Artificial sequence
<220> FEATURE:
<223> OTHER INFORMATION: Immunogenic fragment

<400> SEQUENCE: 206

```
Leu Gln Leu Ser Gln Leu Ala Ala Ile His Leu Glu Lys Ser Lys
1               5                   10                  15
```

<210> SEQ ID NO 207
<211> LENGTH: 15
<212> TYPE: PRT
<213> ORGANISM: Artificial sequence
<220> FEATURE:
<223> OTHER INFORMATION: Immunogenic fragment

<400> SEQUENCE: 207

```
Glu Leu Gly Leu Lys Gly Val Arg Val Asn Ser Ile Asn Pro Gly
1               5                   10                  15
```

<210> SEQ ID NO 208
<211> LENGTH: 15
<212> TYPE: PRT
<213> ORGANISM: Artificial sequence
<220> FEATURE:
<223> OTHER INFORMATION: Immunogenic fragment

<400> SEQUENCE: 208

```
Asn His Thr Leu Leu Lys Phe Leu Ala Gln Pro Asp Glu Ile Ala
1               5                   10                  15
```

<210> SEQ ID NO 209
<211> LENGTH: 15
<212> TYPE: PRT
<213> ORGANISM: Artificial sequence
<220> FEATURE:
<223> OTHER INFORMATION: Immunogenic fragment

<400> SEQUENCE: 209

```
Met Thr Gly Ser Ile Val Val Ser Asp Thr Gly Ser Leu Leu Val
1               5                   10                  15
```

<210> SEQ ID NO 210
<211> LENGTH: 15
<212> TYPE: PRT
<213> ORGANISM: Artificial sequence
<220> FEATURE:
<223> OTHER INFORMATION: Immunogenic fragment

<400> SEQUENCE: 210

Lys Ala Val Val Val Leu Lys Gly Glu Pro Asn Val Thr Gly Thr

<210> SEQ ID NO 211
<211> LENGTH: 15
<212> TYPE: PRT
<213> ORGANISM: Artificial sequence
<220> FEATURE:
<223> OTHER INFORMATION: Immunogenic fragment

<400> SEQUENCE: 211

Val Ala Asn Val Val Ile Glu Asp Ser Leu Ile Ser Leu Thr Gly
1               5                   10                  15

<210> SEQ ID NO 212
<211> LENGTH: 15
<212> TYPE: PRT
<213> ORGANISM: Artificial sequence
<220> FEATURE:
<223> OTHER INFORMATION: Immunogenic fragment

<400> SEQUENCE: 212

Ile Glu Asp Ser Leu Ile Ser Leu Thr Gly Glu Arg Ser Ile Val
1               5                   10                  15

<210> SEQ ID NO 213
<211> LENGTH: 15
<212> TYPE: PRT
<213> ORGANISM: Artificial sequence
<220> FEATURE:
<223> OTHER INFORMATION: Immunogenic fragment

<400> SEQUENCE: 213

Ile Ser Leu Thr Gly Glu Arg Ser Ile Val Gly Arg Ser Leu Val
1               5                   10                  15

<210> SEQ ID NO 214
<211> LENGTH: 15
<212> TYPE: PRT
<213> ORGANISM: Artificial sequence
<220> FEATURE:
<223> OTHER INFORMATION: Immunogenic fragment

<400> SEQUENCE: 214

Glu Lys Ser Ile Val Gly Arg Ser Leu Val Val His Ala Asp Pro
1               5                   10                  15

<210> SEQ ID NO 215
<211> LENGTH: 15
<212> TYPE: PRT
<213> ORGANISM: Artificial sequence
<220> FEATURE:
<223> OTHER INFORMATION: Immunogenic fragment

<400> SEQUENCE: 215

Tyr Cys Asn Gly Ala Ala Ile Val Ser Ala Ala Arg Ser Gln Ile
1               5                   10                  15

<210> SEQ ID NO 216
<211> LENGTH: 15
<212> TYPE: PRT
<213> ORGANISM: Artificial sequence
<220> FEATURE:
<223> OTHER INFORMATION: Immunogenic fragment

<400> SEQUENCE: 216

Ala Ile Val Ser Ala Ala Arg Ser Gln Ile Gly Val Pro Tyr Ser
1               5                   10                  15

```
<210> SEQ ID NO 217
<211> LENGTH: 15
<212> TYPE: PRT
<213> ORGANISM: Artificial sequence
<220> FEATURE:
<223> OTHER INFORMATION: Immunogenic fragment

<400> SEQUENCE: 217

Ser Val Tyr Gln Gly Thr His Lys Val Leu Ala Arg Val Ala Ser
1               5                   10                  15

<210> SEQ ID NO 218
<211> LENGTH: 15
<212> TYPE: PRT
<213> ORGANISM: Artificial sequence
<220> FEATURE:
<223> OTHER INFORMATION: Immunogenic fragment

<400> SEQUENCE: 218

Gly Asp Leu Val Phe Phe Gly Asn Pro Ile His His Val Gly Ile
1               5                   10                  15

<210> SEQ ID NO 219
<211> LENGTH: 15
<212> TYPE: PRT
<213> ORGANISM: Artificial sequence
<220> FEATURE:
<223> OTHER INFORMATION: Immunogenic fragment

<400> SEQUENCE: 219

Asn Pro Ile His His Val Gly Ile Val Ser Ala His Gly Arg Met
1               5                   10                  15

<210> SEQ ID NO 220
<211> LENGTH: 15
<212> TYPE: PRT
<213> ORGANISM: Artificial sequence
<220> FEATURE:
<223> OTHER INFORMATION: Immunogenic fragment

<400> SEQUENCE: 220

Val Gly Ile Val Ser Ala His Gly Arg Met Ile Asn Ala Pro His
1               5                   10                  15

<210> SEQ ID NO 221
<211> LENGTH: 15
<212> TYPE: PRT
<213> ORGANISM: Artificial sequence
<220> FEATURE:
<223> OTHER INFORMATION: Immunogenic fragment

<400> SEQUENCE: 221

Leu Lys Pro Glu Phe Leu Lys Val Asn Pro Phe His Lys Ile Pro
1               5                   10                  15

<210> SEQ ID NO 222
<211> LENGTH: 15
<212> TYPE: PRT
<213> ORGANISM: Artificial sequence
<220> FEATURE:
<223> OTHER INFORMATION: Immunogenic fragment

<400> SEQUENCE: 222

Leu Lys Val Asn Pro Phe His Lys Ile Pro Thr Phe Val Asp Thr
1               5                   10                  15
```

<210> SEQ ID NO 223
<211> LENGTH: 15
<212> TYPE: PRT
<213> ORGANISM: Artificial sequence
<220> FEATURE:
<223> OTHER INFORMATION: Immunogenic fragment

<400> SEQUENCE: 223

Phe His Lys Ile Pro Thr Phe Val Asp Thr Asp Gly Phe Thr Ile
1               5                   10                  15

<210> SEQ ID NO 224
<211> LENGTH: 15
<212> TYPE: PRT
<213> ORGANISM: Artificial sequence
<220> FEATURE:
<223> OTHER INFORMATION: Immunogenic fragment

<400> SEQUENCE: 224

Asp Gly Phe Thr Ile Asp Glu Ser Arg Val Ile Ala Met Tyr Leu
1               5                   10                  15

<210> SEQ ID NO 225
<211> LENGTH: 15
<212> TYPE: PRT
<213> ORGANISM: Artificial sequence
<220> FEATURE:
<223> OTHER INFORMATION: Immunogenic fragment

<400> SEQUENCE: 225

Gln Ile Thr Leu Ala Asp Ile Ala Met Tyr Phe Ser Cys Asn Thr
1               5                   10                  15

<210> SEQ ID NO 226
<211> LENGTH: 15
<212> TYPE: PRT
<213> ORGANISM: Artificial sequence
<220> FEATURE:
<223> OTHER INFORMATION: Immunogenic fragment

<400> SEQUENCE: 226

Asp Ile Ala Met Tyr Phe Ser Cys Asn Thr Met Glu Ile Tyr Ser
1               5                   10                  15

<210> SEQ ID NO 227
<211> LENGTH: 15
<212> TYPE: PRT
<213> ORGANISM: Artificial sequence
<220> FEATURE:
<223> OTHER INFORMATION: Immunogenic fragment

<400> SEQUENCE: 227

Asp Thr Lys Glu Ile Arg Trp Tyr Met Asp Gly Asn Lys Tyr Phe
1               5                   10                  15

<210> SEQ ID NO 228
<211> LENGTH: 15
<212> TYPE: PRT
<213> ORGANISM: Artificial sequence
<220> FEATURE:
<223> OTHER INFORMATION: Immunogenic fragment

<400> SEQUENCE: 228

Gln Lys His Thr Met Glu Ile Asp Tyr Val Arg Val Tyr Gln Trp
1               5                   10                  15

```
<210> SEQ ID NO 229
<211> LENGTH: 15
<212> TYPE: PRT
<213> ORGANISM: Artificial sequence
<220> FEATURE:
<223> OTHER INFORMATION: Immunogenic fragment

<400> SEQUENCE: 229

Ser Leu Arg Gly Val Thr Ile Arg Asn Ala Pro Phe Leu Glu Glu
1               5                   10                  15

<210> SEQ ID NO 230
<211> LENGTH: 15
<212> TYPE: PRT
<213> ORGANISM: Artificial sequence
<220> FEATURE:
<223> OTHER INFORMATION: Immunogenic fragment

<400> SEQUENCE: 230

Glu Ala Arg Glu Asn Tyr Ile Thr Phe Thr Glu Pro Phe Met Ile
1               5                   10                  15

<210> SEQ ID NO 231
<211> LENGTH: 15
<212> TYPE: PRT
<213> ORGANISM: Artificial sequence
<220> FEATURE:
<223> OTHER INFORMATION: Immunogenic fragment

<400> SEQUENCE: 231

Tyr Ile Thr Phe Thr Glu Pro Phe Met Ile Asn Gln Leu Ala Ala
1               5                   10                  15

<210> SEQ ID NO 232
<211> LENGTH: 15
<212> TYPE: PRT
<213> ORGANISM: Artificial sequence
<220> FEATURE:
<223> OTHER INFORMATION: Immunogenic fragment

<400> SEQUENCE: 232

Glu Pro Phe Met Ile Asn Gln Leu Ala Ala Leu Ile Arg Arg Glu
1               5                   10                  15

<210> SEQ ID NO 233
<211> LENGTH: 15
<212> TYPE: PRT
<213> ORGANISM: Artificial sequence
<220> FEATURE:
<223> OTHER INFORMATION: Immunogenic fragment

<400> SEQUENCE: 233

His Lys Pro Ile Ile Leu Gly Thr Leu Arg Asn Gly Ala Thr Asn
1               5                   10                  15

<210> SEQ ID NO 234
<211> LENGTH: 15
<212> TYPE: PRT
<213> ORGANISM: Artificial sequence
<220> FEATURE:
<223> OTHER INFORMATION: Immunogenic fragment

<400> SEQUENCE: 234

Leu Gly Thr Leu Arg Asn Gly Ala Thr Asn His Phe Leu Ser Lys
1               5                   10                  15

<210> SEQ ID NO 235
```

```
<211> LENGTH: 15
<212> TYPE: PRT
<213> ORGANISM: Artificial sequence
<220> FEATURE:
<223> OTHER INFORMATION: Immunogenic fragment

<400> SEQUENCE: 235

Gly Tyr Ala Phe Ile Met Glu Ser Ser Ser Ala Glu His Glu Ile
1               5                   10                  15

<210> SEQ ID NO 236
<211> LENGTH: 15
<212> TYPE: PRT
<213> ORGANISM: Artificial sequence
<220> FEATURE:
<223> OTHER INFORMATION: Immunogenic fragment

<400> SEQUENCE: 236

Leu Thr Met Leu Leu Asp Trp Arg Asn Leu Tyr Pro Arg Lys Tyr
1               5                   10                  15

<210> SEQ ID NO 237
<211> LENGTH: 15
<212> TYPE: PRT
<213> ORGANISM: Artificial sequence
<220> FEATURE:
<223> OTHER INFORMATION: Immunogenic fragment

<400> SEQUENCE: 237

Asp Trp Arg Asn Leu Tyr Pro Arg Lys Tyr Ala Phe Ala Leu Pro
1               5                   10                  15

<210> SEQ ID NO 238
<211> LENGTH: 15
<212> TYPE: PRT
<213> ORGANISM: Artificial sequence
<220> FEATURE:
<223> OTHER INFORMATION: Immunogenic fragment

<400> SEQUENCE: 238

Tyr Pro Arg Lys Tyr Ala Phe Ala Leu Pro Lys Asp Ser Gln Tyr
1               5                   10                  15

<210> SEQ ID NO 239
<211> LENGTH: 15
<212> TYPE: PRT
<213> ORGANISM: Artificial sequence
<220> FEATURE:
<223> OTHER INFORMATION: Immunogenic fragment

<400> SEQUENCE: 239

Lys Asp Ser Gln Tyr Leu Gln His Phe Asn Asn Ala Ile Lys Gln
1               5                   10                  15

<210> SEQ ID NO 240
<211> LENGTH: 15
<212> TYPE: PRT
<213> ORGANISM: Artificial sequence
<220> FEATURE:
<223> OTHER INFORMATION: Immunogenic fragment

<400> SEQUENCE: 240

Leu Gln His Phe Asn Asn Ala Ile Lys Gln Leu Asn Thr Glu Asp
1               5                   10                  15

<210> SEQ ID NO 241
<211> LENGTH: 15
```

```
<212> TYPE: PRT
<213> ORGANISM: Artificial sequence
<220> FEATURE:
<223> OTHER INFORMATION: Immunogenic fragment

<400> SEQUENCE: 241

Asn Lys Phe Thr Val Phe Thr Ser Gly Lys Pro Val Ser Gly Leu
1               5                   10                  15

<210> SEQ ID NO 242
<211> LENGTH: 15
<212> TYPE: PRT
<213> ORGANISM: Artificial sequence
<220> FEATURE:
<223> OTHER INFORMATION: Immunogenic fragment

<400> SEQUENCE: 242

Thr Gly Gly Ile Ser Phe Ala Met Glu Gly Pro Ala Lys Val Glu
1               5                   10                  15

<210> SEQ ID NO 243
<211> LENGTH: 15
<212> TYPE: PRT
<213> ORGANISM: Artificial sequence
<220> FEATURE:
<223> OTHER INFORMATION: Immunogenic fragment

<400> SEQUENCE: 243

Ile Thr Val Ile Tyr Lys Pro Pro Thr Pro Gly Asp Tyr Lys Leu
1               5                   10                  15

<210> SEQ ID NO 244
<211> LENGTH: 15
<212> TYPE: PRT
<213> ORGANISM: Artificial sequence
<220> FEATURE:
<223> OTHER INFORMATION: Immunogenic fragment

<400> SEQUENCE: 244

Gly Asp Tyr Lys Leu His Leu Lys Phe Asn Asp Ile His Leu Pro
1               5                   10                  15

<210> SEQ ID NO 245
<211> LENGTH: 15
<212> TYPE: PRT
<213> ORGANISM: Artificial sequence
<220> FEATURE:
<223> OTHER INFORMATION: Immunogenic fragment

<400> SEQUENCE: 245

Ile Arg Glu Tyr Arg Val Glu Ala Ile Lys Val Met Leu Glu Thr
1               5                   10                  15

<210> SEQ ID NO 246
<211> LENGTH: 15
<212> TYPE: PRT
<213> ORGANISM: Artificial sequence
<220> FEATURE:
<223> OTHER INFORMATION: Immunogenic fragment

<400> SEQUENCE: 246

Val Glu Ala Ile Lys Val Met Leu Glu Thr Asp Arg Lys Leu Leu
1               5                   10                  15

<210> SEQ ID NO 247
<211> LENGTH: 15
<212> TYPE: PRT
```

```
<213> ORGANISM: Artificial sequence
<220> FEATURE:
<223> OTHER INFORMATION: Immunogenic fragment

<400> SEQUENCE: 247

Asp Arg Lys Leu Leu Thr Leu Asn Asn Ser Gln Ile Ile Leu Asn
1               5                   10                  15

<210> SEQ ID NO 248
<211> LENGTH: 15
<212> TYPE: PRT
<213> ORGANISM: Artificial sequence
<220> FEATURE:
<223> OTHER INFORMATION: Immunogenic fragment

<400> SEQUENCE: 248

Gln Ile Ile Leu Asn Ile Gln Tyr Gln Lys Lys Lys Ile Arg Cys
1               5                   10                  15

<210> SEQ ID NO 249
<211> LENGTH: 15
<212> TYPE: PRT
<213> ORGANISM: Artificial sequence
<220> FEATURE:
<223> OTHER INFORMATION: Immunogenic fragment

<400> SEQUENCE: 249

Leu Ser Glu Leu Leu Thr Met His Leu Leu Ala Tyr Lys Gln Gly
1               5                   10                  15

<210> SEQ ID NO 250
<211> LENGTH: 15
<212> TYPE: PRT
<213> ORGANISM: Artificial sequence
<220> FEATURE:
<223> OTHER INFORMATION: Immunogenic fragment

<400> SEQUENCE: 250

Gly Pro His His Phe Asn Val Asp Phe Ser Lys Asp Phe His Asn
1               5                   10                  15

<210> SEQ ID NO 251
<211> LENGTH: 15
<212> TYPE: PRT
<213> ORGANISM: Artificial sequence
<220> FEATURE:
<223> OTHER INFORMATION: Immunogenic fragment

<400> SEQUENCE: 251

Trp Ser Asn Ser Ser Ala Lys Lys Leu Leu Lys Asn Asp Ile Asp
1               5                   10                  15

<210> SEQ ID NO 252
<211> LENGTH: 15
<212> TYPE: PRT
<213> ORGANISM: Artificial sequence
<220> FEATURE:
<223> OTHER INFORMATION: Immunogenic fragment

<400> SEQUENCE: 252

Arg Ser Thr Leu Lys Leu Phe Gly Thr Ile Lys Met Phe Met Lys
1               5                   10                  15

<210> SEQ ID NO 253
<211> LENGTH: 15
<212> TYPE: PRT
<213> ORGANISM: Artificial sequence
```

```
<220> FEATURE:
<223> OTHER INFORMATION: Immunogenic fragment

<400> SEQUENCE: 253

Leu Phe Gly Thr Ile Lys Met Phe Met Lys Glu Leu Leu Asp Asp
1               5                   10                  15

<210> SEQ ID NO 254
<211> LENGTH: 15
<212> TYPE: PRT
<213> ORGANISM: Artificial sequence
<220> FEATURE:
<223> OTHER INFORMATION: Immunogenic fragment

<400> SEQUENCE: 254

Thr His Phe Ile Asn Ala Ile Val Pro Leu Arg Gln Gln Leu Gly
1               5                   10                  15

<210> SEQ ID NO 255
<211> LENGTH: 15
<212> TYPE: PRT
<213> ORGANISM: Artificial sequence
<220> FEATURE:
<223> OTHER INFORMATION: Immunogenic fragment

<400> SEQUENCE: 255

Ala Ile Val Pro Leu Arg Gln Gln Leu Gly Glu Tyr Val Asp Ile
1               5                   10                  15

<210> SEQ ID NO 256
<211> LENGTH: 15
<212> TYPE: PRT
<213> ORGANISM: Artificial sequence
<220> FEATURE:
<223> OTHER INFORMATION: Immunogenic fragment

<400> SEQUENCE: 256

Glu Tyr Val Asp Ile Asp Leu Val Pro Phe Gly Asn Ala His Ile
1               5                   10                  15

<210> SEQ ID NO 257
<211> LENGTH: 15
<212> TYPE: PRT
<213> ORGANISM: Artificial sequence
<220> FEATURE:
<223> OTHER INFORMATION: Immunogenic fragment

<400> SEQUENCE: 257

Thr Gly Gln Lys Gly Phe Glu Leu Ile Lys Val Met Ala Arg Lys
1               5                   10                  15

<210> SEQ ID NO 258
<211> LENGTH: 15
<212> TYPE: PRT
<213> ORGANISM: Artificial sequence
<220> FEATURE:
<223> OTHER INFORMATION: Immunogenic fragment

<400> SEQUENCE: 258

Phe Glu Leu Ile Lys Val Met Ala Arg Lys Thr Pro Arg His Asn
1               5                   10                  15

<210> SEQ ID NO 259
<211> LENGTH: 15
<212> TYPE: PRT
<213> ORGANISM: Artificial sequence
<220> FEATURE:
```

-continued

<223> OTHER INFORMATION: Immunogenic fragment

<400> SEQUENCE: 259

Tyr Val Pro Trp Thr Thr Val Glu Ser Arg Thr Val Asp Val Asn
1               5                   10                  15

<210> SEQ ID NO 260
<211> LENGTH: 15
<212> TYPE: PRT
<213> ORGANISM: Artificial sequence
<220> FEATURE:
<223> OTHER INFORMATION: Immunogenic fragment

<400> SEQUENCE: 260

Val Asp Leu Val Lys Tyr Ile Cys Asp Asn Tyr Leu Asn Asn Val
1               5                   10                  15

<210> SEQ ID NO 261
<211> LENGTH: 130
<212> TYPE: PRT
<213> ORGANISM: Dermatophagoides farinae
<220> FEATURE:
<221> NAME/KEY: misc_feature
<222> LOCATION: (42)..(42)
<223> OTHER INFORMATION: Xaa is serine, alanine, or 2-aminobutyric acid
<220> FEATURE:
<221> NAME/KEY: misc_feature
<222> LOCATION: (71)..(71)
<223> OTHER INFORMATION: Xaa is serine, alanine, or 2-aminobutyric acid
<220> FEATURE:
<221> NAME/KEY: misc_feature
<222> LOCATION: (129)..(129)
<223> OTHER INFORMATION: Xaa is serine, alanine, or 2-aminobutyric acid

<400> SEQUENCE: 261

Asp Gly Ser His Ile Val Lys Ala Ala Arg Ser Gln Ile Gly Val Pro
1               5                   10                  15

Tyr Ser Trp Gly Gly Gly Gly Ile His Gly Lys Ser Lys Gly Ile Gly
            20                  25                  30

Glu Gly Ala Asn Ile Val Gly Phe Asp Xaa Ser Gly Leu Ala Gln Tyr
        35                  40                  45

Ser Ile Tyr Gln Gly Thr His Lys Thr Ile Ala Arg Thr Ala Ala Ala
    50                  55                  60

Gln Tyr Asn Asp Asn His Xaa His His Val Ala Tyr Gly Ser His Gln
65                  70                  75                  80

Pro Gly Asp Leu Val Phe Phe Gly Asn Pro Ile Tyr His Val Gly Ile
                85                  90                  95

Val Ser Ala His Gly Arg Met Val Asn Ala Pro Lys Pro Gly Thr Lys
            100                 105                 110

Val Arg Glu Glu Asn Ile Trp Ser Tyr His Ile Ser His Val Ala Arg
        115                 120                 125

Xaa Trp
    130

<210> SEQ ID NO 262
<211> LENGTH: 132
<212> TYPE: PRT
<213> ORGANISM: Dermatophagoides farinae
<220> FEATURE:
<221> NAME/KEY: misc_feature
<222> LOCATION: (42)..(42)
<223> OTHER INFORMATION: Xaa is serine, alanine, or 2-aminobutyric acid
<220> FEATURE:
<221> NAME/KEY: misc_feature
<222> LOCATION: (86)..(86)

<223> OTHER INFORMATION: Xaa is serine, alanine, or 2-aminobutyric acid
<220> FEATURE:
<221> NAME/KEY: misc_feature
<222> LOCATION: (114)..(114)
<223> OTHER INFORMATION: Xaa is serine, alanine, or 2-aminobutyric acid

<400> SEQUENCE: 262

Met Ala Ile Asp Gly Lys Tyr Gln Met Glu Ser Ser Glu His Phe Glu
1               5                   10                  15

Glu Phe Val Lys Glu Met Gly Leu Asp Val Asp Met Thr Asn Val Asp
                20                  25                  30

Leu Ser Lys Thr Ser Thr Met Glu Ile Xaa Lys Asp Gly Asp Val Tyr
            35                  40                  45

His Ile Lys Ser Glu Thr Ala Gly Ile Ala His Glu Ile Lys Phe Lys
        50                  55                  60

Val Gly Glu Glu Phe Glu Asp Asp Met Asn Gly His Lys Phe Lys Asn
65                  70                  75                  80

Val Val Thr Met Glu Xaa Asp Asn Lys Met Val Gln Lys Lys Thr Ser
                85                  90                  95

Ala Asp Gly Gly Lys Val Val Asn Val Val Arg Glu Phe Thr Asp Ala
            100                 105                 110

Gly Xaa Thr Val Lys Ser Thr Tyr Asn Thr Val Thr Trp Thr Arg Val
        115                 120                 125

Tyr Lys Arg Met
        130

<210> SEQ ID NO 263
<211> LENGTH: 132
<212> TYPE: PRT
<213> ORGANISM: Dermatophagoides pteronyssinus
<220> FEATURE:
<221> NAME/KEY: misc_feature
<222> LOCATION: (42)..(42)
<223> OTHER INFORMATION: Xaa is serine, alanine, or 2-aminobutyric acid
<220> FEATURE:
<221> NAME/KEY: misc_feature
<222> LOCATION: (86)..(86)
<223> OTHER INFORMATION: Xaa is serine, alanine, or 2-aminobutyric acid
<220> FEATURE:
<221> NAME/KEY: misc_feature
<222> LOCATION: (114)..(114)
<223> OTHER INFORMATION: Xaa is serine, alanine, or 2-aminobutyric acid

<400> SEQUENCE: 263

Met Ala Ile Asp Gly Lys Tyr Gln Met Glu Ser Ser Glu His Phe Glu
1               5                   10                  15

Glu Phe Val Lys Glu Met Gly Leu Asp Val Asp Met Thr Asn Val Asp
                20                  25                  30

Leu Ser Lys Thr Ser Thr Met Glu Ile Xaa Lys Asp Gly Asp Val Tyr
            35                  40                  45

His Ile Lys Ser Glu Thr Ala Gly Ile Ala His Glu Ile Lys Phe Lys
        50                  55                  60

Val Gly Glu Glu Phe Glu Asp Asp Met Asn Gly His Lys Phe Lys Asn
65                  70                  75                  80

Val Val Thr Met Glu Xaa Asp Asn Lys Met Val Gln Lys Lys Thr Ser
                85                  90                  95

Ala Asp Gly Gly Lys Val Val Asn Val Val Arg Glu Phe Thr Asp Ala
            100                 105                 110

Gly Xaa Thr Val Lys Ser Thr Tyr Asn Thr Val Thr Trp Thr Arg Val
        115                 120                 125

```
Tyr Lys Arg Met
    130

<210> SEQ ID NO 264
<211> LENGTH: 134
<212> TYPE: PRT
<213> ORGANISM: Dermatophagoides pteronyssinus
<220> FEATURE:
<221> NAME/KEY: misc_feature
<222> LOCATION: (4)..(4)
<223> OTHER INFORMATION: Xaa is serine, alanine, or 2-aminobutyric acid
<220> FEATURE:
<221> NAME/KEY: misc_feature
<222> LOCATION: (46)..(46)
<223> OTHER INFORMATION: Xaa is serine, alanine, or 2-aminobutyric acid
<220> FEATURE:
<221> NAME/KEY: misc_feature
<222> LOCATION: (75)..(75)
<223> OTHER INFORMATION: Xaa is serine, alanine, or 2-aminobutyric acid
<220> FEATURE:
<221> NAME/KEY: misc_feature
<222> LOCATION: (133)..(133)
<223> OTHER INFORMATION: Xaa is serine, alanine, or 2-aminobutyric acid

<400> SEQUENCE: 264

Gln Val Tyr Xaa Asn Gly Ala Ala Ile Val Ser Ala Ala Arg Ser Gln
1               5                   10                  15

Ile Gly Val Pro Tyr Ser Trp Gly Gly Gly Ile His Gly Lys Ser
            20                  25                  30

Arg Gly Ile Gly Glu Gly Ala Asn Thr Val Gly Phe Asp Xaa Ser Gly
        35                  40                  45

Leu Ala Gln Tyr Ser Val Tyr Gln Gly Thr His Lys Val Leu Ala Arg
    50                  55                  60

Val Ala Ser Gly Gln Tyr Ser Asp Pro Lys Xaa His His Val Ala Tyr
65                  70                  75                  80

Gly Ser His Gln Pro Gly Asp Leu Val Phe Phe Gly Asn Pro Ile His
                85                  90                  95

His Val Gly Ile Val Ser Ala His Gly Arg Met Ile Asn Ala Pro His
            100                 105                 110

Thr Gly Thr Asn Val Arg Glu Glu Asn Ile Trp Ser Asp His Ile Ala
        115                 120                 125

Asn Val Ala Arg Xaa Trp
    130

<210> SEQ ID NO 265
<211> LENGTH: 152
<212> TYPE: PRT
<213> ORGANISM: Dermatophagoides farinae
<220> FEATURE:
<221> NAME/KEY: misc_feature
<222> LOCATION: (56)..(56)
<223> OTHER INFORMATION: Xaa is serine, alanine, or 2-aminobutyric acid
<220> FEATURE:
<221> NAME/KEY: misc_feature
<222> LOCATION: (145)..(145)
<223> OTHER INFORMATION: Xaa is serine, alanine, or 2-aminobutyric acid

<400> SEQUENCE: 265

Met Val Lys Ala Val Val Val Leu Lys Gly Glu Pro Asn Val Thr Gly
1               5                   10                  15

Thr Ile Phe Phe Glu Gln Gln Asp Asn Gly Pro Val Lys Val Ser Gly
            20                  25                  30

Thr Val Gln Gly Leu Lys Ser Gly Leu His Gly Phe His Val His Glu
        35                  40                  45
```

```
Phe Gly Asp Asn Thr Asn Gly Xaa Thr Ser Ala Gly Ala His Tyr Asn
 50                  55                  60

Pro Phe Asn Lys Thr His Gly Ala Pro Ala Asp Glu Glu Arg His Val
 65                  70                  75                  80

Gly Asp Leu Gly Asn Val Glu Ala Asn Asp Ala Gly Ile Ala Asn Val
                 85                  90                  95

Ala Ile Glu Asp Ser Leu Ile Ser Leu Thr Gly Glu Arg Ser Ile Val
                100                 105                 110

Gly Arg Ser Leu Val Val His Ala Asp Pro Asp Leu Gly Arg Gly
                115                 120                 125

Gly His Glu Leu Ser Lys Thr Thr Gly Asn Ala Gly Gly Arg Leu Ala
                130                 135                 140

Xaa Gly Val Ile Gly Val Thr Lys
145                 150

<210> SEQ ID NO 266
<211> LENGTH: 152
<212> TYPE: PRT
<213> ORGANISM: Dermatophagoides pteronyssinus
<220> FEATURE:
<221> NAME/KEY: misc_feature
<222> LOCATION: (56)..(56)
<223> OTHER INFORMATION: Xaa is serine, alanine, or 2-aminobutyric acid
<220> FEATURE:
<221> NAME/KEY: misc_feature
<222> LOCATION: (145)..(145)
<223> OTHER INFORMATION: Xaa is serine, alanine, or 2-aminobutyric acid

<400> SEQUENCE: 266

Met Val Lys Ala Val Val Leu Lys Gly Asp Pro Asn Val Ser Gly
 1               5                  10                  15

Thr Ile Phe Phe Glu Gln Gln Asp Asn Gly Pro Val Lys Val Thr Gly
                 20                  25                  30

Ser Val Gln Gly Leu Lys Pro Gly Leu His Gly Phe His Val His Glu
                 35                  40                  45

Phe Gly Asp Asn Thr Asn Gly Xaa Thr Ser Ala Gly Ala His Tyr Asn
 50                  55                  60

Pro Leu Asn Lys Thr His Gly Ala Pro Asn Asp Glu Glu Arg His Val
 65                  70                  75                  80

Gly Asp Leu Gly Asn Ile Glu Ala Asn Asp Lys Gly Val Ala Asn Val
                 85                  90                  95

Val Ile Glu Asp Ser Leu Ile Ser Leu Thr Gly Glu Lys Ser Ile Val
                100                 105                 110

Gly Arg Ser Leu Val Val His Ala Asp Pro Asp Leu Gly Arg Gly
                115                 120                 125

Gly His Glu Leu Ser Lys Thr Thr Gly Asn Ala Gly Gly Arg Leu Val
                130                 135                 140

Xaa Gly Val Ile Gly Val Thr Lys
145                 150

<210> SEQ ID NO 267
<211> LENGTH: 154
<212> TYPE: PRT
<213> ORGANISM: Dermatophagoides farinae
<220> FEATURE:
<221> NAME/KEY: misc_feature
<222> LOCATION: (110)..(110)
<223> OTHER INFORMATION: Xaa is serine, alanine, or 2-aminobutyric acid

<400> SEQUENCE: 267
```

Met Ser Ala Asn Thr Glu Arg Thr Phe Ile Met Leu Lys Pro Asp Ala
1               5                   10                  15

Val Gln Arg Gly Ile Val Gly Glu Ile Ile Arg Arg Phe Glu Ala Lys
            20                  25                  30

Gly Phe Lys Leu Val Ala Met Lys Phe Met Met Ala Ser Glu Asp Leu
        35                  40                  45

Leu Lys Lys His Tyr Ala Asp Leu Ala Ala Arg Pro Phe Phe Pro Gly
    50                  55                  60

Leu Ile Lys Tyr Met Gln Met Gly Pro Val Val Pro Met Val Trp Glu
65                  70                  75                  80

Gly Leu Asn Ala Val Lys Thr Gly Arg Val Met Leu Gly Glu Thr Asn
                85                  90                  95

Pro Ala Glu Ser Lys Pro Gly Thr Ile Arg Gly Asp Leu Xaa Ile Gln
            100                 105                 110

Thr Gly Arg Asn Ile Ile His Gly Ser Asp Ser Val Glu Thr Ala Lys
            115                 120                 125

Arg Glu Ile Asp Leu Trp Phe Arg Pro Glu Glu Leu Val Asp Tyr Lys
            130                 135                 140

Pro Ser Gln Tyr Glu Trp Val Tyr Glu Asn
145                 150

<210> SEQ ID NO 268
<211> LENGTH: 154
<212> TYPE: PRT
<213> ORGANISM: Dermatophagoides pteronyssinus
<220> FEATURE:
<221> NAME/KEY: misc_feature
<222> LOCATION: (110)..(110)
<223> OTHER INFORMATION: Xaa is serine, alanine, or 2-aminobutyric acid

<400> SEQUENCE: 268

Met Ser Ala Asn Thr Glu Arg Thr Phe Ile Met Leu Lys Pro Asp Ala
1               5                   10                  15

Val Gln Arg Gly Ile Val Gly Glu Ile Ile Arg Arg Phe Glu Ala Lys
            20                  25                  30

Gly Phe Lys Leu Val Ala Met Lys Phe Met Met Ala Ser Glu Asp Leu
        35                  40                  45

Leu Lys Lys His Tyr Ala Asp Leu Ala Ala Arg Pro Phe Phe Pro Gly
    50                  55                  60

Leu Ile Lys Tyr Met Gln Met Gly Pro Val Val Pro Met Val Trp Glu
65                  70                  75                  80

Gly Leu Asn Ala Val Lys Thr Gly Arg Val Met Leu Gly Glu Thr Asn
                85                  90                  95

Pro Ala Glu Ser Lys Pro Gly Thr Ile Arg Gly Asp Leu Xaa Ile Gln
            100                 105                 110

Thr Gly Arg Asn Ile Ile His Gly Ser Asp Ser Val Glu Thr Ala Lys
            115                 120                 125

Arg Glu Ile Asp Leu Trp Phe Arg Pro Glu Glu Leu Val Asn Tyr Lys
            130                 135                 140

Pro Ser Gln Tyr Glu Trp Val Tyr Glu Asn
145                 150

<210> SEQ ID NO 269
<211> LENGTH: 171
<212> TYPE: PRT
<213> ORGANISM: Dermatophagoides farinae
<220> FEATURE:
<221> NAME/KEY: misc_feature

```
<222> LOCATION: (13)..(13)
<223> OTHER INFORMATION: Xaa is serine, alanine, or 2-aminobutyric acid
<220> FEATURE:
<221> NAME/KEY: misc_feature
<222> LOCATION: (16)..(16)
<223> OTHER INFORMATION: Xaa is serine, alanine, or 2-aminobutyric acid
<220> FEATURE:
<221> NAME/KEY: misc_feature
<222> LOCATION: (54)..(54)
<223> OTHER INFORMATION: Xaa is serine, alanine, or 2-aminobutyric acid
<220> FEATURE:
<221> NAME/KEY: misc_feature
<222> LOCATION: (61)..(61)
<223> OTHER INFORMATION: Xaa is serine, alanine, or 2-aminobutyric acid
<220> FEATURE:
<221> NAME/KEY: misc_feature
<222> LOCATION: (69)..(69)
<223> OTHER INFORMATION: Xaa is serine, alanine, or 2-aminobutyric acid
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (102)..(102)
<223> OTHER INFORMATION: Xaa is serine, alanine, or 2-aminobutyric acid
<220> FEATURE:
<221> NAME/KEY: misc_feature
<222> LOCATION: (116)..(116)
<223> OTHER INFORMATION: Xaa is serine, alanine, or 2-aminobutyric acid
<220> FEATURE:
<221> NAME/KEY: misc_feature
<222> LOCATION: (160)..(160)
<223> OTHER INFORMATION: Xaa is serine, alanine, or 2-aminobutyric acid
<220> FEATURE:
<221> NAME/KEY: misc_feature
<222> LOCATION: (170)..(170)
<223> OTHER INFORMATION: Xaa is serine, alanine, or 2-aminobutyric acid

<400> SEQUENCE: 269

Asn Arg Val Ser Val Gly Val Tyr Tyr Glu Thr Ile Xaa Ser Gly Xaa
1               5                   10                  15

Arg Thr His Phe Ile Asn Ala Ile Val Pro Leu Arg Gln Gln Leu Gly
            20                  25                  30

Glu Tyr Val Asp Ile Asp Leu Val Pro Phe Gly Asn Ala His Ile Tyr
        35                  40                  45

Ser Asn Gly Pro Gln Xaa Gln His Gly Ala Leu Glu Xaa Tyr Gly Asn
    50                  55                  60

Ala Phe Gln Ala Xaa Ser Leu Asp Met Asn Gly Phe Asp Thr Gly Phe
65                  70                  75                  80

Lys Leu Val Glu Xaa Met Phe Arg Ser Ser Tyr Tyr Ser Asn Pro Gln
                85                  90                  95

Tyr Ser Ala Lys Arg Xaa Ala Gln Gln Leu Asn Leu Asn Tyr Asp Gln
            100                 105                 110

Leu His Ser Xaa Ala Thr Gly Gln Lys Gly Phe Glu Leu Ile Lys Val
        115                 120                 125

Met Ala Arg Lys Thr Pro Arg His Asn Tyr Val Pro Trp Thr Thr Val
    130                 135                 140

Glu Ser Arg Thr Val Asp Val Asn Val Asp Leu Val Lys Tyr Ile Xaa
145                 150                 155                 160

Asp Asn Tyr Leu Asn Asn Val Pro Ala Xaa Asn
                165                 170

<210> SEQ ID NO 270
<211> LENGTH: 172
<212> TYPE: PRT
<213> ORGANISM: Dermatophagoides pteronyssinus
```

-continued

```
<220> FEATURE:
<221> NAME/KEY: misc_feature
<222> LOCATION: (14)..(14)
<223> OTHER INFORMATION: Xaa is serine, alanine, or 2-aminobutyric acid
<220> FEATURE:
<221> NAME/KEY: misc_feature
<222> LOCATION: (17)..(17)
<223> OTHER INFORMATION: Xaa is serine, alanine, or 2-aminobutyric acid
<220> FEATURE:
<221> NAME/KEY: misc_feature
<222> LOCATION: (55)..(55)
<223> OTHER INFORMATION: Xaa is serine, alanine, or 2-aminobutyric acid
<220> FEATURE:
<221> NAME/KEY: misc_feature
<222> LOCATION: (62)..(62)
<223> OTHER INFORMATION: Xaa is serine, alanine, or 2-aminobutyric acid
<220> FEATURE:
<221> NAME/KEY: misc_feature
<222> LOCATION: (70)..(70)
<223> OTHER INFORMATION: Xaa is serine, alanine, or 2-aminobutyric acid
<220> FEATURE:
<221> NAME/KEY: misc_feature
<222> LOCATION: (86)..(86)
<223> OTHER INFORMATION: Xaa is serine, alanine, or 2-aminobutyric acid
<220> FEATURE:
<221> NAME/KEY: misc_feature
<222> LOCATION: (103)..(103)
<223> OTHER INFORMATION: Xaa is serine, alanine, or 2-aminobutyric acid
<220> FEATURE:
<221> NAME/KEY: misc_feature
<222> LOCATION: (117)..(117)
<223> OTHER INFORMATION: Xaa is serine, alanine, or 2-aminobutyric acid
<220> FEATURE:
<221> NAME/KEY: misc_feature
<222> LOCATION: (161)..(161)
<223> OTHER INFORMATION: Xaa is serine, alanine, or 2-aminobutyric acid
<220> FEATURE:
<221> NAME/KEY: misc_feature
<222> LOCATION: (171)..(171)
<223> OTHER INFORMATION: Xaa is serine, alanine, or 2-aminobutyric acid

<400> SEQUENCE: 270

Thr Gln Arg Val Thr Val Gly Val Tyr Tyr Glu Thr Ile Xaa Pro Gly
1               5                   10                  15

Xaa Arg Ser His Phe Ile Gln Ala Ile Val Pro Leu Lys Asn Gln Leu
            20                  25                  30

Gly Gln Tyr Val Asn Ile Asp Leu Val Pro Phe Gly Asn Ala His Phe
        35                  40                  45

Tyr Ser Asn Gly Pro Gln Xaa Gln His Gly Gln Leu Glu Xaa Tyr Gly
    50                  55                  60

Asn Ala Phe Gln Ala Xaa Ser Leu Asp Met Asn Gly Phe Glu Thr Ala
65                  70                  75                  80

Phe Lys Leu Val Glu Xaa Met Phe Arg Ser Asn Tyr Phe Ser Asn Pro
                85                  90                  95

Glu Tyr Ser Ser Lys Gln Xaa Ser Gln Gln Leu Asn Leu Asp Tyr Gln
            100                 105                 110

Gln Leu Asp Ser Xaa Ala Asn Gly Gln Lys Gly Leu Gln Leu Ile Arg
        115                 120                 125

Glu Met Ala Asn Lys Thr Pro Ser His Gln Tyr Val Pro Trp Thr Thr
130                 135                 140

Val Gln Gly Arg Phe Val Asp Gly Asn Val Asp Leu Val Asp Tyr Ile
145                 150                 155                 160

Xaa Glu Asn Tyr Leu Asn Gly Val Pro Ala Xaa Asn
                165                 170

<210> SEQ ID NO 271
<211> LENGTH: 188
```

```
<212> TYPE: PRT
<213> ORGANISM: Dermatophagoides farinae
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (123)..(123)
<223> OTHER INFORMATION: Xaa is serine, alanine, or 2-aminobutyric acid

<400> SEQUENCE: 271

Met Ser Ile Ser Ala His Gly Gly Gly Leu Val Asn Gly Ile Ala Gly
1               5                   10                  15

Met Glu Asn Lys Phe Thr Val Phe Thr Ser Gly Lys Pro Val Ser Gly
                20                  25                  30

Leu Thr Val Ala Phe Glu Gly Pro Thr Lys Pro Glu Ile Asn Phe Asn
            35                  40                  45

Ser Thr Lys Asp Gly Ser Val Asp Val Gly Tyr Thr Pro Lys Ala Gly
        50                  55                  60

Gly Gln Tyr Lys Ile His Ile Lys Tyr Glu Gly Lys Glu Ile Val Gly
65                  70                  75                  80

Ser Pro Phe Lys Xaa Asn Ile Ser Gly Asp Glu Ala Thr His Arg Lys
                85                  90                  95

Leu Thr Glu Lys Val Lys Val Gly Gly Pro Asn Ile Asn Ala Gly Lys
            100                 105                 110

Val Asn Gln Asp Asn Gln Leu Thr Ile Asp Xaa Lys Glu Ala Gly Ile
        115                 120                 125

Thr Gly Gly Ile Ser Phe Ala Met Glu Gly Pro Ala Lys Val Glu Val
    130                 135                 140

Ser Phe Arg Asn Asn Asn Asp Gly Thr Ile Thr Val Ile Tyr Lys Pro
145                 150                 155                 160

Pro Thr Pro Gly Asp Tyr Lys Leu His Leu Lys Phe Asn Asp Ile His
                165                 170                 175

Leu Pro Gly Ser Pro Tyr Pro Ile Val Val Ala Ala
            180                 185

<210> SEQ ID NO 272
<211> LENGTH: 188
<212> TYPE: PRT
<213> ORGANISM: Dermatophagoides pteronyssinus
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (123)..(123)
<223> OTHER INFORMATION: Xaa is serine, alanine, or 2-aminobutyric acid

<400> SEQUENCE: 272

Met Ser Ile Ser Ala His Gly Gly Gly Leu Val Asn Gly Ile Ala Gly
1               5                   10                  15

Met Glu Asn Lys Phe Thr Val Phe Thr Ser Gly Lys Pro Val Ser Gly
                20                  25                  30

Leu Thr Val Ala Phe Glu Gly Pro Thr Lys Pro Glu Ile Asn Phe Asn
            35                  40                  45

Ser Thr Lys Asp Gly Ser Val Asp Val Gly Tyr Ile Pro Lys Ala Gly
        50                  55                  60

Gly Gln Tyr Lys Ile His Ile Lys Tyr Glu Gly Lys Glu Ile Val Gly
65                  70                  75                  80
```

```
Ser Pro Phe Lys Xaa Asn Ile Ser Gly Asp Glu Ser Thr His Arg Lys
                 85                  90                  95

Leu Thr Glu Lys Val Lys Val Gly Gly Pro Asn Ile Ser Thr Gly Lys
            100                 105                 110

Val Asn Gln Asp Asn Gln Leu Thr Ile Asp Xaa Lys Glu Ala Gly Ile
        115                 120                 125

Thr Gly Gly Ile Ser Phe Ala Met Glu Gly Pro Ala Lys Val Glu Val
    130                 135                 140

Ser Phe Arg Asn Asn Asn Asp Gly Thr Ile Thr Val Ile Tyr Lys Pro
145                 150                 155                 160

Pro Thr Pro Gly Asp Tyr Lys Leu His Leu Lys Phe Asn Asp Ile His
                165                 170                 175

Leu Pro Gly Ser Pro Tyr Pro Ile Val Val Ser Ala
            180                 185

<210> SEQ ID NO 273
<211> LENGTH: 222
<212> TYPE: PRT
<213> ORGANISM: Dermatophagoides farinae
<220> FEATURE:
<221> NAME/KEY: misc_feature
<222> LOCATION: (6)..(6)
<223> OTHER INFORMATION: Xaa is serine, alanine, or 2-aminobutyric acid
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
<222> LOCATION: (43)..(43)
<223> OTHER INFORMATION: Xaa is serine, alanine, or 2-aminobutyric acid
<220> FEATURE:
<221> NAME/KEY: misc_feature
<222> LOCATION: (52)..(52)
<223> OTHER INFORMATION: Xaa is serine, alanine, or 2-aminobutyric acid
<220> FEATURE:
<221> NAME/KEY: misc_feature
<222> LOCATION: (60)..(60)
<223> OTHER INFORMATION: Xaa is serine, alanine, or 2-aminobutyric acid
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (100)..(100)
<223> OTHER INFORMATION: Xaa is serine, alanine, or 2-aminobutyric acid
<220> FEATURE:
<221> NAME/KEY: misc_feature
<222> LOCATION: (111)..(111)
<223> OTHER INFORMATION: Xaa is serine, alanine, or 2-aminobutyric acid
<220> FEATURE:
<221> NAME/KEY: misc_feature
<222> LOCATION: (136)..(137)
<223> OTHER INFORMATION: Xaa is serine, alanine, or 2-aminobutyric acid
<220> FEATURE:
<221> NAME/KEY: misc_feature
<222> LOCATION: (145)..(145)
<223> OTHER INFORMATION: Xaa is serine, alanine, or 2-aminobutyric acid
<220> FEATURE:
<221> NAME/KEY: misc_feature
<222> LOCATION: (158)..(158)
<223> OTHER INFORMATION: Xaa is serine, alanine, or 2-aminobutyric acid
<220> FEATURE:
<221> NAME/KEY: misc_feature
<222> LOCATION: (182)..(182)
<223> OTHER INFORMATION: Xaa is serine, alanine, or 2-aminobutyric acid
<220> FEATURE:
<221> NAME/KEY: misc_feature
<222> LOCATION: (190)..(190)
<223> OTHER INFORMATION: Xaa is serine, alanine, or 2-aminobutyric acid
```

<400> SEQUENCE: 273

Lys Lys Thr Lys Asp Xaa Asp Val Glu Lys Pro Ile Arg Glu Xaa Leu
1               5                   10                  15

Lys Asn Gly Leu Leu Arg Tyr Ser Asp Gly Gln Lys Ile Asn Gln Phe
            20                  25                  30

Pro Asp Ser Ile Glu Asp Leu Asn Arg Ala Xaa Glu Glu Leu Lys Lys
        35                  40                  45

Ser Glu Thr Xaa Ala Arg Asn Phe Ile Asp Thr Xaa Thr Glu Thr Ser
50                  55                  60

Tyr Glu Lys Arg Ser Leu Asp Ser Leu Asp Gly Ile Gln Arg Val
65                  70                  75                  80

Leu Lys Arg Leu Xaa Arg Ser Gln Ser Lys Lys Glu Gln Leu Leu Gln
                85                  90                  95

Asn Val Gly Xaa Ala Asn Ser Val Val Gln Asp Thr Lys Leu Xaa Leu
            100                 105                 110

Lys Asn Tyr Arg Met Leu Val Phe Ala Ala Asn Lys Leu Asn Asp Lys
            115                 120                 125

Ser Lys Ile Met Arg Ile Leu Xaa Xaa Lys Ser Arg Lys Val Ala Pro
130                 135                 140

Xaa Ile Gly Glu Ala Met Lys Ser Lys Gly Asn Ala Val Xaa Ser Ala
145                 150                 155                 160

Lys Asn Ile Asp Tyr Phe Arg Glu Met His Gln Asn Ile Lys Ala Glu
                165                 170                 175

Met Thr Ala Val Val Xaa Ser Asp Phe Glu Arg Asp Gln Xaa Glu Asn
            180                 185                 190

Val Glu Val Pro Ala Ile Thr Glu Ala Glu Tyr Lys Asp Gln Asn Ile
            195                 200                 205

Phe Asn Pro Leu Arg Asp Leu Tyr Lys Lys Val Ile Leu Ala
            210                 215                 220

<210> SEQ ID NO 274
<211> LENGTH: 222
<212> TYPE: PRT
<213> ORGANISM: Dermatophagoides pteronyssinus
<220> FEATURE:
<221> NAME/KEY: misc_feature
<222> LOCATION: (6)..(6)
<223> OTHER INFORMATION: Xaa is serine, alanine, or 2-aminobutyric acid
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
<222> LOCATION: (43)..(43)
<223> OTHER INFORMATION: Xaa is serine, alanine, or 2-aminobutyric acid
<220> FEATURE:
<221> NAME/KEY: misc_feature
<222> LOCATION: (52)..(52)
<223> OTHER INFORMATION: Xaa is serine, alanine, or 2-aminobutyric acid
<220> FEATURE:
<221> NAME/KEY: misc_feature
<222> LOCATION: (60)..(60)
<223> OTHER INFORMATION: Xaa is serine, alanine, or 2-aminobutyric acid
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (100)..(100)
<223> OTHER INFORMATION: Xaa is serine, alanine, or 2-aminobutyric acid
<220> FEATURE:

```
<221> NAME/KEY: misc_feature
<222> LOCATION: (111)..(111)
<223> OTHER INFORMATION: Xaa is serine, alanine, or 2-aminobutyric acid
<220> FEATURE:
<221> NAME/KEY: misc_feature
<222> LOCATION: (136)..(137)
<223> OTHER INFORMATION: Xaa is serine, alanine, or 2-aminobutyric acid
<220> FEATURE:
<221> NAME/KEY: misc_feature
<222> LOCATION: (145)..(145)
<223> OTHER INFORMATION: Xaa is serine, alanine, or 2-aminobutyric acid
<220> FEATURE:
<221> NAME/KEY: misc_feature
<222> LOCATION: (158)..(158)
<223> OTHER INFORMATION: Xaa is serine, alanine, or 2-aminobutyric acid
<220> FEATURE:
<221> NAME/KEY: misc_feature
<222> LOCATION: (182)..(182)
<223> OTHER INFORMATION: Xaa is serine, alanine, or 2-aminobutyric acid
<220> FEATURE:
<221> NAME/KEY: misc_feature
<222> LOCATION: (190)..(190)
<223> OTHER INFORMATION: Xaa is serine, alanine, or 2-aminobutyric acid

<400> SEQUENCE: 274

Lys Lys Ser Pro Asp Xaa Asp Ile Glu Arg Pro Ile Arg Glu Xaa Leu
1               5                   10                  15

Lys Asp Gly Leu Leu Arg Tyr Ser Ser Gly Gln Lys Ile Asn Gln Phe
            20                  25                  30

Pro Asp Thr Ile Gln Asp Leu Asn Arg Ala Xaa Glu Glu Leu Lys Lys
        35                  40                  45

Ser Glu Thr Xaa Ala Arg Thr Phe Ile Asp Thr Xaa Thr Glu Ser Ser
    50                  55                  60

Tyr Glu Lys Arg Ser Leu Asp Ser Leu Leu Asp Gly Ile Gln Arg Val
65                  70                  75                  80

Met Lys Arg Leu Xaa Arg Ser Gln Thr Lys Glu Lys Leu Leu Glu
                85                  90                  95

Asn Val Gly Xaa Ala Asn Ser Val Val Gln Asp Thr Lys Gln Xaa Leu
            100                 105                 110

Lys Asn Tyr Arg Met Leu Val Phe Ala Ala Asn Lys Leu Asp Asn Lys
            115                 120                 125

Asn Lys Ile Met Arg Ile Leu Xaa Xaa Lys Ser Arg Lys Val Ala Pro
130                 135                 140

Xaa Ile Gly Glu Ala Met Lys Ala Lys Gly Thr Ala Val Xaa Ser Ala
145                 150                 155                 160

Lys Asn Ile Asp Tyr Phe Lys Asp Val His Gln Asn Ile Lys Gln Glu
                165                 170                 175

Met Thr Ala Val Val Xaa Ser Asp Phe Glu Arg Asp Gln Xaa Glu Asn
            180                 185                 190

Val Asp Val Pro Asn Ile Ser Glu Ser Glu Tyr Lys Asp Gln Asn Ile
            195                 200                 205

Phe Asn Pro Leu Arg Asp Leu Tyr Lys Lys Val Ile Leu Gly
            210                 215                 220

<210> SEQ ID NO 275
<211> LENGTH: 228
<212> TYPE: PRT
<213> ORGANISM: Dermatophagoides farinae
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
```

```
<222> LOCATION: (118)..(118)
<223> OTHER INFORMATION: Xaa is serine, alanine, or 2-aminobutyric acid
<220> FEATURE:
<221> NAME/KEY: misc_feature
<222> LOCATION: (169)..(169)
<223> OTHER INFORMATION: Xaa is serine, alanine, or 2-aminobutyric acid

<400> SEQUENCE: 275

Met Ser Lys Pro Thr Phe Tyr Phe His Pro Phe Ser Gly Pro Xaa Arg
1               5                   10                  15

Thr Val Ser Thr Val Ala Lys Ile Leu Asn Val Glu Met Glu Met Lys
            20                  25                  30

Lys Leu Asp Leu Leu Thr Gln Glu His Leu Lys Pro Glu Phe Leu Lys
        35                  40                  45

Val Asn Pro Phe His Lys Ile Pro Thr Phe Val Asp Thr Asp Gly Phe
    50                  55                  60

Thr Ile Asp Glu Ser Arg Val Ile Ala Met Tyr Leu Leu Gln Ser Arg
65                  70                  75                  80

Lys Pro Asp Ser Phe Leu Tyr Pro Asn Asn Asp Leu Lys Lys Arg Thr
                85                  90                  95

Gln Ile Asp Arg Trp Leu His Tyr Asp Ile Ser Phe Ala Thr Ile Ile
            100                 105                 110

Ser Thr Pro Met Tyr Xaa Lys Phe Arg Gly Lys Pro Val Gln Asp His
        115                 120                 125

Gln Val Glu Gln Gly Lys Glu Thr Leu Lys Thr Leu Asp Gly Val Met
    130                 135                 140

Ala Ser Phe Gly Gly Lys Phe Leu Thr Gly Ser Asp Gln Ile Thr Leu
145                 150                 155                 160

Ala Asp Ile Ala Met Tyr Phe Ser Xaa Asn Thr Met Glu Ile Tyr Ser
                165                 170                 175

Glu Tyr Phe Lys Phe Asp Asp Tyr Pro Asn Leu Lys Ser Trp Tyr Gln
            180                 185                 190

Arg Val Ala Glu Ala Leu Lys Gln Tyr Asp Thr Glu Gly Glu Ile Pro
        195                 200                 205

Lys Ala Ile Glu Met Ile Lys Gln Phe Ala Gln Gln Arg Met Ala Glu
    210                 215                 220

Ser Ala Lys Gln
225

<210> SEQ ID NO 276
<211> LENGTH: 228
<212> TYPE: PRT
<213> ORGANISM: Dermatophagoides pteronyssinus
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
<222> LOCATION: (118)..(118)
<223> OTHER INFORMATION: Xaa is serine, alanine, or 2-aminobutyric acid

<400> SEQUENCE: 276

Met Ser Lys Pro Ile Phe Tyr Tyr His Pro Phe Ser Gly Pro Xaa Arg
1               5                   10                  15

Thr Val Ser Thr Val Ala Lys Ile Leu Asn Val Asp Met Glu Met Lys
            20                  25                  30

Lys Leu Asp Leu Leu Thr Lys Glu His Leu Asn Pro Glu Phe Leu Lys
        35                  40                  45
```

-continued

Val Asn Pro Phe His Lys Val Pro Thr Phe Val Asp Ser Asp Gly Phe
 50                  55                  60

Val Val Asp Glu Ser Arg Val Ile Ala Met Tyr Leu Val Glu Ser Arg
 65                  70                  75                  80

Lys Pro Asp Ser Phe Leu Tyr Pro Lys Asn Asp Leu Lys Lys Arg Ile
                 85                  90                  95

Gln Ile Asp Arg Trp Leu His Tyr Asp Ile Asn Leu Ser Thr Thr Ile
            100                 105                 110

Ser Ala Pro Met Phe Xaa Val Phe Arg Gly His Gln Val Gln Asp Tyr
            115                 120                 125

Gln Val Glu Gln Gly Lys Glu Thr Leu Lys Thr Leu Asp Gly Val Met
130                 135                 140

Gln Ser Phe Glu Gly Lys Phe Leu Thr Gly Ala Asp Gln Phe Thr Leu
145                 150                 155                 160

Ala Asp Ile Ala Met Tyr Phe Ser Leu Asn Thr Met Glu Val Tyr Pro
                165                 170                 175

Lys Tyr Phe Lys Phe Asp Asp Tyr Pro Asn Leu Lys Ser Trp Tyr His
            180                 185                 190

Arg Val Ala Glu Ala Leu Lys Gln Tyr Asp Thr Glu Gly Thr Ile Pro
            195                 200                 205

Lys Ala Ile Glu Thr Met Lys Gln Phe Ile Gln Gln Arg Ala Ala Glu
210                 215                 220

Ala Glu Lys His
225

<210> SEQ ID NO 277
<211> LENGTH: 233
<212> TYPE: PRT
<213> ORGANISM: Dermatophagoides farinae
<220> FEATURE:
<221> NAME/KEY: misc_feature
<222> LOCATION: (11)..(11)
<223> OTHER INFORMATION: Xaa is serine, alanine, or 2-aminobutyric acid
<220> FEATURE:
<221> NAME/KEY: misc_feature
<222> LOCATION: (88)..(88)
<223> OTHER INFORMATION: Xaa is serine, alanine, or 2-aminobutyric acid

<400> SEQUENCE: 277

Glu Ser Leu Phe Ile Tyr Asp Asp Tyr Ser Xaa Gly Ser Tyr Gly His
 1               5                  10                  15

Asp Val Asn Glu Leu Ile Glu Gln Phe Gln Leu Phe Lys Lys Asn Glu
             20                  25                  30

His Asn Gln Asn Glu Ser Ile Glu Ile Gly His Phe Leu Lys Lys
         35                  40                  45

Ile Arg Glu Tyr Arg Val Glu Ala Ile Lys Val Met Leu Glu Thr Asp
 50                  55                  60

Arg Lys Leu Leu Thr Leu Asn Asn Ser Gln Ile Ile Leu Asn Ile Gln
 65                  70                  75                  80

Tyr Gln Lys Lys Lys Ile Arg Xaa Glu Asn Leu Lys His Leu Ser Glu
                 85                  90                  95

Leu Leu Thr Met His Leu Leu Ala Tyr Lys Gln Gly Met Phe Asp Phe
            100                 105                 110

Ala Glu Glu Ile Asp Pro Asp Val Asn Phe Asp Arg Gln Phe Lys Asn
            115                 120                 125

Phe Leu Asp Arg Ser Ser Glu Val Met Asn Ile Asn Glu Phe Ser Asp
130                 135                 140

```
Ile Glu Lys Lys Trp Ser Asn Ser Ser Ala Lys Lys Leu Leu Lys Asn
145                 150                 155                 160

Asp Ile Asp Gly Leu Ile Thr Ala Leu Asp Asp Leu Arg Glu Asp Phe
                165                 170                 175

Leu Lys Asn Ile Ile Leu Pro Glu Phe Asp Ala Gln Ser Arg Tyr Asp
            180                 185                 190

Leu Tyr Phe Ser Ile Gln Asp Gln Ile Asn Ile Arg Ser Thr Leu Lys
        195                 200                 205

Leu Phe Gly Thr Ile Lys Met Phe Met Lys Glu Leu Asp Asp Leu
    210                 215                 220

Asn Gln Pro Asp Phe Glu Ile Leu Tyr
225                 230
```

<210> SEQ ID NO 278
<211> LENGTH: 229
<212> TYPE: PRT
<213> ORGANISM: Dermatophagoides pteronyssinus
<220> FEATURE:
<221> NAME/KEY: misc_feature
<222> LOCATION: (12)..(12)
<223> OTHER INFORMATION: Xaa is serine, alanine, or 2-aminobutyric acid
<220> FEATURE:
<221> NAME/KEY: misc_feature
<222> LOCATION: (88)..(88)
<223> OTHER INFORMATION: Xaa is serine, alanine, or 2-aminobutyric acid

<400> SEQUENCE: 278

```
Gln Ser Leu Phe Val Asp Tyr Asn Asp Tyr Ser Xaa Gly Ser Ser Gln
1               5                   10                  15

Asn Glu Thr Asn Glu Leu Ile Gln Glu Phe Lys Ile Phe Lys Lys Asn
                20                  25                  30

Ile Asn Gly Asn Glu Asn Phe Lys Lys Ile Asn Asp Phe Ile Glu Lys
            35                  40                  45

Ala Arg Leu Phe Arg Asp Asn Ala Ala Lys Gln Met Leu Glu Ile Asp
        50                  55                  60

Gln Gln Leu Leu Thr Leu Asn Val Ile Gln Ile Ser Gln Arg Ile Lys
65                  70                  75                  80

Leu Glu Asn Asn Lys Ile Gln Xaa Glu Lys Leu Thr Lys Phe Ser Glu
                85                  90                  95

Leu Leu Ser Met Gln Leu Leu Ala Tyr Glu Val Gly Met Phe Glu Phe
                100                 105                 110

Ala Glu Glu Ile Asp Pro Asn Ile Asp Phe Asp Arg Lys Met Lys Asn
            115                 120                 125

Phe Leu Asp Glu Thr Ser Arg Leu Phe Asn Leu Ala Glu Phe Glu Lys
        130                 135                 140

Leu Glu Lys Lys Phe Arg Asn Ala Thr Ser Ile Glu Lys Leu Lys Asn
145                 150                 155                 160

Tyr Ile Asp Gly Glu Leu Val Ala Leu Asn Asp Tyr Ile Asn Glu Phe
                165                 170                 175

Leu Lys Asp Ile Ile Met Ser Glu Phe Thr Val Gln Ser Arg Tyr Tyr
            180                 185                 190

Leu Asn Phe Ser Ile Glu Asp Gln Val Gln Ile Asp Ser Thr Leu Met
        195                 200                 205

Thr Phe Ser Ala Leu Lys Ile Leu Leu Asn Asp Leu Lys Asp Tyr Leu
    210                 215                 220

Glu His Leu Asp Asn
225
```

<210> SEQ ID NO 279
<211> LENGTH: 252
<212> TYPE: PRT
<213> ORGANISM: Dermatophagoides farinae

<400> SEQUENCE: 279

Glu Trp Arg Leu Val Trp Gln Asp Glu Phe Asn Gly Asn Gln Leu Asp
1               5                   10                  15

Leu Asn Gln Trp Ser Tyr Glu Val Gly Gly Asn Gly Trp Gly Asn Asn
            20                  25                  30

Glu Leu Glu Phe Tyr Thr Tyr Asn Arg Thr Glu Asn Ala Arg Ile Glu
        35                  40                  45

Asn Gly Asn Leu Val Ile Asp Val Arg Val Glu Asn Tyr Arg Glu Arg
    50                  55                  60

Gln Phe Thr Ser Ala Arg Leu His Thr Arg Gln Ala Trp Thr Tyr Gly
65                  70                  75                  80

Arg Phe Glu Ala Arg Ala Arg Met Pro Tyr Gly His Asn Leu Trp Pro
                85                  90                  95

Ala Ile Trp Met Met Pro Gln Asp Ser Ile Tyr Gly Ile Trp Ala Ala
            100                 105                 110

Ser Gly Glu Ile Asp Ile Val Glu Tyr Arg Gly Asp Asn Pro Asp Arg
        115                 120                 125

Ile Glu Gly Thr Ala His Tyr Gly Gly Thr Trp Pro Asn His Ile Tyr
    130                 135                 140

Ser Gly Ser Gly Pro Arg Ser Phe Ser Val Asn Phe Ser Gln Asp Phe
145                 150                 155                 160

His Thr Phe Ala Leu Glu Trp Asp His Lys Gln Leu Arg Trp Tyr Met
                165                 170                 175

Asp Asn Gln Gln Tyr Phe Thr Leu Asp Ile Asp Arg Met Leu Trp Ser
            180                 185                 190

Gly Lys Gly Val Asn Pro Tyr Thr Lys Asn Gly Gln Pro Phe Asp Gln
        195                 200                 205

Pro Phe His Trp Met Leu Asn Val Ala Val Gly Gly Asn Phe Phe Gly
    210                 215                 220

Pro Gly Pro Tyr Val Thr Pro Asp Gln Ala Arg Gln Trp Pro Lys His
225                 230                 235                 240

Thr Leu Glu Ile Asp Tyr Val Arg Val Tyr Gln Gln
                245                 250

<210> SEQ ID NO 280
<211> LENGTH: 253
<212> TYPE: PRT
<213> ORGANISM: Dermatophagoides pteronyssinus

<400> SEQUENCE: 280

Asn Trp Gln Met Val Trp Gln Asp Glu Phe Asn Gly Gly His Leu Asp
1               5                   10                  15

Gln Asn His Trp Glu Phe Glu Thr Gly Gly Gly Gly Trp Gly Asn Asn
            20                  25                  30

Glu Leu Glu Phe Tyr Thr Ala Asn Arg Ser Gln Asn Val Arg Val Glu
        35                  40                  45

Asn Gly His Leu Val Ile Asp Val Arg Val Glu Ser Tyr Gly Gly Arg
    50                  55                  60

Asp Phe Thr Ser Gly Arg Ile His Ser Lys Gln Ala Trp Ala Tyr Gly
65                  70                  75                  80

```
Lys Phe Glu Ala Arg Ala Arg Leu Pro Ser Gly His His Leu Trp Pro
                 85                  90                  95

Ala Ile Trp Met Phe Pro Arg Asp Ser Lys Tyr Gly Pro Trp Ala Ala
            100                 105                 110

Ser Gly Glu Ile Asp Ile Met Glu Tyr Arg Gly Asp Val His Asp Lys
            115                 120                 125

Ile Glu Gly Thr Ile His Tyr Gly Gly Gln Trp Pro Asn Asn Ile Tyr
            130                 135                 140

Thr Gly Ser Gly Pro His His Phe Asn Val Asp Phe Ser Lys Asp Phe
145                 150                 155                 160

His Asn Phe Ala Val Glu Trp Asp Thr Lys Glu Ile Arg Trp Tyr Met
                165                 170                 175

Asp Gly Asn Lys Tyr Phe Ser Val Asn Ile Asp Arg Asn Met Trp Ser
            180                 185                 190

Gly Lys Gly Asn Asn Pro Tyr Asn Lys Asn Gly Gln Pro Phe Asp Gln
            195                 200                 205

Pro Phe Arg Trp Ile Leu Asn Val Ala Val Gly Asn Phe Phe Gly
            210                 215                 220

Pro Gly Pro Tyr Val Thr Pro Asp Gln Ala Arg His Trp Gln Lys His
225                 230                 235                 240

Thr Met Glu Ile Asp Tyr Val Arg Val Tyr Gln Trp Arg
                245                 250

<210> SEQ ID NO 281
<211> LENGTH: 261
<212> TYPE: PRT
<213> ORGANISM: Dermatophagoides farinae

<400> SEQUENCE: 281

Met Ser Ser Ser Ser Gly Lys Lys Tyr Asp Phe Ser Gly Lys Val Ala
1               5                   10                  15

Leu Val Thr Gly Ser Ser Gly Ile Gly Ala Ala Ile Ala Val Gln
            20                  25                  30

Phe Ala Gln Tyr Gly Ala Lys Leu Thr Ile Thr Gly Arg Asp Gly Ala
            35                  40                  45

Ala Leu Glu Ser Val Ala Lys Lys Ile Glu Ile Glu Ser Gly His Gln
50                  55                  60

Pro Leu Gln Ile Val Gly Asp Leu Leu Asp Gln Ser Leu Pro Ala Lys
65                  70                  75                  80

Leu Ile Asn Glu Thr Val Ser Lys Phe Gly Arg Leu Asp Phe Leu Val
                85                  90                  95

Asn Asn Ala Gly Gly Ser Thr Ala His Arg Glu Leu Asn Asp Glu Lys
            100                 105                 110

Leu Met Glu Ala Phe Asp Lys Val Phe Ala Leu Asn Val Arg Ala Val
            115                 120                 125

Leu Gln Leu Ser Gln Leu Ala Ala Ile His Leu Glu Lys Ser Lys Gly
            130                 135                 140

Asn Ile Ile Asn Ile Ser Ser Ile Val Ser Met Lys Pro Tyr Gly His
145                 150                 155                 160

Val Tyr Ser Ser Ser Lys Ala Ala Leu Asp Met Ile Thr Lys Thr Leu
                165                 170                 175

Ala Lys Glu Leu Gly Leu Lys Gly Val Arg Val Asn Ser Ile Asn Pro
            180                 185                 190

Gly Pro Val Ala Thr Gly Phe Leu Arg Ser Val Gly Met Ser Ala Thr
            195                 200                 205
```

-continued

Ala Tyr Thr Asp Leu Ala Asp Thr Met Ile Asn His Thr Leu Leu Lys
            210                 215                 220

Phe Leu Ala Gln Pro Asp Glu Ile Ala Asn Leu Ala Ser Phe Leu Ala
225                 230                 235                 240

Ser Asp Asp Ala Arg Asn Met Thr Gly Ser Ile Val Val Ser Asp Thr
            245                 250                 255

Gly Ser Leu Leu Val
            260

<210> SEQ ID NO 282
<211> LENGTH: 262
<212> TYPE: PRT
<213> ORGANISM: Dermatophagoides pteronyssinus
<220> FEATURE:
<221> NAME/KEY: misc_feature
<222> LOCATION: (14)..(14)
<223> OTHER INFORMATION: Xaa is serine, alanine, or 2-aminobutyric acid
<220> FEATURE:
<221> NAME/KEY: misc_feature
<222> LOCATION: (39)..(39)
<223> OTHER INFORMATION: Xaa is serine, alanine, or 2-aminobutyric acid

<400> SEQUENCE: 282

Gln Ser Arg Asp Arg Asn Asn Lys Pro Tyr Arg Ile Val Xaa Tyr Trp
1               5                   10                  15

Gly Thr Trp Ala Phe Tyr Arg Pro Gly Thr Gly Lys Phe Glu Ala Glu
            20                  25                  30

Asn Val Asn Pro Asn Leu Xaa Thr His Leu Met Tyr Gly Phe Ala Lys
            35                  40                  45

Leu Gln Asn Asn Lys Ile Ala Leu Tyr Asp Pro Asp Leu Asp Asp Gly
    50                  55                  60

Asp Glu Asp Trp Asn Ser Gly Leu Asn Trp Gly His Gly Met Ile Arg
65                  70                  75                  80

Arg Met Val Asn Leu Arg Thr Tyr Asn Pro His Leu Thr Thr Met Ile
                85                  90                  95

Ser Ile Gly Gly Trp Asn Glu Gly Ser Asp Lys Tyr Ser Met Met Val
            100                 105                 110

Arg Asp Pro Ser Ser Arg Lys Ile Phe Ile Gln Ser Val Leu Asp Leu
        115                 120                 125

Leu Ala Glu Phe Asp Leu Asp Gly Leu Asp Phe Asp Trp Glu Tyr Pro
    130                 135                 140

Ser Met Lys Ala Thr Gly Asp Asn Asp Arg Lys Pro Gly Arg Asp Glu
145                 150                 155                 160

Asp Lys Glu Asp Phe Ile Thr Leu Leu Arg Glu Leu His Glu Ala Phe
                165                 170                 175

Gln Pro His Gly Tyr Leu Leu Ser Ser Ala Val Ser Ala Gly Lys Pro
            180                 185                 190

Thr Ile Asp Arg Ala Tyr Asn Ile Pro Glu Val Ser Lys Tyr Leu Asp
        195                 200                 205

Phe Ile Asn Leu Met Ser Tyr Asp Tyr His Gly Gly Trp Glu Ser His
    210                 215                 220

Thr Gly His Asn Ala Pro Leu Asn Ser Tyr Asp Asn Ala Asn Glu Leu
225                 230                 235                 240

Asp Lys Glu Phe Thr Val Thr Tyr Ser Val Asp Tyr Trp Leu Ser His
                245                 250                 255

Gly Val Asp Ala Lys Asn
            260

<210> SEQ ID NO 283
<211> LENGTH: 270
<212> TYPE: PRT
<213> ORGANISM: Dermatophagoides farinae
<220> FEATURE:
<221> NAME/KEY: misc_feature
<222> LOCATION: (205)..(205)
<223> OTHER INFORMATION: Xaa is serine, alanine, or 2-aminobutyric acid
<220> FEATURE:
<221> NAME/KEY: misc_feature
<222> LOCATION: (260)..(260)
<223> OTHER INFORMATION: Xaa is serine, alanine, or 2-aminobutyric acid

<400> SEQUENCE: 283

Ser Pro Ala Gln Arg Pro Ser Leu Arg Gly Val Thr Ile Arg Asn Ala
1               5                   10                  15

Pro Phe Leu Glu Glu Ile Asp Gly Lys Phe Lys Gly Phe Ile Pro Asp
            20                  25                  30

Leu Met Asp Ala Ile Ala Glu Lys Ala Gly Phe Asp Tyr Thr Leu Tyr
        35                  40                  45

Leu Ser Pro Asp Gly Arg Tyr Gly Asn Ala Asp Lys Glu Gly Asn Val
50                  55                  60

Thr Gly Met Ile Gly Glu Val Tyr Asn Lys Lys Ala Asp Phe Ala Ala
65                  70                  75                  80

Ala Asp Leu Thr Met Thr Glu Ala Arg Glu Asn Tyr Ile Thr Phe Thr
                85                  90                  95

Glu Pro Phe Met Ile Asn Gln Leu Ala Ala Leu Ile Arg Arg Glu Asp
            100                 105                 110

Ala Glu Gly Met Asn Thr Leu Glu Asp Leu Val Asn Ala Gly Lys Thr
        115                 120                 125

Gln Pro Asn His Lys Pro Ile Ile Leu Gly Thr Leu Arg Asn Gly Ala
    130                 135                 140

Thr Asn His Phe Leu Ser Lys Ser Asp Asp Pro Leu Ala Lys Lys Met
145                 150                 155                 160

Tyr Glu Gln Ile Lys Ala Asn Asp Gln Ser Ala Thr Thr Ser Ile Ser
                165                 170                 175

Lys Gly Ile Glu Arg Val Asp Lys Gln Gly Gly Tyr Ala Phe Ile Met
            180                 185                 190

Glu Ser Ser Ser Ala Glu His Glu Ile Ala Asn Asn Xaa Lys Leu Thr
        195                 200                 205

Met Leu Leu Asp Trp Arg Asn Leu Tyr Pro Arg Lys Tyr Ala Phe Ala
    210                 215                 220

Leu Pro Lys Asp Ser Gln Tyr Leu Gln His Phe Asn Asn Ala Ile Lys
225                 230                 235                 240

Gln Leu Asn Thr Glu Asp Lys Ile Ala Glu Leu Arg Arg Lys Tyr Trp
                245                 250                 255

Ser Asn Asn Xaa Ser Asn Thr Gln Thr Lys Asn Thr Gly Ala
            260                 265                 270

<210> SEQ ID NO 284
<211> LENGTH: 271
<212> TYPE: PRT
<213> ORGANISM: Dermatophagoides pteronyssinus
<220> FEATURE:
<221> NAME/KEY: misc_feature
<222> LOCATION: (206)..(206)
<223> OTHER INFORMATION: Xaa is serine, alanine, or 2-aminobutyric acid
<220> FEATURE:
<221> NAME/KEY: misc_feature
<222> LOCATION: (261)..(261)
<223> OTHER INFORMATION: Xaa is serine, alanine, or 2-aminobutyric acid

<400> SEQUENCE: 284

Asp Pro Val Gln Gln Arg Pro Thr Leu Arg Gly Val Thr Val Arg Val
1               5                   10                  15

Gly Pro Phe Val Lys Glu Asn Asn Gly Lys Phe Glu Gly Phe Ile Pro
            20                  25                  30

Asp Leu Val Gln Ala Ile Ser Glu Lys Val Gly Phe Asp Tyr Thr Leu
        35                  40                  45

Tyr Leu Ser Pro Asp Gly Arg Tyr Gly Asn Val Ile Ser Asp Gly Asn
    50                  55                  60

Val Thr Gly Met Ile Gly Glu Val Tyr Asn Lys Lys Ala Asp Phe Ala
65                  70                  75                  80

Ala Ala Asp Leu Thr Met Thr Glu Ala Arg Glu Asn Tyr Ile Thr Phe
                85                  90                  95

Thr Glu Pro Phe Met Ile Asn Gln Leu Ala Ala Leu Ile Arg Arg Glu
            100                 105                 110

Asp Ala Glu Gly Leu Asn Thr Leu Glu Asp Leu Ala Lys Ala Gln Glu
        115                 120                 125

Thr Phe Pro Lys Arg Lys Arg Ile Val Leu Gly Thr Leu Arg Asn Gly
    130                 135                 140

Ala Thr Asn Tyr Phe Leu Ser Lys Ser Asp Asp Pro Leu Ala Lys Lys
145                 150                 155                 160

Ile Tyr Glu Gln Ile Lys Ala Asp Asp Gln Ser Val Val Lys Ser Ile
                165                 170                 175

Ser Glu Gly Val Glu Arg Val Asp Lys Gln Gly Gly Tyr Ala Phe Ile
            180                 185                 190

Met Glu Ser Ala Ser Ala Glu His Glu Ile Ala Asn Asn Xaa Lys Leu
        195                 200                 205

Thr Met Leu Leu Asp Trp Arg Asn Leu Phe Pro Arg Lys Tyr Ala Phe
    210                 215                 220

Ala Leu Pro Lys Asp Ser Pro Tyr Leu Glu His Phe Asn Asn Ala Ile
225                 230                 235                 240

Lys Gln Leu Asn Ser Glu Gly Lys Ile Ala Glu Leu Arg Arg Lys Tyr
                245                 250                 255

Trp Ala Asn Asn Xaa Ala Glu Asn Lys Thr Lys Asp Asp Lys Asn
            260                 265                 270

<210> SEQ ID NO 285
<211> LENGTH: 275
<212> TYPE: PRT
<213> ORGANISM: Dermatophagoides pteronyssinus

<400> SEQUENCE: 285

Met Ser Ser Ser Gly Lys Lys Tyr Asp Phe Ser Gly Lys Val Ala
1               5                   10                  15

Leu Val Thr Gly Ser Ser Ser Gly Ile Gly Ala Ala Ile Ala Leu Gln
            20                  25                  30

Phe Ala Gln Tyr Gly Ala Gln Val Thr Ile Thr Gly Arg Asp Ala Ala
        35                  40                  45

Ala Leu Glu Ser Val Ala Lys Arg Ile Glu Ala Glu Ser Gly His Gln
    50                  55                  60

Pro Leu Gln Ile Val Gly Asn Leu Leu Asp Gln Ser Leu Pro Ala Lys
65                  70                  75                  80

Leu Ile Asp Gly Thr Ile Ser Lys Tyr Gly Arg Leu Asp Phe Leu Val
            85                  90                  95

Asn Asn Ala Gly Phe Ser Thr Gln His Arg Asp Ile His Asp Glu Lys
            100                 105                 110

Leu Met Glu Ala Phe Asp Gln Val Tyr Gly Leu Asn Val Arg Ala Val
            115                 120                 125

Val Gln Leu Ser Gln Leu Ala Ala Thr His Leu Glu Lys Ser Lys Gly
            130                 135                 140

Asn Ile Ile Asn Ile Ser Ser Asn Leu Ser Met Met Pro Val His Ile
145                 150                 155                 160

Ile Tyr Ser Ser Ser Lys Ala Ala Leu Asp Met Ile Thr Lys Thr Met
                165                 170                 175

Ala Met Glu Phe Gly Lys Lys Gly Val Arg Val Asn Ser Ile Asn Pro
            180                 185                 190

Gly Pro Val Ala Thr Gln Phe Met Arg Ser Leu Gly Met Pro Val Thr
            195                 200                 205

Phe Leu Lys Glu Asn Gly Glu Phe Val Lys Glu Leu Thr Leu Leu Lys
            210                 215                 220

Phe Val Ala Gln Pro Val Glu Ile Ala Asn Leu Ala Ser Phe Leu Ala
225                 230                 235                 240

Ser Asp Asp Ala Arg Asn Met Thr Gly Ser Ile Val Val Asn Asp Thr
                245                 250                 255

Gly Ser Leu Leu Ala Pro Arg Val Asp Phe Lys Lys Leu Asp Glu Ile
            260                 265                 270

Lys Lys Lys
        275

<210> SEQ ID NO 286
<211> LENGTH: 310
<212> TYPE: PRT
<213> ORGANISM: Dermatophagoides farinae
<220> FEATURE:
<221> NAME/KEY: misc_feature
<222> LOCATION: (89)..(89)
<223> OTHER INFORMATION: Xaa is serine, alanine, or 2-aminobutyric acid
<220> FEATURE:
<221> NAME/KEY: misc_feature
<222> LOCATION: (117)..(117)
<223> OTHER INFORMATION: Xaa is serine, alanine, or 2-aminobutyric acid
<220> FEATURE:
<221> NAME/KEY: misc_feature
<222> LOCATION: (119)..(120)
<223> OTHER INFORMATION: Xaa is serine, alanine, or 2-aminobutyric acid
<220> FEATURE:
<221> NAME/KEY: misc_feature
<222> LOCATION: (128)..(128)
<223> OTHER INFORMATION: Xaa is serine, alanine, or 2-aminobutyric acid
<220> FEATURE:
<221> NAME/KEY: misc_feature
<222> LOCATION: (151)..(151)
<223> OTHER INFORMATION: Xaa is serine, alanine, or 2-aminobutyric acid
<220> FEATURE:
<221> NAME/KEY: misc_feature
<222> LOCATION: (157)..(157)
<223> OTHER INFORMATION: Xaa is serine, alanine, or 2-aminobutyric acid
<220> FEATURE:
<221> NAME/KEY: misc_feature
<222> LOCATION: (180)..(180)
<223> OTHER INFORMATION: Xaa is serine, alanine, or 2-aminobutyric acid
<220> FEATURE:
<221> NAME/KEY: misc_feature
<222> LOCATION: (189)..(189)
<223> OTHER INFORMATION: Xaa is serine, alanine, or 2-aminobutyric acid
<220> FEATURE:
<221> NAME/KEY: misc_feature
<222> LOCATION: (203)..(203)

<223> OTHER INFORMATION: Xaa is serine, alanine, or 2-aminobutyric acid

<400> SEQUENCE: 286

Ser Pro Thr Ser Ile Arg Thr Phe Glu Glu Phe Lys Arg Gln Phe Asn
1               5                   10                  15

Lys Gln Tyr Gln Ser Ile Glu His Glu Ile Ala Arg Lys Asn Phe
            20                  25                  30

Gln Glu Thr Leu Arg Tyr Val Gln Ala Asn Gln Asp Lys Ala Val Ile
        35                  40                  45

Asn Glu Tyr Ala Asp Leu Ser Ala Glu Glu Phe Ala Asp Gly Tyr Leu
    50                  55                  60

Met Asn Val Gln Asp Val Gln Asp Leu Glu Ala Glu Met Asp Ala His
65                  70                  75                  80

Lys Glu Tyr Phe Asp Asp Pro Asp Xaa Lys Leu His Gly Asp Phe Asn
                85                  90                  95

Pro Pro Lys Glu Phe Asp Leu Arg Pro His Leu Thr Pro Ile Lys Lys
            100                 105                 110

Gln Ile Lys Asn Xaa Gly Xaa Xaa Trp Ala Leu Ser Thr Ile Ser Xaa
        115                 120                 125

Val Glu Thr Ala Tyr Leu Ala Gln Lys Asn Val Ser Leu Gln Leu Ser
130                 135                 140

Thr Gln Glu Leu Val Asn Xaa Ala Lys Glu His Gly Xaa Lys Lys Gly
145                 150                 155                 160

Thr Val Leu Asp Gly Ile Glu Tyr Ile Met Ala Asn Gly Thr Thr Thr
                165                 170                 175

Glu Glu Ala Xaa Pro Phe Ile Ser Glu Ser Thr Xaa Asp Gln Ser
            180                 185                 190

Lys Lys Pro Arg Tyr Glu Ile Ser Asn Trp Xaa Tyr Phe Lys Pro Val
        195                 200                 205

Glu Asp Asp Ile Arg Lys Asn Leu Val Leu Arg Arg Thr Ser Val Ser
210                 215                 220

Val Ser Met Asn Ile Glu Asn Leu Lys Ala Phe Val His Tyr Asp Gly
225                 230                 235                 240

Ser Phe Val Ile Arg Glu Asn Ser Phe Pro Ser Ile Gly Asn Lys Ser
                245                 250                 255

Tyr His Ala Val Asn Ile Val Gly Phe Gly Thr Lys Asp Asp Ile Asp
            260                 265                 270

His Trp Ile Val Arg Asn Ser Trp Gly Glu Lys Trp Gly Asp Lys Gly
        275                 280                 285

Tyr Phe Tyr Val Glu Arg Asp Ile Asn Leu Trp Gly Ile Lys Asp Trp
    290                 295                 300

Ala Phe Thr Thr Ile Val
305                 310

<210> SEQ ID NO 287
<211> LENGTH: 321
<212> TYPE: PRT
<213> ORGANISM: Dermatophagoides pteronyssinus
<220> FEATURE:
<221> NAME/KEY: misc_feature
<222> LOCATION: (94)..(94)
<223> OTHER INFORMATION: Xaa is serine, alanine, or 2-aminobutyric acid
<220> FEATURE:
<221> NAME/KEY: misc_feature
<222> LOCATION: (122)..(122)
<223> OTHER INFORMATION: Xaa is serine, alanine, or 2-aminobutyric acid
<220> FEATURE:
<221> NAME/KEY: misc_feature

```
<222> LOCATION: (124)..(125)
<223> OTHER INFORMATION: Xaa is serine, alanine, or 2-aminobutyric acid
<220> FEATURE:
<221> NAME/KEY: misc_feature
<222> LOCATION: (156)..(156)
<223> OTHER INFORMATION: Xaa is serine, alanine, or 2-aminobutyric acid
<220> FEATURE:
<221> NAME/KEY: misc_feature
<222> LOCATION: (162)..(162)
<223> OTHER INFORMATION: Xaa is serine, alanine, or 2-aminobutyric acid
<220> FEATURE:
<221> NAME/KEY: misc_feature
<222> LOCATION: (194)..(194)
<223> OTHER INFORMATION: Xaa is serine, alanine, or 2-aminobutyric acid
<220> FEATURE:
<221> NAME/KEY: misc_feature
<222> LOCATION: (208)..(208)
<223> OTHER INFORMATION: Xaa is serine, alanine, or 2-aminobutyric acid

<400> SEQUENCE: 287

Ser Pro Thr Gly Trp Asn Ile Arg Thr Phe Glu Gln Phe Lys Ile Gln
 1               5                  10                  15

Phe Asn Lys His Tyr Asp Ser Ile Glu Gln Glu Glu His Ala Arg Glu
            20                  25                  30

Asn Phe Leu Glu Thr Leu Lys Tyr Val Asp Ala Asn Pro Asp Lys Ala
        35                  40                  45

Val Ile Asn Glu Phe Ala Asp Leu Ser Ala Glu Glu Phe Ala Asp Gly
 50                  55                  60

Tyr Leu Met Ser Glu Glu Ser Met Gln Asp Ser Glu Gln Gln Leu Lys
 65                  70                  75                  80

Leu Leu Arg Ala Gly Tyr Asp Tyr His Asp Pro Glu Xaa Leu Phe
                85                  90                  95

Asp Glu Asn Leu Glu Ala Pro Lys Gln Val Asp Leu Arg Pro Asp Leu
            100                 105                 110

Ser Pro Ile Met Arg Gln Thr Leu His Xaa Gly Xaa Xaa Trp Ala Ile
        115                 120                 125

Ser Pro Ile Ser Ser Ala Glu Ser Ala Tyr Lys Ala Arg Tyr Asn Val
    130                 135                 140

Ser Ile Gln Leu Ser Val Gln Glu Leu Val Asn Xaa Ala Val Glu His
145                 150                 155                 160

Gly Xaa Glu Ile Gly Lys Thr Ala Ile Ala Phe Asn Tyr Leu Val Thr
                165                 170                 175

Asn Gly Thr Thr Thr Gln Lys Ala Tyr Pro Tyr Thr Ala Lys Glu Gly
            180                 185                 190

Ala Xaa Asn Pro Pro Glu Lys Pro Arg Tyr Thr Leu Glu Asn Trp Xaa
        195                 200                 205

Ala Tyr Ile Asp Pro Ser Ile Lys Asn Lys Asn Lys Pro Asp Leu Arg
    210                 215                 220

Lys Val Leu Ala Gln Lys Arg Thr Ser Ile Thr Val Gln Ile Ser Ile
225                 230                 235                 240

Lys Asn Val Lys Ala Phe Ala His His Asn Gly Ser Phe Ile Ile Arg
                245                 250                 255

Glu Asn Ser Phe Pro Asp Glu Gly Lys Pro Ser Gly His Ala Ile Asn
            260                 265                 270

Ile Val Gly Tyr Gly Thr Lys Asp Gly Val Asp Tyr Trp Ile Val Arg
        275                 280                 285

Asn Ser Trp Ser Thr Gly Trp Gly Asp Lys Gly Tyr Phe Tyr Val Glu
    290                 295                 300

Arg Gly Val Asn Trp Trp Gly Ile Glu Glu Tyr Ala Phe Ile Ala Thr
```

```
305                 310                 315                 320

Phe

<210> SEQ ID NO 288
<211> LENGTH: 332
<212> TYPE: PRT
<213> ORGANISM: Dermatophagoides farinae
<220> FEATURE:
<221> NAME/KEY: misc_feature
<222> LOCATION: (149)..(149)
<223> OTHER INFORMATION: Xaa is serine, alanine, or 2-aminobutyric acid
<220> FEATURE:
<221> NAME/KEY: misc_feature
<222> LOCATION: (153)..(153)
<223> OTHER INFORMATION: Xaa is serine, alanine, or 2-aminobutyric acid

<400> SEQUENCE: 288
```

Met Val Lys Ile Gly Ile Asn Gly Phe Gly Arg Ile Gly Arg Leu Val
1               5                   10                  15

Leu Arg Ala Ala Val Lys Lys Gly Val Glu Val Val Ala Val Asn Asp
                20                  25                  30

Pro Phe Leu Asp Val Lys Tyr Met Val Tyr Met Phe Lys Phe Asp Ser
            35                  40                  45

Thr His Gly Arg Tyr Gln Gly Glu Val Lys Glu Glu Gly Gly Leu Leu
        50                  55                  60

Val Val Asp Gly Gln Lys Ile Gln Val Phe Gln Glu Arg Asn Pro Ala
65                  70                  75                  80

Asp Ile Pro Trp Gly Lys Val Gly Ala Asp Tyr Val Val Glu Ser Thr
                85                  90                  95

Gly Val Phe Thr Thr Ile Glu Lys Ala Lys Ala His Leu Ala Gly Gly
            100                 105                 110

Ala Lys Lys Val Val Ile Ser Ala Pro Ser Ala Asp Ala Pro Met Tyr
        115                 120                 125

Val Met Gly Val Asn His Asp Lys Tyr Asp Pro Ser Gln Gln Ile Ile
130                 135                 140

Ser Asn Ala Ser Xaa Thr Thr Asn Xaa Leu Ala Pro Leu Ala Lys Val
145                 150                 155                 160

Ile Asn Asp Lys Phe Gly Ile Glu Asn Gly Leu Met Thr Thr Val His
                165                 170                 175

Ala Val Thr Ala Thr Gln Lys Thr Val Asp Gly Pro Ser Gly Lys Met
            180                 185                 190

Trp Arg Asp Gly Arg Gly Ala Gly Gln Asn Ile Ile Pro Ala Ser Thr
        195                 200                 205

Gly Ala Ala Lys Ala Val Gly Lys Val Ile Pro Glu Leu Asn Gly Lys
210                 215                 220

Leu Thr Gly Met Ala Leu Arg Val Pro Val Pro Asp Val Ser Val Val
225                 230                 235                 240

Asp Leu Thr Val Thr Leu Lys Asn Pro Ala Ser Tyr Asp Glu Ile Lys
                245                 250                 255

Ala Ala Ile Lys Ala Ala Ala Glu Ser Asp His Trp Lys Gly Ile Leu
            260                 265                 270

Glu Tyr Thr Asp Glu Glu Val Val Ser Ser Asp Phe Ile Ser Asp Thr
        275                 280                 285

His Ser Ser Ile Phe Asp Ala Lys Ala Gly Ile Ala Leu Thr Pro Thr
290                 295                 300

Phe Val Lys Leu Ile Ala Trp Tyr Asp Asn Glu Phe Gly Tyr Ser Asn
305                 310                 315                 320

Arg Val Ile Asp Leu Ile Lys Tyr Val Ala Ser Lys
            325                 330

<210> SEQ ID NO 289
<211> LENGTH: 332
<212> TYPE: PRT
<213> ORGANISM: Dermatophagoides pteronyssinus
<220> FEATURE:
<221> NAME/KEY: misc_feature
<222> LOCATION: (149)..(149)
<223> OTHER INFORMATION: Xaa is serine, alanine, or 2-aminobutyric acid
<220> FEATURE:
<221> NAME/KEY: misc_feature
<222> LOCATION: (153)..(153)
<223> OTHER INFORMATION: Xaa is serine, alanine, or 2-aminobutyric acid

<400> SEQUENCE: 289

Met Val Lys Ile Gly Ile Asn Gly Phe Gly Arg Ile Gly Arg Leu Val
1               5                   10                  15

Leu Arg Ala Ala Ile Lys Lys Gly Val Glu Val Ala Ala Ile Asn Asp
            20                  25                  30

Pro Phe Leu Asp Val Lys Tyr Met Val Tyr Met Phe Lys Phe Asp Ser
        35                  40                  45

Thr His Gly Arg Tyr Gln Gly Glu Val Lys Glu Glu Gly Gly Leu Leu
    50                  55                  60

Val Val Asp Gly Gln Lys Ile Gln Val Phe Gln Glu Arg Asn Pro Ala
65                  70                  75                  80

Glu Ile Pro Trp Gly Lys Val Gly Ala Asp Tyr Val Val Glu Ser Thr
                85                  90                  95

Gly Val Phe Thr Thr Ile Glu Lys Ala Lys Ala His Leu Ala Gly Gly
            100                 105                 110

Ala Lys Lys Val Ile Ile Ser Ala Pro Ser Ala Asp Ala Pro Met Tyr
        115                 120                 125

Val Met Gly Val Asn His Asp Lys Tyr Asp Pro Lys Gln Gln Ile Ile
    130                 135                 140

Ser Asn Ala Ser Xaa Thr Thr Asn Xaa Leu Ala Pro Leu Ala Lys Val
145                 150                 155                 160

Ile Asn Asp Lys Phe Gly Ile Glu Asn Gly Leu Met Thr Thr Val His
                165                 170                 175

Ala Ile Thr Ala Thr Gln Lys Thr Val Asp Gly Pro Ser Gly Lys Leu
            180                 185                 190

Trp Arg Asp Gly Arg Gly Ala Gly Gln Asn Ile Ile Pro Ala Ser Thr
        195                 200                 205

Gly Ala Ala Lys Ala Val Gly Lys Val Ile Pro Glu Leu Asn Gly Lys
    210                 215                 220

Leu Thr Gly Met Ala Leu Arg Val Pro Val Pro Asp Val Ser Val Val
225                 230                 235                 240

Asp Leu Thr Val Thr Leu Lys Asn Pro Ala Ser Tyr Asp Glu Ile Lys
                245                 250                 255

Ala Ala Val Lys Ala Ala Ala Glu Ser Asp His Trp Lys Gly Ile Leu
            260                 265                 270

Glu Tyr Thr Asp Glu Glu Val Val Ser Ser Asp Phe Ile Ser Asp Thr
        275                 280                 285

His Ser Ser Ile Phe Asp Ala Lys Ala Gly Ile Ala Leu Thr Pro Thr
    290                 295                 300

Phe Val Lys Leu Ile Ala Trp Tyr Asp Asn Glu Phe Gly Tyr Ser Asn
305                 310                 315                 320

```
Arg Val Val Asp Leu Ile Lys Tyr Val Ala Ser Lys
                325                 330

<210> SEQ ID NO 290
<211> LENGTH: 361
<212> TYPE: PRT
<213> ORGANISM: Dermatophagoides farinae
<220> FEATURE:
<221> NAME/KEY: misc_feature
<222> LOCATION: (133)..(133)
<223> OTHER INFORMATION: Xaa is serine, alanine, or 2-aminobutyric acid
<220> FEATURE:
<221> NAME/KEY: misc_feature
<222> LOCATION: (141)..(141)
<223> OTHER INFORMATION: Xaa is serine, alanine, or 2-aminobutyric acid
<220> FEATURE:
<221> NAME/KEY: misc_feature
<222> LOCATION: (148)..(148)
<223> OTHER INFORMATION: Xaa is serine, alanine, or 2-aminobutyric acid
<220> FEATURE:
<221> NAME/KEY: misc_feature
<222> LOCATION: (175)..(176)
<223> OTHER INFORMATION: Xaa is serine, alanine, or 2-aminobutyric acid
<220> FEATURE:
<221> NAME/KEY: misc_feature
<222> LOCATION: (200)..(200)
<223> OTHER INFORMATION: Xaa is serine, alanine, or 2-aminobutyric acid
<220> FEATURE:
<221> NAME/KEY: misc_feature
<222> LOCATION: (238)..(238)
<223> OTHER INFORMATION: Xaa is serine, alanine, or 2-aminobutyric acid

<400> SEQUENCE: 290

Met Ala Lys Phe Asn Tyr Leu Pro Val Asp Val Gln Glu Glu Leu Arg
1               5                   10                  15

Asn Thr Ala Asn Ala Ile Val Ser Val Gly Lys Gly Ile Leu Ala Ala
            20                  25                  30

Asp Glu Ser Thr Gly Thr Ile Gly Lys Arg Phe Ala Asp Ile Asn Val
        35                  40                  45

Glu Asn Val Glu Pro Asn Arg Arg Ala Tyr Arg Gln Leu Leu Phe Tyr
    50                  55                  60

Ser Glu Asn Ile Glu Gln Tyr Ile Ser Gly Val Ile Leu Phe Asp Glu
65                  70                  75                  80

Thr Val Tyr Gln Lys Asp Asp Asn Asn Thr Pro Phe Pro Glu Leu Leu
                85                  90                  95

Lys Lys Lys Gly Ile Ile Pro Gly Ile Lys Val Asp Thr Gly Val Val
            100                 105                 110

Thr Leu Gln Gly Thr Asn Gly Glu Ser Thr Thr Gln Gly Leu Asp Asn
        115                 120                 125

Leu Thr Lys Arg Xaa Gln Glu Tyr Tyr Asn His Gly Xaa Arg Phe Ala
    130                 135                 140

Lys Trp Arg Xaa Val Leu Lys Ile Gly Lys Asp Glu Pro Ser Ala Leu
145                 150                 155                 160

Ala Ile Leu Glu Asn Ala Asn Val Leu Ala Arg Tyr Ala Ser Xaa Xaa
                165                 170                 175

Gln Gln Ala Arg Ile Val Pro Ile Val Glu Pro Glu Ile Leu Pro Asp
            180                 185                 190

Gly Asp His Asp Leu Glu Arg Xaa Gln Lys Val Thr Glu Thr Val Leu
        195                 200                 205

Ala Ala Val Tyr Lys Ala Leu Asn Asp His His Val Tyr Leu Glu Gly
    210                 215                 220

Ser Leu Leu Lys Pro Asn Met Val Thr Pro Gly Gln Ser Xaa Pro Gln
```

```
                225                 230                 235                 240
Lys Ala Ser Pro Gln Asp Ile Ala Arg Ala Thr Val Thr Ala Leu Gln
                245                 250                 255

Arg Thr Val Pro Ala Ala Val Pro Gly Val Val Phe Leu Ser Gly Gly
                260                 265                 270

Gln Ser Glu Glu Ala Ser Val Asn Leu Asn Ala Ile Asn Gln Tyr
            275                 280                 285

Gln Gly Lys Lys Pro Trp Ala Leu Ser Phe Ser Tyr Gly Arg Ala Leu
            290                 295                 300

Gln Ala Ser Ala Leu Arg Ala Trp Gln Gly Lys Pro Glu Asn Ile Ser
305                 310                 315                 320

Ala Gly Gln Lys Glu Phe Leu Gln Arg Ala Lys Ala Asn Ser Leu Ser
                325                 330                 335

Ala Gln Gly Gln Tyr Thr Gly Gly Val Val Gly Ala Ala Ala Asp Gln
            340                 345                 350

Asp Leu Phe Ile Lys Asp His Gln Tyr
            355                 360

<210> SEQ ID NO 291
<211> LENGTH: 362
<212> TYPE: PRT
<213> ORGANISM: Dermatophagoides pteronyssinus
<220> FEATURE:
<221> NAME/KEY: misc_feature
<222> LOCATION: (133)..(133)
<223> OTHER INFORMATION: Xaa is serine, alanine, or 2-aminobutyric acid
<220> FEATURE:
<221> NAME/KEY: misc_feature
<222> LOCATION: (141)..(141)
<223> OTHER INFORMATION: Xaa is serine, alanine, or 2-aminobutyric acid
<220> FEATURE:
<221> NAME/KEY: misc_feature
<222> LOCATION: (148)..(148)
<223> OTHER INFORMATION: Xaa is serine, alanine, or 2-aminobutyric acid
<220> FEATURE:
<221> NAME/KEY: misc_feature
<222> LOCATION: (175)..(176)
<223> OTHER INFORMATION: Xaa is serine, alanine, or 2-aminobutyric acid
<220> FEATURE:
<221> NAME/KEY: misc_feature
<222> LOCATION: (200)..(200)
<223> OTHER INFORMATION: Xaa is serine, alanine, or 2-aminobutyric acid
<220> FEATURE:
<221> NAME/KEY: misc_feature
<222> LOCATION: (238)..(238)
<223> OTHER INFORMATION: Xaa is serine, alanine, or 2-aminobutyric acid

<400> SEQUENCE: 291

Met Ala Lys Phe Asn Tyr Leu Pro Val Asp Val Gln Glu Glu Leu Arg
1               5                   10                  15

Asn Thr Ala Asn Ala Ile Val Ser Val Gly Lys Gly Ile Leu Ala Ala
                20                  25                  30

Asp Glu Ser Thr Gly Thr Ile Gly Lys Arg Phe Ala Asp Ile Asn Val
            35                  40                  45

Glu Asn Val Glu Gln Asn Arg Gln Ala Tyr Arg Gln Leu Leu Phe Tyr
    50                  55                  60

Ser Glu Gly Ile Glu Gln Tyr Ile Ser Gly Val Ile Leu Phe Asp Glu
65                  70                  75                  80

Thr Val Tyr Gln Lys Asp Asp Lys Gly Val Pro Phe Pro Glu Leu Leu
                85                  90                  95

Lys Lys Lys Gly Ile Ile Pro Gly Ile Lys Val Asp Thr Gly Val Val
            100                 105                 110
```

-continued

Thr Leu Gln Gly Thr Asn Gly Glu Ser Thr Thr Gln Gly Leu Asp Asn
            115                 120                 125

Leu Thr Lys Arg Xaa Gln Glu Tyr Tyr Asn Gly Xaa Arg Phe Ala
    130                 135                 140

Lys Trp Arg Xaa Val Leu Lys Ile Gly Gln Asp Glu Pro Ser Ser Leu
145                 150                 155                 160

Ala Ile Val Glu Asn Ala Asn Val Leu Ala Arg Tyr Ala Ser Xaa Xaa
                165                 170                 175

Gln Gln Ala Arg Ile Val Pro Ile Val Glu Pro Glu Ile Leu Pro Asp
            180                 185                 190

Gly Asp His Asn Leu Glu Arg Xaa Gln Lys Val Thr Glu Thr Val Leu
            195                 200                 205

Ala Ala Val Tyr Lys Ala Leu Asn Asp His His Val Tyr Leu Glu Gly
            210                 215                 220

Thr Leu Leu Lys Pro Asn Met Val Thr Pro Gly Gln Ser Xaa Pro Gln
225                 230                 235                 240

Lys Ala Ser Pro Gln Glu Val Ala Gln Ala Thr Val Thr Ala Leu Gln
                245                 250                 255

Arg Thr Val Pro Ala Ala Val Pro Gly Ile Val Phe Leu Ser Gly Gly
            260                 265                 270

Gln Ser Glu Glu Glu Ala Ser Val Asn Leu Asn Ala Ile Asn Gln Tyr
            275                 280                 285

Gln Gly Lys Lys Pro Trp Ala Leu Ser Phe Ser Tyr Gly Arg Ala Leu
        290                 295                 300

Gln Ala Ser Ala Leu Arg Ala Trp Gln Gly Lys Pro Glu Asn Ile Gly
305                 310                 315                 320

Ala Gly Gln Lys Glu Leu Leu Gln Arg Ala Lys Ala Asn Val Leu Ala
                325                 330                 335

His Lys Gly Gln Tyr Val Ala Gly Ser Ile Pro Ser Leu Ala Ser Ala
            340                 345                 350

Lys Ser Asn Phe Val Ala Gln His Lys Tyr
        355                 360

<210> SEQ ID NO 292
<211> LENGTH: 429
<212> TYPE: PRT
<213> ORGANISM: Dermatophagoides farinae
<220> FEATURE:
<221> NAME/KEY: misc_feature
<222> LOCATION: (172)..(172)
<223> OTHER INFORMATION: Xaa is serine, alanine, or 2-aminobutyric acid
<220> FEATURE:
<221> NAME/KEY: misc_feature
<222> LOCATION: (274)..(274)
<223> OTHER INFORMATION: Xaa is serine, alanine, or 2-aminobutyric acid
<220> FEATURE:
<221> NAME/KEY: misc_feature
<222> LOCATION: (282)..(282)
<223> OTHER INFORMATION: Xaa is serine, alanine, or 2-aminobutyric acid

<400> SEQUENCE: 292

Ile Glu Gln Val His Ile Ser Leu Gly Thr Asn Ala Thr Glu Met Ile
1               5                   10                  15

Val Thr Trp Thr Glu Pro Gln Lys His Thr Asp Ile Asp Ile Asp Ala
            20                  25                  30

Val Val Tyr Tyr Gly Arg Ala Ser Ser Phe Asp Gln Ala Ala Ile
        35                  40                  45

Ala Lys Ser Glu His Phe Lys Asp Asp Glu Thr Lys Tyr Thr Thr Phe
    50                  55                  60

```
Arg Ala Leu Leu Thr Gly Leu Glu Ser Asp Thr Arg Tyr His Tyr Lys
 65                  70                  75                  80

Ile Gln Leu Asp Asp Lys Glu Ser Ser Ile Phe Ala Phe Lys Thr Leu
             85                  90                  95

Lys Leu Asp Glu Asn Trp Leu Pro Arg Phe Ala Ile Tyr Gly Asp Leu
            100                 105                 110

Gly Tyr Val Asn Glu Gln Ser Leu Pro Tyr Leu Lys Lys Asp Val Glu
            115                 120                 125

Lys Asn Met Phe Asp Val Ile Phe His Ile Gly Asp Ile Ala Tyr Asp
            130                 135                 140

Leu Gln Asp Glu Asn Gly Glu Val Gly Asn Asn Phe Met Arg Ser Ile
145                 150                 155                 160

Glu Ser Ile Ala Ser Lys Ile Pro Tyr Met Thr Xaa Pro Gly Asn His
                165                 170                 175

Glu Arg His Ser Asn Phe Ser His Tyr Asp Ser Arg Phe Ser Met Ile
            180                 185                 190

Gly Asp Arg Ser Gln Pro Asn His Gln Asp Ser Leu Asp Lys Arg Ile
            195                 200                 205

Asn Asn His Phe His Ser Met Glu Ile Gly Pro Ala Thr Ile Ile Met
210                 215                 220

Phe Ser Thr Glu Tyr Tyr Tyr Thr Tyr Tyr Gly Trp Glu Gln Ile
225                 230                 235                 240

Glu Arg Gln Tyr Arg Phe Leu Glu Lys Glu Leu Ile Arg Ala Asn Glu
                245                 250                 255

Asn Arg Asn Lys Arg Pro Trp Ile Ile Ala Met Gly His Arg Pro Leu
            260                 265                 270

Tyr Xaa Leu Lys Met Gly Asp Ser Ser Xaa Asp His Gln Thr Met Glu
            275                 280                 285

Arg Pro Glu Ile Arg Gln Gly Ile Arg Met His Asp Gln Gly Glu Arg
            290                 295                 300

Gln Tyr Gly Leu Glu Asp Leu Phe His Lys Tyr Gly Val Asp Ile Gln
305                 310                 315                 320

Phe Tyr Gly His Glu His Phe Tyr Ala Arg Met Phe Pro Ile Tyr Lys
                325                 330                 335

Tyr Gln Met Tyr Lys Gly Lys Gln Ser Asp Asn Pro Tyr Asp His Ala
            340                 345                 350

Asp Gly Pro Ile His Ile Thr Thr Gly Ser Ala Gly Asn Lys Glu Ile
            355                 360                 365

His Pro Leu Phe Asn His Leu Lys Glu Trp Val Ala His His Phe Tyr
            370                 375                 380

Asp Tyr Gly Tyr Thr Arg Leu Ile Phe Glu Asn Gln Tyr Arg Ile Arg
385                 390                 395                 400

Leu Gln Gln Val Ser Asp Asp Gln His Gly Lys Val Leu Asp Glu Ile
                405                 410                 415

Glu Ile Ile Lys Ser Ser Pro Gln Pro His Trp Met Pro
            420                 425

<210> SEQ ID NO 293
<211> LENGTH: 434
<212> TYPE: PRT
<213> ORGANISM: Dermatophagoides pteronyssinus
<220> FEATURE:
<221> NAME/KEY: misc_feature
<222> LOCATION: (173)..(173)
<223> OTHER INFORMATION: Xaa is serine, alanine, or 2-aminobutyric acid
```

```
<220> FEATURE:
<221> NAME/KEY: misc_feature
<222> LOCATION: (275)..(275)
<223> OTHER INFORMATION: Xaa is serine, alanine, or 2-aminobutyric acid
<220> FEATURE:
<221> NAME/KEY: misc_feature
<222> LOCATION: (283)..(283)
<223> OTHER INFORMATION: Xaa is serine, alanine, or 2-aminobutyric acid

<400> SEQUENCE: 293
```

| | | | | | | | | | | | | | | |
|---|---|---|---|---|---|---|---|---|---|---|---|---|---|---|
| Ile | Glu | Gln | Val | His | Ile | Ala | Leu | Gly | Ser | Asn | Glu | Thr | Glu | Ile | Ile |
| 1 | | | | 5 | | | | | 10 | | | | | 15 |

Val Thr Trp Thr Glu Pro His Lys His Asp Asp Lys Thr Ser Asp Ala
              20                  25                  30

Val Val Tyr Tyr Gly Gln Ala Lys Ser Ser Phe Asp Gln Lys Val Lys
         35                  40                  45

Ala Ile Ser Glu Tyr Phe Lys Asp Asp Lys Thr Lys Tyr Thr Thr Tyr
    50                  55                  60

Arg Ala Leu Leu Thr Gly Leu Leu Pro Gly Thr Glu Tyr His Tyr Arg
65                  70                  75                  80

Ile Gln Met Asp Asp Leu Glu Ser Ser Ile Phe Glu Phe Lys Thr Leu
                85                  90                  95

Lys Thr Gly Glu Glu Asn Trp Leu Pro Arg Phe Ala Ile Tyr Gly Asp
            100                 105                 110

Leu Gly Tyr Val Asn Glu Gln Ser Leu Pro Tyr Leu Lys Lys Asp Val
        115                 120                 125

Glu Gln Asn Leu Phe Asp Val Ile Phe His Ile Gly Asp Phe Ala Tyr
    130                 135                 140

Asp Leu Asn Asp Glu His Gly Lys Val Gly His His Phe Met Arg Ser
145                 150                 155                 160

Ile Glu Pro Val Ala Ser Lys Val Ala Tyr Met Thr Xaa Pro Gly Asn
                165                 170                 175

His Glu Arg His Asp Asn Phe Ser His Tyr Asp Ser Arg Phe Ser Met
            180                 185                 190

Ile Gly Asp Arg Ser Gln Pro Ile His Ser Asp Lys Leu Asn Lys Arg
        195                 200                 205

Leu Asn Asn His Phe His Ser Met Thr Ile Gly Pro Ala Thr Ile Ile
    210                 215                 220

Leu Phe Ser Thr Glu Tyr Tyr Tyr Thr Lys Tyr Gly Trp Gln Gln
225                 230                 235                 240

Ile Glu His Gln Tyr Arg Trp Leu Glu Gln Glu Leu Lys Arg Ala Asn
                245                 250                 255

Glu Asn Arg Gln Lys His Pro Trp Ile Ile Val Met Gly His Arg Pro
            260                 265                 270

Leu Tyr Xaa Leu Lys Met Gly Asp Asp Ser Xaa Asp His Gln Thr Met
        275                 280                 285

Glu Arg Lys Glu Ile Arg Gln Gly Ile Arg Met His Asp Glu Gly Glu
    290                 295                 300

Arg Gln Tyr Gly Leu Glu Asp Leu Phe Phe Lys Tyr Gly Val Asp Ile
305                 310                 315                 320

Gln Phe Tyr Gly His Glu His Pro Tyr Ala Arg Leu Phe Pro Ile Tyr
                325                 330                 335

Lys Tyr Lys Met Tyr Asn Gly Thr Lys Ser Asn Pro Tyr Asp His
            340                 345                 350

Pro Gly Ala Pro Ile His Ile Thr Thr Gly Ser Ala Gly Asn Lys Glu
        355                 360                 365

-continued

```
Leu His Pro Glu Phe Asn His Leu Asn Asp Trp Val Ala Glu His Phe
    370                 375                 380

Tyr Asp Tyr Gly Tyr Thr Arg Leu Met Phe Glu Asp Lys Tyr Arg Ile
385                 390                 395                 400

Arg Leu Gln Gln Ile Ser Asp Asp Gln His Gly Lys Val Leu Asp Glu
                405                 410                 415

Ile Glu Ile Val Lys Ser Ser Pro Gln Pro His Trp Met Asn Val Glu
            420                 425                 430

His His
```

<210> SEQ ID NO 294
<211> LENGTH: 462
<212> TYPE: PRT
<213> ORGANISM: Dermatophagoides farinae
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
<222> LOCATION: (374)..(374)
<223> OTHER INFORMATION: Xaa is serine, alanine, or 2-aminobutyric acid
<220> FEATURE:
<221> NAME/KEY: misc_feature
<222> LOCATION: (442)..(442)
<223> OTHER INFORMATION: Xaa is serine, alanine, or 2-aminobutyric acid

<400> SEQUENCE: 294

```
Asp Ser Asn Ser Asp Thr Thr Phe Ile Phe Asn Gly Asp Gly Xaa Glu
1               5                   10                  15

Gln Asn His Leu Phe Gln Thr Arg Tyr Arg Pro Gln Ile Gln Gln Leu
                20                  25                  30

Ala Ser Asp Val Gln Arg Ile Ile Asp His Val Met Ser Val Asn Glu
            35                  40                  45

Ser Gly Arg Thr Tyr Arg Gln Leu Ala Glu Phe Val Asp Arg Phe Gly
        50                  55                  60

Ser Arg Leu Thr Gly Thr Lys Asn Leu Glu Asp Ser Ile Asp Tyr Met
65                  70                  75                  80

Ile Asp Leu Leu Arg Gln Glu Gly His Asp Asn Val His Gly Glu Ser
                85                  90                  95

Val Gln Val Pro Arg Trp Thr Gly Asn Glu Trp Ala Arg Met Ile
            100                 105                 110

Lys Pro Arg Glu Lys Lys Leu Asn Ile Leu Gly Leu Gly Tyr Ser Glu
            115                 120                 125

Gly Thr Asn Gly Gln Thr Ile Glu Ala Pro Ile Val Val Arg Asn
        130                 135                 140

Phe Thr Glu Leu Glu Gln Lys Ser Arg Leu Ile Pro Gly Lys Ile Val
145                 150                 155                 160

Val Tyr Asn Phe His Tyr Glu Ser Tyr Gly Lys Gln Ala Ile Tyr Arg
                165                 170                 175

His Ser Gly Ala Ser Arg Ala Ala Glu Phe Gly Ala Val Ala Ala Met
            180                 185                 190

Ile Arg Ser Leu Thr Pro Phe Ser Ile Asp Ser Pro His Thr Gly Met
        195                 200                 205

Gln Thr Tyr Asp Val Asn Val Thr Arg Ile Pro Ala Ile Ser Ile Thr
    210                 215                 220

Ala Glu Asp Ala Asp Leu Phe Gln Arg Phe Ser Asp Arg Asn Glu Glu
225                 230                 235                 240
```

```
Val Ile Val Gln Ile Tyr Ser Glu Asn Arg Asn Glu Lys Glu Gln Gly
                245                 250                 255

Ile Ser Arg Asn Thr Val Ser Asp Ile Arg Gly Glu Gln Tyr Pro Asp
            260                 265                 270

Glu Ile Val Leu Val Ser Gly His Ile Asp Ser Trp Asp Val Gly Gln
            275                 280                 285

Gly Ala Leu Asp Asp Gly Ala Gly Ser Phe Ile Ser Trp Arg Ala Leu
        290                 295                 300

Ser Val Ile Lys Gln Leu Gly Leu Arg Pro Lys Arg Thr Met Arg Ser
305                 310                 315                 320

Ile Leu Trp Thr Gly Glu Glu Phe Gly Leu Ile Gly Val Tyr Asp Tyr
                325                 330                 335

Val Lys Lys His Gln Asn Glu Leu Lys Asn Tyr Val Leu Ala Met Glu
            340                 345                 350

Ser Asp Ile Gly Thr Phe Thr Pro Lys Gly Ile Thr Phe Ser Gly Arg
            355                 360                 365

Asn Ser Thr Ser Gln Xaa Thr Leu Trp Glu Ile Leu Gln Leu Met His
        370                 375                 380

Pro Ile Asn Ala Thr Thr Leu Thr Ile Ser Thr Glu Gly Ser Asp Val
385                 390                 395                 400

Gln Ala Phe Tyr Glu Asn Gly Val Pro Ile Ser Ser Leu Asp Thr Ala
                405                 410                 415

Asn Asp Lys Tyr Phe Tyr Phe His His Thr Gln Gly Asp Thr Met Thr
            420                 425                 430

Val Glu Gln Ser Asp Asp Leu Asp Lys Xaa Gln Ala Leu Trp Thr Ser
            435                 440                 445

Ile Ser Tyr Ala Leu Ala Met Leu Asp Asp Arg Leu Pro Arg
        450                 455                 460

<210> SEQ ID NO 295
<211> LENGTH: 462
<212> TYPE: PRT
<213> ORGANISM: Dermatophagoides pteronyssinus
<220> FEATURE:
<221> NAME/KEY: misc_feature
<222> LOCATION: (15)..(15)
<223> OTHER INFORMATION: Xaa is serine, alanine, or 2-aminobutyric acid
<220> FEATURE:
<221> NAME/KEY: misc_feature
<222> LOCATION: (374)..(374)
<223> OTHER INFORMATION: Xaa is serine, alanine, or 2-aminobutyric acid
<220> FEATURE:
<221> NAME/KEY: misc_feature
<222> LOCATION: (442)..(442)
<223> OTHER INFORMATION: Xaa is serine, alanine, or 2-aminobutyric acid

<400> SEQUENCE: 295

Asp Ser Asn Pro Gly Glu Thr Ser Ile Phe Asn Gly Glu Gly Xaa Ala
1               5                   10                  15

Asn Asp Gln Leu Phe Gln Thr Arg Ile Arg Pro Gln Ile Gln Gln Leu
            20                  25                  30

Ala Ser Asn Val Gln Arg Ile Ile Asp His Val Met Ser Ala Asn Glu
        35                  40                  45

Ser Gly Arg Thr Tyr Arg Gln Leu Ala Glu Phe Val Asp Arg Phe Gly
    50                  55                  60

Ser Arg Leu Thr Gly Thr Lys Asn Leu Glu Asp Ser Ile Asp Tyr Met
65                  70                  75                  80

Ile Asp Leu Leu Lys Gln Glu Gly His Asp Asn Val His Gly Glu Pro
```

```
                        85                  90                  95
Val Gln Val Pro Lys Trp Thr Arg Gly Asn Glu Trp Ala Arg Met Ile
                100                 105                 110

Lys Pro Arg Asp Lys Lys Leu Asn Ile Leu Gly Leu Gly Tyr Ser Glu
                115                 120                 125

Gly Thr Asn Gly Gln Thr Ile Glu Ala Pro Ile Val Val Arg Asn
                130                 135                 140

Phe Thr Glu Leu Glu Gln Lys Ala Gly Leu Ile Pro Gly Lys Ile Val
145                 150                 155                 160

Val Tyr Asn Phe Lys Tyr Glu Ser Tyr Gly Lys Gln Ala Ile Tyr Arg
                165                 170                 175

His Ser Gly Ala Ser Arg Ala Ala Lys Phe Gly Ala Val Ala Ala Met
                180                 185                 190

Ile Arg Ser Leu Thr Pro Phe Ser Ile Asp Ser Pro His Thr Gly Met
                195                 200                 205

Gln Ser Tyr Asp Val Asn Val Thr Lys Ile Pro Ala Ile Ser Ile Thr
                210                 215                 220

Thr Glu Asp Ala Asp Leu Phe Gln Arg Phe Ser Asp Arg Asn Glu Glu
225                 230                 235                 240

Val Ile Val Gln Ile Tyr Ser Glu Asn His Asn Glu Lys Asp Lys Gly
                245                 250                 255

Ile Ser Arg Asn Thr Val Ser Asp Val Arg Gly Glu Lys Tyr Pro Asn
                260                 265                 270

Glu Ile Val Leu Val Ser Gly His Ile Asp Ser Trp Asp Val Gly Gln
                275                 280                 285

Gly Ala Ser Asp Asp Gly Ala Gly Ala Phe Ile Ser Trp Arg Ala Leu
                290                 295                 300

Ser Val Ile Lys Lys Leu Gly Leu Arg Pro Lys Arg Thr Leu Arg Ser
305                 310                 315                 320

Val Leu Trp Thr Gly Glu Glu Phe Gly Leu Ile Gly Val Tyr Asp Tyr
                325                 330                 335

Ile Lys Lys His Arg Asn Glu Leu Lys Asp Tyr Val Ile Ala Met Glu
                340                 345                 350

Ser Asp Ile Gly Thr Phe Thr Pro Arg Gly Ile Thr Tyr Ser Gly Lys
                355                 360                 365

Asn Ser Thr Ser Gln Xaa Thr Leu Trp Glu Ile Leu Gln Leu Met His
                370                 375                 380

Pro Ile Asn Ala Thr Thr Leu Thr Ile Ser Thr Glu Gly Ser Asp Val
385                 390                 395                 400

Gln Ala Phe Tyr Glu Asn Gly Val Pro Ile Ser Ser Leu Asp Thr Ala
                405                 410                 415

Asn Asp Lys Tyr Phe Tyr Phe His His Thr Gln Gly Asp Thr Met Thr
                420                 425                 430

Val Glu Gln Pro Asp Asp Leu Asp Lys Xaa Gln Ala Leu Trp Thr Ser
                435                 440                 445

Val Ser Tyr Ala Leu Ala Met Leu Asp Asp Arg Leu Ser Arg
450                 455                 460

<210> SEQ ID NO 296
<211> LENGTH: 463
<212> TYPE: PRT
<213> ORGANISM: Dermatophagoides farinae
<220> FEATURE:
<221> NAME/KEY: misc_feature
<222> LOCATION: (6)..(6)
```

```
<223> OTHER INFORMATION: Xaa is serine, alanine, or 2-aminobutyric acid
<220> FEATURE:
<221> NAME/KEY: misc_feature
<222> LOCATION: (30)..(30)
<223> OTHER INFORMATION: Xaa is serine, alanine, or 2-aminobutyric acid
<220> FEATURE:
<221> NAME/KEY: misc_feature
<222> LOCATION: (96)..(96)
<223> OTHER INFORMATION: Xaa is serine, alanine, or 2-aminobutyric acid
<220> FEATURE:
<221> NAME/KEY: misc_feature
<222> LOCATION: (114)..(114)
<223> OTHER INFORMATION: Xaa is serine, alanine, or 2-aminobutyric acid
<220> FEATURE:
<221> NAME/KEY: misc_feature
<222> LOCATION: (243)..(243)
<223> OTHER INFORMATION: Xaa is serine, alanine, or 2-aminobutyric acid
<220> FEATURE:
<221> NAME/KEY: misc_feature
<222> LOCATION: (246)..(246)
<223> OTHER INFORMATION: Xaa is serine, alanine, or 2-aminobutyric acid
<220> FEATURE:
<221> NAME/KEY: misc_feature
<222> LOCATION: (279)..(279)
<223> OTHER INFORMATION: Xaa is serine, alanine, or 2-aminobutyric acid
<220> FEATURE:
<221> NAME/KEY: misc_feature
<222> LOCATION: (286)..(286)
<223> OTHER INFORMATION: Xaa is serine, alanine, or 2-aminobutyric acid
<220> FEATURE:
<221> NAME/KEY: misc_feature
<222> LOCATION: (309)..(309)
<223> OTHER INFORMATION: Xaa is serine, alanine, or 2-aminobutyric acid
<220> FEATURE:
<221> NAME/KEY: misc_feature
<222> LOCATION: (319)..(319)
<223> OTHER INFORMATION: Xaa is serine, alanine, or 2-aminobutyric acid
<220> FEATURE:
<221> NAME/KEY: misc_feature
<222> LOCATION: (329)..(329)
<223> OTHER INFORMATION: Xaa is serine, alanine, or 2-aminobutyric acid
<220> FEATURE:
<221> NAME/KEY: misc_feature
<222> LOCATION: (348)..(348)
<223> OTHER INFORMATION: Xaa is serine, alanine, or 2-aminobutyric acid
<220> FEATURE:
<221> NAME/KEY: misc_feature
<222> LOCATION: (449)..(449)
<223> OTHER INFORMATION: Xaa is serine, alanine, or 2-aminobutyric acid

<400> SEQUENCE: 296

Asp Thr Pro Ala Asn Xaa Thr Tyr Glu Asp Ile Lys Gly Leu Trp Leu
1               5                   10                  15

Phe Glu Glu Ser Thr Pro Ile Asn Asp Arg Thr Glu Lys Xaa Asp Asn
            20                  25                  30

Gly Arg Arg Glu Tyr Thr Lys Lys Ile Tyr Val Arg Leu Asp Phe Pro
        35                  40                  45

Asn Thr Ala Val Asp Lys Phe Gly Asn Val Gly Thr Trp Thr Leu Ile
    50                  55                  60

Tyr Asn Gln Gly Phe Glu Val Ile Ile Asn Tyr Arg Lys Tyr Phe Ala
65                  70                  75                  80

Phe Ser Ala Tyr Glu Arg Lys Ser Asn Ser Lys Val Ile Ser Tyr Xaa
                85                  90                  95

His Lys Thr Ile Pro Gly Trp Ser His Asp Leu Leu Gly Asn Asn Trp
            100                 105                 110

Ala Xaa Tyr Ile Gly His Lys Val Asn Asp Trp Asn Ser Ser Pro Leu
        115                 120                 125

Gln Lys Ile Gly Ser Glu Gln Phe Pro Ile Lys Glu His Ile Glu Gln
    130                 135                 140
```

```
Pro Leu Tyr Leu Lys Asn Ile Asp Leu Ser His Ala Leu Ser Gln Asn
145                 150                 155                 160

His Val Asp Gln Ile Asn Ser Lys Gln Lys Ser Trp Lys Ala Thr Val
                165                 170                 175

Tyr Pro Glu Met Gln Ser Lys Thr Val Glu His Leu Ile Lys Met Ala
            180                 185                 190

Gly Gly Glu Lys Ser Arg Ile Met Ser Arg Pro Lys Pro Ile Arg Ala
        195                 200                 205

Thr Glu Gln Gln Arg His Glu Ala Arg Gly Leu Pro Glu Ser Phe Asp
    210                 215                 220

Trp Arg Asn Val Asp Gly Ile Asn Tyr Val Ser Pro Val Arg Asn Gln
225                 230                 235                 240

Gly Asn Xaa Gly Ser Xaa Tyr Ala Phe Ala Ser Met Ala Met Leu Glu
                245                 250                 255

Ala Arg Ile Arg Ile Ala Thr Asn Asn Thr Ala Lys Pro Val Phe Ser
                260                 265                 270

Pro Gln Glu Val Val Asp Xaa Ser Glu Tyr Ser Gln Gly Xaa Asp Gly
            275                 280                 285

Gly Phe Gly Tyr Leu Ile Ala Gly Lys Tyr Ala Gln Asp Phe Gly Val
        290                 295                 300

Val Glu Glu Ser Xaa Tyr Pro Tyr Lys Ala Tyr Thr Gly Lys Xaa Lys
305                 310                 315                 320

Leu Asp Tyr Asn Thr Thr Ala Lys Xaa Gln Gln Arg Thr Tyr Thr Ile
                325                 330                 335

Lys Tyr Asn Tyr Leu Gly Gly Tyr Phe Gly Ala Xaa Asn Glu Glu Ala
                340                 345                 350

Met Arg Ile Glu Leu Val Lys Asn Gly Pro Ile Ala Val Gly Phe Glu
                355                 360                 365

Val Tyr Lys Asp Phe Met Thr Tyr Arg Arg Gly Ile Tyr Ser His Asp
            370                 375                 380

Ser Asp Tyr Glu Thr Glu Gln Lys Val Gly Val Glu Phe Asn Pro Phe
385                 390                 395                 400

Val Leu Thr Asn His Ala Val Leu Ile Val Gly Tyr Gly Arg Asp Glu
                405                 410                 415

Lys Ser Gly Glu Asn Tyr Trp Ile Val Lys Asn Ser Trp Gly Glu Gln
                420                 425                 430

Trp Gly Ile Asp Gly Tyr Phe Leu Ile Arg Arg Gly Thr Asn Glu
            435                 440                 445

Xaa Gly Ile Glu Ser Ile Ala Met Ala Ala Thr Pro Ile Pro Asn
    450                 455                 460
```

<210> SEQ ID NO 297
<211> LENGTH: 474
<212> TYPE: PRT
<213> ORGANISM: Dermatophagoides pteronyssinus
<220> FEATURE:
<221> NAME/KEY: misc_feature
<222> LOCATION: (6)..(6)
<223> OTHER INFORMATION: Xaa is serine, alanine, or 2-aminobutyric acid
<220> FEATURE:
<221> NAME/KEY: misc_feature
<222> LOCATION: (30)..(30)
<223> OTHER INFORMATION: Xaa is serine, alanine, or 2-aminobutyric acid
<220> FEATURE:
<221> NAME/KEY: misc_feature
<222> LOCATION: (99)..(99)
<223> OTHER INFORMATION: Xaa is serine, alanine, or 2-aminobutyric acid
<220> FEATURE:
<221> NAME/KEY: misc_feature

```
<222> LOCATION: (117)..(117)
<223> OTHER INFORMATION: Xaa is serine, alanine, or 2-aminobutyric acid
<220> FEATURE:
<221> NAME/KEY: misc_feature
<222> LOCATION: (249)..(249)
<223> OTHER INFORMATION: Xaa is serine, alanine, or 2-aminobutyric acid
<220> FEATURE:
<221> NAME/KEY: misc_feature
<222> LOCATION: (252)..(252)
<223> OTHER INFORMATION: Xaa is serine, alanine, or 2-aminobutyric acid
<220> FEATURE:
<221> NAME/KEY: misc_feature
<222> LOCATION: (285)..(285)
<223> OTHER INFORMATION: Xaa is serine, alanine, or 2-aminobutyric acid
<220> FEATURE:
<221> NAME/KEY: misc_feature
<222> LOCATION: (292)..(292)
<223> OTHER INFORMATION: Xaa is serine, alanine, or 2-aminobutyric acid
<220> FEATURE:
<221> NAME/KEY: misc_feature
<222> LOCATION: (315)..(315)
<223> OTHER INFORMATION: Xaa is serine, alanine, or 2-aminobutyric acid
<220> FEATURE:
<221> NAME/KEY: misc_feature
<222> LOCATION: (325)..(325)
<223> OTHER INFORMATION: Xaa is serine, alanine, or 2-aminobutyric acid
<220> FEATURE:
<221> NAME/KEY: misc_feature
<222> LOCATION: (338)..(338)
<223> OTHER INFORMATION: Xaa is serine, alanine, or 2-aminobutyric acid
<220> FEATURE:
<221> NAME/KEY: misc_feature
<222> LOCATION: (357)..(357)
<223> OTHER INFORMATION: Xaa is serine, alanine, or 2-aminobutyric acid
<220> FEATURE:
<221> NAME/KEY: misc_feature
<222> LOCATION: (460)..(460)
<223> OTHER INFORMATION: Xaa is serine, alanine, or 2-aminobutyric acid

<400> SEQUENCE: 297

Asp Thr Pro Ala Asn Xaa Thr Tyr Glu Asp Ile Lys Gly Leu Trp Leu
1               5                   10                  15

Phe Glu Glu Thr Glu Pro Ile Lys Asp Arg Trp Glu Lys Xaa Pro Glu
            20                  25                  30

His Gln Gln Gln Arg Glu Lys Tyr Ser Lys Lys Ile Phe Ile Arg Leu
        35                  40                  45

Asp Phe Pro Asn Val Ala Val Asp Lys Phe Gly Asn Ile Gly Glu Trp
    50                  55                  60

Thr Met Ile Tyr Asn Gln Gly Phe Glu Val Lys Ile Asn Tyr Arg Lys
65                  70                  75                  80

Tyr Phe Ala Phe Ser Ala Tyr Glu Arg Lys Ser Glu Asn Asn Val Leu
                85                  90                  95

Ser Tyr Xaa His Lys Thr Gln Pro Gly Trp Ser His Asp Val Leu Gly
            100                 105                 110

Asn Asn Trp Ala Xaa Tyr Val Gly His Lys Val Asn Asn Trp Asn Asp
        115                 120                 125

Asp Asp Val Ser Lys Thr Thr Thr Val Gly Ala Glu Lys Phe Pro Val
    130                 135                 140

Lys Gln His Ser Glu Arg Glu Leu Tyr Leu Gln Asn Ile Asn Val Glu
145                 150                 155                 160

His Ile Leu Ser Gln Lys His Ile Asp His Leu Asn Ser Gln Gln Lys
                165                 170                 175

Ser Trp Lys Ala Ile Val Tyr Pro Asp Leu Gln Ser Lys Ser Ile Glu
            180                 185                 190

His Leu Ile Gln Met Ala Gly Gly Arg Lys Ser Arg Ile Ile Asn Arg
        195                 200                 205
```

```
Pro Lys Pro Leu Arg Ala Thr Glu Gln Gln Lys Gln Leu Ala Arg Ser
    210                 215                 220

Leu Pro Glu Ser Phe Asp Trp Arg Asn Leu Asn Gly Ile Asp Tyr Val
225                 230                 235                 240

Ser Pro Val Arg Asp Gln Gly Lys Xaa Gly Ser Xaa Tyr Thr Phe Ala
                245                 250                 255

Ser Met Ala Met Leu Glu Ser Arg Ile Arg Ile Gln Thr Asn Asn Thr
            260                 265                 270

Phe Lys Pro Ile Phe Ser Thr Gln Glu Val Val Asp Xaa Ser Glu Tyr
        275                 280                 285

Ser Gln Gly Xaa Asp Gly Gly Phe Ser Tyr Leu Ile Ala Gly Lys Tyr
    290                 295                 300

Ala Gln Asp Phe Gly Val Ile Asp Glu Ser Xaa Tyr Pro Tyr Lys Gly
305                 310                 315                 320

Val Thr Gly Lys Xaa Gln Asn Gln Gln Asn Phe Asn Gln Thr Asn Glu
                325                 330                 335

Lys Xaa Lys Gln Arg Thr Tyr Thr Ile Asp Tyr Lys Tyr Val Gly Gly
            340                 345                 350

Tyr Phe Gly Ala Xaa Asn Glu Glu Ala Met Gln Ile Glu Leu Val Gln
    355                 360                 365

Asn Gly Pro Ile Ala Val Gly Phe Glu Val Tyr Gly Asp Phe Phe Gly
370                 375                 380

Tyr Ser Glu Gly Ile Tyr Ser His Gln Pro Ser Asn Glu Ser Asn Asp
385                 390                 395                 400

Gln His Gln Gln Ile Lys Ala Glu Phe Asn Pro Phe Glu Met Thr Asn
                405                 410                 415

His Ala Val Leu Ile Val Gly Tyr Gly Lys Asp Lys Lys Thr Gly Glu
            420                 425                 430

Lys Tyr Trp Ile Val Lys Asn Ser Trp Gly Lys Gln Trp Gly Met Asp
    435                 440                 445

Gly Tyr Phe Trp Met Arg Arg Gly Thr Asp Glu Xaa Ala Ile Glu Ser
450                 455                 460

Leu Ala Met Ala Ala Thr Pro Ile Pro Asn
465                 470

<210> SEQ ID NO 298
<211> LENGTH: 509
<212> TYPE: PRT
<213> ORGANISM: Dermatophagoides farinae
<220> FEATURE:
<221> NAME/KEY: misc_feature
<222> LOCATION: (14)..(14)
<223> OTHER INFORMATION: Xaa is serine, alanine, or 2-aminobutyric acid
<220> FEATURE:
<221> NAME/KEY: misc_feature
<222> LOCATION: (39)..(39)
<223> OTHER INFORMATION: Xaa is serine, alanine, or 2-aminobutyric acid
<220> FEATURE:
<221> NAME/KEY: misc_feature
<222> LOCATION: (310)..(310)
<223> OTHER INFORMATION: Xaa is serine, alanine, or 2-aminobutyric acid
<220> FEATURE:
<221> NAME/KEY: misc_feature
<222> LOCATION: (374)..(374)
<223> OTHER INFORMATION: Xaa is serine, alanine, or 2-aminobutyric acid
<220> FEATURE:
<221> NAME/KEY: misc_feature
<222> LOCATION: (462)..(462)
<223> OTHER INFORMATION: Xaa is serine, alanine, or 2-aminobutyric acid
<220> FEATURE:
<221> NAME/KEY: misc_feature
```

<222> LOCATION: (480)..(480)
<223> OTHER INFORMATION: Xaa is serine, alanine, or 2-aminobutyric acid
<220> FEATURE:
<221> NAME/KEY: misc_feature
<222> LOCATION: (494)..(494)
<223> OTHER INFORMATION: Xaa is serine, alanine, or 2-aminobutyric acid
<220> FEATURE:
<221> NAME/KEY: misc_feature
<222> LOCATION: (507)..(507)
<223> OTHER INFORMATION: Xaa is serine, alanine, or 2-aminobutyric acid

<400> SEQUENCE: 298

Gln Ser Arg Asp Arg Asn Asp Lys Pro Tyr Arg Ile Val Xaa Tyr Trp
1               5                   10                  15

Gly Thr Trp Ala Phe Tyr Arg Pro Ala Ser Gly Lys Phe Gln Ala Glu
            20                  25                  30

Asn Val Asn Pro Asn Leu Xaa Thr His Ile Met Tyr Gly Phe Ala Lys
        35                  40                  45

Leu Gln Asn Asn Lys Ile Ala Leu Tyr Asp Pro Asp Leu Asp Asp Gly
    50                  55                  60

Asp Glu Asp Trp Asn Ser Gly Leu Gln Trp Gly His Gly Met Ile Arg
65                  70                  75                  80

Arg Met Val Asn Leu Arg Thr Tyr Asn Pro His Leu Thr Thr Met Ile
                85                  90                  95

Ser Leu Gly Gly Trp Asn Glu Gly Ser Asp Lys Tyr Ser Ile Met Val
            100                 105                 110

Arg Asp Pro Ala Ser Arg Lys Ile Phe Ile Gln Ser Val Leu His Leu
        115                 120                 125

Leu Ala Glu Phe Asp Leu Asp Gly Leu Asp Phe Asp Trp Glu Tyr Pro
    130                 135                 140

Ala Met Gln Ala Ser Gly Asp Ser Asp Arg Lys Pro Gly Arg Ala Glu
145                 150                 155                 160

Asp Lys Glu Asp Phe Val Thr Leu Leu Arg Glu Leu His Glu Ala Phe
                165                 170                 175

Gln Pro His Gly Tyr Val Leu Ser Ser Ala Val Ser Ala Gly Lys Pro
            180                 185                 190

Thr Ile Asp Arg Ala Tyr Asn Ile Pro Glu Val Ser Lys Tyr Leu Asp
        195                 200                 205

Phe Ile Asn Leu Met Ser Tyr Asp Tyr His Gly Gly Trp Glu Ser His
    210                 215                 220

Thr Gly His Asn Ala Pro Leu Asn Ser Tyr Lys Asn Ala Asn Glu Leu
225                 230                 235                 240

Asp Lys Glu Phe Thr Val Thr Tyr Ser Val Glu Tyr Trp Leu Asn His
                245                 250                 255

Gly Val Asp Pro Lys Lys Leu Val Leu Gly Ile Pro Leu Tyr Gly Arg
            260                 265                 270

Thr Phe Thr Leu Ala Gly Ser Glu His Gly Ile Gly Ala Pro Thr Ile
        275                 280                 285

Gly Lys Gly Gly Glu Ser Gly Thr Ile Thr Arg Thr Ile Gly Met Leu
    290                 295                 300

Gly Tyr Asn Glu Ile Xaa Thr Met Ile Lys Gln Gly Trp Gln Leu Tyr
305                 310                 315                 320

Arg Asp Glu Ile Glu Arg Ile Pro Tyr Ala Val His Ala Asn Gln Trp
                325                 330                 335

Ile Gly Tyr Asp Asp Arg Glu Ser Val Asn Glu Lys Leu Asn Leu Leu
            340                 345                 350

```
Met Ala Lys His Leu Gly Gly Ala Met Val Trp Ser Ile Asp Thr Asp
            355                 360                 365

Asp Phe Val Gly Asn Xaa Val Gly Val Lys Tyr Pro Leu Leu Arg Ser
    370                 375                 380

Ile Ser Lys Lys Leu Asn Asn Val Asp Gly Pro Asp Pro Asp Ile Lys
385                 390                 395                 400

Arg Tyr His Tyr His Thr Ser Thr Ala Lys Pro His Thr Asp Gly Thr
                405                 410                 415

Thr Ser Thr His His Asp His Lys Thr Thr Thr Lys His His Lys
                420                 425                 430

Thr Thr Gln Pro His His Lys Thr Thr Gln Pro His His Thr Gln Thr
                435                 440                 445

Ile Thr Thr Thr Thr Glu Arg Pro His Gly Lys Phe Gln Xaa His Gln
        450                 455                 460

Ala Gly Phe Phe Ala Asp Pro Glu Asn Pro Arg Lys Phe His Gln Xaa
465                 470                 475                 480

Val Asp Phe Gly Gly His Leu Lys Asp Tyr Glu Phe Met Xaa Gly Glu
                485                 490                 495

Gly Thr His Tyr Asp Glu Lys Leu His Ile Xaa Val Arg
                500                 505

<210> SEQ ID NO 299
<211> LENGTH: 520
<212> TYPE: PRT
<213> ORGANISM: Dermatophagoides farinae
<220> FEATURE:
<221> NAME/KEY: misc_feature
<222> LOCATION: (7)..(7)
<223> OTHER INFORMATION: Xaa is serine, alanine, or 2-aminobutyric acid
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (98)..(98)
<223> OTHER INFORMATION: Xaa is serine, alanine, or 2-aminobutyric acid
<220> FEATURE:
<221> NAME/KEY: misc_feature
<222> LOCATION: (117)..(117)
<223> OTHER INFORMATION: Xaa is serine, alanine, or 2-aminobutyric acid
<220> FEATURE:
<221> NAME/KEY: misc_feature
<222> LOCATION: (129)..(129)
<223> OTHER INFORMATION: Xaa is serine, alanine, or 2-aminobutyric acid
<220> FEATURE:
<221> NAME/KEY: misc_feature
<222> LOCATION: (187)..(187)
<223> OTHER INFORMATION: Xaa is serine, alanine, or 2-aminobutyric acid
<220> FEATURE:
<221> NAME/KEY: misc_feature
<222> LOCATION: (292)..(292)
<223> OTHER INFORMATION: Xaa is serine, alanine, or 2-aminobutyric acid
<220> FEATURE:
<221> NAME/KEY: misc_feature
<222> LOCATION: (338)..(338)
<223> OTHER INFORMATION: Xaa is serine, alanine, or 2-aminobutyric acid
<220> FEATURE:
<221> NAME/KEY: misc_feature
<222> LOCATION: (343)..(344)
<223> OTHER INFORMATION: Xaa is serine, alanine, or 2-aminobutyric acid
<220> FEATURE:
<221> NAME/KEY: misc_feature
<222> LOCATION: (400)..(400)
<223> OTHER INFORMATION: Xaa is serine, alanine, or 2-aminobutyric acid
<220> FEATURE:
<221> NAME/KEY: misc_feature
<222> LOCATION: (405)..(405)
<223> OTHER INFORMATION: Xaa is serine, alanine, or 2-aminobutyric acid
```

```
<220> FEATURE:
<221> NAME/KEY: misc_feature
<222> LOCATION: (419)..(419)
<223> OTHER INFORMATION: Xaa is serine, alanine, or 2-aminobutyric acid

<400> SEQUENCE: 299
```

Lys Lys Ala Pro Glu Gly Xaa Phe Arg Ala Ala Val Leu Asp His Val
1               5                   10                  15

His Gln Thr Asn Val Arg Gln Leu Ser Asp Phe Ala Lys Ile Ile Glu
            20                  25                  30

Leu Asn Phe Lys Val Tyr Glu Asp Ala Ala Leu Ala Lys Lys Gln
        35                  40                  45

Gly Ala Asp Ile Ile Val Phe Pro Glu Asp Gly Leu Ile Tyr Asn Ile
50                  55                  60

Ala Ser Arg Glu Lys Ala Asp Glu Phe Ala Ser Asp Ile Pro Asp Gly
65                  70                  75                  80

Glu Thr Asn Ala Xaa Thr Leu Glu Thr Lys Ser Val Tyr Asn Arg Leu
                85                  90                  95

Ala Xaa Leu Ala Gln Lys His Glu Ile Phe Val Val Ala Asp Leu Ile
    100                 105                 110

Asp Arg Lys Ser Xaa Glu Glu Leu Gly Ile Ser Asn Thr Ser Asp Ser
            115                 120                 125

Xaa Pro Ala Asp Lys Lys Phe Leu Phe Asn Thr Ala Val Leu Phe Asp
130                 135                 140

Arg Gln Gly Lys Leu Leu Gly Arg Tyr His Lys Met His Leu Phe Gly
145                 150                 155                 160

Glu Met Thr Met Asn Ile Pro Pro Lys Pro Glu Leu Leu Val Ile Asp
                165                 170                 175

Thr Glu Leu Gly Arg Leu Gly Met Gln Ile Xaa Phe Asp Met Ile Phe
            180                 185                 190

Lys Thr Pro Gly His Phe Leu Ala Glu Gln Asn Lys Phe Asp Thr Met
        195                 200                 205

Leu Phe Pro Thr Trp Trp Phe Asp Glu Ala Pro Met Leu Ser Ser Ser
210                 215                 220

Gln Tyr Gln Met Ala Trp Ala Phe Gly Asn Asn Val Thr Leu Leu Ala
225                 230                 235                 240

Ser Asn Ile His Arg Val Glu Leu Gly Ser Arg Gly Ser Gly Ile Tyr
                245                 250                 255

Val Gly Pro His Gln Thr Leu Ala Thr Ala Leu Tyr Asp Asp Ser Val
            260                 265                 270

Glu Arg Leu Val Leu Ala Asn Val Pro Ile Lys Pro Arg Glu Thr Asp
        275                 280                 285

Lys Ser Val Xaa Pro Leu Asp Ser Glu Ile Ile Glu Val Pro Gln Gln
290                 295                 300

Ile Pro Ile Pro Asn Ser Val Lys Tyr His His Leu Asn Met Asn Leu
305                 310                 315                 320

Leu Asp Val Thr Leu Val Glu Leu Ser Ser Lys Asp Ser Glu Phe His
                325                 330                 335

Ile Xaa Tyr Lys Gly Val Xaa Xaa Gln Ile Glu Tyr Arg Leu Ala Val
            340                 345                 350

Lys Asp Gln Pro Arg Glu Ser Trp Val Asp Arg Val Pro Leu Leu Ala
        355                 360                 365

Asn Met Leu Glu Tyr Phe Thr Pro Glu Glu Arg Tyr Tyr Leu Met Val
370                 375                 380

-continued

```
Ala Asn Arg Thr Arg Pro Gly Thr Tyr Arg Trp Thr Glu Glu Ile Xaa
385                 390                 395                 400

Ala Val Val Val Xaa Pro Ser Ser Arg Trp Asn Ile Gly Lys Val Glu
            405                 410                 415

Lys Asp Xaa Ser Gln Phe Gly Ser Asn Gln Glu Leu Asn Ser Arg Phe
        420                 425                 430

Val Tyr Ala Lys Leu Arg Gly Ala Phe Ser Glu Ser Thr Ala Val Tyr
        435                 440                 445

Pro Ser Ala Val Gly Pro Lys Asn Gln Leu Ile Asn Pro Glu Asn Lys
    450                 455                 460

Trp Lys Tyr Trp Lys Val Asn Val Pro Asp Lys Pro Glu His Phe Val
465                 470                 475                 480

Glu Leu Gly Ala Lys Asp Asn Pro Glu Ser Lys Ala Ile Glu Leu Ser
            485                 490                 495

Thr Leu Ala Leu Tyr Gly Arg Asn Tyr Asp Leu Asp Pro Thr Tyr Lys
        500                 505                 510

Gln Lys Pro Val Pro Ile Asn Leu
        515                 520

<210> SEQ ID NO 300
<211> LENGTH: 519
<212> TYPE: PRT
<213> ORGANISM: Dermatophagoides pteronyssinus
<220> FEATURE:
<221> NAME/KEY: misc_feature
<222> LOCATION: (7)..(7)
<223> OTHER INFORMATION: Xaa is serine, alanine, or 2-aminobutyric acid
<220> FEATURE:
<221> NAME/KEY: misc_feature
<222> LOCATION: (85)..(85)
<223> OTHER INFORMATION: Xaa is serine, alanine, or 2-aminobutyric acid
<220> FEATURE:
<221> NAME/KEY: misc_feature
<222> LOCATION: (98)..(98)
<223> OTHER INFORMATION: Xaa is serine, alanine, or 2-aminobutyric acid
<220> FEATURE:
<221> NAME/KEY: misc_feature
<222> LOCATION: (117)..(117)
<223> OTHER INFORMATION: Xaa is serine, alanine, or 2-aminobutyric acid
<220> FEATURE:
<221> NAME/KEY: misc_feature
<222> LOCATION: (129)..(129)
<223> OTHER INFORMATION: Xaa is serine, alanine, or 2-aminobutyric acid
<220> FEATURE:
<221> NAME/KEY: misc_feature
<222> LOCATION: (187)..(187)
<223> OTHER INFORMATION: Xaa is serine, alanine, or 2-aminobutyric acid
<220> FEATURE:
<221> NAME/KEY: misc_feature
<222> LOCATION: (292)..(292)
<223> OTHER INFORMATION: Xaa is serine, alanine, or 2-aminobutyric acid
<220> FEATURE:
<221> NAME/KEY: misc_feature
<222> LOCATION: (338)..(338)
<223> OTHER INFORMATION: Xaa is serine, alanine, or 2-aminobutyric acid
<220> FEATURE:
<221> NAME/KEY: misc_feature
<222> LOCATION: (343)..(344)
<223> OTHER INFORMATION: Xaa is serine, alanine, or 2-aminobutyric acid
<220> FEATURE:
<221> NAME/KEY: misc_feature
<222> LOCATION: (400)..(400)
<223> OTHER INFORMATION: Xaa is serine, alanine, or 2-aminobutyric acid
<220> FEATURE:
<221> NAME/KEY: misc_feature
<222> LOCATION: (405)..(405)
<223> OTHER INFORMATION: Xaa is serine, alanine, or 2-aminobutyric acid
<220> FEATURE:
<221> NAME/KEY: misc_feature
<222> LOCATION: (419)..(419)
```

<223> OTHER INFORMATION: Xaa is serine, alanine, or 2-aminobutyric acid

<400> SEQUENCE: 300

| | | | | | | | | | | | | | | |
|---|---|---|---|---|---|---|---|---|---|---|---|---|---|---|
| Lys | Ser | Ala | Pro | Glu | Gly | Xaa | Phe | Arg | Ala | Ala | Val | Leu | Asp | His | Val |
| 1 | | | | 5 | | | | | 10 | | | | | 15 | |

| His | Gln | Thr | Asp | Ala | Arg | His | Leu | Ser | Asn | Thr | Ala | Lys | Ile | Ile | Asp |
|---|---|---|---|---|---|---|---|---|---|---|---|---|---|---|---|
| | | | 20 | | | | | 25 | | | | | 30 | | |

| Leu | Asn | Phe | Lys | Val | Tyr | Glu | Asp | Ala | Ala | Leu | Ala | Lys | Lys | Gln |
|---|---|---|---|---|---|---|---|---|---|---|---|---|---|---|
| | | 35 | | | | | 40 | | | | | 45 | | |

| Gly | Ala | Asp | Ile | Ile | Val | Phe | Pro | Glu | Asn | Gly | Leu | Ile | Tyr | Ser | Ile |
|---|---|---|---|---|---|---|---|---|---|---|---|---|---|---|---|
| 50 | | | | | 55 | | | | | 60 | | | | | |

| Leu | Ser | Arg | Glu | Lys | Ala | Asp | Glu | Phe | Ala | Ser | Asp | Ile | Pro | Asp | Ala |
|---|---|---|---|---|---|---|---|---|---|---|---|---|---|---|---|
| 65 | | | | 70 | | | | | 75 | | | | | 80 | |

| Glu | Val | Asn | Ala | Xaa | Thr | Leu | Asp | Ser | Lys | Phe | Val | Tyr | Asn | Arg | Leu |
|---|---|---|---|---|---|---|---|---|---|---|---|---|---|---|---|
| | | | | 85 | | | | | 90 | | | | | 95 | |

| Ala | Xaa | Leu | Ala | Gln | Lys | His | Gln | Met | Phe | Val | Val | Ala | Asp | Leu | Ile |
|---|---|---|---|---|---|---|---|---|---|---|---|---|---|---|---|
| | | | 100 | | | | | 105 | | | | | 110 | | |

| Asp | Arg | Lys | Ser | Xaa | Glu | Glu | Leu | Gly | Ile | Asn | Asn | Val | Ser | Asp | Ser |
|---|---|---|---|---|---|---|---|---|---|---|---|---|---|---|---|
| | | | 115 | | | | | 120 | | | | | 125 | | |

| Xaa | Pro | Ala | Asp | Lys | Lys | Phe | Leu | Phe | Asn | Thr | Ala | Val | Leu | Phe | Asp |
|---|---|---|---|---|---|---|---|---|---|---|---|---|---|---|---|
| 130 | | | | | 135 | | | | | 140 | | | | | |

| Arg | Gln | Gly | Lys | Leu | Leu | Gly | Arg | Tyr | His | Lys | Met | His | Leu | Phe | Gly |
|---|---|---|---|---|---|---|---|---|---|---|---|---|---|---|---|
| 145 | | | | | 150 | | | | | 155 | | | | | 160 |

| Glu | Ile | Ser | Met | Asn | Pro | Pro | Lys | Pro | Glu | Leu | Leu | Val | Ile | Asp |
|---|---|---|---|---|---|---|---|---|---|---|---|---|---|---|
| | | | | 165 | | | | | 170 | | | | | 175 |

| Thr | Glu | Leu | Gly | Arg | Leu | Gly | Met | Gln | Ile | Xaa | Phe | Asp | Met | Ile | Phe |
|---|---|---|---|---|---|---|---|---|---|---|---|---|---|---|---|
| | | | 180 | | | | | 185 | | | | | 190 | | |

| Lys | Thr | Pro | Gly | Tyr | Leu | Leu | Ala | Gln | Glu | Asn | Lys | Phe | Asp | Thr | Met |
|---|---|---|---|---|---|---|---|---|---|---|---|---|---|---|---|
| | | 195 | | | | | 200 | | | | | 205 | | | |

| Leu | Phe | Pro | Thr | Trp | Trp | Phe | Asp | Glu | Ser | Pro | Met | Leu | Ser | Ser | Ser |
|---|---|---|---|---|---|---|---|---|---|---|---|---|---|---|---|
| | 210 | | | | | 215 | | | | | 220 | | | | |

| Gln | Tyr | Gln | Met | Ala | Trp | Ala | Phe | Gly | Asn | Asn | Val | Thr | Leu | Leu | Ala |
|---|---|---|---|---|---|---|---|---|---|---|---|---|---|---|---|
| 225 | | | | | 230 | | | | | 235 | | | | | 240 |

| Ser | Asn | Ile | His | Arg | Ile | Glu | Val | Gly | Ser | Arg | Gly | Ser | Gly | Ile | Tyr |
|---|---|---|---|---|---|---|---|---|---|---|---|---|---|---|---|
| | | | | 245 | | | | | 250 | | | | | 255 | |

| Val | Gly | Pro | His | Arg | Thr | Leu | Ala | Ala | Ala | Leu | Tyr | Asp | Asp | Ser | Val |
|---|---|---|---|---|---|---|---|---|---|---|---|---|---|---|---|
| | | | 260 | | | | | 265 | | | | | 270 | | |

| Glu | Arg | Leu | Val | Leu | Ala | Asn | Val | Pro | Ile | Lys | Pro | Lys | Glu | Thr | Asp |
|---|---|---|---|---|---|---|---|---|---|---|---|---|---|---|---|
| | 275 | | | | | 280 | | | | | 285 | | | | |

| Gln | Ser | Ala | Xaa | Pro | Leu | Asp | Ser | Glu | Ile | Ile | Glu | Val | Pro | Gln | Gln |
|---|---|---|---|---|---|---|---|---|---|---|---|---|---|---|---|
| 290 | | | | | 295 | | | | | 300 | | | | | |

| Ile | Pro | Ile | Pro | Lys | Ser | Val | Lys | Tyr | His | His | Gln | Asn | Leu | Asn | Leu |
|---|---|---|---|---|---|---|---|---|---|---|---|---|---|---|---|
| 305 | | | | | 310 | | | | | 315 | | | | | 320 |

| Lys | Asp | Val | Thr | Leu | Leu | Gln | Leu | Ser | Ser | Asn | Glu | Ser | Glu | Val | His |
|---|---|---|---|---|---|---|---|---|---|---|---|---|---|---|---|
| | | | 325 | | | | | 330 | | | | | 335 | | |

| Leu | Xaa | His | Lys | Gly | Val | Xaa | Xaa | Gln | Phe | Glu | Tyr | Arg | Leu | Ala | Met |
|---|---|---|---|---|---|---|---|---|---|---|---|---|---|---|---|
| | | | 340 | | | | | 345 | | | | | 350 | | |

| Lys | Asp | Gln | Pro | Gln | Glu | Ser | Trp | Val | Asp | Arg | Val | Pro | Leu | Leu | Ala |
|---|---|---|---|---|---|---|---|---|---|---|---|---|---|---|---|
| | | | 355 | | | | | 360 | | | | | 365 | | |

| Asn | Met | Leu | His | Tyr | Leu | Thr | Pro | Glu | Glu | Arg | Tyr | Tyr | Leu | Leu | Ile |
|---|---|---|---|---|---|---|---|---|---|---|---|---|---|---|---|
| | 370 | | | | | 375 | | | | | 380 | | | | |

| Ala | Asn | Arg | Thr | Arg | Pro | Gly | Ala | Tyr | Pro | Trp | Ser | Glu | Glu | Phe | Xaa |
|---|---|---|---|---|---|---|---|---|---|---|---|---|---|---|---|
| 385 | | | | | 390 | | | | | 395 | | | | | 400 |

```
Ala Val Val Val Xaa Pro Ser Ser Arg Trp Asn Phe Gly Lys Met Gln
            405                 410                 415

Lys Asp Xaa Ser Lys Ile Gly Ser Asn Gln Glu Leu Ser Ser Arg Phe
        420                 425                 430

Val His Ala Lys Leu Arg Gly Lys Phe Ser Glu Asp Thr Ala Val Tyr
            435                 440                 445

Pro Ser Ala Val Gly Ser Lys Asn Gln Leu Ile Tyr Pro Glu Asn Lys
        450                 455                 460

Trp Lys Phe Trp Lys Val Asn Val Pro Asn Glu Pro Glu Tyr Phe Ile
465                 470                 475                 480

Glu Leu Gly Ala Lys Asp Asn Ser Glu Ser Arg Ala Met Glu Leu Gly
            485                 490                 495

Ala Leu Val Leu Tyr Gly Arg Asn Tyr Asn Arg Asp Pro Arg Tyr Glu
        500                 505                 510

Gln Lys Ala Leu Pro Ile Asn
        515
```

```
<210> SEQ ID NO 301
<211> LENGTH: 887
<212> TYPE: PRT
<213> ORGANISM: Dermatophagoides pteronyssinus
<220> FEATURE:
<221> NAME/KEY: misc_feature
<222> LOCATION: (8)..(8)
<223> OTHER INFORMATION: Xaa is serine, alanine, or 2-aminobutyric acid
<220> FEATURE:
<221> NAME/KEY: misc_feature
<222> LOCATION: (19)..(19)
<223> OTHER INFORMATION: Xaa is serine, alanine, or 2-aminobutyric acid
<220> FEATURE:
<221> NAME/KEY: misc_feature
<222> LOCATION: (30)..(30)
<223> OTHER INFORMATION: Xaa is serine, alanine, or 2-aminobutyric acid
<220> FEATURE:
<221> NAME/KEY: misc_feature
<222> LOCATION: (35)..(36)
<223> OTHER INFORMATION: Xaa is serine, alanine, or 2-aminobutyric acid
<220> FEATURE:
<221> NAME/KEY: misc_feature
<222> LOCATION: (61)..(61)
<223> OTHER INFORMATION: Xaa is serine, alanine, or 2-aminobutyric acid
<220> FEATURE:
<221> NAME/KEY: misc_feature
<222> LOCATION: (311)..(311)
<223> OTHER INFORMATION: Xaa is serine, alanine, or 2-aminobutyric acid
<220> FEATURE:
<221> NAME/KEY: misc_feature
<222> LOCATION: (382)..(382)
<223> OTHER INFORMATION: Xaa is serine, alanine, or 2-aminobutyric acid
<220> FEATURE:
<221> NAME/KEY: misc_feature
<222> LOCATION: (472)..(472)
<223> OTHER INFORMATION: Xaa is serine, alanine, or 2-aminobutyric acid
<220> FEATURE:
<221> NAME/KEY: misc_feature
<222> LOCATION: (499)..(499)
<223> OTHER INFORMATION: Xaa is serine, alanine, or 2-aminobutyric acid
<220> FEATURE:
<221> NAME/KEY: misc_feature
<222> LOCATION: (589)..(589)
<223> OTHER INFORMATION: Xaa is serine, alanine, or 2-aminobutyric acid
<220> FEATURE:
<221> NAME/KEY: misc_feature
<222> LOCATION: (600)..(600)
<223> OTHER INFORMATION: Xaa is serine, alanine, or 2-aminobutyric acid

<400> SEQUENCE: 301

Leu Asp Ser Asp Pro Met Lys Xaa Asn Ser Ile Arg Asn Glu Asp Arg
1               5                   10                  15
```

```
Ile Asp Xaa Asn Pro Asp Pro Pro Ile Ser Lys Glu Ile Xaa Glu Gln
            20                  25                  30

Arg Gly Xaa Xaa Trp Asn Ala Gly Asn Thr Asp Asp Gly Asn Leu
        35                  40                  45

Ile Ser Arg Ala Leu Pro His Leu Gly Val Pro Ser Xaa Tyr Tyr Gly
    50                  55                  60

Glu Asn Tyr Ile Gly Tyr Lys Ile Glu Lys Ile Tyr Ile Lys Asp Glu
65                  70                  75                  80

Asp Leu Ser Met Thr Lys Leu Lys Arg Val Arg Pro Ser Gly Phe Pro
                85                  90                  95

Lys Asp Ile Glu Asn Val Asn Ile Glu Ile His Gln Leu Asn Asp Gln
                100                 105                 110

Val Leu Arg Leu Lys Phe Ile Asp Ala Asn Gln Lys Arg Tyr Glu Val
            115                 120                 125

Pro Thr Pro Lys Leu Asn Ile Pro Ser Val Ser Lys Ser Ser Asn Ser
            130                 135                 140

Arg Leu Tyr Ser Thr Glu Ile Ser Gly Ser His Leu Ile Val Arg Arg
145                 150                 155                 160

Arg Glu Thr Asn Gln Ser Ile Phe Asp Ile Asn Leu Ala Gln Met Val
                165                 170                 175

Tyr Ser Asp Gln Leu Ile His Leu Thr Ser Lys Leu Pro Ser Lys Tyr
            180                 185                 190

Ile Tyr Gly Ile Gly Glu His Arg Glu Pro Phe Arg Lys Thr Thr Asp
            195                 200                 205

Trp Lys Arg Tyr Thr Gln Trp Thr Arg Asp Gln Val Pro Ile Ser Asp
    210                 215                 220

His Ala Leu Tyr Gly Ser His Pro Phe Tyr Met Met Val Glu Asn Lys
225                 230                 235                 240

Thr Lys Leu Ala Ser Gly Val Phe Leu Phe Asn Ser Asn Ala Met Asp
                245                 250                 255

Ile Leu Thr Gln Pro Ser Pro Ala Ile Thr Phe Arg Thr Val Gly Gly
                260                 265                 270

Ile Leu Asp Phe Phe Ile Phe Phe Gly Pro Lys Pro Glu Gln Val Val
            275                 280                 285

Gln Gln Tyr His Asn Leu Ile Gly Leu Pro Ala Met Pro Pro Phe Trp
    290                 295                 300

Ser Leu Gly Tyr Gln Gln Xaa Arg Tyr Gly Tyr Asn Asn Phe Thr Asn
305                 310                 315                 320

Leu Asn Gln Thr Tyr Trp Arg Thr Arg Gln Ala Gly Ile Pro Met Asp
                325                 330                 335

Val Gln Trp Thr Asp Ile Asp Met Phe Asp Ser Tyr Asn Asp Phe Thr
            340                 345                 350

Tyr Asn His Lys Gln Phe Lys Glu Leu Pro Asp Phe Ile Arg Asn Val
        355                 360                 365

Leu His Lys Asn Gly Gln Lys Phe Ile Pro Met Phe Asp Xaa Gly Ile
    370                 375                 380

Ser Ser Gly Glu Lys Ala His Ser Tyr Arg Pro Tyr Asp Tyr Gly Val
385                 390                 395                 400

Glu Leu Asp Ile Phe Val Lys Asn Ser Ser Lys Gln Ile Phe Asn Gly
                405                 410                 415

Lys Val Trp Asn Gly Lys Ser Thr Val Trp Pro Asp Phe Ser His Pro
            420                 425                 430

Asn Ala Thr Lys Tyr Trp Ser Lys Met Phe Glu Glu Tyr His Lys Ile
```

```
            435                 440                 445
Ile Glu Phe Asp Gly Ala Trp Ile Asp Met Asn Glu Pro Ser Asn Phe
450                 455                 460

Tyr Asp Gly Gln Ile Asp Gly Xaa Pro Lys Thr Glu Ile Glu Asn Pro
465                 470                 475                 480

Gln Tyr Val Pro Gly Met Thr Asp Asp Ser Leu Thr Leu Arg His Lys
                485                 490                 495

Thr Leu Xaa Met Thr Ala Arg His Tyr Asn Asp Gln Leu His Tyr Asn
            500                 505                 510

Leu His Asn Leu Tyr Gly Phe Gln Glu Ala Ile Ala Thr Asn Glu Ala
        515                 520                 525

Leu Lys Thr Thr Leu Asn Lys Arg Pro Phe Ile Ile Ser Arg Ser Ser
    530                 535                 540

Ala Pro Gly His Gly His Trp Ala Ser His Trp Asp Gly Asp Val Ile
545                 550                 555                 560

Ser Asp Trp Ser Ser Met Arg Trp Thr Ile Pro Ser Ile Leu Asn Phe
                565                 570                 575

Asn Leu Phe Gly Val Pro Met Ile Gly Ala Asp Ile Xaa Gly Phe Asn
            580                 585                 590

Gly Asp Thr Thr Val Glu Leu Xaa Arg Arg Trp Tyr Gln Leu Gly Ala
        595                 600                 605

Phe Tyr Ser Phe Val Arg Asn His Asn Thr Asp Asn Ala Ile Asp Gln
    610                 615                 620

Asp Pro Val Ala Leu Gly Glu Thr Val Val Arg Thr Ala Arg Ser Ala
625                 630                 635                 640

Leu Thr Tyr Arg Tyr Ala Phe Leu Pro Tyr Leu Tyr Thr Leu Phe Tyr
                645                 650                 655

Asn Val His Gln Asn Gly Gly Thr Val Leu Arg Pro Met Phe Phe Glu
            660                 665                 670

Phe Pro Asp Asp His Leu Tyr Asp Ile Glu Thr Gln Phe Met Trp
        675                 680                 685

Gly Asp Ser Met Leu Ile Ala Pro Ile Leu Tyr Pro Asn Gln Thr Glu
    690                 695                 700

Asn Lys Val Tyr Leu Pro Lys Gly Thr Trp His Asn Met Arg Gln Thr
705                 710                 715                 720

Phe Glu Ser Gln Gly Gln Tyr Phe Thr Ile Lys Asp Ser Leu Asp Asp
                725                 730                 735

Ile Asn Tyr Val Phe Phe Arg Ser Gly Ser Ile Ile Pro Ile Gln Gly
            740                 745                 750

Pro Gln Asn Asn Thr Glu Met Met Lys Ser Lys Asp Phe Gly Leu Val
        755                 760                 765

Val Ile Leu Asp Ser Lys Asn Pro Glu Pro Tyr Ala Lys Gly Ser Leu
    770                 775                 780

Tyr Leu Asp Ser Gly Asp Ser Leu Asp Pro Val Lys Lys Gly Glu Tyr
785                 790                 795                 800

Asn Phe Tyr Asn Phe Glu Val Lys Asn Asn Thr Leu Thr Ile Glu Ser
                805                 810                 815

Gln His Leu Gly Tyr Gln Thr Asn Gln Ser Ile Ile Leu Glu Ile
            820                 825                 830

Leu Gly Ile Asp Arg Lys Pro Thr Ser Ile Ile Phe Asp Gly Lys Pro
        835                 840                 845

Tyr Tyr Gln Phe Ile Tyr Thr Thr Asn Asn Met Leu Ile Ile Gln Thr
    850                 855                 860
```

```
Lys Leu Ser Ile Phe Asn Asp Asn Asp Lys Ser Lys Ile His Tyr
865                 870                 875                 880

Gln Phe Glu Trp Lys Phe Asn
                885

<210> SEQ ID NO 302
<211> LENGTH: 885
<212> TYPE: PRT
<213> ORGANISM: Dermatophagoides farinae
<220> FEATURE:
<221> NAME/KEY: misc_feature
<222> LOCATION: (5)..(5)
<223> OTHER INFORMATION: Xaa is serine, alanine, or 2-aminobutyric acid
<220> FEATURE:
<221> NAME/KEY: misc_feature
<222> LOCATION: (16)..(16)
<223> OTHER INFORMATION: Xaa is serine, alanine, or 2-aminobutyric acid
<220> FEATURE:
<221> NAME/KEY: misc_feature
<222> LOCATION: (27)..(27)
<223> OTHER INFORMATION: Xaa is serine, alanine, or 2-aminobutyric acid
<220> FEATURE:
<221> NAME/KEY: misc_feature
<222> LOCATION: (32)..(33)
<223> OTHER INFORMATION: Xaa is serine, alanine, or 2-aminobutyric acid
<220> FEATURE:
<221> NAME/KEY: misc_feature
<222> LOCATION: (57)..(57)
<223> OTHER INFORMATION: Xaa is serine, alanine, or 2-aminobutyric acid
<220> FEATURE:
<221> NAME/KEY: misc_feature
<222> LOCATION: (306)..(306)
<223> OTHER INFORMATION: Xaa is serine, alanine, or 2-aminobutyric acid
<220> FEATURE:
<221> NAME/KEY: misc_feature
<222> LOCATION: (377)..(377)
<223> OTHER INFORMATION: Xaa is serine, alanine, or 2-aminobutyric acid
<220> FEATURE:
<221> NAME/KEY: misc_feature
<222> LOCATION: (467)..(467)
<223> OTHER INFORMATION: Xaa is serine, alanine, or 2-aminobutyric acid
<220> FEATURE:
<221> NAME/KEY: misc_feature
<222> LOCATION: (494)..(494)
<223> OTHER INFORMATION: Xaa is serine, alanine, or 2-aminobutyric acid
<220> FEATURE:
<221> NAME/KEY: misc_feature
<222> LOCATION: (583)..(583)
<223> OTHER INFORMATION: Xaa is serine, alanine, or 2-aminobutyric acid
<220> FEATURE:
<221> NAME/KEY: misc_feature
<222> LOCATION: (594)..(594)
<223> OTHER INFORMATION: Xaa is serine, alanine, or 2-aminobutyric acid

<400> SEQUENCE: 302

Asp Ser Leu Lys Xaa Ser Ser Ile Arg Asn Glu Asp Arg Ile Asp Xaa
1               5                   10                  15

Asn Pro Asp Pro Pro Ile Ser Lys Asn Val Xaa Glu Gln Arg Gly Xaa
                20                  25                  30

Xaa Trp Lys Thr Ala Gly Asn Asp Leu Lys Asn Leu Ser Ser Lys Val
        35                  40                  45

Leu Pro Asn Leu Asn Val Pro Tyr Xaa Tyr Tyr Gly Glu Asn Tyr Ile
    50                  55                  60

Gly Tyr Lys Ile Glu Lys His Ser Lys Asn Leu Ile Gln Leu Lys Arg
65                  70                  75                  80

Asn Arg Ser Ser Gly Phe Ala Arg Asp Ile Glu Asn Ile Asn Ile Glu
                85                  90                  95

Ile His Glu Leu Asn Asp Lys Val Ile Arg Leu Lys Phe Ile Asp Ala
                100                 105                 110
```

```
Asn Lys Lys Arg Tyr Glu Val Pro Ile Pro Lys Leu Asn Leu Pro Ser
            115                 120                 125

Thr Thr Ser Ser Ser Ser Asn Ser Arg Leu Tyr Ser Val Glu Leu
    130                 135                 140

Asp Gly Ser His Leu Ile Val Arg Arg Glu Thr Asn Gln Ser Ile
145                 150                 155                 160

Phe Asp Ile Asn Leu Ala Tyr Met Val Tyr Ser Asp Gln Leu Ile His
                165                 170                 175

Val Thr Ser Arg Leu Pro Ser Lys Tyr Ile Tyr Gly Leu Gly Glu His
            180                 185                 190

Arg Ala Pro Phe Arg Lys Asn Thr Asn Trp Lys Arg Tyr Thr Gln Trp
            195                 200                 205

Thr Arg Asp Gln Tyr Pro Val Thr Asp Lys Ala Leu Tyr Gly Asn His
    210                 215                 220

Pro Phe Tyr Leu Thr Val Glu Asp Glu Ser Pro Lys Lys Ser Ala Ser
225                 230                 235                 240

Gly Val Phe Leu Phe Asn Ser Asn Ala Met Asp Ile Ile Thr Gln Pro
                245                 250                 255

Ser Pro Ala Ile Thr Phe Arg Thr Ile Gly Gly Ile Leu Asp Phe Phe
            260                 265                 270

Val Phe Phe Gly Pro Lys Pro Glu Asp Val Ile Ser Gln Tyr Gln Asn
            275                 280                 285

Leu Ile Gly Leu Pro Ala Met Pro Pro Phe Trp Ser Leu Gly Tyr Gln
            290                 295                 300

Gln Xaa Arg Tyr Gly Tyr Asn Asn Phe Thr Asn Leu Asn Thr Thr Tyr
305                 310                 315                 320

Thr Arg Asn Arg Ala Val Gly Ile Pro Met Asp Val Gln Trp Thr Asp
                325                 330                 335

Ile Asp Ala Phe Asn Ser Asn Asn Asp Phe Thr Tyr Asp His Lys Arg
                340                 345                 350

Phe Lys Glu Leu Pro Asp Phe Ile Asn Asn Val Leu His Pro Asn Gly
            355                 360                 365

Gln Lys Phe Ile Pro Met Phe Asp Xaa Gly Ile Ser Ser Gly Glu Pro
            370                 375                 380

Ala Gly Ser Tyr Lys Pro Phe Asp Ser Gly Val Glu Leu Asp Val Phe
385                 390                 395                 400

Val Lys Asn Ser Ser Asn Lys Ile Phe Arg Gly Lys Val Trp Asn Gly
            405                 410                 415

Lys Ser Thr Val Trp Pro Asp Phe Ser His Pro Asn Ala Thr Glu Tyr
            420                 425                 430

Trp Met Asp Met Phe Ala Glu Tyr His Lys Thr Ile Ala Phe Asp Gly
            435                 440                 445

Ala Trp Leu Asp Met Asn Glu Pro Ser Asn Phe Tyr Asn Gly Glu Glu
    450                 455                 460

His Gly Xaa Pro Glu Ser Glu Ile Glu Asn Pro Gln Tyr Val Pro Gly
465                 470                 475                 480

Met Thr Asp Asp Ser Leu Thr Leu Arg His Lys Thr Leu Xaa Met Thr
                485                 490                 495

Ala Arg His Tyr Asn Asp Gln Leu His Tyr Asn Leu His Asn Leu Tyr
            500                 505                 510

Ser Leu Ser Met Ala Met Ala Thr Asn Ala Ala Leu Thr Lys Leu Asn
            515                 520                 525
```

```
Lys Arg Pro Phe Ile Ile Ser Arg Ala Thr Ala Pro Gly His Gly His
530                 535                 540
Trp Ala Tyr His Trp Asn Gly Asp Ile Leu Ser Asp Trp Ser Ser Met
545                 550                 555                 560
Arg Trp Thr Ile Pro Ser Ile Leu Asn Phe Asn Met Phe Gly Ile Pro
                565                 570                 575
Met Val Gly Ala Asp Ile Xaa Gly Phe Gly Gly Asn Thr Ala Glu Glu
            580                 585                 590
Leu Xaa Ile Arg Trp Tyr Gln Leu Gly Ala Phe Tyr Ser Phe Ala Arg
    595                 600                 605
Asn His Asn Asp Ile His Ser Ile Asp Gln Asp Pro Ala Ala Leu Gly
610                 615                 620
Glu Ser Val Ile Arg Ala Ala Arg Ser Ser Leu Gln Tyr Arg Tyr Arg
625                 630                 635                 640
Phe Leu Ala His Leu Tyr Thr Leu Phe Tyr His Val His Lys Asn Gly
                645                 650                 655
Gly Thr Val Leu Arg Pro Met Phe Phe Glu Phe Pro His Asp Glu His
            660                 665                 670
Thr Tyr Glu Ile Glu Thr Gln Phe Met Trp Gly Asp Ser Val Leu Ile
    675                 680                 685
Ala Pro Ile Leu Tyr Pro Asn Gln Thr Gln His Lys Ile Tyr Leu Pro
690                 695                 700
Lys Gly Thr Trp Tyr Asn Arg Lys Val Ser Phe Glu Ser Gln Gly Gln
705                 710                 715                 720
Tyr Ile Thr Met Asn Asp Ser Tyr Asp Ile Asp Tyr Val Phe Val
                725                 730                 735
Arg Gly Gly Ser Ile Ile Pro Thr Gln Glu Pro His Asp Asn Thr Glu
            740                 745                 750
Leu Met Lys Thr Lys Asp Phe Leu Leu Ile Val Ala Leu Asp Asn Gln
    755                 760                 765
Thr Ser Tyr Ala Lys Gly Ser Leu Tyr Trp Asp Ser Gly Asp Ser Leu
770                 775                 780
Asn Pro Asp Lys Thr Gly His Tyr Asn Phe Tyr Asn Phe Asp Ala Val
785                 790                 795                 800
Asn Asn Thr Leu Thr Ile Gln Ser Gln Trp Leu Gly Tyr Gln Thr Thr
                805                 810                 815
Gln Asn Ile Asn Phe Ile Asn Ile Leu Gly Val Pro Lys Leu Pro Thr
            820                 825                 830
Ser Phe Lys Leu Asn Gly His Val Ser Asp Pro Arg Ile Ile Arg Phe
    835                 840                 845
Asn Tyr Asp Glu Gln Thr Asn Ile Leu Thr Val Glu Thr Lys Leu Pro
850                 855                 860
Ile Tyr Asn Gln Asp Ser Ser His Asp Arg Ile His Tyr Gln Phe
865                 870                 875                 880
Glu Trp Ile Met Glu
            885

<210> SEQ ID NO 303
<211> LENGTH: 975
<212> TYPE: PRT
<213> ORGANISM: Dermatophagoides farinae
<220> FEATURE:
<221> NAME/KEY: misc_feature
<222> LOCATION: (12)..(12)
<223> OTHER INFORMATION: Xaa is serine, alanine, or 2-aminobutyric acid
<220> FEATURE:
```

```
<221> NAME/KEY: misc_feature
<222> LOCATION: (17)..(17)
<223> OTHER INFORMATION: Xaa is serine, alanine, or 2-aminobutyric acid
<220> FEATURE:
<221> NAME/KEY: misc_feature
<222> LOCATION: (148)..(148)
<223> OTHER INFORMATION: Xaa is serine, alanine, or 2-aminobutyric acid
<220> FEATURE:
<221> NAME/KEY: misc_feature
<222> LOCATION: (316)..(316)
<223> OTHER INFORMATION: Xaa is serine, alanine, or 2-aminobutyric acid
<220> FEATURE:
<221> NAME/KEY: misc_feature
<222> LOCATION: (370)..(370)
<223> OTHER INFORMATION: Xaa is serine, alanine, or 2-aminobutyric acid
<220> FEATURE:
<221> NAME/KEY: misc_feature
<222> LOCATION: (426)..(426)
<223> OTHER INFORMATION: Xaa is serine, alanine, or 2-aminobutyric acid
<220> FEATURE:
<221> NAME/KEY: misc_feature
<222> LOCATION: (449)..(449)
<223> OTHER INFORMATION: Xaa is serine, alanine, or 2-aminobutyric acid
<220> FEATURE:
<221> NAME/KEY: misc_feature
<222> LOCATION: (457)..(457)
<223> OTHER INFORMATION: Xaa is serine, alanine, or 2-aminobutyric acid

<400> SEQUENCE: 303

Val Val Ile Lys Val Glu Asn Leu Pro Glu Arg Xaa Asp Tyr Ser Gln
1               5                   10                  15

Xaa Pro Lys Trp Asp Pro Asn Asp Ile Asn Val His Leu Val Ala His
            20                  25                  30

Thr His Asp Asp Val Gly Trp Leu Lys Thr Val Glu Gln Tyr Tyr Tyr
        35                  40                  45

Gly Leu Lys Asn Asp Ile Gln Arg Ala Gly Val Gln Tyr Ile Leu Asp
    50                  55                  60

Thr Val Ile Glu Glu Leu Ile Arg Asn Lys Gln Arg Arg Phe Ile Tyr
65                  70                  75                  80

Val Glu Ile Ala Phe Phe Trp Lys Trp Gln Glu Gln Asp Glu Asp
                85                  90                  95

Gln Arg Met Ile Val Arg Glu Leu Val Arg Thr Gly Gln Leu Glu Phe
            100                 105                 110

Ile Asn Gly Gly Trp Ser Met Pro Asp Glu Ala Ala Thr His Tyr Asn
        115                 120                 125

Ser Leu Ile Asp Gln Ser Thr Trp Gly Leu Arg Gln Leu Asn Asp Thr
    130                 135                 140

Phe Gly Lys Xaa Gly His Pro Lys Val Thr Trp Gln Ile Asp Pro Phe
145                 150                 155                 160

Gly His Ser Arg Glu Met Ala Asn Leu Tyr Ala Gln Met Gly Tyr Asp
                165                 170                 175

Ala Leu Phe Phe Ala Arg Gln Asp Tyr Gln Asp Arg Glu Asn Arg Met
            180                 185                 190

Thr Asn Arg Lys Leu Glu His Val Trp Gln Gly Ser Asp Asp Leu Gly
        195                 200                 205

Thr Ala Gly Asp Ile Phe Thr Gly Met Met Phe Ser Gly Tyr Gly Pro
    210                 215                 220

Ile Glu Phe Asn Trp Asp Ile Thr Asn Gly Pro Glu Asp Ala Val Val
225                 230                 235                 240

Asp Asn Pro Glu Ser Glu Glu Tyr Asn Val Pro Asp Lys Ile Arg Arg
                245                 250                 255

Phe Val Glu Lys Ala Lys Tyr Phe Ala Gln Tyr Tyr Ala Thr Asn His
```

```
                260                 265                 270
Phe Met Phe Pro Met Gly Thr Asp Phe Gln Tyr Gly Asp Ala His Thr
            275                 280                 285
Trp Phe Lys Asn Leu Asp Lys Leu Ile Lys Ala Val Asn Asn Ala Gly
            290                 295                 300
Lys Gly Val Arg Ala Phe Tyr Ser Thr Pro Ser Xaa Tyr Ala Arg Ala
305                 310                 315                 320
Leu Tyr Glu Thr Asn Arg Thr Trp Thr Thr Lys Thr Asp Asp Phe Phe
                325                 330                 335
Pro Tyr Ala Ser Asp Glu His Ala Tyr Trp Thr Gly Tyr Phe Thr Ser
            340                 345                 350
Arg Pro Ala Leu Lys Arg Met Glu Arg Met Gly Asn Asn Leu Leu Gln
            355                 360                 365
Ala Xaa Lys Gln Leu Asp Ile Leu Ala Gly Asn Asp Gly Arg Phe Glu
            370                 375                 380
Met Asn Ile Thr Arg Leu Arg Glu Ala Met Gly Val Met Gln His His
385                 390                 395                 400
Asp Ala Val Thr Gly Thr Glu Lys Gln His Val Ala Phe Asn Tyr Ala
                405                 410                 415
Lys Met Leu Asp Ser Ala Met Leu Gln Xaa Arg His Val Ile Ser Glu
            420                 425                 430
Ser Tyr Arg Lys Leu Phe Pro Thr Gln Thr Lys Glu Gln His Glu Phe
            435                 440                 445
Xaa Pro Tyr Leu Asn Ile Ser Ser Xaa Pro Ser Thr Glu Met Gly Glu
450                 455                 460
Ser Arg Thr Ile His Leu Tyr Asn Pro Leu Gly His Arg Leu Val Asn
465                 470                 475                 480
Arg Thr Ile Arg Val Pro Val Lys Asp Gly Tyr Tyr Tyr Gln Val Arg
            485                 490                 495
Asp Gln Asn Asp His Ser Ile Pro Ala Val Leu Ile Ser Ile Pro Glu
            500                 505                 510
Phe Val Arg Lys Ile Pro Gly Arg Lys Ser Val Ala Thr Lys Glu Leu
            515                 520                 525
Val Phe Arg Val Pro Ile Ile Glu Ser Leu Gly Ile Arg Arg Phe His
            530                 535                 540
Met Ile Ala Thr Lys Glu Lys Gln Gln Asp Ser Ala Val Glu Ile Gln
545                 550                 555                 560
Gly Glu Lys Phe Val Gly His Lys Gly Gln Arg Phe Gln Leu Lys Asp
                565                 570                 575
Gly Leu Ile Ile Glu Phe Asp Ser Asn Gly Lys Ile Ala Thr Met Ile
            580                 585                 590
Arg Asn Asn Gln Ser Ile Ser Ile Ser Asn Glu Phe Arg Leu Phe His
            595                 600                 605
Gly Ala Asp Ile Gly Arg His Ser Gly Ala Tyr Ile Phe Arg Pro Ser
            610                 615                 620
Glu Gln Lys Thr Phe Pro Val Thr Glu Lys Met Glu Ala Thr Leu Tyr
625                 630                 635                 640
Val Asp Gln Lys Phe Gly Ile Val Gln Glu Val His Gln Gln Phe Asp
                645                 650                 655
Ser Phe Val Gly Gln Ile Ile Arg Leu Asp Lys Gln Gly Asp Tyr Val
            660                 665                 670
Glu Phe Asp Phe Val Val Gly Pro Ile Pro Val Asp Asp Leu Ile Gly
            675                 680                 685
```

Lys Glu Ile Ile Thr Arg Tyr Asn Thr Asn Leu Ala Asn Asp Glu Thr
690                 695                 700

Phe Phe Thr Asp Ser Asn Gly Arg Gln Met Leu Arg Arg Arg Trp Asn
705                 710                 715                 720

Tyr Arg Pro Ser Trp Lys Tyr Glu Ile Glu Glu Pro Val Ser Gly Asn
            725                 730                 735

Tyr Tyr Pro Val Asn Ser Arg Ile Ala Ile Arg Asp Asp Arg Lys Ser
            740                 745                 750

Leu Gln Met Thr Ile Met Thr Asp Arg Ser Gln Gly Gly Ser Leu Ser
        755                 760                 765

Pro Glu Gln Ile Asn Gly Ser Val Asp Leu Met Val His Arg Arg Leu
770                 775                 780

Leu His Asp Asp Tyr Phe Gly Val Asp Glu Pro Leu Asn Glu Pro Gly
785                 790                 795                 800

Val Asp Gly His Gly Ile Val Ile Arg Gly Arg His Leu Leu Leu Leu
            805                 810                 815

Asp Thr Leu Glu Lys Ala Ala Glu Lys His Arg Pro Leu Ala Gln Glu
            820                 825                 830

Met Phe Met Glu Pro Ile Ile Ser Phe Thr Ser Ser Met Glu Lys Asn
        835                 840                 845

Gln Pro Ile Tyr Lys Gly Leu Thr Lys Asp Leu Pro Gly Asn Val His
850                 855                 860

Leu Leu Thr Leu Glu Gln Trp His Ser Lys Arg Tyr Leu Leu Arg Leu
865                 870                 875                 880

Glu His Phe Tyr Gln Arg Phe Glu Asp Pro Ser Leu Ser Asn Pro Ala
            885                 890                 895

Thr Val Ser Leu Arg His Leu Phe Gln Ser Phe Glu Ile Thr Ala Val
            900                 905                 910

Glu Glu Leu Thr Leu Gly Ala Asn Gln Pro Ile Ser Ala Leu Lys Asn
        915                 920                 925

Arg Leu Gln Tyr Arg Tyr Ile Arg Pro Leu Asn Glu Gln Gln Ser Ser
930                 935                 940

Ile Ile Thr Asp Pro Ile Ile Glu Gly Glu Asn Phe Asp Ile His Leu
945                 950                 955                 960

Glu Pro Met Gln Ile Arg Thr Phe Leu Ile Asp Ile Lys Arg Asn
            965                 970                 975

<210> SEQ ID NO 304
<211> LENGTH: 990
<212> TYPE: PRT
<213> ORGANISM: Dermatophagoides pteronyssinus
<220> FEATURE:
<221> NAME/KEY: misc_feature
<222> LOCATION: (12)..(12)
<223> OTHER INFORMATION: Xaa is serine, alanine, or 2-aminobutyric acid
<220> FEATURE:
<221> NAME/KEY: misc_feature
<222> LOCATION: (17)..(17)
<223> OTHER INFORMATION: Xaa is serine, alanine, or 2-aminobutyric acid
<220> FEATURE:
<221> NAME/KEY: misc_feature
<222> LOCATION: (148)..(148)
<223> OTHER INFORMATION: Xaa is serine, alanine, or 2-aminobutyric acid
<220> FEATURE:
<221> NAME/KEY: misc_feature
<222> LOCATION: (316)..(316)
<223> OTHER INFORMATION: Xaa is serine, alanine, or 2-aminobutyric acid
<220> FEATURE:
<221> NAME/KEY: misc_feature
<222> LOCATION: (370)..(370)

```
<223> OTHER INFORMATION: Xaa is serine, alanine, or 2-aminobutyric acid
<220> FEATURE:
<221> NAME/KEY: misc_feature
<222> LOCATION: (426)..(426)
<223> OTHER INFORMATION: Xaa is serine, alanine, or 2-aminobutyric acid
<220> FEATURE:
<221> NAME/KEY: misc_feature
<222> LOCATION: (449)..(449)
<223> OTHER INFORMATION: Xaa is serine, alanine, or 2-aminobutyric acid
<220> FEATURE:
<221> NAME/KEY: misc_feature
<222> LOCATION: (457)..(457)
<223> OTHER INFORMATION: Xaa is serine, alanine, or 2-aminobutyric acid

<400> SEQUENCE: 304

Val Val Ile Lys Val Glu Asn Leu Pro Glu Gln Xaa Asp Tyr Thr Gln
1               5                   10                  15

Xaa Pro Lys Trp Ser Lys Asp Asp Ile Asn Val His Leu Val Ala His
                20                  25                  30

Thr His Asp Asp Val Gly Trp Leu Lys Thr Val Glu Gln Tyr Tyr Tyr
            35                  40                  45

Gly Leu Lys Asn Asp Ile Gln Arg Ala Gly Val Gln Tyr Ile Leu Asp
        50                  55                  60

Thr Met Ile Glu Glu Leu Ile Arg Asn Lys Asp Arg Arg Phe Ile Tyr
65                  70                  75                  80

Val Glu Ile Ala Phe Phe Trp Lys Trp Trp Gln Glu Gln Asn Glu Glu
                85                  90                  95

Gln Arg Met Ile Val Lys Glu Leu Val Arg Thr Gly Gln Leu Glu Phe
            100                 105                 110

Ile Asn Gly Gly Trp Ser Met Pro Asp Glu Ala Ala Thr His Tyr Asn
        115                 120                 125

Ser Leu Ile Asp Gln Ser Thr Trp Gly Leu Arg Gln Leu Asn Asp Thr
130                 135                 140

Phe Gly Arg Xaa Gly His Pro Lys Val Thr Trp Gln Ile Asp Pro Phe
145                 150                 155                 160

Gly His Ser Lys Glu Met Ala Asn Leu Tyr Ala Gln Met Gly Tyr Asp
                165                 170                 175

Ala Leu Phe Phe Ala Arg Gln Asp Tyr Gln Asp Arg Glu Asn Arg Met
            180                 185                 190

Ser Asn Arg Thr Leu Glu His Val Trp Gln Gly Ser Asp Asp Leu Gly
        195                 200                 205

Glu Ile Gly Asp Ile Phe Thr Gly Met Met Phe Ser Gly Tyr Gly Pro
210                 215                 220

Ile Glu Phe Asn Trp Asp Ile Thr Asn Gly Pro Glu Asp Ala Val Val
225                 230                 235                 240

Asp Asn Pro Glu Ser Glu Glu Tyr Asn Val Pro Asp Lys Ile Arg Arg
                245                 250                 255

Phe Val Glu Lys Ala Lys Tyr Phe Gly Gln Phe Tyr Ala Thr Asn His
            260                 265                 270

Phe Met Phe Pro Met Gly Thr Asp Phe Gln Tyr Thr Asp Ala His Thr
        275                 280                 285

Trp Phe Lys Asn Leu Asp Lys Leu Ile Asn Ala Val Asn Lys Ala Gly
290                 295                 300

Lys Gly Val Arg Ala Phe Tyr Ser Thr Pro Ser Xaa Tyr Ala His Ala
305                 310                 315                 320

Leu Tyr Glu Gln Asn Arg Thr Trp Thr Thr Lys Thr Asp Asp Phe Phe
                325                 330                 335
```

-continued

Pro Tyr Ala Ser Asp Glu His Ala Tyr Trp Thr Gly Tyr Phe Thr Ser
            340                 345                 350

Arg Pro Ala Ile Lys Arg Met Glu Arg Ile Gly Asn Asn Leu Leu Gln
        355                 360                 365

Ala Xaa Lys Gln Leu Asp Val Leu Ala Asp Asn Asn Gly Arg Phe Glu
    370                 375                 380

Met Asn Leu Thr Lys Met Arg Glu Ala Met Gly Val Met Gln His His
385                 390                 395                 400

Asp Ala Val Thr Gly Thr Glu Lys Gln His Val Ala Phe Asn Tyr Ala
                405                 410                 415

Lys Met Leu Asp Ser Ala Met Leu Gln Xaa Arg His Ile Ile Asn Glu
            420                 425                 430

Ser Tyr Lys Lys Leu Leu Pro Lys Ser Ser Thr Ser Glu His Glu Phe
        435                 440                 445

Xaa Pro Tyr Leu Asn Ile Ser Ser Xaa Pro Thr Thr Glu Met Gly Glu
    450                 455                 460

Ser Arg Ile Ile Tyr Leu Tyr Asn Pro Leu Gly His Arg Leu Ile Asn
465                 470                 475                 480

His Thr Val Arg Leu Pro Ile Lys Asn Gly Tyr Tyr Arg Ile Gln
                485                 490                 495

Asp Gln Asn Asn Gln Ser Val Pro Ser Val Leu Val Pro Ile Pro Glu
            500                 505                 510

Phe Val Gln Lys Ile Pro Gly Arg Lys Ser Val Ala Thr Lys Glu Leu
        515                 520                 525

Val Phe Arg Val Pro Val Ile Glu Pro Leu Gly Ile Thr Thr Met Tyr
    530                 535                 540

Met Tyr Val Asp Lys Asn Glu Gln Pro Asn Ser Ala Ile Glu Ile Lys
545                 550                 555                 560

Gly Glu Asn Pro Asp Asp Asn Asp Asp Lys Ser Lys Trp Leu Val Leu
                565                 570                 575

Thr Lys Asn Leu Ile Val Glu Phe Tyr Ser Asn Gly Thr Ile Ser Arg
            580                 585                 590

Ile Ser Ile Asp Lys Leu His Gln Ser Ile Ser Ile Ser Asn Glu Phe
        595                 600                 605

Arg Leu Tyr His Gly Ala Gly Gly Thr Gly Arg His Ser Gly Ala Tyr
    610                 615                 620

Ile Phe Arg Pro Asn Glu Gln Lys Thr Phe Pro Val Thr Asn Lys Ile
625                 630                 635                 640

Lys Ser Thr Phe Phe Ile Asp Arg Lys Tyr His Ile Val Gln Glu Val
                645                 650                 655

His Gln Gln Phe Asp Ser Ser Phe Val Gly Gln Ile Ile Arg Met Asp
            660                 665                 670

Lys Tyr Asn Asp Asn Val Glu Phe Asp Phe Val Val Gly Pro Ile Pro
        675                 680                 685

Val Asn Asp Gln Ile Gly Lys Glu Ile Ile Ala Ser Tyr Lys Thr Asp
    690                 695                 700

Leu Glu Asn Asp Glu Thr Phe Tyr Thr Asp Ala Asn Gly Arg Gln Met
705                 710                 715                 720

Leu Arg Arg Arg Trp Asn Tyr Arg Pro Ser Trp Lys Tyr Asn Val Gln
                725                 730                 735

Glu Pro Ile Ser Gly Asn Tyr Tyr Pro Val Asn Ser Arg Ile Ala Ile
            740                 745                 750

Arg Asp Glu Lys Gln Ser Leu Gln Met Thr Ile Met Thr Asp Arg Ser

```
                    755                 760                 765
Gln Gly Gly Ser Leu Ser Pro Glu Gln Ile Asn Gly Ser Ile Asp Ile
770                 775                 780

Met Ile His Arg Arg Leu Leu His Asp Asp Tyr Phe Gly Val Gly Glu
785                 790                 795                 800

Ala Leu Asn Glu Pro Gly Val Asp Gly His Gly Leu Val Ile Arg Gly
                805                 810                 815

Lys His Leu Leu Leu Asn Ser Ile Lys Gln Ser Ala Ser Glu His
                820                 825                 830

Arg Pro Leu Ala Gln Gln Met Phe Met Glu Pro Ile Ile Ser Phe Thr
                835                 840                 845

Ser Ile Glu Ser Asn Lys Gln Ala Glu Lys Gln Ser Asn Gln Tyr Ile
850                 855                 860

Gly Leu Asn Asn Asp Leu Pro Ser Asn Val His Leu Leu Thr Leu Glu
865                 870                 875                 880

Gln Trp His Ser Lys Arg Tyr Leu Leu Arg Leu Glu His Phe Tyr Gln
                885                 890                 895

Ser Asn Glu Asp Thr Glu Leu Ser Lys Pro Val Lys Leu Ser Leu Arg
                900                 905                 910

His Leu Phe Lys Ser Phe Glu Ile Ile Ala Val Glu Glu Leu Thr Leu
                915                 920                 925

Gly Ala Asn Gln Pro Ile Ser Ser Leu Lys Asn Arg Leu His Tyr Arg
                930                 935                 940

Tyr Asn Arg Pro Leu Glu Gln Arg Gln Gln Gln Ser Ser Leu Leu
945                 950                 955                 960

Leu Asp Asp Pro Lys Ile Glu Gly Asn Phe Asp Ile His Leu Ser
                965                 970                 975

Pro Met Gln Ile Arg Thr Phe Leu Ile Asp Ile Lys Arg Asn
                980                 985                 990

<210> SEQ ID NO 305
<211> LENGTH: 125
<212> TYPE: PRT
<213> ORGANISM: Blomia tropicalis

<400> SEQUENCE: 305

Gly Lys Tyr Gln Leu Glu Ser Ser Glu Asn Phe Asp Glu Phe Leu Lys
1               5                   10                  15

Glu Leu Gly Val Asn Phe Ile Leu Arg Asn Leu Ala Lys Thr Ser Lys
                20                  25                  30

Pro Thr Ile Glu Ile Thr Leu Asp Gly Asp Thr Tyr Thr Ile Lys Thr
                35                  40                  45

Ile Thr Thr Leu Lys Thr Ser Val Ile Thr Phe Lys Ile Gly Glu Glu
                50                  55                  60

Phe Glu Glu Ser Arg Met Asp Gly Lys Thr Val Lys Thr Val Ile Thr
65                  70                  75                  80

Gln Glu Gly Asp Lys Leu Ile Gln Val Gln Gln Gly Asp Lys Glu Val
                85                  90                  95

Lys Ile Val Arg Glu Phe Thr Glu Thr His Leu Thr Thr Ile Cys Thr
                100                 105                 110

Val Gly Glu Ile Thr Ser Thr Arg Val Tyr Lys Arg Val
                115                 120                 125

<210> SEQ ID NO 306
<211> LENGTH: 363
```

<212> TYPE: PRT
<213> ORGANISM: Blomia tropicalis

<400> SEQUENCE: 306

```
Met Ser Ile Ile Gln Asn Leu Pro Ala Asp Val Gln Glu Glu Leu Arg
1               5                   10                  15
Lys Thr Ala Asn Ala Ile Val Thr Pro Gly Lys Gly Ile Leu Ala Ala
            20                  25                  30
Asp Glu Ser Thr Gly Thr Ile Gly Lys Arg Phe Ala Asp Ile Asn Val
        35                  40                  45
Glu Asn Val Glu Asn Asn Arg Arg Thr Tyr Arg Asp Leu Leu Phe Ser
    50                  55                  60
Ala Pro Asp Glu Val Asn Asn Tyr Ile Ser Gly Val Ile Leu Phe Asp
65                  70                  75                  80
Glu Thr Val Tyr Gln Lys Asn Ala Ala Gly Val Pro Phe Pro Gln Val
                85                  90                  95
Leu Ala Lys Arg Gly Ile Ile Pro Gly Ile Lys Val Asp Thr Gly Val
            100                 105                 110
Val Val Leu Gln Gly Thr Asn Gly Glu Ser Thr Thr Gln Gly Leu Asp
        115                 120                 125
Asn Leu Thr Lys Arg Cys Gln Ala Tyr Tyr Glu Gln Gly Cys Arg Phe
    130                 135                 140
Ala Lys Trp Arg Cys Val Leu Lys Ile Gly Asp Asn Glu Pro Ser Pro
145                 150                 155                 160
Leu Ala Ile Leu Glu Asn Ala Asn Val Leu Ala Arg Tyr Ala Ser Cys
                165                 170                 175
Cys Gln Gln Ala Arg Ile Val Pro Ile Val Glu Pro Glu Ile Leu Pro
            180                 185                 190
Asp Gly Ala His Asp Ile Glu Arg Cys Gln Lys Val Thr Glu Lys Val
        195                 200                 205
Leu Ala Ala Val Tyr Lys Ala Leu Asn Asp His Asn Val Phe Leu Glu
    210                 215                 220
Gly Thr Leu Leu Lys Pro Asn Met Val Thr Ala Gly Gln Ser Phe Ala
225                 230                 235                 240
Gly Pro Lys Pro Ser Pro Gln Glu Val Ala Arg Ala Thr Val Thr Ala
                245                 250                 255
Leu Gln Arg Thr Val Pro Ala Ala Val Pro Gly Ile Val Phe Leu Ser
            260                 265                 270
Gly Gly Gln Ser Glu Glu Glu Ala Ser Ile Asn Leu Asn Ala Ile Asn
        275                 280                 285
Gln Phe Glu Gly Lys Lys Pro Trp Ala Leu Ser Phe Ser Tyr Gly Arg
    290                 295                 300
Ala Leu Gln Ala Ser Val Leu Arg Ala Trp Gln Gly Lys Asp Glu Leu
305                 310                 315                 320
Ile Ala Ala Gly Gln Lys Glu Leu Val Asn Arg Ser Lys Ala Asn Ser
                325                 330                 335
Asp Ala Ser Leu Gly Lys Tyr Ser Gly Gly Ile Val Gly Ala Ala Gly
            340                 345                 350
Glu Gln Asp Leu Phe Ile Lys Asp His Gln Tyr
        355                 360
```

<210> SEQ ID NO 307
<211> LENGTH: 973
<212> TYPE: PRT
<213> ORGANISM: Blomia tropicalis

<400> SEQUENCE: 307

```
Val Val Ile Lys Val Glu Asn Leu Pro Ala Arg Cys Asp Tyr Thr Lys
1               5                   10                  15

Cys Pro Lys Ser Asp Pro Asn Lys Ile Asn Val His Leu Val Pro His
                20                  25                  30

Thr His Asp Asp Val Gly Trp Leu Lys Thr Val Glu Gln Tyr Tyr Tyr
            35                  40                  45

Gly Ser Lys Thr Tyr Tyr Gln Lys Ala Gly Val Gln Tyr Ile Leu Asp
        50                  55                  60

Ser Val Met Asn Glu Leu Ile His Asn Lys Glu Arg Lys Phe Ile Tyr
65                  70                  75                  80

Val Glu Thr Ala Phe Phe Trp Lys Trp Trp Met Glu Gln Asp Tyr Gly
                85                  90                  95

Met Arg Asn Ile Val Lys Glu Leu Val Glu Thr Gly Gln Leu Glu Phe
                100                 105                 110

Ile Asn Ala Gly Trp Ser Met Asn Asp Glu Ala Ser Thr His Tyr Asn
            115                 120                 125

Ser Ile Ile Asp Gln Met Ser Trp Gly Phe Tyr Arg Leu Gln Thr Thr
        130                 135                 140

Phe Gly Arg Cys Gly Val Pro Lys Val Ala Trp Gln Ile Asp Pro Phe
145                 150                 155                 160

Gly His Ser Lys Glu Gln Ala Ala Leu Phe Ala Leu Met Asn Phe Asp
                165                 170                 175

Ala Leu Phe Phe Ala Arg Glu Asp Trp Gln Glu Gln Ser His Arg Arg
                180                 185                 190

Lys Asn Arg Thr Leu Glu His Val Trp Gln Ala Ser Ser Asp Leu Gly
            195                 200                 205

Lys Ser Ala Asp Leu Phe Thr Gly Met Met Asn Phe Gly Tyr Gly Pro
        210                 215                 220

Pro Gln Gly Phe Asn Trp Asp Leu Val Gly Gly Ala Asp Glu Pro Val
225                 230                 235                 240

Ile Asp Asp Pro Glu Ser Asp Glu Tyr Asn Val Pro Arg Arg Val Lys
                245                 250                 255

Glu Leu Ile Asp Leu Ala Lys Thr Tyr Gln Lys Tyr Tyr Ala Thr Asn
                260                 265                 270

Asn Val Met Phe Pro Met Gly Thr Asp Phe Gln Tyr Gln Asp Ala His
            275                 280                 285

Ile Tyr Phe Lys Asn Met Asp Lys Leu Ile Lys Tyr Val Asn Glu Asn
        290                 295                 300

Ser Thr Glu Val Asn Ile Phe Tyr Ser Thr Pro Ser Cys Tyr Ala Lys
305                 310                 315                 320

Ser Leu Lys Asp Ser Gly Lys Thr Phe Thr Ala Lys Asn Asp Asp Tyr
                325                 330                 335

Phe Pro Tyr Ala Ser Asp Pro His Ser Tyr Trp Thr Gly Tyr Phe Thr
                340                 345                 350

Ser Arg Pro Ala Ile Lys Arg Phe Glu Arg Val Gly Asn Asn Tyr Leu
            355                 360                 365

Gln Val Cys Lys Gln Met Asp Thr Tyr Thr Gly His Gln Ala Thr Arg
        370                 375                 380

Asp Arg His Thr Thr Lys Leu Arg Glu Ile Met Gly Val Met Gln His
385                 390                 395                 400

His Asp Ala Val Ser Gly Thr Glu Lys Gln His Val Ala Phe Asn Tyr
```

```
                    405                 410                 415
Ala Lys His Leu Gln Ser Gly Ile Glu Ser Cys Arg Lys Val Ile Ser
                420                 425                 430
Glu Ala Tyr Gln Leu Leu Gln His Pro His Thr Lys Thr Val Gln Thr
                435                 440                 445
Phe Cys Asp Tyr Leu Asn Ile Ser Ser Cys Ala Ile Thr Glu Ser Gly
                450                 455                 460
Gln Asn Phe Val Val Asn Ile Tyr Asn Pro Leu Ser Lys Thr Leu Lys
465                 470                 475                 480
Asn His Pro Ile Arg Leu Pro Ile Asn Ser Asp Lys Tyr Tyr Asn Val
                485                 490                 495
Val Asp Asp Glu Gly Lys Ser Val Tyr Ser Glu Leu Thr Phe Ile Pro
                500                 505                 510
Glu Tyr Val Gln Ala Ile Pro Glu Arg Thr Thr Asn Ala Thr Thr Asp
                515                 520                 525
Leu Val Phe Leu Ala Ser Ile Pro Pro Leu Gly Tyr Ala Ser Tyr Phe
                530                 535                 540
Val Gln Ala Thr Thr Thr Lys Ser Pro Asp Ser Ala Asn Ala Val Thr
545                 550                 555                 560
Val Thr Lys Ile Thr Asn Glu Thr Arg Leu Ser Ser Gly Asn Phe Ser
                565                 570                 575
Val Val Phe Asp Ser Thr Gly Ala Leu Ser Lys Val Glu Leu Pro Ser
                580                 585                 590
Gly Glu Ser Ile Pro Phe Lys Asn Glu Phe Arg Tyr Tyr Asn Gly Ala
                595                 600                 605
Ala Asp Asn Ile Arg Ala Ser Gly Ala Tyr Ile Phe Arg Pro Lys Glu
                610                 615                 620
Gln Gln Thr Phe Pro Phe Ala Lys Leu Val Ser Ala Asn Leu Leu Thr
625                 630                 635                 640
Arg Thr Ser Ser Gly Gly Ile Val His Glu Val His Gln Lys Phe Asp
                645                 650                 655
Ser Asn Val Glu Gln Val Ile Arg Val Leu Pro Asp Ser Asp Ser Ile
                660                 665                 670
Glu Phe Glu Tyr Val Val Gly Pro Ile Pro Val Lys Asp Gly Ile Gly
                675                 680                 685
Lys Glu Val Val Leu Thr Tyr Glu Thr Asp Phe Lys Asn Asn Lys Thr
                690                 695                 700
Phe Tyr Thr Asp Ala Asn Gly Arg Gln Met Met Lys Arg Lys Trp Asp
705                 710                 715                 720
Tyr Arg Pro Glu Phe Lys Met Glu Val Thr Glu Pro Ile Ser Gly Asn
                725                 730                 735
Tyr Tyr Pro Ile Asn Ser Arg Ile Tyr Leu Gln Asp Glu Lys Lys Gly
                740                 745                 750
Met Gln Met Thr Ile Leu Asn Asp Arg Ser Gln Gly Gly Thr Ser Pro
                755                 760                 765
Arg Asp Gly Val Ile Glu Ile Met Val His Arg Arg Leu Leu His Asp
                770                 775                 780
Asp Gly Phe Gly Val Gly Glu Ala Leu Asn Glu Pro Gly Val Asp Asn
785                 790                 795                 800
Lys Gly Leu Ile Ile Arg Gly Arg His Leu Val Gln Phe Ser Asp Ile
                805                 810                 815
Lys Thr Ala Ala Ser Lys His Arg Pro Lys Ala Gln Gln Leu Phe Met
                820                 825                 830
```

```
Ala Pro Val Leu Ser Phe Val Pro Asp Val Ser Asp Tyr Glu Thr Tyr
            835                 840                 845

Lys Arg Ser His Leu Thr Lys Tyr Ser Ala Leu Ile Asn Pro Leu Pro
            850                 855                 860

Glu Gln Ile His Leu Leu Thr Leu Glu Arg Trp Met Glu Gly His Phe
865                 870                 875                 880

Leu Leu Arg Leu Glu His Tyr Phe Gln Thr Asn Glu Asp Ala Glu Leu
                885                 890                 895

Ser Lys Pro Val Thr Leu Asn Leu Lys His Met Phe Lys Ser Phe Lys
            900                 905                 910

Ile Phe Glu Ala Glu Glu Leu Thr Leu Gly Gly Asn Gln Pro Ile Phe
            915                 920                 925

Glu Thr Lys His Arg Met Lys Phe Asn Tyr Ile Pro Val Glu Asn Val
            930                 935                 940

Thr Glu Pro Pro Glu His Ser Phe Asp Pro Thr Lys Leu Glu Val Lys
945                 950                 955                 960

Leu Tyr Pro Met Gln Ile Arg Thr Phe Ser Val Arg Val
                965                 970

<210> SEQ ID NO 308
<211> LENGTH: 889
<212> TYPE: PRT
<213> ORGANISM: Blomia tropicalis

<400> SEQUENCE: 308

Gln Cys Met Ala Ile Pro Pro Asn Ser Arg Ile Asp Cys Asn Pro Asp
1               5                   10                  15

Pro Pro Ile Ser Ala Glu Val Cys Gln Ser Arg Gly Cys Cys Trp Met
            20                  25                  30

Pro Ser Ser Asn Glu Ser Ser Glu Asn Met Asn Leu Leu Lys Lys Asn
        35                  40                  45

Val Leu Pro Pro Leu Asn Val Pro Tyr Cys Phe Phe Gly Ser Asp Tyr
    50                  55                  60

His Gly Tyr Asn Val Ser Asn Val Gln Thr Ile Asn Asp Asn Gln Lys
65                  70                  75                  80

Val Ile Asn Leu Gln Arg Ile Arg Asp Ser Gly Phe Val Asn Asp Val
                85                  90                  95

Lys Asn Val Arg Ile Gln Ile Asp Glu Leu Ser Ser Asn Val Leu Arg
            100                 105                 110

Ile Lys Met Ile Asp Ser Asp Ser Ser Arg Tyr Glu Val Pro Ile Pro
            115                 120                 125

Val Leu Asn Leu Pro Lys Arg Asn Glu Val Leu Glu Ser Leu Asn Glu
        130                 135                 140

Lys Met Tyr Gln Val Glu Met Asn Ser Thr Asp Phe Met Leu Thr Val
145                 150                 155                 160

Tyr Arg Ala Lys Thr Lys Ala Ile Val Phe Asn Val Asn Leu Gly Gln
                165                 170                 175

Leu Ile Tyr Ser Asn Gln Phe Ile Gln Ile Thr Asn Lys Leu Ala Ser
            180                 185                 190

Asn Phe Ile Phe Gly Ile Gly Glu Asn Arg Glu Ser Phe Arg Lys Leu
            195                 200                 205

Thr Asn Trp Lys Arg Tyr Thr Leu Phe Ala Arg Asp Gln Trp Pro Val
        210                 215                 220

Pro Asp Arg Ala Leu Tyr Gly Ser His Pro Phe Tyr Leu Ala Thr Glu
```

```
                225                 230                 235                 240
Ser Asp Asn Ser Ser His Gly Val Phe Leu Phe Asn Ser Asn Ala Met
                245                 250                 255

Asp Ile Ile Thr Gln Pro Met Pro Ala Ile Thr Tyr Arg Thr Ile Gly
                260                 265                 270

Gly Ile Leu Asp Phe Phe Leu Phe Gly Pro Thr Ser Glu Asn Val
                275                 280                 285

Ile Glu Gln Tyr His Gln Leu Ile Gly Leu Pro Thr Met Pro Ala Tyr
                290                 295                 300

Trp Thr Leu Gly Phe His Leu Ser Arg Tyr Gly Tyr Arg Asn Leu Ser
305                 310                 315                 320

Asn Leu Glu Lys Thr Phe Arg Arg Thr Arg Lys Ala Glu Ile Pro Phe
                325                 330                 335

Asp Val Gln Trp Thr Asp Ile Asp Met Phe Asp Ser Asn Asn Asp Phe
                340                 345                 350

Thr Tyr Asp Arg Lys Arg Phe Asp Gly Leu Pro Lys Phe Ile Glu His
                355                 360                 365

Leu His Ser Ile Asn Met Arg Phe Val Pro Met Phe Asp Cys Gly Ile
    370                 375                 380

Ser Ser Gly Glu His Pro Pro Gln Ser Tyr Leu Pro Tyr Lys Met Gly
385                 390                 395                 400

Leu Glu Met Asn Val Phe Val Arg Asn Gly Thr Asn Gln Pro Phe Glu
                405                 410                 415

Gly Lys Val Trp Asn Ser Lys Ser Thr Val Trp Pro Asp Phe Thr His
                420                 425                 430

Pro Asn Ala Thr Lys Tyr Trp Thr Arg Gln Phe Ala Glu Tyr His Lys
                435                 440                 445

Thr Ile Gln Phe Asp Gly Ala Trp Ile Asp Met Asn Glu Pro Ser Asn
    450                 455                 460

Phe Leu Asp Gly Ala Phe Asn Gly Cys Pro Thr Asn Ser Thr Leu Glu
465                 470                 475                 480

Thr Pro Gln Tyr Thr Pro Gly Met Val Glu Asp Ser Leu Thr Leu Asn
                485                 490                 495

His Lys Thr Leu Cys Met Ser Ala Arg His Ser Ile Gly Leu His Tyr
                500                 505                 510

Asn Leu His Asn Leu Tyr Gly Ile Ser Glu Ala Ile Val Thr Lys Ser
                515                 520                 525

Ala Leu Glu Ser Val Leu Lys Arg Arg Ser Phe Ile Leu Ser Arg Ser
                530                 535                 540

Thr Ala Pro Gly His Gly His Phe Ala His Trp Asp Gly Asp Ile
545                 550                 555                 560

Leu Ser Asp Trp Pro Ser Met Lys Trp Ser Ile Ser Ser Ile Leu Asn
                565                 570                 575

Phe Asn Ile Phe Gly Val Pro Leu Ile Gly Ala Asp Ile Cys Gly Phe
                580                 585                 590

Asn Gly Asn Thr Thr Ile Glu Leu Cys Ala Arg Trp His Gln Leu Gly
                595                 600                 605

Ala Phe Tyr Thr Phe Val Arg Asn His Asn Thr Asp Asn Ala Ile Asp
                610                 615                 620

Gln Asp Pro Val Ala Leu Gly Pro Leu Val Val Lys Ala Ala Lys Asn
625                 630                 635                 640

Ala Leu Lys Leu Arg Tyr Ala Leu Leu Pro Tyr Leu Tyr Thr Gln Phe
                645                 650                 655
```

-continued

Tyr Arg Val His Arg Lys Gly Gly Thr Ile Leu Arg Pro Leu Phe Phe
              660                 665                 670

Glu Phe Val His Asp Gln Val Leu Glu Ile Glu Thr Gln Phe Met
          675                 680                 685

Trp Gly Ser Ser Ile Met Val Ala Pro Ala Leu Ser Ile Asn Glu Thr
690                 695                 700

Glu Thr Ser Val Tyr Phe Pro Ser Gly Thr Trp Phe His Ser Tyr Asn
705                 710                 715                 720

Phe Thr Arg Ile Asn Thr Ile Gly Lys Phe Leu Pro Gln Leu Ala Ser
              725                 730                 735

Phe Asp Tyr Pro Asn Val Tyr Phe Arg Ala Gly Ser Ile Ile Pro Thr
          740                 745                 750

Leu Arg Pro Met Leu Thr Thr Asp Glu Thr His Ser Gly Asn Phe Thr
      755                 760                 765

Leu Leu Val Ala Leu Ser Asn Glu Asn Gly His Ala Glu Gly Asp Leu
  770                 775                 780

Tyr Leu Asp Ser Gly Asp Gly Leu Asp Thr Glu Val Leu Gly His Tyr
785                 790                 795                 800

Asn Leu Tyr Ser Phe Lys Val Glu Lys Lys Ile Leu Glu Ile Lys Ser
              805                 810                 815

Ser His Leu Gly Tyr Ser Thr Glu Gln Met Ile Asp Asn Val Leu Ile
          820                 825                 830

Leu Gly Ile Asp Lys Ser Pro Ile Glu Ile Lys Ile Asn Gly Arg Ser
      835                 840                 845

Met Lys Ser Trp Ser Tyr Ser Lys Asn Lys Ile His Ile Asn Ser Leu
  850                 855                 860

Asn Leu Pro Leu Tyr Asp Leu Lys Thr Ile Asp Lys Ser Lys Leu Ile
865                 870                 875                 880

Gln Ile His Tyr Gln Ile Glu Trp Val
              885

<210> SEQ ID NO 309
<211> LENGTH: 482
<212> TYPE: PRT
<213> ORGANISM: Blomia tropicalis

<400> SEQUENCE: 309

Gly Cys Phe Arg Ala Ala Val Leu Asp His Val His Gln Ser Ser Arg
1               5                   10                  15

Asn Gly Gly Gly Thr Lys Glu Asn Ile Lys Leu Asn Leu Lys Leu Tyr
            20                  25                  30

Glu Thr Ala Ala Lys Thr Ala Lys Glu Gln Gly Ala Asp Ile Ile Val
        35                  40                  45

Phe Pro Glu Asn Gly Ile Val Tyr Gly Ile Gly Ser Arg Ala Asn Ala
    50                  55                  60

Leu Lys Tyr Gly Glu Ile Leu Pro Glu Ser Lys Thr Ser Met Cys Thr
65                  70                  75                  80

Asp Ser Tyr Ala Ser Ser His Pro Ile Ala Tyr Gln Leu Ala Cys Leu
                85                  90                  95

Ala Lys Glu His Gln Met Phe Val Ala Ala Asp Met Ile Asp Val Gln
            100                 105                 110

Thr Cys Gln Thr Lys Ser Cys Pro Ile Asp Lys Lys Tyr Ala Phe Asn
        115                 120                 125

Thr Ala Val Leu Phe Asp Arg Asn Gly Tyr Leu Leu Gly Lys Tyr His

```
            130                 135                 140
Lys Met His Pro Phe Gly Glu Leu Gln Phe Asn Val Pro Pro Lys Asp
145                 150                 155                 160

Glu Leu Val Val Ile Glu Thr Glu Ile Gly Arg Leu Ser Met Gln Val
                165                 170                 175

Cys Phe Asp Leu Ile Tyr Asn Lys Pro Gly Val Val Leu Ala Ser Gln
                180                 185                 190

Asp Lys Ile Asp Thr Met Leu Phe Pro Thr Trp Trp Phe Asp Glu Leu
                195                 200                 205

Pro Phe Leu Ala Ala Ser Gln Tyr Gln Met Ser Trp Ala Phe Gly Asn
        210                 215                 220

Lys Ile Asn Leu Leu Ala Ser Asn Ile His Leu Val Ala Val Gly Ser
225                 230                 235                 240

Lys Gly Ser Gly Ile Phe Ala Gly Gly His Gly Gln Phe Glu Val Ile
                245                 250                 255

Ser Glu Pro Asp Ala Lys Ala Arg Ile Leu Val Ala Thr Leu Pro Ile
                260                 265                 270

Asn Ala Arg Ser Asp Ala Gln Cys Ser Met Asp Ser Lys Lys Ile Glu
                275                 280                 285

Val Pro Gln Met Val Pro Ile Pro Ser Asn Val Ile Tyr Asn Tyr Gln
        290                 295                 300

Met Met Asn Leu Thr Glu Asn Thr Val Lys Lys Leu Asp Pro Ser Met
305                 310                 315                 320

Glu Ala Ile Ser Ala Cys Asp Gly Gly Val Cys Cys Gln Leu Asn Tyr
                325                 330                 335

Gln Met Asp Gln Ser Ser Ile Lys Ser Asp Glu Glu Tyr Tyr Leu Ile
                340                 345                 350

Val Thr Asn Arg Thr Arg Pro Gly Ala Tyr Pro Trp Thr Glu Glu Tyr
                355                 360                 365

Cys Gly Leu Val Leu Cys Pro His Met Thr Lys Leu Asp Thr Cys Lys
        370                 375                 380

Gln Ile Ser Ser Asn Asn Pro Leu Gln Thr Lys Phe Leu Tyr Ala Lys
385                 390                 395                 400

Leu Ser Gly Glu Phe Ser Ser Glu Thr His Val Tyr Pro Ser Val Ile
                405                 410                 415

Gly Ser Glu His Lys Val Leu Pro Lys Asp Gly Gly Leu Trp Thr Tyr
                420                 425                 430

Glu Asp Glu Lys Thr Asp Val Gly Ala Lys Lys Gln Lys Phe Phe Ile
                435                 440                 445

Thr Phe Gly Asn Lys Glu Glu Arg Lys Ser Tyr Thr Ile Ser Thr Ile
        450                 455                 460

Gly Leu Tyr Gly Arg Val Tyr Ala Arg Asp Pro Pro Tyr Glu Gln Lys
465                 470                 475                 480

Pro Leu

<210> SEQ ID NO 310
<211> LENGTH: 491
<212> TYPE: PRT
<213> ORGANISM: Blomia tropicalis

<400> SEQUENCE: 310

Asp Arg Asn Lys Leu Pro His Lys Val Val Cys Tyr Trp Gly Thr Trp
1               5                   10                  15

Ala Phe Tyr Arg Pro Gly Ser Asp Gly Lys Phe Glu Ala Glu Asn Ile
```

```
            20                  25                  30
Asn Pro Asn Leu Cys Thr His Ile Asn Tyr Gly Phe Ala Lys Leu Val
            35                  40                  45
Gly Asn Lys Ile Ala Leu Phe Asp Pro Asp Leu Asp Thr Gly Asp Glu
 50                  55                  60
Asp Trp Ala Ser Gly Leu Thr Trp Gly His Gly Met Ile Arg Arg Leu
 65                  70                  75                  80
Asn Glu Leu Arg Lys Tyr Asn Lys Asn Leu Ser Thr Leu Ile Ser Ile
                85                  90                  95
Gly Gly Trp Asn Glu Gly Ser Asn Lys Tyr Ser Thr Met Val Ser Thr
                100                 105                 110
Ala Gly Gly Arg Ser Glu Phe Val Lys Ser Val Ile Glu Phe Leu Gln
                115                 120                 125
Lys Tyr Glu Phe Asp Gly Leu Asp Leu Asp Trp Glu Tyr Pro Gly Met
                130                 135                 140
Ser Ala Ser Gly Asp Ala Asp Arg Lys Pro Gly Arg Glu Gln Asp Lys
145                 150                 155                 160
Ala Asp Tyr Ile Glu Leu Leu Lys Glu Leu Arg Gln Ala Phe Glu Pro
                165                 170                 175
His Gly Tyr Ile Leu Ser Ala Ala Val Ser Ala Gly Ala Pro Thr Ile
                180                 185                 190
Asp Arg Ala Tyr Asn Val Pro Glu Val Ser Lys His Leu His Phe Ile
                195                 200                 205
Asn Leu Met Ala Tyr Asp Phe His Gly Gly Trp Asp Thr Lys Thr Ala
                210                 215                 220
His Asn Ala Pro Leu Tyr Ala Leu Pro Gly Ala Glu Gly Ile Asp Lys
225                 230                 235                 240
Glu Phe Thr Val Ser Tyr Ala Val Glu Tyr Trp Ile Ser Lys Gly Ala
                245                 250                 255
Asp Pro Lys Lys Leu Val Leu Gly Ile Pro Leu Tyr Gly Arg Thr Phe
                260                 265                 270
Thr Leu Ala Gly Pro Asn His Asp Ile Gly Ala Pro Val Thr Gly His
                275                 280                 285
Gly Gly Gln Ala Gly Pro Ile Thr Arg Leu Ile Gly Met Leu Gly Tyr
                290                 295                 300
Asn Glu Ile Cys Ser Met Val Lys Asn Gly Trp Glu Ile His Trp Asn
305                 310                 315                 320
Asp Ile Gln Gln Ile Pro Tyr Ala Thr His Ala Ser Gln Trp Ile Gly
                325                 330                 335
Tyr Asp Asn Glu Lys Ser Ile Glu Lys Lys Leu Asp Tyr Val His Gln
                340                 345                 350
Lys Asn Leu Gly Gly Gly Met Val Trp Ser Ile Asp Thr Asp Asp Phe
                355                 360                 365
Ser Gly His Cys Gly Val Lys Tyr Pro Leu Leu Lys Thr Ile Ser Arg
                370                 375                 380
Arg Leu Asn Asn Ile Asp Gly Pro Asp Val Val Ile Pro Arg Thr His
385                 390                 395                 400
Ala Thr Thr Pro His Pro Asp His Asp His Thr Thr Lys Arg Pro
                405                 410                 415
Asp Asp Pro His Thr Asp Pro His Thr Glu Pro His His Asp Lys Thr
                420                 425                 430
Thr Ser Ala Pro Asn Pro Asp Gly Lys Phe Gln Cys His Ser Thr Gly
                435                 440                 445
```

```
Phe Phe Lys Asp Pro Ser Asp Pro Arg Lys Phe His Gln Cys Val Asp
    450                 455                 460

Ile Gly Asn Gly Lys Leu Lys Asp Tyr Glu Phe Asn Cys Pro Leu Gly
465                 470                 475                 480

Ser His Tyr Asp Glu Gln Leu His Val Cys Val
                485                 490

<210> SEQ ID NO 311
<211> LENGTH: 459
<212> TYPE: PRT
<213> ORGANISM: Blomia tropicalis

<400> SEQUENCE: 311

Asp Thr Pro Ala Asn Cys Thr Tyr Glu Asp Ile Arg Gly Glu Trp Glu
1               5                   10                  15

Phe His Glu Thr Glu Arg Ile Ala Ser Arg Lys Glu Val Cys Asp Asp
                20                  25                  30

Asn Ser Val Ser Thr Thr Lys His Thr Val Tyr Leu Lys Leu Glu Phe
            35                  40                  45

Pro Asn Ile Ala Thr Asp Gln His Gly Asn Val Gly His Trp Thr Ile
50                  55                  60

Ile Tyr Asn Gln Gly Phe Glu Val Ser Ile Asn Tyr Arg Lys Tyr Phe
65                  70                  75                  80

Ala Phe Ser Leu Tyr Lys Gln Val Gly Lys Gln Val Thr Ser Tyr Cys
                85                  90                  95

Asp Ser Thr Phe Pro Gly Trp Ser His Asp Val Leu Gly Asn Asn Trp
            100                 105                 110

Ala Cys Phe Lys Gly Arg Lys Val Asn Arg Gln Gln Glu Lys Ser Phe
        115                 120                 125

Asp Glu Thr Met Ile Asn Asn Gly Lys Thr His Thr Val Gln Pro Phe
130                 135                 140

Leu Leu Glu Ser Val Pro Val Asn His Asn Leu Ile Gln Met Asn Val
145                 150                 155                 160

Asn Lys Ile Asn Met Lys Gln Ser Ser Trp Lys Ala Lys Phe Tyr Pro
                165                 170                 175

His Leu Met Asn Leu Asn Thr Glu Asp Leu Ile Arg Met Ala Gly Gly
            180                 185                 190

Arg Gly Ser Ala Ile Val Asn Arg Pro Ser Thr Val Pro Ala Ser Glu
        195                 200                 205

Glu Ile Lys Glu Lys Val Arg Gln Leu Pro Glu Ser Phe Asp Trp Arg
210                 215                 220

Asn Val Asn Gly Ile Asn Tyr Val Ser Pro Val Arg Asp Gln Gly Lys
225                 230                 235                 240

Cys Gly Ser Cys Tyr Ile Phe Ser Ser Met Ala Gln Leu Glu Ala Arg
                245                 250                 255

Val Arg Ile Ala Thr Asn Asn Ser Glu Gln Pro Ile Phe Ser Thr Gln
            260                 265                 270

Glu Val Val Asp Cys Ser Lys Tyr Ser Gln Gly Cys Asp Gly Gly Phe
        275                 280                 285

Pro Tyr Leu Ile Ala Gly Lys Tyr Gly Arg Asp Tyr Gly Val Ile Ala
290                 295                 300

Asp Glu Cys Tyr Pro Tyr Lys Gly Lys Asn Gly Lys Cys Ser Leu Pro
305                 310                 315                 320

Tyr Asn Ser Thr Gly Thr Lys Cys Met Lys Arg Ser Tyr Thr Leu His
```

325                 330                 335

Tyr His Tyr Val Gly Gly Tyr Tyr Gly Gly Cys Asn Glu Glu Leu Met
            340                 345                 350

Leu Leu Glu Leu Val Lys Asn Gly Pro Ile Thr Val Gly Phe Glu Val
        355                 360                 365

Tyr Asp Asp Phe Thr Ser Tyr Ser Gly Gly Ile Tyr Ser His Asp Lys
    370                 375                 380

Ser Lys Asp Gln Trp Arg Asn Gly Val His Phe Asn Pro Phe Gln Leu
385                 390                 395                 400

Thr Asn His Ala Val Leu Ile Val Gly Tyr Gly Val Asp Lys Gln Ser
                405                 410                 415

Gly Glu Lys Tyr Trp Ile Val Lys Asn Ser Trp Gly Lys Asp Trp Gly
            420                 425                 430

Leu Asp Gly Tyr Phe Trp Ile Lys Arg Gly Asn Asp Glu Cys Gly Ile
        435                 440                 445

Glu Ser Leu Ala Val Ser Val Thr Pro Ile Pro
    450                 455

<210> SEQ ID NO 312
<211> LENGTH: 309
<212> TYPE: PRT
<213> ORGANISM: Blomia tropicalis

<400> SEQUENCE: 312

Ile Lys Thr Phe Glu Gln Phe Lys Lys Val Phe Gly Lys Val Tyr Arg
1               5                   10                  15

Asn Ala Glu Glu Glu Ala Arg Arg Glu His His Phe Lys Glu Gln Leu
            20                  25                  30

Lys Trp Val Glu Glu His Asn Gly Ile Asp Gly Val Glu Tyr Ala Ile
        35                  40                  45

Asn Glu Tyr Ser Asp Met Ser Glu Gln Glu Phe Ser Phe His Leu Ser
    50                  55                  60

Gly Gly Gly Leu Asn Phe Thr Tyr Met Lys Met Glu Ala Ala Lys Glu
65                  70                  75                  80

Pro Leu Ile Asn Thr Tyr Gly Ser Leu Pro Gln Asn Phe Asp Trp Arg
                85                  90                  95

Gln Lys Ala Arg Leu Thr Arg Ile Arg Gln Gln Gly Ala Cys Gly Ser
            100                 105                 110

Cys Trp Ala Phe Ala Ala Ala Gly Val Ala Glu Ser Leu Tyr Ser Ile
        115                 120                 125

Gln Lys Gln Gln Ser Ile Glu Leu Ser Glu Gln Glu Leu Val Asp Cys
    130                 135                 140

Thr Tyr Asn Arg Tyr Asp Ser Ser Tyr Gln Cys Asn Gly Cys Gly Ser
145                 150                 155                 160

Gly Tyr Ser Thr Glu Ala Phe Lys Tyr Met Ile Arg Thr Gly Leu Val
                165                 170                 175

Glu Glu Arg Asn Tyr Pro Tyr Asn Met Arg Thr Gln Trp Cys Asp Pro
            180                 185                 190

Asp Val Glu Gly Gln Arg Tyr His Val Ser Gly Tyr Gln Gln Leu Arg
        195                 200                 205

Tyr Gln Ser Ser Asp Glu Asp Val Met Tyr Thr Ile Gln Gln His Gly
    210                 215                 220

Pro Val Val Ile Tyr Met His Gly Ser Asn Asn Tyr Phe Arg Asn Leu
225                 230                 235                 240

```
Gly Asn Gly Val Leu Arg Gly Val Ala Tyr Asn Asp Ala Tyr Thr Asp
                    245                 250                 255

His Ala Val Ile Leu Val Gly Trp Gly Thr Val Gln Gly Val Asp Tyr
            260                 265                 270

Trp Ile Ile Arg Asn Ser Trp Gly Thr Gly Trp Gly Asn Gly Gly Tyr
        275                 280                 285

Gly Tyr Val Glu Arg Gly His Asn Ser Leu Gly Ile Asn Asn Phe Val
    290                 295                 300

Thr Tyr Ala Thr Leu
305

<210> SEQ ID NO 313
<211> LENGTH: 260
<212> TYPE: PRT
<213> ORGANISM: Blomia tropicalis

<400> SEQUENCE: 313

Ser Leu Thr Asn Lys Lys Tyr Asp Phe Ser Gly Lys Val Ala Leu Val
1               5                   10                  15

Thr Gly Ser Ser Ser Gly Ile Gly Ala Ala Ile Ala Ile Gln Phe Ala
            20                  25                  30

Gln Tyr Gly Ala Lys Val Thr Ile Thr Gly Arg Asn Ala Glu Asn Leu
        35                  40                  45

Asp Lys Ile Ala Lys Lys Ile Ala Glu Val Ser Asn Gly Val Glu Ala
    50                  55                  60

Leu Gln Ile Ile Gly Asp Leu Thr Ile Asp Asp Ser Leu Pro Lys Arg
65                  70                  75                  80

Leu Ile Asp Glu Thr Val Thr Lys Phe Gly Arg Leu Asp Phe Leu Val
                85                  90                  95

Asn Asn Ala Gly Gly Ala Thr Pro Gln Gly Thr Leu Ala Ser Pro Asp
            100                 105                 110

Leu Leu Lys Gly Phe Asp Asp Val Phe Lys Leu Asn Val Arg Ser Val
        115                 120                 125

Ile Glu Leu Thr Gln Leu Ala Met Pro His Leu Glu Lys Thr Lys Gly
    130                 135                 140

Asn Ile Ile Asn Ile Ser Ser Val Ala Ser Ile Lys Pro Tyr Met Val
145                 150                 155                 160

Val Tyr Ser Ser Ser Lys Ala Ala Leu Asp Met Ile Thr Lys Thr Ser
                165                 170                 175

Ala Leu Glu Leu Gly Pro Lys Gly Ile Arg Val Asn Ser Ile Asn Pro
            180                 185                 190

Gly Pro Val Val Thr Ala Phe Gly Arg Ser Met Gly Val Asp Pro Ser
        195                 200                 205

His His Lys Lys Met Phe Asp Ser Phe Glu Lys Gln Met Leu Met Glu
    210                 215                 220

Arg Val Gly Gln Pro Glu Asp Ile Ala Asn Leu Ala Ser Phe Leu Ala
225                 230                 235                 240

Ser Asp Asp Ala Ile Asn Ile Thr Gly Ser Ile Met Val Asn Asp Ser
                245                 250                 255

Gly Cys Leu Leu
            260

<210> SEQ ID NO 314
<211> LENGTH: 150
<212> TYPE: PRT
<213> ORGANISM: Blomia tropicalis
```

<400> SEQUENCE: 314

| Lys | Ala | Val | Val | Leu | Lys | Gly | Asp | Ser | Pro | Val | Ser | Gly | Thr | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Phe Phe Glu Gln Lys Asp Asn Gly Pro Val Ser Val Thr Gly Thr Val
          20                  25                  30

Asn Gly Leu Thr Ala Gly Asp His Gly Phe His Val His Glu Phe Gly
             35                  40                  45

Asp Asn Thr Asn Gly Cys Thr Ser Ala Gly Ala His Phe Asn Pro Phe
        50                  55                  60

Gly Lys Thr His Gly Ala Pro Ala Asp Gln Glu Arg His Val Gly Asp
65                  70                  75                  80

Leu Gly Asn Val Thr Ala Asp Ala Asn Gly Val Ala Asn Val Asn Ile
                85                  90                  95

Gln Asp Ser Leu Ile Thr Leu Glu Gly Ala Asn Thr Ile Val Gly Arg
            100                 105                 110

Ser Leu Val Val His Ala Asp Pro Asp Leu Gly Arg Gly His
            115                 120                 125

Glu Leu Ser Lys Thr Thr Gly Asn Ala Gly Gly Arg Val Ala Cys Gly
        130                 135                 140

Val Ile Gly Leu Thr Lys
145             150

<210> SEQ ID NO 315
<211> LENGTH: 137
<212> TYPE: PRT
<213> ORGANISM: Blomia tropicalis

<400> SEQUENCE: 315

Gln Ala Met Ala Gly Gly His Glu Ile Val Thr Ala Ala Arg Ser Gln
1               5                   10                  15

Leu Gly Val Pro Tyr Ser Trp Gly Gly Asn Trp Ala Gly Lys Ser
          20                  25                  30

Lys Gly Ile Asp Ser Gly Ala His Thr Val Gly Phe Asp Cys Ser Gly
            35                  40                  45

Leu Ala Gln Tyr Ala Val Tyr His Gly Thr His Lys Lys Ile Ala Arg
    50                  55                  60

Val Ala Ser Ala Gln Tyr Ala Asp His Gln Cys His His Val Pro Tyr
65                  70                  75                  80

Ala Gln His Leu Pro Gly Asp Leu Val Phe Phe Asn Asp Gly Gly Ser
                85                  90                  95

Ile His His Val Ala Ile Ile Ser Gly Lys Asn Thr Met Ile His Ala
            100                 105                 110

Pro His Thr Gly Asp His Val Arg Glu Ala Ala Val Tyr Val Lys Gly
        115                 120                 125

Arg Met Ser Thr Val Gln Arg Cys Phe
    130                 135

<210> SEQ ID NO 316
<211> LENGTH: 233
<212> TYPE: PRT
<213> ORGANISM: Blomia tropicalis

<400> SEQUENCE: 316

Met Ser Lys Pro Thr Leu Tyr Tyr Met Trp Glu Ser Pro Pro Cys Cys
1               5                   10                  15

```
Thr Val Ile Ala Ile Ala Arg Ile Leu Asn Ile Glu Leu Asp Met Lys
         20                  25                  30

His Val Asp Leu Thr Lys Lys Asp Gln Asn Asn Pro Glu Phe Lys Lys
     35                  40                  45

Ile Asn Pro Phe Ala Ile Val Pro Thr Phe Val Glu Thr Asp Gly Tyr
 50                  55                  60

Thr Leu Trp Glu Ser Arg Ala Ile Ser Thr Tyr Leu Val Gln Ser Arg
65                  70                  75                  80

Ser Pro Asp Ser Thr Leu Tyr Pro Gly Ser Asp Leu Lys Lys Arg Ser
                 85                  90                  95

Thr Ile Asp Lys Phe Leu Gln Tyr Asp Leu Gly Thr Phe Asn Arg Ala
             100                 105                 110

Ile Tyr Asp Val Val Ser Glu Ile Phe Lys Ser Gly Lys Leu Asn Glu
         115                 120                 125

Gln Asn Ile Pro Arg Leu Gly Glu Val Leu Lys Thr Leu Glu Glu Thr
    130                 135                 140

Leu Ala Ala Asn Asn Glu Ser Asn Gly Gly Pro Phe Ile Thr Gly Asp
145                 150                 155                 160

Asp Gln Leu Thr Ile Ala Asp Ile Ser Met His Phe Ser Trp Thr Leu
                165                 170                 175

Leu Ser Leu Leu Pro Glu Arg Leu Ile Asp Gln Ser Ser Tyr Pro Thr
            180                 185                 190

Ile Arg Ala Trp Asn Gln Ala Val Ile Gln Ala Leu Lys Pro Tyr Asn
        195                 200                 205

Arg Asp Gln Lys Phe Thr Glu Ala Gln Arg Arg Leu Lys Ala Phe Ile
    210                 215                 220

Thr Met Met Ile Glu Ser Ala Lys Asn
225                 230

<210> SEQ ID NO 317
<211> LENGTH: 252
<212> TYPE: PRT
<213> ORGANISM: Blomia tropicalis

<400> SEQUENCE: 317

Asn Trp Gln Leu Val Trp Ser Asp Glu Phe Asn Gly Asn Gly Leu Asp
1               5                   10                  15

Glu Asn Asn Trp Asn Tyr Gln Thr Gly Cys Ser Gln Gln Asn Asp Glu
             20                  25                  30

Leu Glu Cys Tyr Thr Ser His Arg His Glu Asn Val Arg Val Glu Asn
         35                  40                  45

Gly His Leu Val Ile Glu Ala Arg Pro Glu Glu Tyr Gln Gly His His
     50                  55                  60

Phe Thr Ser Gly Arg Leu His Gly Lys Lys Ala Trp Ala Tyr Gly Lys
65                  70                  75                  80

Phe Glu Ala Arg Ala Lys Met Pro Ser Gly His His Leu Trp Pro Ala
                 85                  90                  95

Ile Trp Met Met Pro Arg Asp Ser Lys Tyr Gly Gly Trp Ala Ala Ser
            100                 105                 110

Gly Glu Ile Asp Ile Leu Glu Leu Arg Gly Asp Lys Pro His Glu Ile
        115                 120                 125

Val Gly Thr Ile His Tyr Gly Gly Ser Trp Pro Asn Asn Ile Tyr His
    130                 135                 140

Gly Ser Gly Glu Arg Tyr Tyr Gln Gln Asp Phe Ser Gln Asp Tyr His
145                 150                 155                 160
```

```
Thr Phe Ala Val Glu Trp Asp Gln Lys Glu Ile Arg Trp Tyr Val Asp
            165                 170                 175

Gly Gln His Tyr His Thr Glu Asn Ile Asp Arg Asn Met Trp Ser Gly
            180                 185                 190

Arg Gly Asn Asn Pro Tyr His Lys Asn Gly Glu Pro Phe Asp Gln Pro
            195                 200                 205

Phe Tyr Trp Ile Leu Asn Val Ala Val Gly Gly Asn Phe Phe Gly Pro
            210                 215                 220

Gly Pro Tyr Val Ser Pro Ala Glu Ala Arg Asn Trp His Lys Arg Thr
225                 230                 235                 240

Met Glu Val Asp Tyr Val Arg Val Tyr Gln Trp Arg
            245                 250

<210> SEQ ID NO 318
<211> LENGTH: 187
<212> TYPE: PRT
<213> ORGANISM: Blomia tropicalis

<400> SEQUENCE: 318

Met Ser Ile Ser Ala His Gly Gly Leu Ile Asn Gly Ile Ala Gly
1               5                   10                  15

Met Glu Asn Lys Phe Thr Val Phe Thr Ser Gly Lys Pro Val Ser Gly
            20                  25                  30

Leu Thr Val Ala Phe Glu Gly Pro Thr Lys Pro Asp Ile Asn Phe Asn
            35                  40                  45

Ser Ala Lys Asp Gly Ser Val Asp Val Ser Tyr Thr Pro Lys Ala Gly
50                  55                  60

Gly Met Tyr Lys Ile His Ile Lys Tyr Asp Gly Lys Glu Ile Ile Gly
65                  70                  75                  80

Ser Pro Phe Lys Thr Asn Ile Thr Gly Asp Glu Ala Thr His Arg Lys
            85                  90                  95

Leu Thr Glu Lys Val Lys Val Gly Gly Pro Asn Val Ser Thr Gly Lys
            100                 105                 110

Ala Asn Ala Asp Asn Glu Leu Thr Ile Asp Cys Lys Glu Ala Gly Ile
            115                 120                 125

Thr Gly Gly Ile Ser Phe Ala Met Glu Gly Pro Ala Lys Val Glu Val
            130                 135                 140

Ser Phe Arg Asn Asn Asn Asp Gly Thr Ile Thr Val Val Tyr Lys Pro
145                 150                 155                 160

Pro Gln Asn Gly Asp Tyr Lys Leu His Leu Lys Phe Asn Asp Ile His
            165                 170                 175

Leu Pro Gly Ser Pro Phe Pro Ile Val Val Ser
            180                 185

<210> SEQ ID NO 319
<211> LENGTH: 125
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (111)..(111)
<223> OTHER INFORMATION: Xaa is serine, alanine, or 2-aminobutyric acid

<400> SEQUENCE: 319

Gly Lys Tyr Gln Leu Glu Ser Ser Glu Asn Phe Asp Glu Phe Leu Lys
1               5                   10                  15
```

```
Glu Leu Gly Val Asn Phe Ile Leu Arg Asn Leu Ala Lys Thr Ser Lys
            20                  25                  30

Pro Thr Ile Glu Ile Thr Leu Asp Gly Asp Thr Tyr Thr Ile Lys Thr
            35                  40                  45

Ile Thr Thr Leu Lys Thr Ser Val Ile Thr Phe Lys Ile Gly Glu Glu
 50                  55                  60

Phe Glu Glu Ser Arg Met Asp Gly Lys Thr Val Lys Thr Val Ile Thr
 65                  70                  75                  80

Gln Gly Asp Lys Leu Ile Gln Val Gln Gln Gly Asp Lys Glu Val
            85                  90                  95

Lys Ile Val Arg Glu Phe Thr Glu Thr His Leu Thr Thr Ile Xaa Thr
            100                 105                 110

Val Gly Glu Ile Thr Ser Thr Arg Val Tyr Lys Arg Val
            115                 120                 125
```

<210> SEQ ID NO 320
<211> LENGTH: 363
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (134)..(134)
<223> OTHER INFORMATION: Xaa is serine, alanine, or 2-aminobutyric acid
<220> FEATURE:
<221> NAME/KEY: misc_feature
<222> LOCATION: (142)..(142)
<223> OTHER INFORMATION: Xaa is serine, alanine, or 2-aminobutyric acid
<220> FEATURE:
<221> NAME/KEY: misc_feature
<222> LOCATION: (149)..(149)
<223> OTHER INFORMATION: Xaa is serine, alanine, or 2-aminobutyric acid
<220> FEATURE:
<221> NAME/KEY: misc_feature
<222> LOCATION: (176)..(177)
<223> OTHER INFORMATION: Xaa is serine, alanine, or 2-aminobutyric acid
<220> FEATURE:
<221> NAME/KEY: misc_feature
<222> LOCATION: (201)..(201)
<223> OTHER INFORMATION: Xaa is serine, alanine, or 2-aminobutyric acid

<400> SEQUENCE: 320

```
Met Ser Ile Ile Gln Asn Leu Pro Ala Asp Val Gln Glu Glu Leu Arg
 1               5                  10                  15

Lys Thr Ala Asn Ala Ile Val Thr Pro Gly Lys Gly Ile Leu Ala Ala
            20                  25                  30

Asp Glu Ser Thr Gly Thr Ile Gly Lys Arg Phe Ala Asp Ile Asn Val
            35                  40                  45

Glu Asn Val Glu Asn Asn Arg Arg Thr Tyr Arg Asp Leu Leu Phe Ser
 50                  55                  60

Ala Pro Asp Glu Val Asn Asn Tyr Ile Ser Gly Val Ile Leu Phe Asp
 65                  70                  75                  80

Glu Thr Val Tyr Gln Lys Asn Ala Ala Gly Val Pro Phe Pro Gln Val
            85                  90                  95

Leu Ala Lys Arg Gly Ile Ile Pro Gly Ile Lys Val Asp Thr Gly Val
            100                 105                 110

Val Val Leu Gln Gly Thr Asn Gly Glu Ser Thr Thr Gln Gly Leu Asp
            115                 120                 125

Asn Leu Thr Lys Arg Xaa Gln Ala Tyr Tyr Glu Gln Gly Xaa Arg Phe
            130                 135                 140
```

```
Ala Lys Trp Arg Xaa Val Leu Lys Ile Gly Asp Asn Glu Pro Ser Pro
145                 150                 155                 160

Leu Ala Ile Leu Glu Asn Ala Asn Val Leu Ala Arg Tyr Ala Ser Xaa
                165                 170                 175

Xaa Gln Gln Ala Arg Ile Val Pro Ile Val Glu Pro Glu Ile Leu Pro
            180                 185                 190

Asp Gly Ala His Asp Ile Glu Arg Xaa Gln Lys Val Thr Glu Lys Val
            195                 200                 205

Leu Ala Ala Val Tyr Lys Ala Leu Asn Asp His Asn Val Phe Leu Glu
            210                 215                 220

Gly Thr Leu Leu Lys Pro Asn Met Val Thr Ala Gly Gln Ser Phe Ala
225                 230                 235                 240

Gly Pro Lys Pro Ser Pro Gln Glu Val Ala Arg Ala Thr Val Thr Ala
                245                 250                 255

Leu Gln Arg Thr Val Pro Ala Ala Val Pro Gly Ile Val Phe Leu Ser
            260                 265                 270

Gly Gly Gln Ser Glu Glu Glu Ala Ser Ile Asn Leu Asn Ala Ile Asn
            275                 280                 285

Gln Phe Glu Gly Lys Lys Pro Trp Ala Leu Ser Phe Ser Tyr Gly Arg
            290                 295                 300

Ala Leu Gln Ala Ser Val Leu Arg Ala Trp Gln Gly Lys Asp Glu Leu
305                 310                 315                 320

Ile Ala Ala Gly Gln Lys Glu Leu Val Asn Arg Ser Lys Ala Asn Ser
                325                 330                 335

Asp Ala Ser Leu Gly Lys Tyr Ser Gly Gly Ile Val Gly Ala Ala Gly
            340                 345                 350

Glu Gln Asp Leu Phe Ile Lys Asp His Gln Tyr
            355                 360

<210> SEQ ID NO 321
<211> LENGTH: 973
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (12)..(12)
<223> OTHER INFORMATION: Xaa is serine, alanine, or 2-aminobutyric acid
<220> FEATURE:
<221> NAME/KEY: misc_feature
<222> LOCATION: (17)..(17)
<223> OTHER INFORMATION: Xaa is serine, alanine, or 2-aminobutyric acid
<220> FEATURE:
<221> NAME/KEY: misc_feature
<222> LOCATION: (148)..(148)
<223> OTHER INFORMATION: Xaa is serine, alanine, or 2-aminobutyric acid
<220> FEATURE:
<221> NAME/KEY: misc_feature
<222> LOCATION: (317)..(317)
<223> OTHER INFORMATION: Xaa is serine, alanine, or 2-aminobutyric acid
<220> FEATURE:
<221> NAME/KEY: misc_feature
<222> LOCATION: (371)..(371)
<223> OTHER INFORMATION: Xaa is serine, alanine, or 2-aminobutyric acid
<220> FEATURE:
<221> NAME/KEY: misc_feature
<222> LOCATION: (427)..(427)
<223> OTHER INFORMATION: Xaa is serine, alanine, or 2-aminobutyric acid
<220> FEATURE:
<221> NAME/KEY: misc_feature
<222> LOCATION: (450)..(450)
<223> OTHER INFORMATION: Xaa is serine, alanine, or 2-aminobutyric acid
<220> FEATURE:
<221> NAME/KEY: misc_feature
```

<222> LOCATION: (458)..(458)
<223> OTHER INFORMATION: Xaa is serine, alanine, or 2-aminobutyric acid

<400> SEQUENCE: 321

```
Val Val Ile Lys Val Glu Asn Leu Pro Ala Arg Xaa Asp Tyr Thr Lys
1               5                   10                  15

Xaa Pro Lys Ser Asp Pro Asn Lys Ile Asn Val His Leu Val Pro His
            20                  25                  30

Thr His Asp Asp Val Gly Trp Leu Lys Thr Val Glu Gln Tyr Tyr Tyr
        35                  40                  45

Gly Ser Lys Thr Tyr Tyr Gln Lys Ala Gly Val Gln Tyr Ile Leu Asp
    50                  55                  60

Ser Val Met Asn Glu Leu Ile His Asn Lys Glu Arg Lys Phe Ile Tyr
65                  70                  75                  80

Val Glu Thr Ala Phe Phe Trp Lys Trp Trp Met Glu Gln Asp Tyr Gly
                85                  90                  95

Met Arg Asn Ile Val Lys Glu Leu Val Glu Thr Gly Gln Leu Glu Phe
            100                 105                 110

Ile Asn Ala Gly Trp Ser Met Asn Asp Glu Ala Ser Thr His Tyr Asn
        115                 120                 125

Ser Ile Ile Asp Gln Met Ser Trp Gly Phe Tyr Arg Leu Gln Thr Thr
    130                 135                 140

Phe Gly Arg Xaa Gly Val Pro Lys Val Ala Trp Gln Ile Asp Pro Phe
145                 150                 155                 160

Gly His Ser Lys Glu Gln Ala Ala Leu Phe Ala Leu Met Asn Phe Asp
                165                 170                 175

Ala Leu Phe Phe Ala Arg Glu Asp Trp Gln Glu Gln Ser His Arg Arg
            180                 185                 190

Lys Asn Arg Thr Leu Glu His Val Trp Gln Ala Ser Ser Asp Leu Gly
        195                 200                 205

Lys Ser Ala Asp Leu Phe Thr Gly Met Met Asn Phe Gly Tyr Gly Pro
    210                 215                 220

Pro Gln Gly Phe Asn Trp Asp Leu Val Gly Gly Ala Asp Glu Pro Val
225                 230                 235                 240

Ile Asp Asp Pro Glu Ser Asp Glu Tyr Asn Val Pro Arg Arg Val Lys
                245                 250                 255

Glu Leu Ile Asp Leu Ala Lys Thr Tyr Gln Lys Tyr Tyr Ala Thr Asn
            260                 265                 270

Asn Val Met Phe Pro Met Gly Thr Asp Phe Gln Tyr Gln Asp Ala His
        275                 280                 285

Ile Tyr Phe Lys Asn Met Asp Lys Leu Ile Lys Tyr Val Asn Glu Asn
    290                 295                 300

Ser Thr Glu Val Asn Ile Phe Tyr Ser Thr Pro Ser Xaa Tyr Ala Lys
305                 310                 315                 320

Ser Leu Lys Asp Ser Gly Lys Thr Phe Thr Ala Lys Asn Asp Asp Tyr
                325                 330                 335

Phe Pro Tyr Ala Ser Asp Pro His Ser Tyr Trp Thr Gly Tyr Phe Thr
            340                 345                 350

Ser Arg Pro Ala Ile Lys Arg Phe Glu Arg Val Gly Asn Asn Tyr Leu
        355                 360                 365

Gln Val Xaa Lys Gln Met Asp Thr Tyr Thr Gly His Gln Ala Thr Arg
    370                 375                 380

Asp Arg His Thr Thr Lys Leu Arg Glu Ile Met Gly Val Met Gln His
385                 390                 395                 400
```

```
His Asp Ala Val Ser Gly Thr Glu Lys Gln His Val Ala Phe Asn Tyr
                405                 410                 415
Ala Lys His Leu Gln Ser Gly Ile Glu Ser Xaa Arg Lys Val Ile Ser
                420                 425                 430
Glu Ala Tyr Gln Leu Leu Gln His Pro His Thr Lys Thr Val Gln Thr
                435                 440                 445
Phe Xaa Asp Tyr Leu Asn Ile Ser Ser Xaa Ala Ile Thr Glu Ser Gly
    450                 455                 460
Gln Asn Phe Val Val Asn Ile Tyr Asn Pro Leu Ser Lys Thr Leu Lys
465                 470                 475                 480
Asn His Pro Ile Arg Leu Pro Ile Asn Ser Asp Lys Tyr Tyr Asn Val
                485                 490                 495
Val Asp Asp Glu Gly Lys Ser Val Tyr Ser Glu Leu Thr Phe Ile Pro
                500                 505                 510
Glu Tyr Val Gln Ala Ile Pro Glu Arg Thr Thr Asn Ala Thr Thr Asp
                515                 520                 525
Leu Val Phe Leu Ala Ser Ile Pro Pro Leu Gly Tyr Ala Ser Tyr Phe
    530                 535                 540
Val Gln Ala Thr Thr Lys Ser Pro Asp Ser Ala Asn Ala Val Thr
545                 550                 555                 560
Val Thr Lys Ile Thr Asn Glu Thr Arg Leu Ser Ser Gly Asn Phe Ser
                565                 570                 575
Val Val Phe Asp Ser Thr Gly Ala Leu Ser Lys Val Glu Leu Pro Ser
                580                 585                 590
Gly Glu Ser Ile Pro Phe Lys Asn Glu Phe Arg Tyr Tyr Asn Gly Ala
                595                 600                 605
Ala Asp Asn Ile Arg Ala Ser Gly Ala Tyr Ile Phe Arg Pro Lys Glu
                610                 615                 620
Gln Gln Thr Phe Pro Phe Ala Lys Leu Val Ser Ala Asn Leu Leu Thr
625                 630                 635                 640
Arg Thr Ser Ser Gly Gly Ile Val His Glu Val His Gln Lys Phe Asp
                645                 650                 655
Ser Asn Val Glu Gln Val Ile Arg Val Leu Pro Asp Ser Asp Ser Ile
                660                 665                 670
Glu Phe Glu Tyr Val Val Gly Pro Ile Pro Val Lys Asp Gly Ile Gly
                675                 680                 685
Lys Glu Val Val Leu Thr Tyr Glu Thr Asp Phe Lys Asn Asn Lys Thr
                690                 695                 700
Phe Tyr Thr Asp Ala Asn Gly Arg Gln Met Met Lys Arg Lys Trp Asp
705                 710                 715                 720
Tyr Arg Pro Glu Phe Lys Met Glu Val Thr Glu Pro Ile Ser Gly Asn
                725                 730                 735
Tyr Tyr Pro Ile Asn Ser Arg Ile Tyr Leu Gln Asp Glu Lys Lys Gly
                740                 745                 750
Met Gln Met Thr Ile Leu Asn Asp Arg Ser Gln Gly Gly Thr Ser Pro
                755                 760                 765
Arg Asp Gly Val Ile Glu Ile Met Val His Arg Arg Leu Leu His Asp
                770                 775                 780
Asp Gly Phe Gly Val Gly Glu Ala Leu Asn Glu Pro Gly Val Asp Asn
785                 790                 795                 800
Lys Gly Leu Ile Ile Arg Gly Arg His Leu Val Gln Phe Ser Asp Ile
                805                 810                 815
```

```
Lys Thr Ala Ala Ser Lys His Arg Pro Lys Ala Gln Gln Leu Phe Met
                820                 825                 830

Ala Pro Val Leu Ser Phe Val Pro Asp Val Ser Asp Tyr Glu Thr Tyr
            835                 840                 845

Lys Arg Ser His Leu Thr Lys Tyr Ser Ala Leu Ile Asn Pro Leu Pro
        850                 855                 860

Glu Gln Ile His Leu Leu Thr Leu Glu Arg Trp Met Glu Gly His Phe
865                 870                 875                 880

Leu Leu Arg Leu Glu His Tyr Phe Gln Thr Asn Glu Asp Ala Glu Leu
                885                 890                 895

Ser Lys Pro Val Thr Leu Asn Leu Lys His Met Phe Lys Ser Phe Lys
            900                 905                 910

Ile Phe Glu Ala Glu Glu Leu Thr Leu Gly Gly Asn Gln Pro Ile Phe
        915                 920                 925

Glu Thr Lys His Arg Met Lys Phe Asn Tyr Ile Pro Val Glu Asn Val
930                 935                 940

Thr Glu Pro Pro Glu His Ser Phe Asp Pro Thr Lys Leu Glu Val Lys
945                 950                 955                 960

Leu Tyr Pro Met Gln Ile Arg Thr Phe Ser Val Arg Val
                965                 970

<210> SEQ ID NO 322
<211> LENGTH: 889
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is serine, alanine, or 2-aminobutyric acid
<220> FEATURE:
<221> NAME/KEY: misc_feature
<222> LOCATION: (13)..(13)
<223> OTHER INFORMATION: Xaa is serine, alanine, or 2-aminobutyric acid
<220> FEATURE:
<221> NAME/KEY: misc_feature
<222> LOCATION: (24)..(24)
<223> OTHER INFORMATION: Xaa is serine, alanine, or 2-aminobutyric acid
<220> FEATURE:
<221> NAME/KEY: misc_feature
<222> LOCATION: (29)..(30)
<223> OTHER INFORMATION: Xaa is serine, alanine, or 2-aminobutyric acid
<220> FEATURE:
<221> NAME/KEY: misc_feature
<222> LOCATION: (58)..(58)
<223> OTHER INFORMATION: Xaa is serine, alanine, or 2-aminobutyric acid
<220> FEATURE:
<221> NAME/KEY: misc_feature
<222> LOCATION: (382)..(382)
<223> OTHER INFORMATION: Xaa is serine, alanine, or 2-aminobutyric acid
<220> FEATURE:
<221> NAME/KEY: misc_feature
<222> LOCATION: (473)..(473)
<223> OTHER INFORMATION: Xaa is serine, alanine, or 2-aminobutyric acid
<220> FEATURE:
<221> NAME/KEY: misc_feature
<222> LOCATION: (501)..(501)
<223> OTHER INFORMATION: Xaa is serine, alanine, or 2-aminobutyric acid
<220> FEATURE:
<221> NAME/KEY: misc_feature
<222> LOCATION: (590)..(590)
<223> OTHER INFORMATION: Xaa is serine, alanine, or 2-aminobutyric acid
<220> FEATURE:
<221> NAME/KEY: misc_feature
<222> LOCATION: (601)..(601)
<223> OTHER INFORMATION: Xaa is serine, alanine, or 2-aminobutyric acid

<400> SEQUENCE: 322
```

```
Gln Xaa Met Ala Ile Pro Pro Asn Ser Arg Ile Asp Xaa Asn Pro Asp
1               5                   10                  15

Pro Pro Ile Ser Ala Glu Val Xaa Gln Ser Arg Gly Xaa Xaa Trp Met
            20                  25                  30

Pro Ser Ser Asn Glu Ser Ser Glu Asn Met Asn Leu Leu Lys Lys Asn
        35                  40                  45

Val Leu Pro Pro Leu Asn Val Pro Tyr Xaa Phe Phe Gly Ser Asp Tyr
    50                  55                  60

His Gly Tyr Asn Val Ser Asn Val Gln Thr Ile Asn Asp Asn Gln Lys
65                  70                  75                  80

Val Ile Asn Leu Gln Arg Ile Arg Asp Ser Gly Phe Val Asn Asp Val
                85                  90                  95

Lys Asn Val Arg Ile Gln Ile Asp Glu Leu Ser Ser Asn Val Leu Arg
            100                 105                 110

Ile Lys Met Ile Asp Ser Asp Ser Arg Tyr Glu Val Pro Ile Pro
            115                 120                 125

Val Leu Asn Leu Pro Lys Arg Asn Glu Val Leu Glu Ser Leu Asn Glu
    130                 135                 140

Lys Met Tyr Gln Val Glu Met Asn Ser Thr Asp Phe Met Leu Thr Val
145                 150                 155                 160

Tyr Arg Ala Lys Thr Lys Ala Ile Val Phe Asn Val Asn Leu Gly Gln
                165                 170                 175

Leu Ile Tyr Ser Asn Gln Phe Ile Gln Ile Thr Asn Lys Leu Ala Ser
            180                 185                 190

Asn Phe Ile Phe Gly Ile Gly Glu Asn Arg Glu Ser Phe Arg Lys Leu
            195                 200                 205

Thr Asn Trp Lys Arg Tyr Thr Leu Phe Ala Arg Asp Gln Trp Pro Val
    210                 215                 220

Pro Asp Arg Ala Leu Tyr Gly Ser His Pro Phe Tyr Leu Ala Thr Glu
225                 230                 235                 240

Ser Asp Asn Ser Ser His Gly Val Phe Leu Phe Asn Ser Asn Ala Met
            245                 250                 255

Asp Ile Ile Thr Gln Pro Met Pro Ala Ile Thr Tyr Arg Thr Ile Gly
            260                 265                 270

Gly Ile Leu Asp Phe Phe Leu Phe Leu Gly Pro Thr Ser Glu Asn Val
    275                 280                 285

Ile Glu Gln Tyr His Gln Leu Ile Gly Leu Pro Thr Met Pro Ala Tyr
    290                 295                 300

Trp Thr Leu Gly Phe His Leu Ser Arg Tyr Gly Tyr Arg Asn Leu Ser
305                 310                 315                 320

Asn Leu Glu Lys Thr Phe Arg Arg Thr Arg Lys Ala Glu Ile Pro Phe
            325                 330                 335

Asp Val Gln Trp Thr Asp Ile Asp Met Phe Asp Ser Asn Asn Asp Phe
            340                 345                 350

Thr Tyr Asp Arg Lys Arg Phe Asp Gly Leu Pro Lys Phe Ile Glu His
            355                 360                 365

Leu His Ser Ile Asn Met Arg Phe Val Pro Met Phe Asp Xaa Gly Ile
    370                 375                 380

Ser Ser Gly Glu His Pro Pro Gln Ser Tyr Leu Pro Tyr Lys Met Gly
385                 390                 395                 400

Leu Glu Met Asn Val Phe Val Arg Asn Gly Thr Asn Gln Pro Phe Glu
            405                 410                 415
```

-continued

Gly Lys Val Trp Asn Ser Lys Ser Thr Val Trp Pro Asp Phe Thr His
            420                 425                 430

Pro Asn Ala Thr Lys Tyr Trp Thr Arg Gln Phe Ala Glu Tyr His Lys
        435                 440                 445

Thr Ile Gln Phe Asp Gly Ala Trp Ile Asp Met Asn Glu Pro Ser Asn
450                 455                 460

Phe Leu Asp Gly Ala Phe Asn Gly Xaa Pro Thr Asn Ser Thr Leu Glu
465                 470                 475                 480

Thr Pro Gln Tyr Thr Pro Gly Met Val Glu Asp Ser Leu Thr Leu Asn
            485                 490                 495

His Lys Thr Leu Xaa Met Ser Ala Arg His Ser Ile Gly Leu His Tyr
        500                 505                 510

Asn Leu His Asn Leu Tyr Gly Ile Ser Glu Ala Ile Val Thr Lys Ser
    515                 520                 525

Ala Leu Glu Ser Val Leu Lys Arg Arg Ser Phe Ile Leu Ser Arg Ser
530                 535                 540

Thr Ala Pro Gly His Gly His Phe Ala Ala His Trp Asp Gly Asp Ile
545                 550                 555                 560

Leu Ser Asp Trp Pro Ser Met Lys Trp Ser Ile Ser Ser Ile Leu Asn
            565                 570                 575

Phe Asn Ile Phe Gly Val Pro Leu Ile Gly Ala Asp Ile Xaa Gly Phe
        580                 585                 590

Asn Gly Asn Thr Thr Ile Glu Leu Xaa Ala Arg Trp His Gln Leu Gly
    595                 600                 605

Ala Phe Tyr Thr Phe Val Arg Asn His Asn Thr Asp Asn Ala Ile Asp
610                 615                 620

Gln Asp Pro Val Ala Leu Gly Pro Leu Val Val Lys Ala Ala Lys Asn
625                 630                 635                 640

Ala Leu Lys Leu Arg Tyr Ala Leu Leu Pro Tyr Leu Tyr Thr Gln Phe
            645                 650                 655

Tyr Arg Val His Arg Lys Gly Gly Thr Ile Leu Arg Pro Leu Phe Phe
        660                 665                 670

Glu Phe Val His Asp Gln Val Val Leu Glu Ile Glu Thr Gln Phe Met
    675                 680                 685

Trp Gly Ser Ser Ile Met Val Ala Pro Ala Leu Ser Ile Asn Glu Thr
690                 695                 700

Glu Thr Ser Val Tyr Phe Pro Ser Gly Thr Trp Phe His Ser Tyr Asn
705                 710                 715                 720

Phe Thr Arg Ile Asn Thr Ile Gly Lys Phe Leu Pro Gln Leu Ala Ser
            725                 730                 735

Phe Asp Tyr Pro Asn Val Tyr Phe Arg Ala Gly Ser Ile Ile Pro Thr
        740                 745                 750

Leu Arg Pro Met Leu Thr Thr Asp Glu Thr His Ser Gly Asn Phe Thr
    755                 760                 765

Leu Leu Val Ala Leu Ser Asn Glu Asn Gly His Ala Glu Gly Asp Leu
770                 775                 780

Tyr Leu Asp Ser Gly Asp Gly Leu Asp Thr Glu Val Leu Gly His Tyr
785                 790                 795                 800

Asn Leu Tyr Ser Phe Lys Val Glu Lys Lys Ile Leu Glu Ile Lys Ser
            805                 810                 815

Ser His Leu Gly Tyr Ser Thr Glu Gln Met Ile Asp Asn Val Leu Ile
        820                 825                 830

Leu Gly Ile Asp Lys Ser Pro Ile Glu Ile Lys Ile Asn Gly Arg Ser

```
                      835                 840                 845
Met Lys Ser Trp Ser Tyr Ser Lys Asn Lys Ile His Ile Asn Ser Leu
            850                 855                 860

Asn Leu Pro Leu Tyr Asp Leu Lys Thr Ile Asp Lys Ser Lys Leu Ile
865                 870                 875                 880

Gln Ile His Tyr Gln Ile Glu Trp Val
                885

<210> SEQ ID NO 323
<211> LENGTH: 482
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is serine, alanine, or 2-aminobutyric acid
<220> FEATURE:
<221> NAME/KEY: misc_feature
<222> LOCATION: (79)..(79)
<223> OTHER INFORMATION: Xaa is serine, alanine, or 2-aminobutyric acid
<220> FEATURE:
<221> NAME/KEY: misc_feature
<222> LOCATION: (95)..(95)
<223> OTHER INFORMATION: Xaa is serine, alanine, or 2-aminobutyric acid
<220> FEATURE:
<221> NAME/KEY: misc_feature
<222> LOCATION: (114)..(114)
<223> OTHER INFORMATION: Xaa is serine, alanine, or 2-aminobutyric acid
<220> FEATURE:
<221> NAME/KEY: misc_feature
<222> LOCATION: (119)..(119)
<223> OTHER INFORMATION: Xaa is serine, alanine, or 2-aminobutyric acid
<220> FEATURE:
<221> NAME/KEY: misc_feature
<222> LOCATION: (177)..(177)
<223> OTHER INFORMATION: Xaa is serine, alanine, or 2-aminobutyric acid
<220> FEATURE:
<221> NAME/KEY: misc_feature
<222> LOCATION: (280)..(280)
<223> OTHER INFORMATION: Xaa is serine, alanine, or 2-aminobutyric acid
<220> FEATURE:
<221> NAME/KEY: misc_feature
<222> LOCATION: (326)..(326)
<223> OTHER INFORMATION: Xaa is serine, alanine, or 2-aminobutyric acid
<220> FEATURE:
<221> NAME/KEY: misc_feature
<222> LOCATION: (331)..(332)
<223> OTHER INFORMATION: Xaa is serine, alanine, or 2-aminobutyric acid
<220> FEATURE:
<221> NAME/KEY: misc_feature
<222> LOCATION: (369)..(369)
<223> OTHER INFORMATION: Xaa is serine, alanine, or 2-aminobutyric acid
<220> FEATURE:
<221> NAME/KEY: misc_feature
<222> LOCATION: (374)..(374)
<223> OTHER INFORMATION: Xaa is serine, alanine, or 2-aminobutyric acid
<220> FEATURE:
<221> NAME/KEY: misc_feature
<222> LOCATION: (383)..(383)
<223> OTHER INFORMATION: Xaa is serine, alanine, or 2-aminobutyric acid

<400> SEQUENCE: 323

Gly Xaa Phe Arg Ala Ala Val Leu Asp His Val His Gln Ser Ser Arg
1               5                   10                  15

Asn Gly Gly Gly Thr Lys Glu Asn Ile Lys Leu Asn Leu Lys Leu Tyr
                20                  25                  30

Glu Thr Ala Ala Lys Thr Ala Lys Glu Gln Gly Ala Asp Ile Ile Val
            35                  40                  45

Phe Pro Glu Asn Gly Ile Val Tyr Gly Ile Gly Ser Arg Ala Asn Ala
```

```
                50                  55                  60
Leu Lys Tyr Gly Glu Ile Leu Pro Glu Ser Lys Thr Ser Met Xaa Thr
 65                  70                  75                  80

Asp Ser Tyr Ala Ser Ser His Pro Ile Ala Tyr Gln Leu Ala Xaa Leu
                 85                  90                  95

Ala Lys Glu His Gln Met Phe Val Ala Ala Asp Met Ile Asp Val Gln
                100                 105                 110

Thr Xaa Gln Thr Lys Ser Xaa Pro Ile Asp Lys Lys Tyr Ala Phe Asn
        115                 120                 125

Thr Ala Val Leu Phe Asp Arg Asn Gly Tyr Leu Leu Gly Lys Tyr His
        130                 135                 140

Lys Met His Pro Phe Gly Glu Leu Gln Phe Asn Val Pro Pro Lys Asp
145                 150                 155                 160

Glu Leu Val Val Ile Glu Thr Glu Ile Gly Arg Leu Ser Met Gln Val
                165                 170                 175

Xaa Phe Asp Leu Ile Tyr Asn Lys Pro Gly Val Val Leu Ala Ser Gln
        180                 185                 190

Asp Lys Ile Asp Thr Met Leu Phe Pro Thr Trp Trp Phe Asp Glu Leu
        195                 200                 205

Pro Phe Leu Ala Ala Ser Gln Tyr Gln Met Ser Trp Ala Phe Gly Asn
210                 215                 220

Lys Ile Asn Leu Leu Ala Ser Asn Ile His Leu Val Ala Val Gly Ser
225                 230                 235                 240

Lys Gly Ser Gly Ile Phe Ala Gly Gly His Gly Gln Phe Glu Val Ile
                245                 250                 255

Ser Glu Pro Asp Ala Lys Ala Arg Ile Leu Val Ala Thr Leu Pro Ile
                260                 265                 270

Asn Ala Arg Ser Asp Ala Gln Xaa Ser Met Asp Ser Lys Lys Ile Glu
        275                 280                 285

Val Pro Gln Met Val Pro Ile Pro Ser Asn Val Ile Tyr Asn Tyr Gln
        290                 295                 300

Met Met Asn Leu Thr Glu Asn Thr Val Lys Lys Leu Asp Pro Ser Met
305                 310                 315                 320

Glu Ala Ile Ser Ala Xaa Asp Gly Gly Val Xaa Xaa Gln Leu Asn Tyr
                325                 330                 335

Gln Met Asp Gln Ser Ser Ile Lys Ser Asp Glu Glu Tyr Tyr Leu Ile
        340                 345                 350

Val Thr Asn Arg Thr Arg Pro Gly Ala Tyr Pro Trp Thr Glu Glu Tyr
        355                 360                 365

Xaa Gly Leu Val Leu Xaa Pro His Met Thr Lys Leu Asp Thr Xaa Lys
        370                 375                 380

Gln Ile Ser Ser Asn Asn Pro Leu Gln Thr Lys Phe Leu Tyr Ala Lys
385                 390                 395                 400

Leu Ser Gly Glu Phe Ser Ser Glu Thr His Val Tyr Pro Ser Val Ile
                405                 410                 415

Gly Ser Glu His Lys Val Leu Pro Lys Asp Gly Gly Leu Trp Thr Tyr
                420                 425                 430

Glu Asp Glu Lys Thr Asp Val Gly Ala Lys Lys Gln Lys Phe Phe Ile
        435                 440                 445

Thr Phe Gly Asn Lys Glu Glu Arg Lys Ser Tyr Thr Ile Ser Thr Ile
        450                 455                 460

Gly Leu Tyr Gly Arg Val Tyr Ala Arg Asp Pro Pro Tyr Glu Gln Lys
465                 470                 475                 480
```

Pro Leu

```
<210> SEQ ID NO 324
<211> LENGTH: 491
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (11)..(11)
<223> OTHER INFORMATION: Xaa is serine, alanine, or 2-aminobutyric acid
<220> FEATURE:
<221> NAME/KEY: misc_feature
<222> LOCATION: (37)..(37)
<223> OTHER INFORMATION: Xaa is serine, alanine, or 2-aminobutyric acid
<220> FEATURE:
<221> NAME/KEY: misc_feature
<222> LOCATION: (308)..(308)
<223> OTHER INFORMATION: Xaa is serine, alanine, or 2-aminobutyric acid
<220> FEATURE:
<221> NAME/KEY: misc_feature
<222> LOCATION: (372)..(372)
<223> OTHER INFORMATION: Xaa is serine, alanine, or 2-aminobutyric acid
<220> FEATURE:
<221> NAME/KEY: misc_feature
<222> LOCATION: (444)..(444)
<223> OTHER INFORMATION: Xaa is serine, alanine, or 2-aminobutyric acid
<220> FEATURE:
<221> NAME/KEY: misc_feature
<222> LOCATION: (462)..(462)
<223> OTHER INFORMATION: Xaa is serine, alanine, or 2-aminobutyric acid
<220> FEATURE:
<221> NAME/KEY: misc_feature
<222> LOCATION: (477)..(477)
<223> OTHER INFORMATION: Xaa is serine, alanine, or 2-aminobutyric acid
<220> FEATURE:
<221> NAME/KEY: misc_feature
<222> LOCATION: (490)..(490)
<223> OTHER INFORMATION: Xaa is serine, alanine, or 2-aminobutyric acid

<400> SEQUENCE: 324

Asp Arg Asn Lys Leu Pro His Lys Val Val Xaa Tyr Trp Gly Thr Trp
1               5                   10                  15

Ala Phe Tyr Arg Pro Gly Ser Asp Gly Lys Phe Glu Ala Glu Asn Ile
            20                  25                  30

Asn Pro Asn Leu Xaa Thr His Ile Asn Tyr Gly Phe Ala Lys Leu Val
        35                  40                  45

Gly Asn Lys Ile Ala Leu Phe Asp Pro Asp Leu Asp Thr Gly Asp Glu
    50                  55                  60

Asp Trp Ala Ser Gly Leu Thr Trp Gly His Gly Met Ile Arg Arg Leu
65                  70                  75                  80

Asn Glu Leu Arg Lys Tyr Asn Lys Asn Leu Ser Thr Leu Ile Ser Ile
                85                  90                  95

Gly Gly Trp Asn Glu Gly Ser Asn Lys Tyr Ser Thr Met Val Ser Thr
            100                 105                 110

Ala Gly Gly Arg Ser Glu Phe Val Lys Ser Val Ile Glu Phe Leu Gln
        115                 120                 125

Lys Tyr Glu Phe Asp Gly Leu Asp Leu Asp Trp Glu Tyr Pro Gly Met
    130                 135                 140

Ser Ala Ser Gly Asp Ala Asp Arg Lys Pro Gly Arg Glu Gln Asp Lys
145                 150                 155                 160

Ala Asp Tyr Ile Glu Leu Leu Lys Glu Leu Arg Gln Ala Phe Glu Pro
                165                 170                 175

His Gly Tyr Ile Leu Ser Ala Ala Val Ser Ala Gly Ala Pro Thr Ile
```

```
                  180                 185                 190
Asp Arg Ala Tyr Asn Val Pro Glu Val Ser Lys His Leu His Phe Ile
            195                 200                 205
Asn Leu Met Ala Tyr Asp Phe His Gly Gly Trp Asp Thr Lys Thr Ala
        210                 215                 220
His Asn Ala Pro Leu Tyr Ala Leu Pro Gly Ala Glu Gly Ile Asp Lys
225                 230                 235                 240
Glu Phe Thr Val Ser Tyr Ala Val Glu Tyr Trp Ile Ser Lys Gly Ala
                245                 250                 255
Asp Pro Lys Lys Leu Val Leu Gly Ile Pro Leu Tyr Gly Arg Thr Phe
            260                 265                 270
Thr Leu Ala Gly Pro Asn His Asp Ile Gly Ala Pro Val Thr Gly His
        275                 280                 285
Gly Gly Gln Ala Gly Pro Ile Thr Arg Leu Ile Gly Met Leu Gly Tyr
    290                 295                 300
Asn Glu Ile Xaa Ser Met Val Lys Asn Gly Trp Glu Ile His Trp Asn
305                 310                 315                 320
Asp Ile Gln Gln Ile Pro Tyr Ala Thr His Ala Ser Gln Trp Ile Gly
                325                 330                 335
Tyr Asp Asn Glu Lys Ser Ile Glu Lys Lys Leu Asp Tyr Val His Gln
            340                 345                 350
Lys Asn Leu Gly Gly Met Val Trp Ser Ile Asp Thr Asp Asp Phe
        355                 360                 365
Ser Gly His Xaa Gly Val Lys Tyr Pro Leu Leu Lys Thr Ile Ser Arg
    370                 375                 380
Arg Leu Asn Asn Ile Asp Gly Pro Asp Val Val Ile Pro Arg Thr His
385                 390                 395                 400
Ala Thr Thr Pro His Pro Asp Asp His Asp Thr Thr Lys Arg Pro
                405                 410                 415
Asp Asp Pro His Thr Asp Pro Thr Glu Pro His His Asp Lys Thr
            420                 425                 430
Thr Ser Ala Pro Asn Pro Asp Gly Lys Phe Gln Xaa His Ser Thr Gly
        435                 440                 445
Phe Phe Lys Asp Pro Ser Asp Pro Arg Lys Phe His Gln Xaa Val Asp
    450                 455                 460
Ile Gly Asn Gly Lys Leu Lys Asp Tyr Glu Phe Asn Xaa Pro Leu Gly
465                 470                 475                 480
Ser His Tyr Asp Glu Gln Leu His Val Xaa Val
                485                 490

<210> SEQ ID NO 325
<211> LENGTH: 459
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: Xaa is serine, alanine, or 2-aminobutyric acid
<220> FEATURE:
<221> NAME/KEY: misc_feature
<222> LOCATION: (30)..(30)
<223> OTHER INFORMATION: Xaa is serine, alanine, or 2-aminobutyric acid
<220> FEATURE:
<221> NAME/KEY: misc_feature
<222> LOCATION: (96)..(96)
<223> OTHER INFORMATION: Xaa is serine, alanine, or 2-aminobutyric acid
<220> FEATURE:
```

<221> NAME/KEY: misc_feature
<222> LOCATION: (114)..(114)
<223> OTHER INFORMATION: Xaa is serine, alanine, or 2-aminobutyric acid
<220> FEATURE:
<221> NAME/KEY: misc_feature
<222> LOCATION: (241)..(241)
<223> OTHER INFORMATION: Xaa is serine, alanine, or 2-aminobutyric acid
<220> FEATURE:
<221> NAME/KEY: misc_feature
<222> LOCATION: (244)..(244)
<223> OTHER INFORMATION: Xaa is serine, alanine, or 2-aminobutyric acid
<220> FEATURE:
<221> NAME/KEY: misc_feature
<222> LOCATION: (277)..(277)
<223> OTHER INFORMATION: Xaa is serine, alanine, or 2-aminobutyric acid
<220> FEATURE:
<221> NAME/KEY: misc_feature
<222> LOCATION: (284)..(284)
<223> OTHER INFORMATION: Xaa is serine, alanine, or 2-aminobutyric acid
<220> FEATURE:
<221> NAME/KEY: misc_feature
<222> LOCATION: (307)..(307)
<223> OTHER INFORMATION: Xaa is serine, alanine, or 2-aminobutyric acid
<220> FEATURE:
<221> NAME/KEY: misc_feature
<222> LOCATION: (317)..(317)
<223> OTHER INFORMATION: Xaa is serine, alanine, or 2-aminobutyric acid
<220> FEATURE:
<221> NAME/KEY: misc_feature
<222> LOCATION: (328)..(328)
<223> OTHER INFORMATION: Xaa is serine, alanine, or 2-aminobutyric acid
<220> FEATURE:
<221> NAME/KEY: misc_feature
<222> LOCATION: (347)..(347)
<223> OTHER INFORMATION: Xaa is serine, alanine, or 2-aminobutyric acid
<220> FEATURE:
<221> NAME/KEY: misc_feature
<222> LOCATION: (446)..(446)
<223> OTHER INFORMATION: Xaa is serine, alanine, or 2-aminobutyric acid

<400> SEQUENCE: 325

Asp Thr Pro Ala Asn Xaa Thr Tyr Glu Asp Ile Arg Gly Glu Trp Glu
1               5                   10                  15

Phe His Glu Thr Glu Arg Ile Ala Ser Arg Lys Glu Val Xaa Asp Asp
            20                  25                  30

Asn Ser Val Ser Thr Thr Lys His Thr Val Tyr Leu Lys Leu Glu Phe
        35                  40                  45

Pro Asn Ile Ala Thr Asp Gln His Gly Asn Val Gly His Trp Thr Ile
    50                  55                  60

Ile Tyr Asn Gln Gly Phe Glu Val Ser Ile Asn Tyr Arg Lys Tyr Phe
65                  70                  75                  80

Ala Phe Ser Leu Tyr Lys Gln Val Gly Lys Gln Val Thr Ser Tyr Xaa
                85                  90                  95

Asp Ser Thr Phe Pro Gly Trp Ser His Asp Val Leu Gly Asn Asn Trp
            100                 105                 110

Ala Xaa Phe Lys Gly Arg Lys Val Asn Arg Gln Gln Glu Lys Ser Phe
        115                 120                 125

Asp Glu Thr Met Ile Asn Asn Gly Lys Thr His Thr Val Gln Pro Phe
    130                 135                 140

Leu Leu Glu Ser Val Pro Val Asn His Asn Leu Ile Gln Met Asn Val
145                 150                 155                 160

Asn Lys Ile Asn Met Lys Gln Ser Ser Trp Lys Ala Lys Phe Tyr Pro
                165                 170                 175

His Leu Met Asn Leu Asn Thr Glu Asp Leu Ile Arg Met Ala Gly Gly
            180                 185                 190

Arg Gly Ser Ala Ile Val Asn Arg Pro Ser Thr Val Pro Ala Ser Glu

```
                195                 200                 205
Glu Ile Lys Glu Lys Val Arg Gln Leu Pro Glu Ser Phe Asp Trp Arg
    210                 215                 220

Asn Val Asn Gly Ile Asn Tyr Val Ser Pro Val Arg Asp Gln Gly Lys
225                 230                 235                 240

Xaa Gly Ser Xaa Tyr Ile Phe Ser Ser Met Ala Gln Leu Glu Ala Arg
                245                 250                 255

Val Arg Ile Ala Thr Asn Asn Ser Glu Gln Pro Ile Phe Ser Thr Gln
            260                 265                 270

Glu Val Val Asp Xaa Ser Lys Tyr Ser Gln Gly Xaa Asp Gly Gly Phe
        275                 280                 285

Pro Tyr Leu Ile Ala Gly Lys Tyr Gly Arg Asp Tyr Gly Val Ile Ala
    290                 295                 300

Asp Glu Xaa Tyr Pro Tyr Lys Gly Lys Asn Gly Lys Xaa Ser Leu Pro
305                 310                 315                 320

Tyr Asn Ser Thr Gly Thr Lys Xaa Met Lys Arg Ser Tyr Thr Leu His
                325                 330                 335

Tyr His Tyr Val Gly Gly Tyr Tyr Gly Gly Xaa Asn Glu Glu Leu Met
            340                 345                 350

Leu Leu Glu Leu Val Lys Asn Gly Pro Ile Thr Val Gly Phe Glu Val
        355                 360                 365

Tyr Asp Asp Phe Thr Ser Tyr Ser Gly Gly Ile Tyr Ser His Asp Lys
    370                 375                 380

Ser Lys Asp Gln Trp Arg Asn Gly Val His Phe Asn Pro Phe Gln Leu
385                 390                 395                 400

Thr Asn His Ala Val Leu Ile Val Gly Tyr Gly Val Asp Lys Gln Ser
                405                 410                 415

Gly Glu Lys Tyr Trp Ile Val Lys Asn Ser Trp Gly Lys Asp Trp Gly
            420                 425                 430

Leu Asp Gly Tyr Phe Trp Ile Lys Arg Gly Asn Asp Glu Xaa Gly Ile
        435                 440                 445

Glu Ser Leu Ala Val Ser Val Thr Pro Ile Pro
    450                 455

<210> SEQ ID NO 326
<211> LENGTH: 309
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (110)..(110)
<223> OTHER INFORMATION: Xaa is serine, alanine, or 2-aminobutyric acid
<220> FEATURE:
<221> NAME/KEY: misc_feature
<222> LOCATION: (113)..(113)
<223> OTHER INFORMATION: Xaa is serine, alanine, or 2-aminobutyric acid
<220> FEATURE:
<221> NAME/KEY: misc_feature
<222> LOCATION: (144)..(144)
<223> OTHER INFORMATION: Xaa is serine, alanine, or 2-aminobutyric acid
<220> FEATURE:
<221> NAME/KEY: misc_feature
<222> LOCATION: (155)..(155)
<223> OTHER INFORMATION: Xaa is serine, alanine, or 2-aminobutyric acid
<220> FEATURE:
<221> NAME/KEY: misc_feature
<222> LOCATION: (158)..(158)
<223> OTHER INFORMATION: Xaa is serine, alanine, or 2-aminobutyric acid
<220> FEATURE:
<221> NAME/KEY: misc_feature
```

<222> LOCATION: (190)..(190)
<223> OTHER INFORMATION: Xaa is serine, alanine, or 2-aminobutyric acid

<400> SEQUENCE: 326

Ile Lys Thr Phe Glu Gln Phe Lys Lys Val Phe Gly Lys Val Tyr Arg
1               5                   10                  15

Asn Ala Glu Glu Ala Arg Arg Glu His Phe Lys Glu Gln Leu
            20                  25                  30

Lys Trp Val Glu Glu His Asn Gly Ile Asp Gly Val Glu Tyr Ala Ile
        35                  40                  45

Asn Glu Tyr Ser Asp Met Ser Glu Gln Glu Phe Ser Phe His Leu Ser
    50                  55                  60

Gly Gly Gly Leu Asn Phe Thr Tyr Met Lys Met Glu Ala Ala Lys Glu
65              70                  75                  80

Pro Leu Ile Asn Thr Tyr Gly Ser Leu Pro Gln Asn Phe Asp Trp Arg
                85                  90                  95

Gln Lys Ala Arg Leu Thr Arg Ile Arg Gln Gln Gly Ala Xaa Gly Ser
            100                 105                 110

Xaa Trp Ala Phe Ala Ala Gly Val Ala Glu Ser Leu Tyr Ser Ile
        115                 120                 125

Gln Lys Gln Gln Ser Ile Glu Leu Ser Glu Gln Glu Leu Val Asp Xaa
130                 135                 140

Thr Tyr Asn Arg Tyr Asp Ser Ser Tyr Gln Xaa Asn Gly Xaa Gly Ser
145                 150                 155                 160

Gly Tyr Ser Thr Glu Ala Phe Lys Tyr Met Ile Arg Thr Gly Leu Val
                165                 170                 175

Glu Glu Arg Asn Tyr Pro Tyr Asn Met Arg Thr Gln Trp Xaa Asp Pro
            180                 185                 190

Asp Val Glu Gly Gln Arg Tyr His Val Ser Gly Tyr Gln Gln Leu Arg
        195                 200                 205

Tyr Gln Ser Ser Asp Glu Asp Val Met Tyr Thr Ile Gln Gln His Gly
    210                 215                 220

Pro Val Val Ile Tyr Met His Gly Ser Asn Asn Tyr Phe Arg Asn Leu
225                 230                 235                 240

Gly Asn Gly Val Leu Arg Gly Val Ala Tyr Asn Asp Ala Tyr Thr Asp
                245                 250                 255

His Ala Val Ile Leu Val Gly Trp Gly Thr Val Gln Gly Val Asp Tyr
            260                 265                 270

Trp Ile Ile Arg Asn Ser Trp Gly Thr Gly Trp Gly Asn Gly Gly Tyr
        275                 280                 285

Gly Tyr Val Glu Arg Gly His Asn Ser Leu Gly Ile Asn Asn Phe Val
    290                 295                 300

Thr Tyr Ala Thr Leu
305

<210> SEQ ID NO 327
<211> LENGTH: 260
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (258)..(258)
<223> OTHER INFORMATION: Xaa is serine, alanine, or 2-aminobutyric acid

<400> SEQUENCE: 327

```
Ser Leu Thr Asn Lys Lys Tyr Asp Phe Ser Gly Lys Val Ala Leu Val
1               5                   10                  15

Thr Gly Ser Ser Ser Gly Ile Gly Ala Ala Ile Ala Ile Gln Phe Ala
            20                  25                  30

Gln Tyr Gly Ala Lys Val Thr Ile Thr Gly Arg Asn Ala Glu Asn Leu
            35                  40                  45

Asp Lys Ile Ala Lys Lys Ile Ala Glu Val Ser Asn Gly Val Glu Ala
            50                  55                  60

Leu Gln Ile Ile Gly Asp Leu Thr Ile Asp Asp Ser Leu Pro Lys Arg
65                  70                  75                  80

Leu Ile Asp Glu Thr Val Thr Lys Phe Gly Arg Leu Asp Phe Leu Val
                85                  90                  95

Asn Asn Ala Gly Gly Ala Thr Pro Gln Gly Thr Leu Ala Ser Pro Asp
            100                 105                 110

Leu Leu Lys Gly Phe Asp Asp Val Phe Lys Leu Asn Val Arg Ser Val
            115                 120                 125

Ile Glu Leu Thr Gln Leu Ala Met Pro His Leu Glu Lys Thr Lys Gly
            130                 135                 140

Asn Ile Ile Asn Ile Ser Ser Val Ala Ser Ile Lys Pro Tyr Met Val
145                 150                 155                 160

Val Tyr Ser Ser Ser Lys Ala Ala Leu Asp Met Ile Thr Lys Thr Ser
                165                 170                 175

Ala Leu Glu Leu Gly Pro Lys Gly Ile Arg Val Asn Ser Ile Asn Pro
            180                 185                 190

Gly Pro Val Val Thr Ala Phe Gly Arg Ser Met Gly Val Asp Pro Ser
            195                 200                 205

His His Lys Lys Met Phe Asp Ser Phe Glu Lys Gln Met Leu Met Glu
            210                 215                 220

Arg Val Gly Gln Pro Glu Asp Ile Ala Asn Leu Ala Ser Phe Leu Ala
225                 230                 235                 240

Ser Asp Asp Ala Ile Asn Ile Thr Gly Ser Ile Met Val Asn Asp Ser
                245                 250                 255

Gly Xaa Leu Leu
            260

<210> SEQ ID NO 328
<211> LENGTH: 150
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (54)..(54)
<223> OTHER INFORMATION: Xaa is serine, alanine, or 2-aminobutyric acid
<220> FEATURE:
<221> NAME/KEY: misc_feature
<222> LOCATION: (143)..(143)
<223> OTHER INFORMATION: Xaa is serine, alanine, or 2-aminobutyric acid

<400> SEQUENCE: 328

Lys Ala Val Val Val Leu Lys Gly Asp Ser Pro Val Ser Gly Thr Ile
1               5                   10                  15

Phe Phe Glu Gln Lys Asp Asn Gly Pro Val Ser Val Thr Gly Thr Val
            20                  25                  30

Asn Gly Leu Thr Ala Gly Asp His Gly Phe His Val His Glu Phe Gly
            35                  40                  45

Asp Asn Thr Asn Gly Xaa Thr Ser Ala Gly Ala His Phe Asn Pro Phe
```

```
                50                  55                  60
Gly Lys Thr His Gly Ala Pro Ala Asp Gln Glu Arg His Val Gly Asp
 65                  70                  75                  80

Leu Gly Asn Val Thr Ala Asp Ala Asn Gly Val Ala Asn Val Asn Ile
                 85                  90                  95

Gln Asp Ser Leu Ile Thr Leu Glu Gly Ala Asn Thr Ile Val Gly Arg
            100                 105                 110

Ser Leu Val Val His Ala Asp Pro Asp Leu Gly Arg Gly Gly His
        115                 120                 125

Glu Leu Ser Lys Thr Thr Gly Asn Ala Gly Gly Arg Val Ala Xaa Gly
        130                 135                 140

Val Ile Gly Leu Thr Lys
145                 150

<210> SEQ ID NO 329
<211> LENGTH: 137
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (46)..(46)
<223> OTHER INFORMATION: Xaa is serine, alanine, or 2-aminobutyric acid
<220> FEATURE:
<221> NAME/KEY: misc_feature
<222> LOCATION: (75)..(75)
<223> OTHER INFORMATION: Xaa is serine, alanine, or 2-aminobutyric acid
<220> FEATURE:
<221> NAME/KEY: misc_feature
<222> LOCATION: (136)..(136)
<223> OTHER INFORMATION: Xaa is serine, alanine, or 2-aminobutyric acid

<400> SEQUENCE: 329

Gln Ala Met Ala Gly Gly His Glu Ile Val Thr Ala Ala Arg Ser Gln
  1               5                  10                  15

Leu Gly Val Pro Tyr Ser Trp Gly Gly Gly Asn Trp Ala Gly Lys Ser
             20                  25                  30

Lys Gly Ile Asp Ser Gly Ala His Thr Val Gly Phe Asp Xaa Ser Gly
         35                  40                  45

Leu Ala Gln Tyr Ala Val Tyr His Gly Thr His Lys Lys Ile Ala Arg
 50                  55                  60

Val Ala Ser Ala Gln Tyr Ala Asp His Gln Xaa His His Val Pro Tyr
 65                  70                  75                  80

Ala Gln His Leu Pro Gly Asp Leu Val Phe Phe Asn Asp Gly Gly Ser
                 85                  90                  95

Ile His His Val Ala Ile Ile Ser Gly Lys Asn Thr Met Ile His Ala
            100                 105                 110

Pro His Thr Gly Asp His Val Arg Glu Ala Ala Val Tyr Val Lys Gly
        115                 120                 125

Arg Met Ser Thr Val Gln Arg Xaa Phe
        130                 135

<210> SEQ ID NO 330
<211> LENGTH: 233
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (15)..(16)
```

<223> OTHER INFORMATION: Xaa is serine, alanine, or 2-aminobutyric acid

<400> SEQUENCE: 330

Met Ser Lys Pro Thr Leu Tyr Tyr Met Trp Glu Ser Pro Pro Xaa Xaa
1               5                   10                  15

Thr Val Ile Ala Ile Ala Arg Ile Leu Asn Ile Glu Leu Asp Met Lys
            20                  25                  30

His Val Asp Leu Thr Lys Lys Asp Gln Asn Asn Pro Glu Phe Lys Lys
        35                  40                  45

Ile Asn Pro Phe Ala Ile Val Pro Thr Phe Val Glu Thr Asp Gly Tyr
    50                  55                  60

Thr Leu Trp Glu Ser Arg Ala Ile Ser Thr Tyr Leu Val Gln Ser Arg
65                  70                  75                  80

Ser Pro Asp Ser Thr Leu Tyr Pro Gly Ser Asp Leu Lys Lys Arg Ser
                85                  90                  95

Thr Ile Asp Lys Phe Leu Gln Tyr Asp Leu Gly Thr Phe Asn Arg Ala
            100                 105                 110

Ile Tyr Asp Val Val Ser Glu Ile Phe Lys Ser Gly Lys Leu Asn Glu
        115                 120                 125

Gln Asn Ile Pro Arg Leu Gly Glu Val Leu Lys Thr Leu Glu Glu Thr
    130                 135                 140

Leu Ala Ala Asn Asn Glu Ser Asn Gly Gly Pro Phe Ile Thr Gly Asp
145                 150                 155                 160

Asp Gln Leu Thr Ile Ala Asp Ile Ser Met His Phe Ser Trp Thr Leu
                165                 170                 175

Leu Ser Leu Leu Pro Glu Arg Leu Ile Asp Gln Ser Ser Tyr Pro Thr
            180                 185                 190

Ile Arg Ala Trp Asn Gln Ala Val Ile Gln Ala Leu Lys Pro Tyr Asn
        195                 200                 205

Arg Asp Gln Lys Phe Thr Glu Ala Gln Arg Leu Lys Ala Phe Ile
    210                 215                 220

Thr Met Met Ile Glu Ser Ala Lys Asn
225                 230

<210> SEQ ID NO 331
<211> LENGTH: 252
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (26)..(26)
<223> OTHER INFORMATION: Xaa is serine, alanine, or 2-aminobutyric acid
<220> FEATURE:
<221> NAME/KEY: misc_feature
<222> LOCATION: (35)..(35)
<223> OTHER INFORMATION: Xaa is serine, alanine, or 2-aminobutyric acid

<400> SEQUENCE: 331

Asn Trp Gln Leu Val Trp Ser Asp Glu Phe Asn Gly Asn Gly Leu Asp
1               5                   10                  15

Glu Asn Asn Trp Asn Tyr Gln Thr Gly Xaa Ser Gln Gln Asn Asp Glu
            20                  25                  30

Leu Glu Xaa Tyr Thr Ser His Arg His Glu Asn Val Arg Val Glu Asn
        35                  40                  45

Gly His Leu Val Ile Glu Ala Arg Pro Glu Glu Tyr Gln Gly His His
    50                  55                  60

```
Phe Thr Ser Gly Arg Leu His Gly Lys Lys Ala Trp Ala Tyr Gly Lys
 65                  70                  75                  80

Phe Glu Ala Arg Ala Lys Met Pro Ser Gly His His Leu Trp Pro Ala
                 85                  90                  95

Ile Trp Met Met Pro Arg Asp Ser Lys Tyr Gly Gly Trp Ala Ala Ser
            100                 105                 110

Gly Glu Ile Asp Ile Leu Glu Leu Arg Gly Asp Lys Pro His Glu Ile
        115                 120                 125

Val Gly Thr Ile His Tyr Gly Gly Ser Trp Pro Asn Asn Ile Tyr His
    130                 135                 140

Gly Ser Gly Glu Arg Tyr Tyr Gln Gln Asp Phe Ser Gln Asp Tyr His
145                 150                 155                 160

Thr Phe Ala Val Glu Trp Asp Gln Lys Glu Ile Arg Trp Tyr Val Asp
                165                 170                 175

Gly Gln His Tyr His Thr Glu Asn Ile Asp Arg Asn Met Trp Ser Gly
            180                 185                 190

Arg Gly Asn Asn Pro Tyr His Lys Asn Gly Glu Pro Phe Asp Gln Pro
        195                 200                 205

Phe Tyr Trp Ile Leu Asn Val Ala Val Gly Gly Asn Phe Phe Gly Pro
    210                 215                 220

Gly Pro Tyr Val Ser Pro Ala Glu Ala Arg Asn Trp His Lys Arg Thr
225                 230                 235                 240

Met Glu Val Asp Tyr Val Arg Val Tyr Gln Trp Arg
                245                 250

<210> SEQ ID NO 332
<211> LENGTH: 187
<212> TYPE: PRT
<213> ORGANISM: Artificial sequene
<220> FEATURE:
<223> OTHER INFORMATION: Synthetic sequence
<220> FEATURE:
<221> NAME/KEY: misc_feature
<222> LOCATION: (123)..(123)
<223> OTHER INFORMATION: Xaa is serine, alanine, or 2-aminobutyric acid

<400> SEQUENCE: 332

Met Ser Ile Ser Ala His Gly Gly Gly Leu Ile Asn Gly Ile Ala Gly
  1               5                  10                  15

Met Glu Asn Lys Phe Thr Val Phe Thr Ser Gly Lys Pro Val Ser Gly
                 20                  25                  30

Leu Thr Val Ala Phe Glu Gly Pro Thr Lys Pro Asp Ile Asn Phe Asn
             35                  40                  45

Ser Ala Lys Asp Gly Ser Val Asp Val Ser Tyr Thr Pro Lys Ala Gly
 50                  55                  60

Gly Met Tyr Lys Ile His Ile Lys Tyr Asp Lys Glu Ile Ile Gly
 65                  70                  75                  80

Ser Pro Phe Lys Thr Asn Ile Thr Gly Asp Glu Ala Thr His Arg Lys
                 85                  90                  95

Leu Thr Glu Lys Val Lys Val Gly Gly Pro Asn Val Ser Thr Gly Lys
            100                 105                 110

Ala Asn Ala Asp Asn Glu Leu Thr Ile Asp Xaa Lys Glu Ala Gly Ile
        115                 120                 125

Thr Gly Gly Ile Ser Phe Ala Met Glu Gly Pro Ala Lys Val Glu Val
    130                 135                 140

Ser Phe Arg Asn Asn Asn Asp Gly Thr Ile Thr Val Val Tyr Lys Pro
145                 150                 155                 160
```

```
Pro Gln Asn Gly Asp Tyr Lys Leu His Leu Lys Phe Asn Asp Ile His
            165                 170                 175

Leu Pro Gly Ser Pro Phe Pro Ile Val Val Ser
            180                 185
```